United States Patent
Zemel et al.

(10) Patent No.: US 9,855,235 B2
(45) Date of Patent: *Jan. 2, 2018

(54) COMPOSITIONS AND METHODS FOR MODULATING METABOLIC PATHWAYS

(71) Applicant: NuSirt Sciences, Inc., Nashville, TN (US)

(72) Inventors: Michael Zemel, Knoxville, TN (US); E. Douglas Grindstaff, II, Nashville, TN (US); Antje Bruckbauer, Knoxville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,911

(22) Filed: May 15, 2017

(65) Prior Publication Data

US 2017/0312240 A1    Nov. 2, 2017

Related U.S. Application Data

(63) Continuation of application No. 15/164,647, filed on May 25, 2016, now Pat. No. 9,682,053, which is a (Continued)

(51) Int. Cl.
*A61K 31/198* (2006.01)
*A61K 31/216* (2006.01)
(Continued)

(52) U.S. Cl.
CPC .............. *A61K 31/198* (2013.01); *A23L 2/52* (2013.01); *A23L 33/175* (2016.08); *A23L 33/30* (2016.08);
(Continued)

(58) Field of Classification Search
CPC .... A61K 31/198; A61K 31/216; A61K 38/22; A61K 31/353; A61K 45/06;
(Continued)

(56) References Cited

U.S. PATENT DOCUMENTS 3,810,994 A    5/1974   Wiegand
3,936,527 A    2/1976   Alper
(Continued)

FOREIGN PATENT DOCUMENTS

CN    1504424 A    6/2004
CN    102077936 A    6/2011
(Continued)

OTHER PUBLICATIONS

Agarwal. Cortisol metabolism and visceral obesity: role of 11beta-hydroxysteroid dehydrogenase type I enzyme and reduced co-factor NADPH. Endocr Res. Nov. 2003; 29(4):411-8.
(Continued)

*Primary Examiner* — Trevor Love
(74) *Attorney, Agent, or Firm* — Wilson Sonsini Goodrich & Rosati

(57) ABSTRACT

Compositions and methods useful for inducing an increase in fatty acid oxidation or mitochondrial biogenesis, reducing weight gain, inducing weight loss, or increasing Sirt1, Sirt3, or AMPK activity are provided herein. Such compositions can contain synergizing amounts of a sirtuin-pathway activators, including but not limited to resveratrol, in combination with beta-hydroxymethylbutyrate (HMB), keto isocaproic acid (KIC), leucine, or combinations of HMB, KIC and leucine.

25 Claims, 39 Drawing Sheets

Related U.S. Application Data continuation of application No. 14/927,255, filed on Oct. 29, 2015, now Pat. No. 9,351,967, which is a continuation of application No. 14/746,516, filed on Jun. 22, 2015, now Pat. No. 9,198,883, which is a continuation of application No. 13/866,936, filed on Apr. 19, 2013, now Pat. No. 9,072,692, which is a continuation of application No. 13/549,381, filed on Jul. 13, 2012, now Pat. No. 8,617,886.

(60) Provisional application No. 61/508,139, filed on Jul. 15, 2011, provisional application No. 61/636,597, filed on Apr. 20, 2012, provisional application No. 61/636,598, filed on Apr. 20, 2012, provisional application No. 61/636,603, filed on Apr. 20, 2012, provisional application No. 61/636,605, filed on Apr. 20, 2012, provisional application No. 61/636,608, filed on Apr. 20, 2012, provisional application No. 61/636,610, filed on Apr. 20, 2012.

(51) Int. Cl.

| | |
|---|---|
| A61K 38/22 | (2006.01) |
| A61K 31/353 | (2006.01) |
| A61K 45/06 | (2006.01) |
| A61K 31/015 | (2006.01) |
| A61K 31/19 | (2006.01) |
| A61K 31/426 | (2006.01) |
| A61K 31/194 | (2006.01) |
| A61K 31/4439 | (2006.01) |
| A61K 31/191 | (2006.01) |
| A61K 31/522 | (2006.01) |
| A61K 31/366 | (2006.01) |
| A61K 31/336 | (2006.01) |
| A61K 31/192 | (2006.01) |
| A61K 31/155 | (2006.01) |
| A61K 36/87 | (2006.01) |
| A23L 2/52 | (2006.01) |
| A23L 33/175 | (2016.01) |
| A23L 33/00 | (2016.01) |
| A61K 31/05 | (2006.01) |

(52) U.S. Cl.
CPC ............ *A61K 31/015* (2013.01); *A61K 31/05* (2013.01); *A61K 31/155* (2013.01); *A61K 31/19* (2013.01); *A61K 31/191* (2013.01); *A61K 31/192* (2013.01); *A61K 31/194* (2013.01); *A61K 31/216* (2013.01); *A61K 31/336* (2013.01); *A61K 31/353* (2013.01); *A61K 31/366* (2013.01); *A61K 31/426* (2013.01); *A61K 31/4439* (2013.01); *A61K 31/522* (2013.01); *A61K 36/87* (2013.01); *A61K 38/22* (2013.01); *A61K 45/06* (2013.01); *A23V 2002/00* (2013.01)

(58) Field of Classification Search
CPC .... A61K 31/015; A61K 31/19; A61K 31/426; A61K 31/194; A61K 31/4439; A61K 31/05; A61K 31/191; A61K 31/522; A61K 31/366; A61K 31/336; A61K 31/192; A61K 31/155; A61K 36/87; A23L 2/52; A23L 33/30; A23L 33/175; A23V 2002/00

See application file for complete search history.

(56) References Cited

U.S. PATENT DOCUMENTS

| | | |
|---|---|---|
| 4,606,909 A | 8/1986 | Bechgaard et al. |
| 4,769,027 A | 9/1988 | Baker et al. |
| 4,803,080 A | 2/1989 | Benedikt et al. |
| 4,897,268 A | 1/1990 | Tice et al. |
| 4,992,470 A | 2/1991 | Nissen |
| 5,069,204 A | 12/1991 | Smith et al. |
| 5,087,624 A | 2/1992 | Boynton et al. |
| 5,250,534 A | 10/1993 | Bell et al. |
| 5,339,771 A | 8/1994 | Axelrod |
| 5,395,626 A | 3/1995 | Kotwal et al. |
| 5,419,283 A | 5/1995 | Leo |
| 5,616,569 A | 4/1997 | Reinhart |
| 5,776,913 A | 7/1998 | Ogilvie et al. |
| 5,886,012 A | 3/1999 | Pang et al. |
| 5,968,569 A | 10/1999 | Cavadini et al. |
| 6,004,996 A | 12/1999 | Shah et al. |
| 6,031,000 A | 2/2000 | Nissen et al. |
| 6,048,903 A | 4/2000 | Toppo |
| 6,063,414 A | 5/2000 | Jones et al. |
| 6,063,820 A | 5/2000 | Cavazza |
| 6,224,861 B1 | 5/2001 | Abe et al. |
| 6,280,779 B1 | 8/2001 | Nadeau et al. |
| 6,338,862 B1 | 1/2002 | Niazi |
| 6,369,042 B1 | 4/2002 | Oberthuer et al. |
| 6,384,087 B1 | 5/2002 | Zemel et al. |
| 6,387,419 B1 | 5/2002 | Christensen |
| 6,426,091 B1 | 7/2002 | Okumura et al. |
| 6,469,012 B1 | 10/2002 | Ellis et al. |
| 6,517,877 B2 | 2/2003 | Gannon |
| 6,527,711 B1 | 3/2003 | Stivoric et al. |
| 6,595,929 B2 | 7/2003 | Stivoric et al. |
| 6,605,038 B1 | 8/2003 | Teller et al. |
| 6,635,268 B2 | 10/2003 | Peery et al. |
| 6,638,545 B1 | 10/2003 | Rombi |
| 6,676,967 B1 | 1/2004 | Cefali et al. |
| 6,764,697 B1 | 7/2004 | Jao et al. |
| 6,790,869 B2 | 9/2004 | Ghai et al. |
| 6,797,283 B1 | 9/2004 | Edgren et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 7,020,508 B2 | 3/2006 | Stivoric et al. |
| 7,109,198 B2 | 9/2006 | Gadde et al. |
| 7,141,254 B2 | 11/2006 | Bhaskaran et al. |
| 7,153,262 B2 | 12/2006 | Stivoric et al. |
| 7,230,009 B2 | 6/2007 | Haque et al. |
| 7,261,690 B2 | 8/2007 | Teller et al. |
| 7,285,090 B2 | 10/2007 | Stivoric et al. |
| 7,354,738 B2 | 4/2008 | Spiegelman et al. |
| 7,495,101 B2 | 2/2009 | Fischesser et al. |
| 7,502,643 B2 | 3/2009 | Farringdon et al. |
| 7,674,485 B2 | 3/2010 | Bhaskaran et al. |
| 7,689,437 B1 | 3/2010 | Teller et al. |
| 7,722,905 B2 | 5/2010 | Khoo |
| 7,744,930 B2 | 6/2010 | Fisher et al. |
| 7,829,556 B2 | 11/2010 | Bemis et al. |
| 7,855,289 B2 | 12/2010 | Nunes et al. |
| 7,870,856 B2 | 1/2011 | Boeck |
| 7,893,086 B2 | 2/2011 | Bemis et al. |
| 7,959,567 B2 | 6/2011 | Stivoric et al. |
| 7,989,007 B2 | 8/2011 | Giuliano et al. |
| 8,008,458 B2 | 8/2011 | Zaloga et al. |
| 8,017,634 B2 | 9/2011 | Sinclair et al. |
| 8,044,198 B2 | 10/2011 | Nunes et al. |
| 8,073,707 B2 | 12/2011 | Teller et al. |
| 8,088,043 B2 | 1/2012 | Andren et al. |
| 8,088,044 B2 | 1/2012 | Tchao et al. |
| 8,088,928 B2 | 1/2012 | Nunes et al. |
| 8,093,401 B2 | 1/2012 | Nunes et al. |
| 8,106,097 B2 | 1/2012 | Najib et al. |
| 8,157,731 B2 | 4/2012 | Teller et al. |
| 8,192,767 B2 | 6/2012 | Carta |
| 8,275,635 B2 | 9/2012 | Stivoric et al. |
| 8,299,083 B2 | 10/2012 | Kass et al. |

(56) References Cited

U.S. PATENT DOCUMENTS

| | | |
|---|---|---|
| 8,369,936 B2 | 2/2013 | Farringdon et al. |
| 8,370,549 B2 | 2/2013 | Burton et al. |
| 8,378,090 B2 | 2/2013 | Petiard et al. |
| 8,382,590 B2 | 2/2013 | Stivoric et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,469,862 B2 | 6/2013 | Andren et al. |
| 8,517,896 B2 | 8/2013 | Robinette et al. |
| 8,557,869 B2 | 10/2013 | Yamka et al. |
| 8,562,489 B2 | 10/2013 | Burton et al. |
| 8,597,677 B2 | 12/2013 | Yamka et al. |
| 8,617,886 B2 | 12/2013 | Zemel et al. |
| 8,623,924 B2 | 1/2014 | Zemel et al. |
| 9,072,692 B2 | 7/2015 | Zemel et al. |
| 9,198,454 B2 | 12/2015 | Zemel et al. |
| 9,198,883 B1 | 12/2015 | Zemel et al. |
| 9,351,967 B2 | 5/2016 | Zemel et al. |
| 9,408,410 B2 | 8/2016 | Zemel et al. |
| 9,408,834 B2 | 8/2016 | Zemel et al. |
| 9,585,876 B2 | 3/2017 | Zemel et al. |
| 9,682,053 B2 | 6/2017 | Zemel et al. |
| 9,707,213 B2 | 7/2017 | Zemel et al. |
| 2001/0043983 A1 | 11/2001 | Hamilton |
| 2003/0035882 A1 | 2/2003 | McDaniel et al. |
| 2003/0187055 A1 | 10/2003 | Riker et al. |
| 2004/0120983 A1 | 6/2004 | Connolly |
| 2004/0186046 A1 | 9/2004 | Burgess et al. |
| 2005/0042362 A1 | 2/2005 | Clark et al. |
| 2005/0064070 A1 | 3/2005 | Liebrecht |
| 2005/0100617 A1 | 5/2005 | Malnoe et al. |
| 2005/0215882 A1 | 9/2005 | Chenevert et al. |
| 2006/0051416 A1 | 3/2006 | Rastogi et al. |
| 2006/0111435 A1 | 5/2006 | Sinclair et al. |
| 2006/0159746 A1 | 7/2006 | Troup et al. |
| 2006/0165824 A1 | 7/2006 | Khambe |
| 2006/0188611 A1 | 8/2006 | Unlu et al. |
| 2006/0194743 A1 | 8/2006 | Oku et al. |
| 2006/0205633 A1 | 9/2006 | Nishitani et al. |
| 2007/0014833 A1 | 1/2007 | Milburn et al. |
| 2007/0065512 A1 | 3/2007 | Dedhiya et al. |
| 2007/0077310 A1 | 4/2007 | Zemel et al. |
| 2007/0092577 A1 | 4/2007 | Zemel et al. |
| 2007/0110850 A1 | 5/2007 | Rifkin |
| 2007/0190171 A1 | 8/2007 | Yamka et al. |
| 2007/0203083 A1 | 8/2007 | Mootha et al. |
| 2007/0244202 A1 | 10/2007 | Murase |
| 2007/0286909 A1 | 12/2007 | Smith et al. |
| 2008/0069862 A1 | 3/2008 | Hurwitz |
| 2008/0076828 A1 | 3/2008 | Dalton et al. |
| 2008/0102137 A1 | 5/2008 | Guffey |
| 2008/0176822 A1 | 7/2008 | Chen |
| 2008/0220092 A1 | 9/2008 | Dipierro et al. |
| 2008/0233245 A1 | 9/2008 | White et al. |
| 2008/0268038 A1 | 10/2008 | Wolfe |
| 2008/0286254 A1 | 11/2008 | Sakamoto et al. |
| 2009/0012183 A1 | 1/2009 | Draijer et al. |
| 2009/0017130 A1 | 1/2009 | Yamka et al. |
| 2009/0054450 A1 | 2/2009 | Currie et al. |
| 2009/0074827 A1 | 3/2009 | Scherl et al. |
| 2009/0105246 A1 | 4/2009 | Bemis et al. |
| 2009/0142336 A1 | 6/2009 | Walsh et al. |
| 2009/0156648 A1 | 6/2009 | Molino et al. |
| 2009/0163476 A1 | 6/2009 | Milburn et al. |
| 2009/0182036 A1 | 7/2009 | Krammer-Lukas |
| 2009/0197820 A1 | 8/2009 | Wolfe et al. |
| 2009/0230013 A1 | 9/2009 | Born et al. |
| 2010/0009992 A1 | 1/2010 | Birnberg et al. |
| 2010/0158956 A1 | 6/2010 | Komorowski |
| 2010/0173024 A1 | 7/2010 | McDaniel |
| 2010/0204204 A1 | 8/2010 | Zaworotko et al. |
| 2010/0210692 A1 | 8/2010 | Farmer et al. |
| 2010/0261793 A1 | 10/2010 | Caterson et al. |
| 2010/0303966 A1 | 12/2010 | Sunvold et al. |
| 2010/0303967 A1 | 12/2010 | Sunvold et al. |
| 2010/0304003 A1 | 12/2010 | Friesen et al. |
| 2010/0316679 A1 | 12/2010 | Sinclair et al. |
| 2010/0324002 A1 | 12/2010 | Fox et al. |
| 2011/0020443 A1 | 1/2011 | Liu et al. |
| 2011/0027416 A1 | 2/2011 | Sunvold et al. |
| 2011/0033559 A1 | 2/2011 | Zemel et al. |
| 2011/0038948 A1 | 2/2011 | Zemel et al. |
| 2011/0064712 A1 | 3/2011 | Amato |
| 2011/0064720 A1 | 3/2011 | Amato |
| 2011/0070258 A1 | 3/2011 | Jimenez Del Rio et al. |
| 2011/0082189 A1 | 4/2011 | Sinclair et al. |
| 2011/0111066 A1 | 5/2011 | Ferguson et al. |
| 2011/0112047 A1 | 5/2011 | Evans et al. |
| 2011/0130387 A1 | 6/2011 | Nunes et al. |
| 2011/0165125 A1 | 7/2011 | Pan |
| 2011/0208153 A1 | 8/2011 | Alvey |
| 2012/0035105 A1 | 2/2012 | Geho et al. |
| 2012/0058088 A1 | 3/2012 | Sardi |
| 2012/0129785 A1 | 5/2012 | Fleuranges et al. |
| 2012/0177730 A1 | 7/2012 | Baron et al. |
| 2012/0225139 A1 | 9/2012 | Ferguson et al. |
| 2012/0289598 A1 | 11/2012 | Yamka et al. |
| 2012/0301559 A1 | 11/2012 | Pridmore-Merten et al. |
| 2013/0017283 A1 | 1/2013 | Zemel et al. |
| 2013/0017284 A1 | 1/2013 | Zemel et al. |
| 2013/0045193 A1 | 2/2013 | Gonzalez et al. |
| 2013/0052286 A1 | 2/2013 | Wada et al. |
| 2013/0151196 A1 | 6/2013 | Yuen et al. |
| 2013/0158369 A1 | 6/2013 | Yuen et al. |
| 2013/0237605 A1 | 9/2013 | Zemel et al. |
| 2013/0323287 A1 | 12/2013 | Komorowski |
| 2014/0057017 A1 | 2/2014 | Yamka et al. |
| 2014/0148488 A1 | 5/2014 | Zemel et al. |
| 2015/0056274 A1 | 2/2015 | Zemel et al. |
| 2016/0000737 A1 | 1/2016 | Zemel et al. |
| 2016/0008329 A1 | 1/2016 | Zemel et al. |
| 2016/0067201 A1 | 3/2016 | Zemel et al. |
| 2016/0279130 A1 | 9/2016 | Zemel et al. |
| 2016/0338983 A1 | 11/2016 | Zemel et al. |
| 2017/0000777 A1 | 1/2017 | Zemel et al. |
| 2017/0000780 A1 | 1/2017 | Zemel et al. |
| 2017/0065545 A1 | 3/2017 | Zemel et al. |

FOREIGN PATENT DOCUMENTS

| | | |
|---|---|---|
| EP | 1685833 A1 | 8/2006 |
| EP | 1818055 A1 | 8/2007 |
| EP | 2308493 A1 | 4/2011 |
| FR | 2710243 A1 | 3/1995 |
| GB | 1584539 A | 2/1981 |
| JP | 3219838 B2 | 10/2001 |
| JP | 2005097273 A | 4/2005 |
| JP | 2007306851 A | 11/2007 |
| JP | 2008063321 A | 3/2008 |
| WO | WO-2004056208 A1 | 7/2004 |
| WO | WO-2004082401 A1 | 9/2004 |
| WO | WO-2005049006 A1 | 6/2005 |
| WO | WO-2005065667 A2 | 7/2005 |
| WO | WO-2007146124 A2 | 12/2007 |
| WO | WO-2007146313 A1 | 12/2007 |
| WO | WO-2011051974 A1 | 5/2011 |
| WO | WO-2012097064 A1 | 7/2012 |
| WO | WO-2013028547 A1 | 2/2013 |
| WO | WO-2013134736 A1 | 9/2013 |
| WO | WO-2013169007 A1 | 11/2013 |
| WO | WO-2014113404 A1 | 7/2014 |
| WO | WO-2014152016 A1 | 9/2014 |
| WO | WO-2015053379 A1 | 4/2015 |

OTHER PUBLICATIONS

Alwine, et al. Method for detection of specific RNAs in agarose gels by transfer to diazobenzyloxymethyl-paper and hybridization with DNA probes. Proc Natl Acad Sci U S A. Dec. 1977; 74(12):5350-4.

Amstad, et al. Mechanism of c-fos induction by active oxygen. Cancer Res. Jul. 15, 1992; 52(14):3952-60.

(56) References Cited

OTHER PUBLICATIONS

Anonymous: "European commission health and consumer protection directorate-general directorate C-scientific opinions c2-management of scientific committees II; scientific co-operation and networks opinion of the scientific committee on food on the tolerable upper intake levels of nicotinic acid and nicotinamide," May 6, 2002.Available at: http://ec.europa.eu/foods/fs/sc/scf/out80j_en.pdf. Retrieved on Sep. 21, 2016.

Anonymous: "GRAS notification for L-Leucine produced by innonio limited," May 27, 2014, Available at: http://www.fda.gov/ucm/groups/fdagov-public/@fdaov-foods-gen/documents/document/ucm407679.pdf. Retrieved on Sep. 21, 2016.

Anthony, et al. Orally Administered Leucine Stimulates Protein Synthesis of Skeletal Muscle of Postabsorptive Rats in Association with Increased elF4F Formation. The Journal of Nutrition. 2000; 130:139-145.

Arend, et al. Inhibition of the production and effects of interleukin-1 and tumor necrosis factor alpha in rheumatoid arthritis. Arthritis Rheum. Feb. 1995; 38(2):151-60.

Argiles, et al. Cross-talk between skeletal muscle and adipose tissue: a link with obesity? Med Res Rev. Jan. 2005; 25(1):49-65.

Atabek, et al. Oxidative stress in childhood obesity. J Pediatr Endocrinol Metab. Aug. 2004; 17(8):1063-8.

Ayala, et al. Chronic treatment with sildenafil improves energy balance and insulin action in high fat-fed conscious mice. Diabetes. Apr. 2007; 56(4):1025-33. Epub Jan. 17, 2007.

Balabolkin, et al., The role of thiazolidinediones in compensation of carbohydrate metabolism in type 2 diabetes and in the prevention of vascular complications of diabetes. 1998-2017. Retrieved from: https://www.Ivrach.ru/2007/02/4534786/.

Banakar, et al. 1alpha, 25-dihydroxyvitamin D3 prevents DNA damage and restores antioxidant enzymes in rat hepatocarcinogenesis induced by diethylnitrosamine and promoted by phenobarbital. World J Gastroenterol. May 1, 2004; 10(9):1268-75.

Bannowsky, A. et al., Recovery of erectile function after nerve-sparing radical prostatectomy: improvement with nightly low-dose sildenafil. BJU Int., Feb. 18, 2008, vol. 101, No. 10, pp. 1279-1283.

Bartges, et al. Calculating a patient's nutritional requirements. Veterinary Medicine. 2004; 99:632.

Bender, et al. Cyclic nucleotide phosphodiesterases: molecular regulation to clinical use. Pharmacol Rev. Sep. 2006; 58(3):488-520.

Berchtold. A simple method for direct cloning and sequencing cDNA by the use of a single specific oligonucleotide and oligo(dT) in a polymerase chain reaction (PCR). Nucleic Acids Res. Jan. 11, 1989; 17(1):453.

Beta-hydroxy Beta-methylbutyrate (HMB). 2009; 1-2. http://exrx.net/Nutrition/Supplements/HMB.html.

Black grape ingredients. Power of resveratrol. Accessed: Sep. 29, 2010. www.blackgrapehealth.com/Tnt37/ingredients.php.

Blum, et al. SIRT1 modulation as a novel approach to the treatment of diseases of aging. J Med Chem. Jan. 27, 2011; 54(2):417-32. Epub Nov. 16, 2010.

BodyBuilding, VitaMinder Power shaker, 2006, BodyBuilding.com, p. 1.

Bostrum, et al. A PGC1-α-dependent myokine that drives brown-fat-like development of white fat and thermogenesis. Nature. Jan. 11, 2012;481(7382):463-8. doi: 10.1038/nature10777.

Botanical Online 2010, 1-3. http//:www.botanical-online.com/english/plantschemicalagents.htm.

Boustany. Diabetes and grapefruit. 2010. ThinkScienceNow. 1-4. http://www.thinksciencenow.com/blog-post/diabetes-and-grapefruit/.

Brand, et al. Mitochondrial superoxide and aging: uncoupling-protein activity and superoxide production. Biochem Soc Symp. 2004;(71):203-13.

Breastfeeding.com. Q&A How many ounces of breast milk should I pump? 2010; 1-2. http://www.breastfeeding.com/breastfeeding-questions/breastfeeding-pumping-basics/qa/how-many-ounces-of-breast-milk-should-i-pumpp.aspx.

Brennan, et al. Inhibitory effect of TNF alpha antibodies on synovial cell interleukin-1 production in rheumatoid arthritis. Lancet. Jul. 29, 1989;2(8657):244-7.

Brookes. Mitochondrial H(+) leak and ROS generation: an odd couple. Free Radic Biol Med. Jan. 1, 2005;38(1):12-23.

Bruckbauer, et al. Synergistic effects of leucine and resveratrol on insulin sensitivity and fat metabolism in adipocytes and mice. Nutr Metab (Lond). Aug. 22, 2012;9(1):77. doi: 10.1186/1743-7075-9-77.

Bruckbauer, et al. Synergistic effects of metformin, resveratrol, and hydroxymethylbutyrate on insulin sensitivity. Diabetes Metab Syndr Obes. 2013;6:93-102. doi: 10.2147/DMSO.S40840. Epub Feb. 13, 2013.

Bruckbauer, et al. Synergistic effects of polyphenols and methylxanthines with leucine on AMPK/sirtuin-mediated metabolism in muscle cells and adipocytes. PLoS One. 9(2):e89166. Feb. 14, 2014.

Bruckbauer, et al. The effects of dairy components on energy partitioning and metabolic risk in mice: a microarray study. J Nutrigenet Nutrigenomics. 2009;2(2):64-77. Epub Mar. 4, 2009.

Busquets, et al. Interleukin-15 decreases proteolysis in skeletal muscle: a direct effect. Int J Mol Med. Sep. 2005;16(3):471-6.

Carbo, et al. Interleukin-15 antagonizes muscle protein waste in tumour-bearing rats. Br J Cancer. Aug. 2000;83(4):526-31.

Carbo, et al. Interleukin-15 mediates reciprocal regulation of adipose and muscle mass: a potential role in body weight control. Biochim Biophys Acta. Apr. 3, 2001;1526(1):17-24.

Carlson, La. Nicotinic acid: the broad-spectrum lipid drug. A 50th anniversary review. J Intern Med. Aug. 2005; 258(2):94-114.

Carroll, et al. Antagonism of the IL-6 cytokine subfamily—a potential strategy for more effective therapy in rheumatoid arthritis. Inflamm Res. Jan. 1998; 47(1):1-7.

Caton, et al., Metformin opposes impaired AMPK and SIRT1 function and deleterious changes in core clock protein expression in white adipose tissue of genetically-obese db/db mice. Diabetes Obes Metab 13, 1097-1104 Dec. 13, 2011.

Cerutti, et al. The role of the cellular antioxidant defense in oxidant carcinogenesis. Environ Health Perspect. Dec. 1994;102 Suppl 10:123-9.

Chalasani, et al. The diagnosis and management of non-alcoholic fatty liver disease: Practice guideline by the American Association for the Study of Liver Diseases, American College of Gastroenterology, and the American Gastroenterological Association. Hepatology 2012; 55:2005-2021.

Chang, et al. Mammalian MAP kinase signalling cascades. Nature. Mar. 1, 2001;410(6824):37-40.

Cheng, et al. Leucine deprivation decreases fat mass by stimulation of lipolysis in white adipose tissue and upregulation of uncoupling protein 1 (UCP1) in brown adipose tissue. Diabetes. Jan. 2010;59(1):17-25. Epub Oct. 15, 2009.

Chung, et al. Contribution of polyol pathway to diabetes-induced oxidative stress. J Am Soc Nephrol. Aug. 2003;14(8 Suppl 3):S233-6.

Clement, et al. Weight loss regulates inflammation-related genes in white adipose tissue of obese subjects. FASEB J. Nov. 2004;18(14):1657-69.

Co-pending U.S. Appl. No. 15/447,049, filed Mar. 1, 2017.
Co-pending U.S. Appl. No. 15/513,115, filed Mar. 21, 2017.
Co-pending U.S. Appl. No. 15/619,406, filed Jun. 9, 2017.
Co-pending U.S. Appl. No. 15/638,241, filed Jun. 29, 2017.

Cottam, et al. The chronic inflammatory hypothesis for the morbidity associated with morbid obesity: implications and effects of weight loss. Obes Surg. May 2004;14(5):589-600.

Creider, et al., Niacin: another look at an underutilized lipid-lowering medication. Nature Reviews Endocrinology, 2012. 8:517-528.

De Souza, et al. Insulin secretory defect in zucker FA/FA rats is improved by ameliorating insulin resistance. Diabetes. Aug. 1995;44(8):984-91.

(56) References Cited

OTHER PUBLICATIONS

Ding, et al. Amino acid composition of lactating mothers' milk and confinement diet in rural North China. Asia Pac J. Clin Nutr. 2010; 19(3):344-349.

Doi, et al. Isoleucine, a Blood Glucose-Lowering Amino Acid, Increases Glucose Uptake in Rat Skeletal Muscle in the Absence of Increases in AMP-Activated Protein Kinase Activity. J Nutr. Sep. 2005;135(9):2103-8.

Donato, et al. Effects of leucine supplementation on the body composition and protein status of rats submitted to food restriction. Nutrition. May 2006;22(5):520-7.

Duval, et al. Increased reactive oxygen species production with antisense oligonucleotides directed against uncoupling protein 2 in murine endothelial cells. Biochem Cell Biol. 2002;80(6):757-64.

Erlanson-Albertsson. The role of uncoupling proteins in the regulation of metabolism. Acta Physiol Scand. Aug. 2003;178(4):405-12.

Ermak, et al. Calcium and oxidative stress: from cell signaling to cell death. Mol Immunol. Feb. 2002;38(10):713-21.

European search report and opinion dated Mar. 9, 2015 for EP Application No. 12814141.3.

European search report and opinion dated May 6, 2016 for EP Application No. 13854549.

European search report and opinion dated Aug. 22, 2016 for EP Application No. 14770824.

European search report and opinion dated Sep. 28, 2015 for EP Application No. 13758140.1.

European Search Report dated Sep. 30, 2016 for European Application No. 14768984.8.

Fain, et al. Comparison of the release of adipokines by adipose tissue, adipose tissue matrix, and adipocytes from visceral and subcutaneous abdominal adipose tissues of obese humans. Endocrinology. May 2004;145(5):2273-82. Epub Jan. 15, 2004.

Feige, et al. Specific SIRT1 activation mimics low energy levels and protects against diet-induced metabolic disorders by enhancing fat oxidation. Cell Metab. Nov. 2008;8(5):347-58. Erratum Cell Metab. Feb. 2009;9(2):210.

Festi, et al. Hepatic steatosis in obese patients: clinical aspects and prognostic significance. Obesity Rev 2004; 5:27-42.

Flatt, et al. Direct and indirect actions of nutrients in the regulation of insulin secretion from the pancreatic beta cells. Proc Nutr Soc. Dec. 1991;50(3):559-66.

Fortamet (Metformin Hydrochloride) Extended-Release Tablets Label. http://www.accessdata.fda.gov/drugsatfda_docs/label/2008/021574s010lbl.pdf. Accessed Jul. 6, 2015.

Fraquelli, M. et al., Reproducibility of transient elastrography in the evaluation of liver fibrosis in patients with chronic liver disease. Gut. Jan. 25, 2007, vol. 56; pp. 968-973; Abstract; pp. 969 1st column, 2nd paragraph; DOI 10.1136/gut.2006.111302.

Fried, et al. Omental and subcutaneous adipose tissues of obese subjects release interleukin-6: depot difference and regulation by glucocorticoid. J Clin Endocrinol Metab. Mar. 1998;83(3):847-50.

Fu, L., et al. Interaction between leucine and phosphodiesterase 5 inhibition in modulating insulin sensitivity and lipid metabolism. Diabetes, Metabolic syndrome and obesity: Targets and therapy. May 6, 2015; vol. 8: pp. 227-239.; abstract; p. 228, 1st column, 3rd paragraph to 2nd column, 1st paragraph.

Furukawa, et al. Increased oxidative stress in obesity and its impact on metabolic syndrome. J Clin Invest. Dec. 2004;114(12):1752-61.

Gerlinger-Romero, et al. Chronic supplementation of beta-hydroxy-beta methylbutyrate (HMβ) increases the activity of the GH/IGF-I axis and induces hyperinsulinemia in rats. Growth Horm IGF Res. Apr. 2011;21(2):57-62. doi: 10.1016/j.ghir.2010.12.006. Epub Jan. 14, 2011.

Gilhuly, K. Niacin Dosage for lowering Triglycerides. Livestrong. Jul. 27, 2015. Available at: http://www.livestrong.com/article/460725-the-dosage-of-niacin-for-lowering-triglycerides/#ixzz2N03KhDZu. Accessed on Jun. 8, 2017.

Giri, et al. Constitutive activation of NF-kappaB causes resistance to apoptosis in human cutaneous T cell lymphoma HuT-78 cells. Autocrine role of tumor necrosis factor and reactive oxygen intermediates. J Biol Chem. May 29, 1998;273(22):14008-14.

Goldman, et al. Generation of reactive oxygen species in a human keratinocyte cell line: role of calcium. Arch Biochem Biophys. Feb. 1, 1998;350(1):10-8.

Goldstein, et al. Adiponectin: A novel adipokine linking adipocytes and vascular function. J Clin Endocrinol Metab. Jun. 2004;89(6):2563-8.

Gordeeva, et al. Cross-talk between reactive oxygen species and calcium in living cells. Biochemistry (Mosc). Oct. 2003;68(10):1077-80.

Hale, et al. Transfer of metformin into human milk. Diabetologia. 2002; 45:1509-1514.

Harwood, et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals. The Journal of Biological Chemistry. Sep. 26, 2003; 278(39):37099-37111.

Haworth, et al. Expression of granulocyte-macrophage colony-stimulating factor in rheumatoid arthritis: regulation by tumor necrosis factor-alpha. Eur J Immunol. Oct. 1991;21(10):2575-9.

Hollander, et al. Induction of fos RNA by DNA-damaging agents. Cancer Res. Apr. 1, 1989;49(7):1687-92.

Hornstra, et al. Essential fatty acids in pregnancy and early human development. Eur J Obstet Gynecol Reprod Biol. Jul. 1995;61(1):57-62.

Hotamisligil, et al. Tumor necrosis factor alpha inhibits signaling from the insulin receptor. Proc Natl Acad Sci U S A. May 24, 1994;91(11):4854-8.

Hou, et al. Sirt1 regulates hepatocyte lipid metabolism through activating AMPK-activated protein kinase. J Biol Chem 2008; 383:20015-20026.

Howells, et al. Phase I randomized, double-blind pilot study of micronized resveratrol (SRT501) in patients with hepatic metastases—safety, pharmacokinetics, and pharmacodynamics. Cancer Prev Res (Phila). Sep. 2011;4(9):1419-25. Epub Jun 16, 2011.

Howitz, K.T. et al., Small molecule activators of sirtuins extend *Saccharomyces cerevisiae* lifespan. Letters to Nature. 2003; 425:191-196.

Hydroxymethyl Butyrate (HMB). Beth Israel Deaconess Medical Center. Accessed Dec. 13, 2012. http://www.bidmc.org/YourHealth/HolisticHealth/HerbsandSupplements.aspx?ChunkID=21551.

Inoguchi, et al. High glucose level and free fatty acid stimulate reactive oxygen species production through protein kinase C—dependent activation of NAD(P)H oxidase in cultured vascular cells. Diabetes. Nov. 2000;49(11):1939-45.

International search report and written opinion dated May 28, 2013 for PCT Application No. US2013/030044.

International search report and written opinion dated Feb. 8, 2007 for PCT Application No. US2006/038854.

International search report and written opinion dated Mar. 10, 2014 for PCT Application No. US2013/069957.

International search report and written opinion dated May 22, 2015 for PCT/US2015/018182.

International search report and written opinion dated Jul. 21, 2014 for PCT/US2014/016592.

International Search report and Written opinion dated Sep. 19, 2016 for Singapore Application No. 11201503774P.

International search report and written opinion dated Nov. 29, 2012 for PCT Application No. US2012/046814.

International search report and written opinion dated Dec. 18, 2015 for PCT/US2015/051793.

International search report dated Jul. 14, 2014 for PCT Application No. US 2014/026816.

International Search Report dated Nov. 28, 2016 for International Application No. PCT/US2016/049272.

Ionut, et al. Novel canine models of obese prediabetes and mild type 2 diabetes. Am J Physiol Endocrinol Metab. Jan. 2010;298(1):E38-48. doi: 10.1152/ajpendo.00466.2009. Epub Oct. 20, 2009.

JillWillRun. Hydration Review Nuun, 2009, pp. 1-8.

(56) References Cited

OTHER PUBLICATIONS

Khan, et al. Induction of renal oxidative stress and cell proliferation response by ferric nitrilotriacetate (Fe-NTA): diminution by soy isoflavones. Chem Biol Interact. Aug. 10, 2004;149(1):23-35.
Kiens. Skeletal Muscle Lipid Metabolism in Exercise and Insulin Resistance. Physiological Reviews. 2006;86: 205-243.
Kies, E. et al., Interrelationship of leucine with lysine, tryptophan, and niacin as they influence protein value of cereal gains for humans. Cereal Chemistry. Apr. 1972; 223-231.
Koren, et al. Vitamin D is a prooxidant in breast cancer cells. Cancer Res. Feb. 15, 2001;61(4):1439-44.
Korshunov, et al. High protonic potential actuates a mechanism of production of reactive oxygen species in mitochondria. FEBS Lett. Oct. 13, 1997;416(1):15-8.
Kouzarides, et al. Leucine zippers of fos, jun and GCN4 dictate dimerization specificity and thereby control DNA binding. Nature. Aug. 17, 1989;340(6234):568-71.
Krishnaswamy, et al. Effect of vitamin B6 on leucine-induced changes in human subjects. Am J Clin Nutr. Feb. 1976;29(2):177-81.
Laflamme. Development and validation of a body condition score system for dogs. Canine Practice. 1997; 22:10-15.
Layman. The role of leucine in weight loss diets and glucose homeostasis. Journal of Nutrition, 2003, 133, 261S-267S.
Lee, et al. The evolving role of inflammation in obesity and the metabolic syndrome. Curr Diab Rep. Feb. 2005;5(1):70-5.
Leenders, et al. Leucine as a pharmaconutrient to prevent and treat sarcopenia and type 2 diabetes. Nutr Rev. Nov. 2011;69(11):675-89. doi: 10.1111/j.1753-4887.2011.00443.x. Abstract only.
Lehman, et al. Assessment of coronary plaque progression in coronary computed tomography angiography using a semiquantitative score. JACC Cardiovasc Imaging. Nov. 2009;2(11):1262-70. doi: 10.1016/j.jcmg.2009.07.007.
Li, et al. Evaluation of antioxidant capacity and aroma quality of breast milk. Nutrition. 2008; 25(1):1-3.
Li, et al. Leucine nutrition in animals and humans: mTOR signaling and beyond. Amino Acids. Nov. 2011;41(5):1185-93. Epub Jul. 20, 2011.
Li, et al. Visceral fat: higher responsiveness of fat mass and gene expression to calorie restriction than subcutaneous fat. Exp Biol Med (Maywood). Nov. 2003;228(10):1118-23.
Lim, et al. Intakes of dietary docosahexaenoic acid ethyl ester and egg phosphatidylcholine improve maze-learning ability in young and old mice. J Nutr. Jun. 2000; 130(6):1629-32.
Lin, et al. Increased oxidative damage with altered antioxidative status in type 2 diabetic patients harboring the 16189 T to C variant of mitochondrial DNA. Ann N Y Acad Sci. May 2005; 1042:64-9.
Lin. Suppression of protein kinase C and nuclear oncogene expression as possible action mechanisms of cancer chemoprevention by Curcumin. Arch Pharm Res. Jul. 2004; 27(7):683-92.
Lind, et al. Evaluation of four different methods to measure endothelium-dependent vasodilation in the human peripheral circulation. Clin Sci (Lond). May 2002; 102(5):561-7.
Lira, et al. Nitric oxide and AMPK cooperatively regulate PGC-1 in skeletal muscle cells. J Physiol. Sep. 15, 2010; 588(Pt 18):3551-66. Epub Jul. 19, 2010.
Lumeng, et al. Plasma content of B6 vitamers and its relationship to hepatic vitamin B6 metabolism. J Clin Invest. Oct. 1980; 66(4): 688-695.
Lynch, et al. Leucine is a direct-acting nutrient signal that regulates protein synthesis in adipose tissue. Am J Physiol Endocrinol Metab. Sep. 2002;283(3):E503-13.
Macotela, et al. Dietary Leucine—an environmental modifier of insulin resistance acting on multiple levels of metabolism. PLoS One. 2011; 6(6):e21187. Epub Jun. 22, 2011.
Mahadev, et al. The NAD(P)H oxidase homolog Nox4 modulates insulin-stimulated generation of H2O2 and plays an integral role in insulin signal transduction. Mol Cell Biol. Mar. 2004; 24(5):1844-54.
Manders, et al. Co-ingestion of a protein hydrolysate with or without additional leucine effectively reduces postprandial blood glucose excursions in type 2 diabetic men 1. May 2006. 1294-1299. http://jn.nutrition.org/content/136/5/1294.full.pdf.
Manea, et al. Changes in oxidative balance in rat pericytes exposed to diabetic conditions. J Cell Mol Med. Jan.-Mar. 2004;8(1):117-26.
Manna, et al., Resveratrol Suppresses TNF-Induced Activation of Nuclear Transcription Factors NF-κB, Activator Protein-1, and Apoptosis: Potential Role of Reactive Oxygen Intermediates and Lipid Peroxidation1. J Immunol 2000; 164:6509-6519.
Mawby, et al. Comparison of various methods for estimating body fat in dogs. J Am Anim Hosp Assoc. Mar.-Apr. 2004; 40(2):109-14.
Melnik. Leucine signaling in the pathogenesis of type 2 diabetes and obesity. World J Diabetes. Mar. 15, 2012; 3(3):38-53. doi: 10.4239/wjd.v3.i3.38.
Melton, et al. Efficient in vitro synthesis of biologically active RNA and RNA hybridization probes from plasmids containing a bacteriophage SP6 promoter. Nucleic Acids Res. Sep. 25, 1984; 12(18):7035-56.
Merck Manual Home Edition online article entitled, "Multiple Sclerosis"-accessed Jun. 20, 2010 at http://www.merck.com/mmhe/print/sec06/ch092/ch092b.html.
Merck Manual Home Edition online article entitled, "Introduction: Coronary Artery Disease"-accessed Jun. 20, 2010 at www.merck.com/mmhe/print/sec03/ch033/ch033a.html.
Miwa, et al. Mitochondrial matrix reactive oxygen species production is very sensitive to mild uncoupling. Biochem Soc Trans. Dec. 2003;31(Pt 6):1300-1.
Mooney, et al., Mechanisms underlying the metabolic actions of galegine that contribute to weight loss in mice. Br J Pharmacal. Apr. 2008; 153(8): 1669-1677. Published online Feb. 25, 2008. doi: 10.1038/bjp.2008.37.
Morris, et al. 1,25-dihydroxyvitamin D3 modulation of adipocyte glucocorticoid function. Obes Res. Apr. 2005;13(4):670-7.
Moser, et al. Interleukin 1 and tumor necrosis factor stimulate human vascular endothelial cells to promote transendothelial neutrophil passage. J Clin Invest. Feb. 1989;83(2):444-55.
Muscle Synergy: Advanced Nitric Oxide and muscle building supplement. Beverly International. Accessed on Oct. 18, 2012. Available at: https://web.archive.org/web/20121018004354/http://www.beverlyinternational.com/products/muscle-synergy.html.
Musso, G. et al., Impact of current treatments on liver disease, glucose metabolism and cardiovascular risk in non-alcoholic fatty liver disease (NAFLD): a systematic review and meta-analysis of randonmised trials. Diabetologia (2012) 55:885-904.
Nagao, et al. Dietary diacylglycerol suppresses accumulation of body fat compared to triacylglycerol in men in a double-blind controlled trial. J Nutr. Apr. 2000; 130(4):792-7.
Nairizi, et al. Leucine supplementation of drinking water does not alter susceptibility to diet-induced obesity in mice. Nutr. Apr. 2009; 139(4):715-9. Epub Feb. 25, 2009.
Nakagawa, I. Effect of an excess intake of leucine, with and without additions of vitamin B6 and/or niacin, on tryptophan and niacin metabolism in rats. Journal of nutritional science and vitaminology. 23(6). Jan. 1, 1977. p. 535-548.
Nin, et al., Role of deleted in breast cancer 1 (DBC1) protein in SIRT1 deacetylase activation induced by protein kinase A and AMP-activated protein kinase. J Biol Chem. Jul. 6, 2012;287(28):23489-501. doi: 10.1074/jbc.M112.365874. Epub May 2, 2012.
Nisoli, et al. Mitochondrial biogenesis by NO yields functionally active mitochondria in mammals. Proc Natl Acad Sci U S A. Nov. 23, 2004;101(47):16507-12. Epub Nov. 15, 2004.
Nisoli, et al. Mitochondrial biogenesis in mammals: the role of endogenous nitric oxide. Science. Feb. 7, 2003;299(5608):896-9.
Nomura, et al. Inhibition of 12-O-tetradecanoylphorbol-13-acetate-induced NF-kappaB activation by tea polyphenols, (-)-epigallocatechin gallate and theaflavins. Carcinogenesis. Oct. 2000;21(10):1885-90.
Notice of allowance dated Feb. 1, 2016 for U.S. Appl. No. 14/927,255.
Notice of allowance dated Feb. 27, 2017 for U.S. Appl. No. 15/164,647.

(56) References Cited

OTHER PUBLICATIONS

Notice of allowance dated Mar. 6, 2015 for U.S. Appl. No. 13/866,936.
Notice of allowance dated Mar. 15, 2013 for U.S. Appl. No. 13/549,381.
Notice of Allowance dated Mar. 23, 2017 for U.S. Appl. No. 15/206,125.
Notice of allowance dated Apr. 11, 2016 for U.S. Appl. No. 14/472,081.
Notice of allowance dated Apr. 11, 2016 for U.S. Appl. No. 14/927,228.
Notice of allowance dated Apr. 25, 2013 for U.S. Appl. No. 11/542,703.
Notice of Allowance dated Apr. 27, 2017 for U.S. Appl. No. 15/119,695.
Notice of allowance dated Apr. 29, 2015 for U.S. Appl. No. 13/866,936.
Notice of allowance dated May 29, 2013 for U.S. Appl. No. 13/549,399.
Notice of allowance dated Aug. 13, 2013 for U.S. Appl. No. 13/549,381.
Notice of allowance dated Aug. 15, 2013 for U.S. Appl. No. 13/549,399.
Notice of allowance dated Sep. 1, 2015 for U.S. Appl. No. 13/662,345.
Notice of allowance dated Sep. 11, 2015 for U.S. Appl. No. 14/746,516.
Notice of Allowance dated Oct. 26, 2016 for U.S. Appl. No. 14/772,366.
Notice of allowance dated Dec. 28, 2012 for U.S. Appl. No. 13/549,399.
Ofei, et al. Effects of an engineered human anti-TNF-alpha antibody (CDP571) on insulin sensitivity and glycemic control in patients with NIDDM. Diabetes. Jul. 1996;45(7):881-5.
Office action dated Feb. 5, 2015 for U.S. Appl. No. 13/662,345.
Office Action dated Apr. 5, 2017 for U.S. Appl. No. 14/843,873.
Office action dated Apr. 22, 2013 for U.S. Appl. No. 13/662,345.
Office action dated Jun. 25, 2010 for U.S. Appl. No. 11/543,171.
Office action dated Jul. 15, 2010 for U.S. Appl. No. 11/542,703.
Office action dated Sep. 16, 2013 for U.S. Appl. No. 13/662,345.
Office action dated Nov. 7, 2012 for U.S. Appl. No. 13/549,381.
Office Action dated Dec. 15, 2016 for U.S. Appl. No. 14/770,418.
Office action dated Dec. 23, 2010 for U.S. Appl. No. 11/542,703.
Office action dated Dec. 23, 2010 for U.S. Appl. No. 11/543,171.
OpenSource Diets. Product Data D12451. Report Repeat Revise Where NutriPhenomics Begins Research Diets, Inc. 20. Last modified: Feb. 28, 2013.
Ouyang, et al., Metformin Activates AMP Kinase through Inhibition of AMP Deaminase. J Biol Chern 286, 1-11 Jan. 7, 2011.
Panichi, et al. Calcitriol modulates in vivo and in vitro cytokine production: a role for intracellular calcium. Kidney Int. Nov. 1998;54(5):1463-9.
Park, et al. Resveratrol ameliorates aging-related metabolic phenotypes by inhibiting cAMP phosphodiesterases. Cell. Feb. 3, 2012;148(3):421-33. doi: 10.1016/j.cell.2012.01.017.
Patterson, et al. Excretion of tryptophan-niacin metabolites by young men: effects of tryptophan, leucine, and vitamin B6 intakes. Am J Clin Nutr. Oct. 1980;33(10):2157-67.
Pearce, et al. Sports supplements: A modern case of caveat emptor. Current Sports Medicine Reports. 2005; 4:171-178.
Peterson, et al. The mechanism of transamination. Function of the histidyl residue at the active site of supernatant aspartate transaminase. J Biol Chem. Feb. 25, 1970;245(4):806-13.
Phan, et al. Effects of niacin on glucose levels, coronary stenosis progression, and clinical events in subjects with normal baseline glucose levels (<100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study. Am J Cardiol. Feb. 1, 2013;111(3):352-5. doi: 10.1016/j.amjcard.2012.09.034. Epub Nov. 17, 2012.
Povolny, et al. The role of recombinant human M-CSF, IL-3, GM-CSF and calcitriol in clonal development of osteoclast precursors in primate bone marrow. Exp Hematol. Apr. 1993;21(4):532-7.
Price, et al. SIRT1 is required for AMPK activation and the beneficial effects of resveratrol on mitochondrial function. Cell Metab. May 2, 2012;15(5):675-90. doi: 10.1016/j.cmet.2012.04.003.
Purushotham, et al. Hepatocyte-specific deletion of Sirt1 alters fatty acid metabolism and results in hepatic steatosis and inflammation. Cell Metabolism 2009; 9:327-338.
Quinn, et al. Interleukin-15 stimulates adiponectin secretion by 3T3-L1 adipocytes: evidence for a skeletal muscle-to-fat signaling pathway. Cell Biol Int. Jun. 2005;29(6):449-57.
Rasmussen, et al. Regulation of fatty acid oxidation in skeletal muscle. Annu Rev Nutr. 1999;19:463-84.
Reeves. Components of the AIN-93 diets as improvements in the AIN-76A diet. J Nutr. May 1997;127(5 Suppl):838S-841S.
Remington's Pharmaceutical Sciences 18th Edition. 1990, Martin ed., Mack Publishing Co., PA.
Roberts, et al. Nutrition and aging: changes in the regulation of energy metabolism with aging. Physiol Rev. Apr. 2006;86(2):651-67.
Rogers. A healthy body, a healthy mind: long-term impact of diet on mood and cognitive function. Proc Nutr Soc. Feb. 2001;60(1):135-43.
S Bear. Nother way to get leucine for the 6 week cure, 2009, pp. 1-5.
Sabatini, et al. Tadalafil alters energy metabolism in C2C12 skeletal muscle cells. Acta Biochim Pol. 2011;58(2):237-41. Epub Jun. 16, 2011.
Saumet, et al. Non-invasive measurement of skin blood flow: comparison between plethysmography, laser-Doppler flowmeter and heat thermal clearance method. Int J Microcirc Clin Exp. 1986;5(1):73-83.
Schulze-Osthoff, et al. Oxidative stress and signal transduction. Int J Vitam Nutr Res. 1997;67(5):336-42.
Sellden, et al. Augmented thermic effect of amino acids under general anaesthesia: a mechanism useful for prevention of anaesthesia-induced hypothermia. Clin Sci (Lond). May 1994;86(5):611-8.
Seshasai, et al. Diabetes mellitus, fasting glucose, and risk of cause-specific death. N Engl J Med. Mar. 3, 2011;364(9):829-41. doi: 10.1056/NEJMoa1008862.
Shalwala, M. B., A novel role of sirt1 in sildenafil induced cardioprotection in mice. Virginia Commonwealth University—Master Thesis, May 2010, pp. 1-56.
Shalwala, M., et al., SIRT1 Activation Mediates Sildenafil-Induced Cardioprotection Against Ischemia/Reperfusion Injury in Mice. Circulation, 122(Suppl 21 ), 2010: A 14584-A 14584.
Shangari, et al. The cytotoxic mechanism of glyoxal involves oxidative stress. Biochem Pharmacol. Oct. 1, 2004;68(7):1433-42.
Shi, et al. 1alpha,25-dihydroxyvitamin D3 inhibits uncoupling protein 2 expression in human adipocytes. FASEB J. Nov. 2002;16(13):1808-10. Epub Sep 5, 2002.
Shi, et al. 1alpha,25-Dihydroxyvitamin D3 modulates human adipocyte metabolism via nongenomic action. FASEB J. Dec. 2001;15(14):2751-3. Epub Oct. 15, 2001.
Simeone, et al. How retinoids regulate breast cancer cell proliferation and apoptosis. Cell Mol Life Sci. Jun. 2004;61(12):1475-84.
Soares, et al. Effects of oxidative stress on adiponectin secretion and lactate production in 3T3-L1 adipocytes. Free Radic Biol Med. Apr. 1, 2005;38(7):882-9.
Solerte, et al. Metabolic effects of orally administered amino acid mixture in elderly subjects with poorly controlled type 2 diabetes mellitus. Am J Cardiol. Apr. 22, 2004;93(8A):23A-29A.
Song, et al. Methionine-induced hyperhomocysteinemia promotes superoxide anion generation and NFkappaB activation in peritoneal macrophages of C57BL/6 mice. J Med Food. 2004 Summer;7(2):229-34.
Sonta, et al. Evidence for contribution of vascular NAD(P)H oxidase to increased oxidative stress in animal models of diabetes and obesity. Free Radic Biol Med. Jul. 1, 2004;37(1):115-23.

(56) References Cited

OTHER PUBLICATIONS

Sorescu, et al. Superoxide production and expression of nox family proteins in human atherosclerosis. Circulation. Mar. 26, 2002;105(12):1429-35.
Stipanuk. Leucine and protein synthesis: mTOR and beyond. Nutr Rev. Mar. 2007;65(3):122-9.
Sun, et al. 1, 25(OH)2D3 and reactive oxygen species interactively stimulate angiotensinogen expression in differentiated 3T3-L1 adipocytes. FASEB J. 2005; 19:A70, No. 67.8 (abstract only).
Sun, et al. Calcium and dairy products inhibit weight and fat regain during ad libitum consumption following energy restriction in Ap2-agouti transgenic mice. J Nutr. Nov. 2004;134(11):3054-60.
Sun, et al. Dietary calcium regulates ROS production in aP2-agouti transgenic mice on high-fat/high-sucrose diets. Int J Obes (Lond). Sep. 2006;30(9):1341-6. Epub Mar. 7, 2006.
Sun, et al. Dual effects of 1-alpha,25-(OH)2-D3 on adipocyte apoptosis. FASEB J. 2004; 18:A49 (abstract only).
Sun, et al. Effects of mitochondrial uncoupling on adipocyte intracellular Ca(2+) and lipid metabolism. J Nutr Biochem. Apr. 2003;14(4):219-26.
Sun, et al. Leucine and calcium regulate fat metabolism and energy partitioning in murine adipocytes and muscle cells. Lipids. Apr. 2007;42(4):297-305. Epub Feb. 20, 2007.
Sun, et al. Leucine modulation of mitochondrial mass and oxygen consumption in skeletal muscle cells and adipocytes. Nutr Metab (Lond). Jun. 5, 2009;6:26. doi:10.1186/1743-7075-6-26.
Sun, et al. Reactive oxygen species stimulate cell proliferation and down-regulate UCP2 expression in 3T3-L1 adipocytes. Obesity Research. 2004; 11: A21, No. 80-OR (abstract only).
Sun, et al. Role of uncoupling protein 2 (UCP2) expression and 1alpha, 25-dihydroxyvitamin D3 in modulating adipocyte apoptosis. FASEB J. Sep. 2004;18(12):1430-2. Epub Jul. 1, 2004.
Suzuki, et al. Oxidants as stimulators of signal transduction. Free Radic Biol Med. 1997;22(1-2):269-85.
Suzuki, et al. Relationship between obesity and serum markers of oxidative stress and inflammation in Japanese. Asian Pac J Cancer Prev. Jul.-Sep. 2003;4(3):259-66.
Tappy, et al. Thermic effect of infused amino acids in healthy humans and in subjects with insulin resistance. Am J Clin Nutr. Jun. 1993;57(6):912-6.
Tennen, et al. Finding a target for resveratrol. Cell. Feb. 3, 2012;148(3):387-9.
Thannickal, et al. Reactive oxygen species in cell signaling. Am J Physiol Lung Cell Mol Physiol. Dec. 2000;279(6):L1005-28.
Thompson, et al. Effect of energy-reduced diets high in dairy products and fiber on weight loss in obese adults. Obes Res. Aug. 2005;13(8):1344-53.
Thomson, et al. Effects of nine weeks of beta-hydroxy-beta-methylbutyrate supplementation on strength and body composition in resistance trained men. Journal of strength and conditioning research / National Strength & Conditioning Association 23: 827-835, 2009.
Truswell, A.S. Effect of surplus leucine intake on serum cholesterol in man. Proceedings of the nutrition society. 23(2). Sep. 1, 1964. pp. XLVI-XLVII.
Sunvold, et al. Dietary fiber for dogs: IV. In vitro fermentation of selected fiber sources by dog fecal inoculum and in vivo digestion and metabolism of fiber-supplemented diets. J Anim Sci. Apr. 1995;73(4):1099-109.
Upham, et al. Hydrogen peroxide inhibits gap junctional intercellular communication in glutathione sufficient but not glutathione deficient cells. Carcinogenesis. Jan. 1997;18(1):37-42.
Valle, et al. Low-grade systemic inflammation, hypoadiponectinemia and a high concentration of leptin are present in very young obese children, and correlate with metabolic syndrome. Diabetes Metab. Feb. 2005;31(1):55-62.
Van Loon. Leucine as a pharmaconutrient in health and disease. Curr Opin Clin Nutr Metab Care. Jan. 2012;15(1):71-7. Abstract only.
Varma, et al. Chronic Tadalafil Therapy Improves Fasting Glucose Levels and Downregulates Microrna-103 and—107 In Obese Diabetic Mice. Circulation2012; 126: A14802. Abstract 14802.
Verdin, et al. Sirtuin regulation of mitochondria: energy production, apoptosis, and signaling. Trends Biochem Sci. Dec. 2010;35(12):669-75. Epub Sep. 20, 2010.
Vernon et al. Systematic review: The epidemiology and natural history of non-alcoholic fatty liver disease and non-alcoholic steatohepatitis in adults. Aliment Pharmacol 2011; 34:274-285.
Volk, et al. Transient Ca2+ changes in endothelial cells induced by low doses of reactive oxygen species: role of hydrogen peroxide. Mol Cell Biochem. Jun. 1997;171(1-2):11-21.
Wajchenberg. Subcutaneous and visceral adipose tissue: their relation to the metabolic syndrome. Endocr Rev. Dec. 2000;21(6):697-738.
Warner. Metformin Linked to B12 Deficiency, 2009, WebMD, pp. 1-2.
Weisberg, et al. Obesity is associated with macrophage accumulation in adipose tissue. J Clin Invest. Dec. 2003;112(12):1796-808.
Weitzman, et al. Free radical adducts induce alterations in DNA cytosine methylation. Proc Natl Acad Sci U S A. Feb. 15, 1994;91(4):1261-4.
Wilson, et al. Effects of beta-hydroxy-beta-methylbutyrate (HMB) on exercise performance and body composition across varying levels of age, sex, and training experience: A review. Nutr Metab (Lond). Jan. 3, 2008;5:1.
Wiseman, et al. Damage to DNA by reactive oxygen and nitrogen species: role in inflammatory disease and progression to cancer. Biochem J. Jan. 1, 1996;313 ( Pt 1):17-29.
Witters, L.A., The blooming of the French lilac. J Clin Invest. Oct. 15, 2001; 108(8): 1105-1107. doi: 10.1172/JCI14178.
Wojtczak, A., "Prevention" in glossary of medical education terms: Parts 1-7. Ed. Medical Teacher. vol. 24, Nos. 2-6 and vol. 25, No. 1 &2. 2002.
Xiao, et al. Leucine deprivation increases hepatic insulin sensitivity via GCN2/mTOR/S6K1 and AMPK pathways. Diabetes. Mar. 2011;60(3):746-56. Epub Jan. 31, 2011.
Xu, et al. Chronic inflammation in fat plays a crucial role in the development of obesity-related insulin resistance. J Clin Invest. Dec. 2003;112(12):1821-30.
Xue, et al. Relationship between human adipose tissue agouti and fatty acid synthase (FAS). J Nutr. Oct. 2000;130(10):2478-81.
Xue, et al. The agouti gene product inhibits lipolysis in human adipocytes via a Ca2+- dependent mechanism. FASEB J. Oct. 1998;12(13):1391-6.
Yalkowsky, et al. Potentiometric titration of monomeric and micellar acylcarnitines. J Pharm Sci. Jun. 1970;59(6):798-802.
Yalkowsky, et al. Some micellar properties of long-chain acylcarnitines. J Colloid Interface Sci. Dec. 1970;34(4):525-33.
Yamka, et al. In vivo measurement of flatulence and nutrient digestibility in dogs fed poultry by-product meal, conventional soybean meal, and low-oligosaccharide low-phytate soybean meal. Am J Vet Res. Jan. 2006;67(1):88-94.
Yang, et al. Leucine metabolism in regulation of insulin secretion from pancreatic beta cells. Nutr Rev. May 2010;68(5):270-9.
Yudkin, et al. Inflammation, obesity, stress and coronary heart disease: is interleukin-6 the link? Atherosclerosis. Feb. 2000;148(2):209-14.
Zanchi, et al. Potential antiproteolytic effects of L-leucine: observations of in vitro and in vivo studies. Nutr Metab (Lond). Jul. 17, 2008;5:20.
Zemel. Calcium and dairy modulation of obesity risk. Obes Res. Jan. 2005;13(1):192-3.
Zemel, et al. Calcium and dairy acceleration of weight and fat loss during energy restriction in obese adults. Obes Res. Apr. 2004;12(4):582-90.
Zemel, et al. Dairy augmentation of total and central fat loss in obese subjects. Int J Obes (Lond). Apr. 2005;29(4):391-7.
Zemel, et al. Effects of dairy compared with soy on oxidative and inflammatory stress in overweight and obese subjects. Am J Clin Nutr. Jan. 2010;91(1):16-22. Epub Nov. 4, 2009.
Zemel, et al. Regulation of adiposity by dietary calcium. FASEB J. Jun. 2000;14(9):1132-8.

(56) References Cited

OTHER PUBLICATIONS

Zemel. Role of calcium and dairy products in energy partitioning and weight management. Am J Clin Nutr. May 2004;79(5):907S-912S.

Zemel. The role of dairy foods in weight management. J Am Coll Nutr. Dec. 2005; 24(6 Suppl):537S-46S.

Zemel, et al. Effects of calcium and dairy on body composition and weight loss in African-American adults. Obes Res. Jul. 2005;13(7):1218-25.

Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.

Zhang, et al. Occurrence of beta-hydroxyl-beta-methyl butyrates in foods and feed. Protein and amini acid nutrition. 1994; A464: 2685-2690.

Zoraghi, et al. Phosphodiesterase-5 Gln817 is critical for cGMP, vardenafil, or sildenafil affinity: its orientation impacts cGMP but not cAMP affinity. J Biol Chem. Mar. 3, 2006;281(9):5553-8. Epub Jan. 5, 2006.

HMB-Resveratrol Synergy in Activation of SIRT3

Resveratrol-HMB synergy in glucose uptake using FDG-PET

Effects of resveratrol, leucine and HMB on adipose tissue Sirt1 activity in diet-induced obese mice

COMPOSITIONS AND METHODS FOR MODULATING METABOLIC PATHWAYS

CROSS-REFERENCE

This application is a continuation application of U.S. application Ser. No. 15/164,647, filed May 25, 2016, which is a continuation application of U.S. patent application Ser. No. 14/927,255, filed Oct. 29, 2015, which is a continuation application of U.S. application Ser. No. 14/746,516, filed Jun. 22, 2015, now U.S. Pat. No. 9,198,883, which is a continuation application of Ser. No. 13/866,936, filed Apr. 19, 2013, now U.S. Pat. No. 9,072,692, which is a continuation application of Ser. No. 13/549,381, filed Jul. 13, 2012, now U.S. Pat. No. 8,617,886, which claims the benefit of U.S. Application No. 61/508,139, filed Jul. 15, 2011; U.S. Application No. 61/636,597, filed Apr. 20, 2012; U.S. Application No. 61/636,598, filed Apr. 20, 2012; U.S. Application No. 61/636,603, filed Apr. 20, 2012; U.S. Application No. 61/636,605, filed Apr. 20, 2012; U.S. Application No. 61/636,608, filed Apr. 20, 2012; U.S. Application No. 61/636,610, filed Apr. 20, 2012; all of which applications are incorporated herein by reference in their entirety.

BACKGROUND OF THE INVENTION

All organisms have developed exquisite metabolic pathways that maintain energy homeostasis by balancing their intake and metabolism of energy with their expenditure needs of the organism. In mammals, these pathways regulate food intake, glucose homeostasis, storage of energy in fat and/or muscle, and mobilization of energy by, for instance, physical activity. Malfunctioning of these pathways, often resulting from excess energy intake relative to energy expenditure, leads to imbalance in energy homeostasis and can lead to a wide range of metabolic disorders, such as obesity, diabetes, hypertension, arteriosclerosis, high cholesterol, and hyperlipidemia.

The high incidence of metabolic disorders in humans and their related impact on health and mortality represents a significant threat to public health. For instance, obesity, clinically defined as a body mass index of over 30 $kg/m^2$, is estimated to affect 35.7% of the U.S. adult population. Obesity increases the likelihood of many diseases, such as heart disease and type II diabetes, which is one of the leading preventable causes of death worldwide. In the U.S., obesity is estimated to cause roughly 110,000-365,000 deaths per year. Diabetes is a metabolic disorder characterized by high blood glucose levels or low glucose tolerance, and is estimated to affect 8% of the U.S. population. Diabetes is also significantly associated with higher risk of death from vascular disease, cancer, renal disease, infectious diseases, external causes, intentional self-harm, nervous system disorders, and chronic pulmonary disease (N Engl J Med 2011; 364:829-841). Metabolic syndrome, in which subjects present with central obesity and at least two other metabolic disorders (such as high cholesterol, high blood pressure, or diabetes), is estimated to affect 25% of the U.S. population.

Sirtuins are highly conserved protein deacetylases and/or ADP-ribosyltransferases that have been shown to extend lifespan in lower model organisms, such as yeast, *C. elegans*, and *drosophila*. In mammals, sirtuins have been shown to act as metabolic sensors, responding to environmental signals to coordinate the activity of genes that regulate multiple energy homeostasis pathways. For example, studies have shown that sirtuin activation mimics the effects of caloric restriction, an intervention demonstrated to significantly extend lifespan, and activates genes that improve glucose homeostasis and the conversion of fat to energy by fatty acid oxidation.

Many efforts have been attempted to develop treatments for metabolic disorders by targeting specific energy metabolism pathways. These efforts have resulted in the development of, for example, isoflavones (U.S. Patent Application No. 20110165125), tetrahydrolipstatin (U.S. Pat. No. 6,004,996), and compositions that modulate the SIRT1 and AMPK pathways (U.S. Patent Application Nos. 20100210692, 20100009992, 20070244202 and 20080176822). However, these efforts are of limited success. For instance, use of the SIRT1 activator resveratrol in humans is hampered by its limited bioavailability, necessitating high dosages which have raised safety concerns. Thus, there remains a great need for treatments that can address a wide range of metabolic disorders by safely regulating metabolic pathways.

SUMMARY OF THE INVENTION

The subject application provides compositions useful for inducing an increase in fatty acid oxidation and mitochondrial biogenesis in a subject. The compositions also cause activation of Sirt1 and Sirt3, thereby mediating beneficial downstream effects, including prevention and treatment of diabetes, cardiovascular disease and inflammatory disease. Such compositions contain synergizing amounts of a sirtuin pathway activator (e.g. resveratrol) in combination with a branched chain amino acid and/or metabolites thereof (e.g. beta-hydroxymethylbutyrate (HMB), leucine, keto-isocaproic acid (KIC) or combinations of HMB, KIC and/or leucine). The subject application also provides methods of increasing fatty acid oxidation in a subject comprising the administration of the disclosed compositions.

The invention provides for a composition comprising: (a) one or more types of branched amino acids (e.g. leucine) and/or metabolites thereof and (b) a sirtuin-pathway activator that optionally may be present in a sub-therapeutic amount, wherein the composition is synergistically effective in increasing the sirtuin-pathway output by at least about 1-fold (e.g. at least about 1, 2, 3, 4, 5 or more fold) as compared to that of component (a) or (b) when it is being used alone. In some embodiments, the synergistic effect is observed when (i) media from myotybes or adipocytes treated with the composition is administered to the other of the myotubes or adipocytes, (ii) the composition is administered to myotubes or adipocytes, and/or (iii) the composition is administered to a subject.

In some embodiments of any aspect described herein, an increase in sirtuin-pathway output is evidenced by an increase in physiological effect selected from the group consisting of mitochondrial biogenesis, fatty acid oxidation, glucose uptake, palmitate uptake, oxygen consumption, carbon dioxide production, weight loss, heat production, visceral adipose tissue loss, respiratory exchange ratio, insulin sensitivity, a inflammation marker level, body temperature, fat cell browning, irisin production, and vasodilatation. An increase in sirtuin-pathway output can be evidenced by an increase in expression or activity level of one or more of the group consisting of SIRT1, SIRT3, and PGC1-α. The increase in sirtuin-pathway output can be at least about 1, 3, 5, 6, 8, 10, 15, 20, or 50 fold.

Another aspect of the invention provides for a composition comprising: (a) one or more types of branched amino acids (e.g. leucine) and/or metabolites thereof, and (b) a sirtuin-pathway activator, wherein molar ratio of component (a) to (b) in said composition is greater than about 20, and wherein the composition when administered to a subject in need thereof synergistically enhances mitochondrial biogenesis as measured by a decrease in weight gain of a subject, a decrease in visceral adipose volume of a subject, an increase in fat oxidation of a subject, an increase in irisin production of a subject, an increase in insulin sensitivity of a subject, an increase of glucose uptake in muscle of a subject, a decrease in inflammation markers, an increase in vasodilatation, and/or an increase in body temperature. In some embodiments, the molar ratio of component (a) to (b) in said composition is greater than about 5, 10, 15, 20, 25, 30, 35, 40, 60, 80, 100, 150, 200, 250, or more.

Another aspect of the invention provides for a composition comprising: a unit dosage suitable for oral ingestion, said unit dosage comprising: (a) one or more types of branched amino acids (e.g. leucine) and/or metabolites thereof, and (b) a substantially homogeneous population of polyphenol or polyphenol precursor molecules, and wherein the unit dosage is effective in inducing an increase in sirtuin pathway output as measured by a decrease in weight gain of a subject, a decrease in visceral adipose volume of a subject, an increase in fat oxidation of a subject, an increase in insulin sensitivity of a subject, an increase of glucose uptake in muscle of a subject, an increase in vasodilatation, and/or an increase in body temperature. In some embodiments, the unit dosage is formulated as a tablet, capsule, or gel capsule.

The polyphenol or polyphenol precursor molecules can be present in an amount effective in increasing sirtuin-pathway output (e.g. by about, less than about, or more than about 1-fold, 3-fold, 5-fold, 6-fold, 8-fold, 10-fold, 15-fold, 20-fold, 50-fold, or more). The polyphenol or polyphenol precursor molecules can be present in an amount effective in sirtuin-pathway output by at least about 1, 2, 3, 4, 5 or more fold. The polyphenol molecules can activate SIRT1 and/or SIRT3. The polyphenol can activate AMPK. The polyphenol can activate PGC1α. The polyphenol can be resveratrol or an analog thereof. The polyphenol can be chlorogenic acid. The polyphenol can be selected from the group consisting of chlorogenic acid, resveratrol, caffeic acid, quinic acid, piceatannol, ellagic acid, epigallocatechin gallate, grape seed extract, cinnamic acid, ferulic acid, and any analog thereof.

Another aspect of the invention provides for a food composition comprising: (a) one or more types of branched amino acids (e.g. leucine) and/or metabolites thereof (b) a sirtuin pathway activator, wherein (a) and (b) are present in an amount that synergistically effect an increase in sirtuin pathway output as measured by a decrease in weight gain of a subject, a decrease in visceral adipose volume of a subject, an increase in fat oxidation of a subject, an increase in insulin sensitivity of a subject, an increase of glucose uptake in muscle of a subject, an increase in vasodilatation, and/or an increase in body temperature; and (c) a food carrier.

The composition can be a dietary supplement packaged as a liquid (e.g. a beverage), solid (e.g. solid food) or semi-solid (e.g. semi-solid food). In some embodiments, the food carrier is a juice, coffee, tea, soda, or snack bar. The composition can be formulated as an oral dosage form. The composition can be packaged as a unit dosage. The unit dosage can be formulated as a tablet, capsule, or gel capsule.

Another aspect of the invention provides for a composition comprising: a synergistically effective amount of (a) one or more types of branched amino acids (e.g. leucine) and/or metabolites thereof and (b) a sirtuin-pathway activator, wherein the composition is substantially free of non-branched amino acids, wherein the combination when administered to a subject in need thereof enhances mitochondrial biogenesis to a greater degree as compared to administering to a subject component (a) or component (b) alone, and wherein the enhanced mitochondrial biogenesis is measured by a decrease in weight of a subject, a decrease in visceral adipose volume of a subject, an increase in fat oxidation of a subject, an increase in insulin sensitivity of a subject, an increase of glucose uptake in muscle of a subject, an increase in vasodilatation, and/or an increase in body temperature. The increase mitochondrial biogenesis can be at least about 1, 2, 3, 4, 5, 6, 8, 10, 15, 20, or 50 fold (where a 1-fold increase is equivalent to a 100% increase). In some embodiments, the change in mitochondrial biogenesis and/or in one or more measures thereof is about or more than about 10%, 20%, 50%, 100%, 200%, 300%, 400%, 500%, 750%, 1000%, 2000%, 5000%, or more.

Another aspect of the invention provides for a composition comprising: (a) one or more types of branched amino acids (e.g. leucine) and/or metabolites thereof, and (b) a signaling molecule downstream of PGC1α in a sirtuin-signaling pathway. The signaling molecule downstream of PGC1α can be irisin or an analog thereof. In some embodiments, the one or more types of branched amino acids and/or metabolites thereof can be selected from the group consisting of leucine, valine, isoleucine, 4-hydroxyisoleucine, keto-isocaproic acid (KIC), alpha-hydroxy-isocaproic acid, and HMB. The composition is substantially free of non-branched amino acids.

In one aspect, the invention provides a composition comprising: (a) one or more types of branched amino acids (e.g. leucine) and/or metabolites thereof, and (b) a sub-therapeutic amount of one or more anti-diabetic agents selected from the group consisting of biguanide, meglitinide, sulfonylurea, thiazolidinedione, alpha glucosidase inhibitor, and ergot alkaloid; wherein the combination when administered to a subject synergistically increases insulin sensitivity in said subject as compared to administering to a subject component (a) or component (b) alone. In some embodiments, the anti-diabetic agent is a sirtuin pathway activator. In some embodiments, the anti-diabetic agent is a biguanide (e.g. metformin or any analog thereof). In some embodiments, the increase in insulin sensitivity is at least about a 1-fold increase (e.g. at least about 1, 2, 3, 4, 5, 6, 8, 10, 15, 20, or 50 fold). In some embodiments, the invention provides a method of potentiating the therapeutic efficacy of a biguanide comprising administering simultaneously or sequentially to a subject component (a) and component (b) of a composition of the invention, wherein the administration of (a) and (b) is in an amount that synergistically increases insulin sensitivity, and wherein component (b) is a biguanide (e.g. metformin).

The invention also provides for a method of potentiating the therapeutic efficacy of one or more anti-diabetic agents selected from the group consisting of biguanide, meglitinide, sulfonylurea, thiazolidinedione, alpha glucosidase inhibitor, and ergot alkaloid, comprising administering simultaneously or sequentially to a subject (a) a sub-therapeutic amount of said anti-diabetic agent, and (b) one or more branched amino acids, wherein the administration of (a) and (b) is effective in ameliorating a diabetic symptom of said subject. Examples of diabetic symptoms include, but are not limited to, polyuria, polydipsia, weight loss, polyphagia, blurred vision, hypertension, abnormalities of lipoprotein metabolism, and periodontal disease. The biguanide can be metformin. The one or more anti-diabetic agent can comprise glipizide and/or metformin. The one or more anti-diabetic agent can be thiazolidinedione.

In one aspect, the invention provides a method of increasing a level of irisin, such as increasing production of irisin by a cell or in a subject. In some embodiments, the method comprises administering a composition comprising: (a) one or more types of branched amino acids (e.g. leucine) and/or metabolites thereof, and (b) a sirtuin pathway activator; wherein the administering increases production of irisin by a cell. In some embodiments, the increase in irisin production (or in an indicator providing evidence thereof) is an increase of about, less than about, or more than about 5%, 10%, 20%, 30%, 40%, 50%, 60%, 70%, 80%, 90%, 100%, 125%, 150%, 175%, 200%, or more. In some embodiments, the increase in irisin production (or in an indicator providing evidence thereof) is an increase of about, less than about, or more than about 1-fold, 3-fold, 5-fold, 6-fold, 8-fold, 10-fold, 15-fold, 20-fold, 50-fold, or more. In some embodiments, the increase in irisin production is evidenced by an increase in FNDC5 expression (e.g. as measured from mRNA and/or protein level). In some embodiments, the increase in irisin production is evidenced by an increase in one or more indicia of fat cell browning (e.g. fatty acid oxidation, and/or an increase in expression of one or more brown fat selective genes in adipose tissue). In some embodiments, the increase in irisin production is evidenced by increased secretion of irisin from the cell or in the subject (e.g. as measured from media in which the cell is cultured, or from circulating plasma in a subject). In some embodiments, the composition comprises leucine and resveratrol. In some embodiments, the composition comprises leucine and cinnamic acid. In some embodiments, the composition comprises HMB and resveratrol. In some embodiments, the composition comprises HMB and cinnamic acid.

In some embodiments of any of the aspects described herein, the composition is suitable for oral consumption. The composition can be a liquid form suitable for non-oral administration to a subject. The composition can be a liquid form suitable for injectable administration to a subject. The composition can be formulated for oral administration to a subject.

The invention provides for a method of enhancing fat oxidation in a subject in need thereof comprising administering to the subject any of the compositions described herein over a time period, wherein the fat oxidation in the subject is increased over the time period. The invention provides for a method of reducing an inflammatory response in a subject in need thereof comprising administering to the subject any of the compositions described herein over a time period, wherein the inflammatory response in the subject is reduced over the time period. The invention provides for a method of increasing or maintaining body temperature in a subject comprising administering to the subject any of the compositions described herein over a time period, wherein the body temperature in the subject is increased over the time period. The invention provides for a method of inducing vasodilatation comprising administering to the subject any of the compositions described herein over a time period, wherein the vasodilation in the subject is induced over the time period. The invention provides for a method of treating diabetes, comprising administering to the subject any of the compositions described herein over a time period, wherein the insulin sensitivity in the subject is increased over the time period. In some embodiments, an increase in insulin sensitivity is evidenced by a decrease in plasma insulin levels, and/or an increase in glucose utilization (e.g. faster glucose uptake in response to glucose challenge). In some embodiments, the increase in fat oxidation and/or the increase in insulin sensitivity is about, less than about, or more than about 5%, 10%, 20%, 30%, 40%, 50%, 60%, 70%, 80%, 90%, 100%, 125%, 150%, 175%, 200%, or more. In some embodiments, the increase in fat oxidation and insulin sensitivity is more than about 5%, 10%, 20%, 30%, 40%, 50%, 60%, 70%, 80%, 90%, 100%, 125%, 150%, 175%, 200%, or more. In some embodiments, the increase in fat oxidation and/or the increase in insulin sensitivity is about, less than about, or more than about 1-fold, 3-fold, 5-fold, 6-fold, 8-fold, 10-fold, 15-fold, 20-fold, 50-fold, or more. In some embodiments, the increase in fat oxidation and/or the increase in insulin sensitivity is more than about 1-fold, 3-fold, 5-fold, 6-fold, 8-fold, 10-fold, 15-fold, 20-fold, 50-fold, or more.

The invention provides for a method of preparing a composition of any of the compositions described herein, comprising mixing the components to form a substantially homogeneous mixture and forming the composition into a unit dosage.

In some embodiments of any of the aspects described herein, the one or more types of branched amino acids and/or metabolites thereof is selected from the group consisting of leucine, valine, isoleucine, 4-hydroxyisoleucine, keto-isocaproic acid (KIC), alpha-hydroxy-isocaproic acid, and hydroxymethylbutyrate (HMB). The composition can be substantially free of non-branched amino acids. The composition can comprise at least about 500 mg leucine and/or at least about 200 mg of the one or more metabolites.

In some embodiments of any of the aspects described herein, the sirtuin-pathway activator can activate one or more of SIRT1, SIRT3, AMPK, and PGC1α. In some embodiments, the sirtuin-pathway activator is a polyphenol or polyphenol precursor. In some embodiments, the sirtuin-pathway activator is resveratrol or an analog thereof. The polyphenol can be chlorogenic acid. The polyphenol or polyphenol precursor can be selected from the group consisting of chlorogenic acid, resveratrol, caffeic acid, cinnamic acid, ferulic acid, piceatannol, ellagic acid, epigallocatechin gallate, grape seed extract, and any analog thereof. The sirtuin-pathway activator can be selected from the group consisting of cinnamic acid, quinic acid, fucoxanthin, a biguanide, rosiglitazone, or any analog thereof. The biguanide can be metformin.

In some embodiments of any of the aspects described herein, the composition has one or more additional characteristics. In some embodiments, the composition is a food composition. The composition can be a food or a dietary supplement packaged as a liquid (e.g. a beverage), a solid (e.g. solid food), or a semi-solid (e.g. semi-solid food). In some embodiments, the composition is formulated as an oral dosage form. In some embodiments, the composition can be packaged as a unit dosage. The unit dosage can be formulated as a tablet, capsule, or gel capsule. In some embodiments, the composition further comprises a pharmaceutically active agent. In some embodiments, the composition further comprises an anti-diabetic agent. The composition can be a pharmaceutical composition further comprising a pharmaceutically acceptable excipient. In some embodiments, administration of a composition to a subject synergistically increases mitochondrial biogenesis by at least about 1-fold, 3-fold, 5-fold, 6-fold, 8-fold, 10-fold, 15-fold, 20-fold, or 50-fold, or more. In some embodiments, administration of a composition to a subject synergistically increases sirtuin pathway output by at least about 1-fold, 3-fold, 5-fold, 6-fold, 8-fold, 10-fold, 15-fold, 20-fold, or 50-fold, or more.

Furthermore, the following non-limiting embodiments are also provided:

The invention provides for a composition comprising a synergizing amount of resveratrol, a synergizing amount of beta-hydroxymethylbutyrate (HMB), a synergizing amount of keto isocaproic acid (KIC); and/or a synergizing amount of leucine. In some embodiments, the composition comprises a synergizing amount of resveratrol and a synergizing amount of HMB, wherein: said synergizing amount of resveratrol is between at least 35 mg and about 500 mg, and said synergizing amount of HMB is between about (or at least) 0.20 g and about 3.0 g.

In some embodiments, the composition comprises a synergizing amount of resveratrol and a synergizing amount of leucine, wherein: said synergizing amount of resveratrol is between at least 35 mg and about 500 mg; and said synergizing amount of leucine is between about (or at least) 0.75 g and about 3.0 g. The composition can comprise a synergizing amount of resveratrol and a synergizing amount of KIC, wherein: said synergizing amount of resveratrol is between at least 35 mg and about 500 mg; and said synergizing amount of KIC is between about (or at least) 0.75 g and about 3.0 g. The composition can comprise a synergizing amount of resveratrol, a synergizing amount of HMB and a synergizing amount of leucine, provided that the total amount of HMB and leucine in said composition is less than (or less than about) 3.0 g, wherein: said synergizing amount of resveratrol is between at least 35 mg and about 500 mg; said synergizing amount of HMB is between about (or at least) 0.20 g and about 3.0 g; and said synergizing amount of leucine is between about (or at least) 0.50 g and about 3.0 g. The composition can comprise a synergizing amount of resveratrol, a synergizing amount of KIC and a synergizing amount of leucine, provided that the total amount of KIC and leucine in said composition is less than (or less than about) 3.0 g, wherein: said synergizing amount of resveratrol is between at least 35 mg and about 500 mg; said synergizing amount of KIC is between about (or at least) 0.50 g and about 3.0 g; and said synergizing amount of leucine is between about (or at least) 0.50 g and about 3.0 g. The composition can comprise a synergizing amount of resveratrol, a synergizing amount of HMB and a synergizing amount of KIC, provided that the total amount of HMB and KIC in said composition is less than (or less than about) 3.0 g, wherein: said synergizing amount of resveratrol is between at least 35 mg and about 500 mg; said synergizing amount of HMB is between about (or at least) 0.20 g and about 3.0 g; and said synergizing amount of KIC is between about (or at least) 0.50 g and about 3.0 g.

The composition can comprise a synergizing amount of resveratrol, a synergizing amount of KIC, a synergizing amount of HMB and a synergizing amount of leucine, provided that the total amount of KIC, HMB and leucine in said composition is less than (or less than about) 3.0 g, wherein: said synergizing amount of resveratrol is between at least 35 mg and about 500 mg; said synergizing amount of HMB is between about (or at least) 0.20 g and about 3.0 g; said synergizing amount of KIC is between about (or at least) 0.50 g and about 3.0 g; and said synergizing amount of leucine is between about (or at least) 0.50 g and about 3.0 g.

In some embodiments, said synergizing amount of resveratrol is between at least 50 mg and about 500 mg; and said synergizing amount of HMB is between about (or at least) 0.40 g and about 3.0 g. In other embodiments, said synergizing amount of resveratrol is between at least 50 mg and about 500 mg; and said synergizing amount of leucine is between about (or at least) 0.75 g and about 3.0 g. In some embodiments, said synergizing amount of resveratrol is between at least 50 mg and about 500 mg; said synergizing amount of HMB is between at least 0.40 g and about 3.0 g; and said synergizing amount of leucine is between at least 0.75 g and about 3.0 g. In other embodiments, said synergizing amount of resveratrol is between at least 50 mg and about 500 mg; said synergizing amount of KIC is between at least 0.75 g and about 3.0 g; and said synergizing amount of leucine is between at least 0.75 g and about 3.0 g. In some embodiments, said synergizing amount of resveratrol is between at least 50 mg and about 500 mg; said synergizing amount of HMB is between at least 0.40 g and about 3.0 g; and said synergizing amount of KIC is between at least 0.75 g and about 3.0 g.

In some embodiments, said synergizing amount of resveratrol is between at least 50 mg and about 500 mg; said synergizing amount of HMB is between at least 0.40 g and about 3.0 g; said synergizing amount of KIC is between at least 0.75 g and about 3.0 g; and said synergizing amount of leucine is between at least 0.75 g and about 3.0 g.

In some of the embodiments described herein, the amount or HMB, KIC, leucine or combinations of leucine, KIC and/or HMB may be less than, or equal to, 3.0 g.

In some of the embodiments described herein, said composition may exclude one or more of the amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine.

In some of the embodiments described herein, the composition may exclude one or more of the following ingredients: niacin, vitamin B6, vitamin B12, pantothenic acid, caffeine, green tea extract, extracts from guarana seed or extracts from guarana plants.

In some of the embodiments described herein, said composition may exclude one or more of the amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine.

In some of the embodiments described herein, the composition may exclude one or more of the following ingredients: niacin, vitamin B6, vitamin B12, pantothenic acid, caffeine, green tea extract, extracts from guarana seed or extracts from guarana plants.

In some of the embodiments described herein, said composition may exclude one or more of the amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. In some embodiments, the composition excludes valine and/or isoleucine.

In some of the embodiments described herein, the composition may further comprise a flavorant. In any one of the embodiments described herein, said composition is a solid, liquid, emulsion, gel or paste.

The invention provides for a method of increasing fatty acid oxidation in a subject comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount effective to increase fatty acid oxidation.

In one aspect, the invention provides for a method of reducing weight gain or inducing weight loss in a subject comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount effective to reduce weight gain or induce weight loss.

In another aspect, the invention provides for a method of stimulating Sirt1 or Sirt3 comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount effective to stimulate SIRT1 or SIRT3.

The invention provides for a method of activating the metabolic activity of adipocytes, smooth muscle, skeletal muscle or cardiac muscle comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount sufficient to activate the metabolic activity of said muscle.

In other embodiments, the invention provides for a method of increasing or maintaining body temperature in a subject comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount sufficient to increase or maintain the body temperature of said subject.

The invention provides for a method of treating type 2 diabetes in a subject comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount sufficient to treat type 2 diabetes in said subject.

The invention also provides for a method of reducing an inflammatory response in a subject comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine to a subject in an amount sufficient to reduce an inflammatory response in said subject.

The invention provides for a method of inducing vasodilation comprising the administration of a composition comprising a synergizing amount of resveratrol, a synergizing amount of beta-hydroxymethylbutyrate (HMB), a synergizing amount of keto isocaproic acid (KIC), and/or a synergizing amount of leucine in an amount sufficient to induce vasodilation in said subject.

In some embodiments, the composition comprises a synergizing amount of resveratrol and a synergizing amount of HMB, wherein: said synergizing amount of resveratrol is between at least 35 mg and about 500 mg, and said synergizing amount of HMB is between about (or at least) 0.20 g and about 3.0 g.

In some embodiments, the composition comprises a synergizing amount of resveratrol and a synergizing amount of leucine, wherein: said synergizing amount of resveratrol is between at least 35 mg and about 500 mg, and said synergizing amount of leucine is between about (or at least) 0.75 g and about 3.0 g.

In other embodiments, the composition comprises a synergizing amount of resveratrol and a synergizing amount of KIC, wherein: said synergizing amount of resveratrol is between at least 35 mg and about 500 mg, and said synergizing amount of KIC is between about (or at least) 0.75 g and about 3.0 g.

In some embodiments, the composition comprises a synergizing amount of resveratrol, a synergizing amount of HMB and a synergizing amount of leucine, provided that the total amount of HMB and leucine in said composition is less than (or less than about) 3.0 g, wherein: said synergizing amount of resveratrol is between at least 35 mg and about 500 mg, said synergizing amount of HMB is between about (or at least) 0.20 g and about 3.0 g, and said synergizing amount of leucine is between about (or at least) 0.50 g and about 3.0 g.

In some embodiments, the composition comprises a synergizing amount of resveratrol, a synergizing amount of KIC and a synergizing amount of leucine, provided that the total amount of KIC and leucine in said composition is less than (or less than about) 3.0 g, wherein: said synergizing amount of resveratrol is between at least 35 mg and about 500 mg, said synergizing amount of KIC is between about (or at least) 0.50 g and about 3.0 g, and said synergizing amount of leucine is between about (or at least) 0.50 g and about 3.0 g.

In other embodiments, the composition comprises a synergizing amount of resveratrol, a synergizing amount of HMB and a synergizing amount of KIC, provided that the total amount of HMB and KIC in said composition is less than (or less than about) 3.0 g, wherein: said synergizing amount of resveratrol is between at least 35 mg and about 500 mg, said synergizing amount of HMB is between about (or at least) 0.20 g and about 3.0 g, and said synergizing amount of KIC is between about (or at least) 0.50 g and about 3.0 g.

In some embodiments, the composition comprises a synergizing amount of resveratrol, a synergizing amount of KIC, a synergizing amount of HMB and a synergizing amount of leucine, provided that the total amount of KIC, HMB and leucine in said composition is less than (or less than about) 3.0 g, wherein: said synergizing amount of resveratrol is between at least 35 mg and about 500 mg, said synergizing amount of HMB is between about (or at least) 0.20 g and about 3.0 g, said synergizing amount of KIC is between about (or at least) 0.50 g and about 3.0 g, and said synergizing amount of leucine is between about (or at least) 0.50 g and about 3.0 g.

In some embodiments, said synergizing amount of resveratrol is between at least 50 mg and about 500 mg, and said synergizing amount of HMB is between about (or at least) 0.40 g and about 3.0 g.

In some embodiments, said synergizing amount of resveratrol is between at least 50 mg and about 500 mg, and said synergizing amount of leucine is between about (or at least) 0.75 g and about 3.0 g.

In some embodiments, said synergizing amount of resveratrol is between at least 50 mg and about 500 mg, said synergizing amount of HMB is between at least 0.40 g and about 3.0 g, and said synergizing amount of leucine is between at least 0.75 g and about 3.0 g.

In some embodiments, said synergizing amount of resveratrol is between at least 50 mg and about 500 mg, said synergizing amount of KIC is between at least 0.75 g and about 3.0 g, and said synergizing amount of leucine is between at least 0.75 g and about 3.0 g.

In some embodiments, said synergizing amount of resveratrol is between at least 50 mg and about 500 mg, said synergizing amount of HMB is between at least 0.40 g and about 3.0 g, and said synergizing amount of KIC is between at least 0.75 g and about 3.0 g.

In some embodiments, said synergizing amount of resveratrol is between at least 50 mg and about 500 mg, said synergizing amount of HMB is between at least 0.40 g and about 3.0 g, said synergizing amount of KIC is between at least 0.75 g and about 3.0 g, and said synergizing amount of leucine is between at least 0.75 g and about 3.0 g.

In some of the embodiments described herein, the amount or HMB, KIC, leucine or combinations of leucine, KIC and/or HMB is less than, or equal to, 3.0 g.

In some of the embodiments described herein, the composition further comprises a flavorant. In any one of the embodiments described herein, said composition is a solid, liquid, emulsion, gel or paste. In any one of the embodiments described herein, the subject is a human or non-human animal. In any one of the embodiments described herein, said composition is administered orally, parenterally, intravenously or intraperitoneally. In any of the embodiments for reducing weight gain or inducing weight loss according to any one of embodiments, said subject is on an unrestricted diet.

In any of the embodiments for reducing weight gain or inducing weight loss according to any one of embodiments, said subject is on a calorie restricted diet. In any one of the embodiments described herein, said composition comprises: a) about 50 to 100 mg resveratrol and about 400 mg to about 500 mg HMB, b) about 50 to 100 mg resveratrol and about 750 mg to about 1250 mg leucine, or c) about 50 to 100 mg resveratrol and about 750 mg to about 1250 mg KIC.

In any one of the embodiments described herein, said composition comprises about 50 mg to about 100 mg resveratrol and a) a combination of HMB and KIC in an amount of about 400 mg and about 1250 mg, b) a combination of HMB and leucine in an amount of about 400 mg and about 1250 mg, c) a combination of KIC and leucine in an amount of about 400 mg and about 1250 mg, or d) a combination of HMB, KIC and leucine in an amount of about 400 mg and about 1250 mg.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
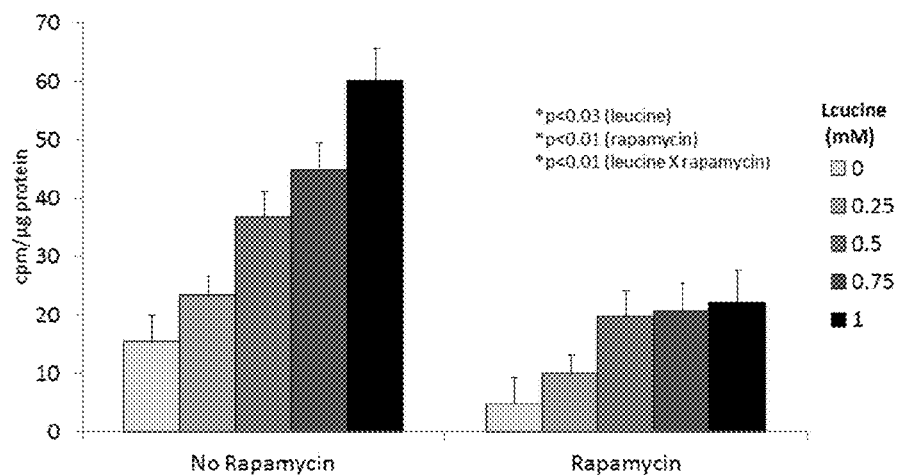
FIG. 1 depicts a graph showing the effects of leucine and rapamycin on fatty acid oxidation.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions are exemplary and not meant to be limited to the recited concentration per se.

As used herein, the term "subject" or "individual" includes mammals. Non-limiting examples of mammals include humans and mice, including transgenic and non-transgenic mice. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The terms "administer", "administered", "administers" and "administering" are defined as the providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition may be preferred.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptomer and polynucleotides), an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "modulator" of a pathway refers to a substance or agent which modulates the activity of one or more cellular proteins mapped to the same specific signal transduction pathway. A modulator may augment or suppress the activity and/or expression level or pattern of a signaling molecule. A modulator can activate a component in a pathway by directly binding to the component. A modulator can also indirectly activate a component in a pathway by interacting with one or more associated components. The output of the pathway can be measured in terms of the expression or activity level of proteins. The expression level of a protein in a pathway can be reflected by levels of corresponding mRNA or related transcription factors as well as the level of the protein in a subcellular location. For instance, certain proteins are activated by translocating in or out of a specific subcellular component, including but not limited to nucleus, mitochondria, endosome, lysosome or other membraneous structure of a cell. The output of the pathway can also be measured in terms of physiological effects, such as mitochondrial biogenesis, fatty acid oxidation, or glucose uptake.

An "activator" refers to a modulator that influences a pathway in a manner that increases the pathway output. Activation of a particular target may be direct (e.g. by interaction with the target) or indirect (e.g. by interaction with a protein upstream of the target in a signaling pathway including the target).

A "suppressor" can be a modulator that influences a pathway in a manner that decreases pathway output.

The term "substantially free", as used herein, refers to compositions that have less than about 10%, less than about 5%, less than about 1%, less than about 0.5%, less than 0.1% or even less of a specified component. For example a composition that is substantially free of non-branched chain amino acids may have less than about 1% of the non-branched chain amino acid lysine.

A "sub-therapeutic amount" of an agent, an activator or a therapy is an amount less than the effective amount for that agent, activator or therapy, but when combined with an effective or sub-therapeutic amount of another agent or therapy can produce a desired result, due to, for example, synergy in the resulting efficacious effects, and/or reduced side effects.

A "synergistic" or "synergizing" effect can be such that the one or more effects of the combination compositions are greater than the one or more effects of each component alone, or they can be greater than the sum of the one or more effects of each component alone. The synergistic effect can be about, or greater than about 10, 20, 30, 50, 75, 100, 110, 120, 150, 200, 250, 350, or 500% or even more than the effect on a subject with one of the components alone, or the additive effects of each of the components when administered individually. The effect can be any of the measurable effects described herein.

Compositions

Figure 11:
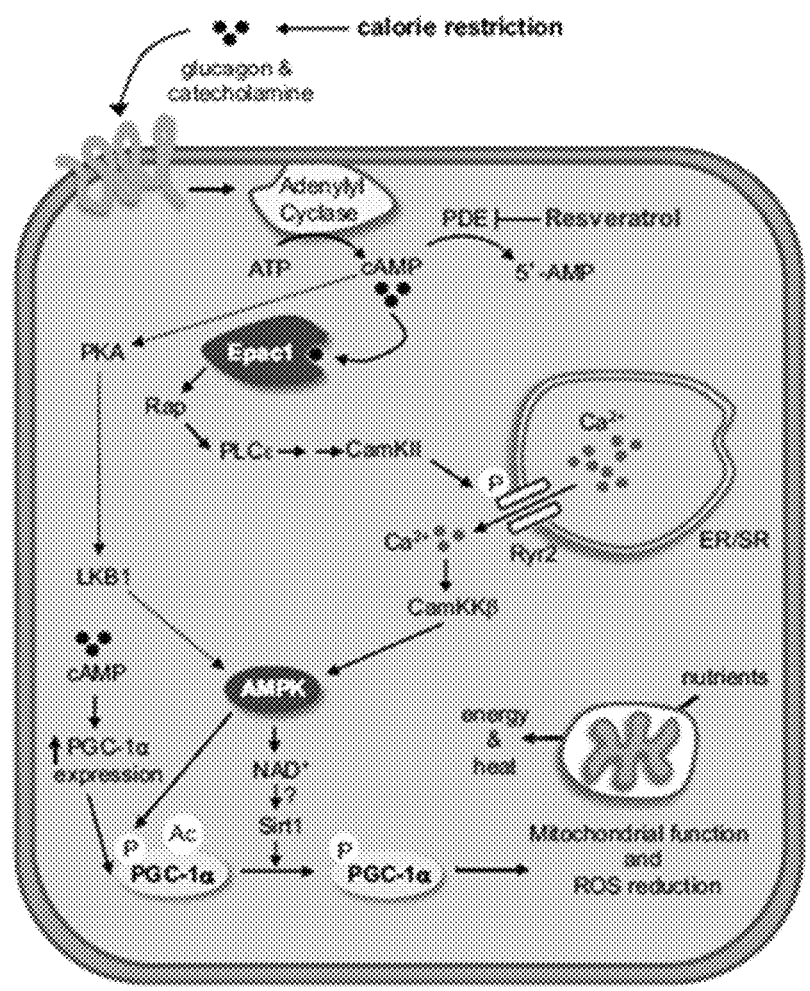
FIG. 11 depicts a diagram showing a sirtuin pathway.

The invention provides for compositions that can increase or modulate the output of a sirtuin pathway. The sirtuin pathway includes, without limitation, signaling molecules such as, Sirt1, Sirt3, and AMPK. The output of the pathway can be determined by the expression level and/or the activity of the pathway and/or a physiological effect. In some embodiments, activation of the Sirt1 pathway includes stimulation of PGC1-α and/or subsequent stimulation of mitochondrial biogenesis and fatty acid oxidation. In general, a sirtuin pathway activator is compound that activates or increases one or more components of a sirtuin pathway. An increase or activation of a sirtuin pathway can be observed by an increase in the activity of a pathway component protein. For example, the protein can be Sirt1, PGC1-α, AMPK, Epac1, Adenylyl cyclase, Sirt3, or any other proteins and their respective associated proteins along the signaling pathway depicted in FIG. 11 (Park et. al., "Resveratrol Ameliorates Aging-Related Metabolic Phenotypes by Inhibiting cAMP Phosphodiesterases," Cell 148, 421-433 Feb. 3, 2012). Non-limiting examples of physiological effects that can serve as measures of sirtuin pathway output include mitochondrial biogenesis, fatty acid oxidation, glucose uptake, palmitate uptake, oxygen consumption, carbon dioxide production, weight loss, heat production, visceral adipose tissue loss, respiratory exchanger ratio, insulin sensitivity, inflammation marker level, vasodilation, browing of fat cells, and irisin production. Examples of indicia of browning of fat cells include, without limitation, increased fatty acid oxidation, and expression of one or more brown-fat-selective genes (e.g. Ucp1, Cidea, Prdm16, and Ndufs1). In some embodiments, changes in one or more physiological effects that can serve as measures of sirtuin pathway output are induced by increasing irisin production, such as by administering a composition of the invention.

An increase in mitochondrial biogenesis can be evidenced by an increase in the formation of new mitochondria and/or by an increase in mitochondrial functions, such as increased fatty acid oxidation, increased heat generation, increased insulin sensitivity, increased in glucose uptake, increased in vasodilation, decreased in weight, decreased in adipose volume, and decreased inflammatory response or markers in a subject.

The compositions can be combination compositions which may include one or more synergistic components. In some embodiments, the synergistic effect of the combination compositions can allow for reduced dosing amounts, leading to reduced side effects to the subject and reduced cost of treatment. In other embodiments, the synergistic effect can allow for results that are not achievable through any other conventional treatments. The subject combination compositions provide a significant improvement in the regulation of energy metabolism.

In some embodiments, the compositions can be combination compositions of one or more branched chain amino acids and/or metabolites thereof and a sirtuin-pathway activator can have one or more characteristics. The combination compositions (a) can have a synergistic effect in increasing the sirtuin-pathway output, (b) increase sirtuin-pathway output by at least about 1, 2, 5, 7, 10, or 20 fold, (c) have a molar ratio of branched chain amino acids and/or metabolites thereof to sirtuin-pathway output that is greater than about 20, (d) be formulated as a unit dosage for oral ingestion, where the sirtuin-pathway activator is a substantially homogeneous population of polyphenol molecules, and (e) can have a synergistic effect and further comprise a food carrier. Any of the compositions described herein can have one or more of these characteristics.

In some embodiments, the present invention provides a composition comprising (a) one or more types of branched amino acids and/or metabolites thereof and (b) a sirtuin-pathway activator present in a sub-therapeutic amount, wherein the composition is synergistically effective in increasing the sirtuin-pathway output by at least about 5, 10, 50, 100, 200, 500 or more fold as compared to that of component (b) when it being used alone.

In some embodiments, the sirtuin-pathway activator or AMPK pathway activator can be a polyphenol. For example, the polyphenol can be chlorogenic acid, resveratrol, caffeic acid, piceatannol, ellagic acid, epigallocatechin gallate (EGCG), grape seed extract, or any analog thereof. In some embodiments, the activator can be resveratrol, an analog thereof, or a metabolite thereof. For example, the activator can be pterostilbene or a small molecule analog of resveratrol. Examples of small molecule analogs of resveratrol are described in U.S. Patent Application Nos. 20070014833, 20090163476, and 20090105246, which are incorporated herein by reference in its entirety.

The polyphenol can be a substantially homogeneous population of polyphenols. The polyphenol can be one type of polyphenol, wherein the composition can exclude all other types of polyphenols. In other embodiments, the composition can comprise two, three, or four types of polyphenols, and exclude all other types of polyphenols. In some embodiments, the composition can comprise 1, 2, 3, or 4 types of polyphenols and less than 0.1, 0.5, 1, or 2% of any other types of polyphenols. In some embodiments, a composition further comprises a phosphodiesterase (PDE) inhibitor, and/or other sirtuin pathway activator.

In some embodiments, a sirtuin activator is any one or more of the compounds shown below:

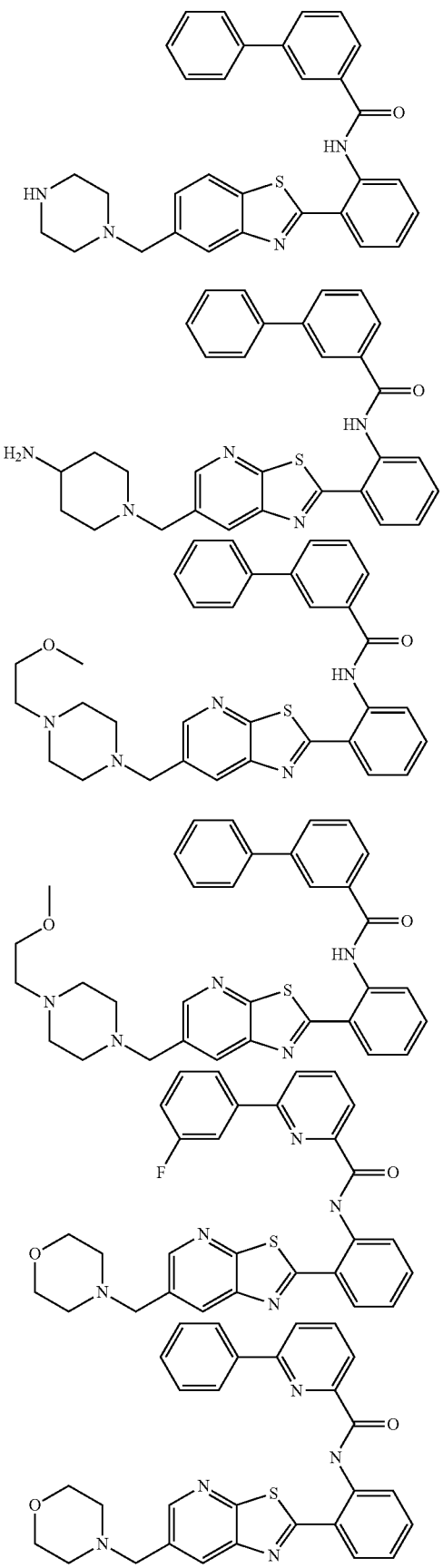

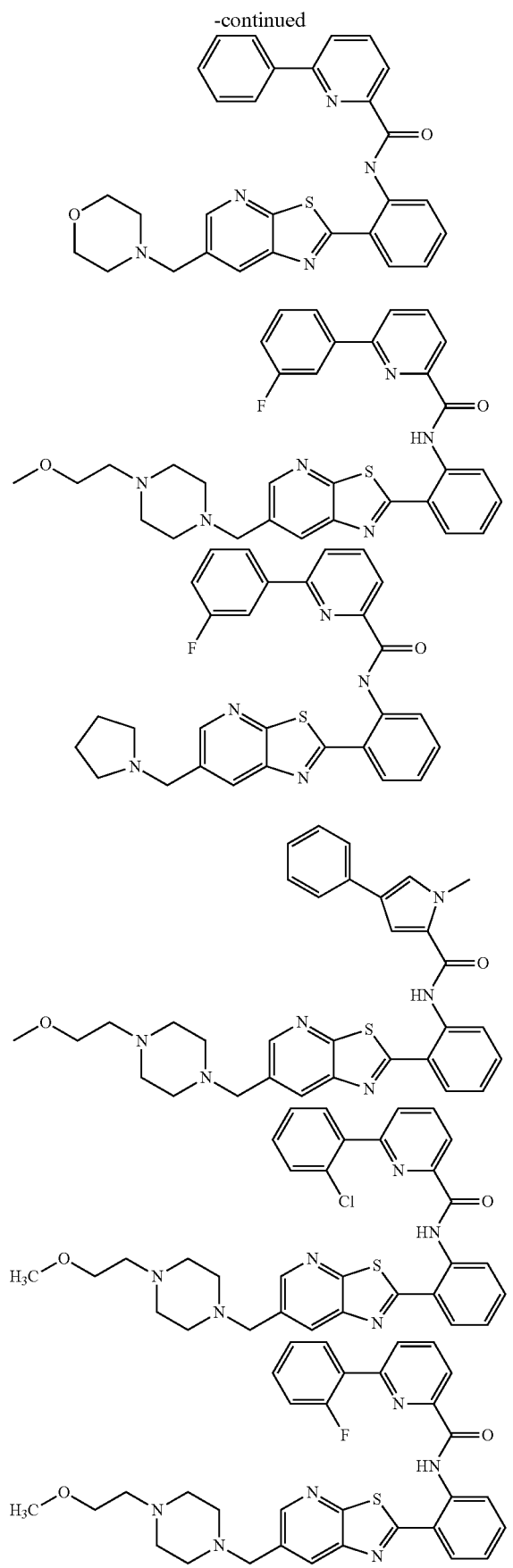
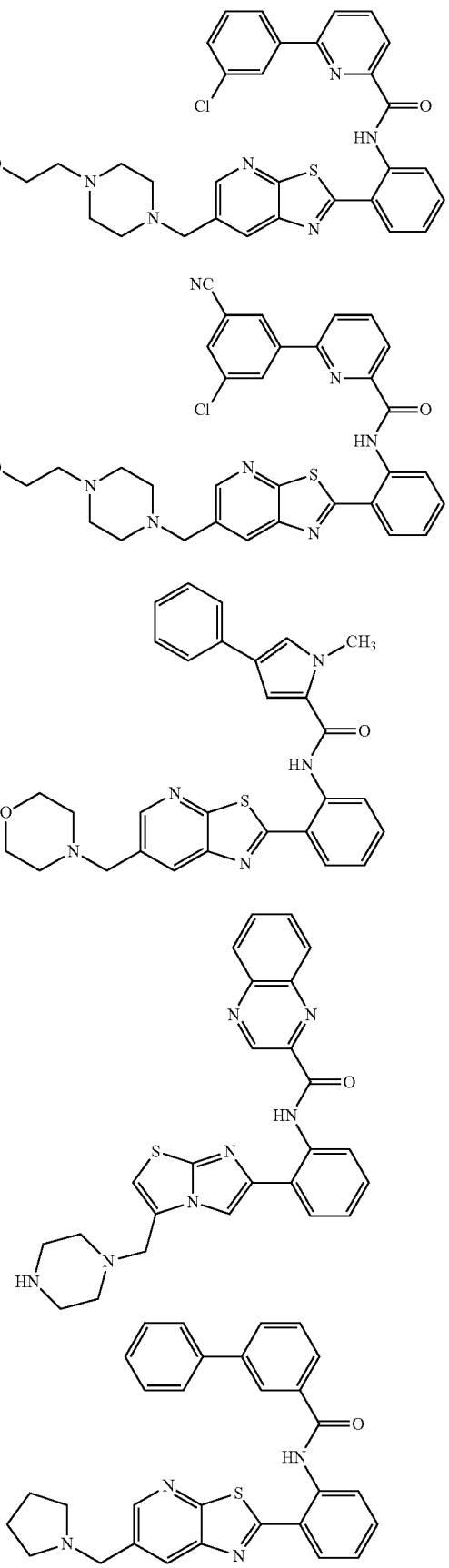

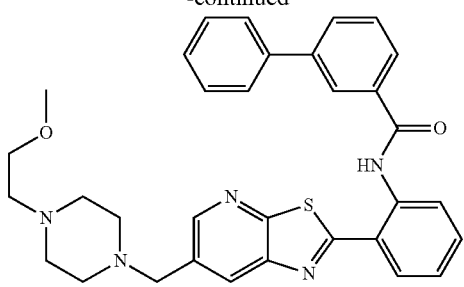
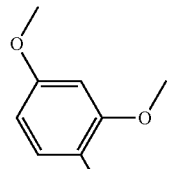
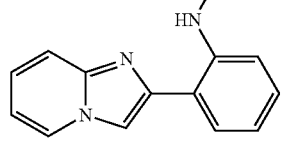
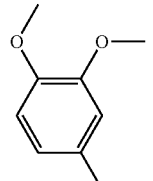
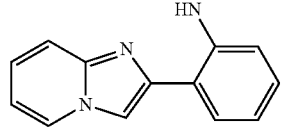
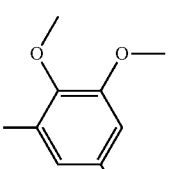
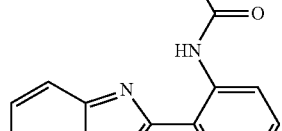
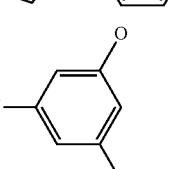
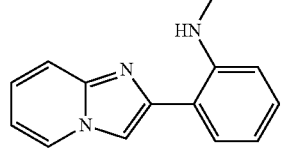
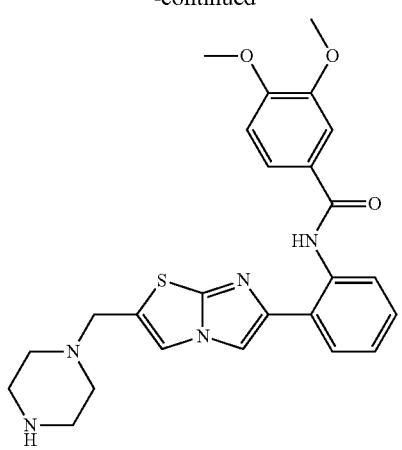
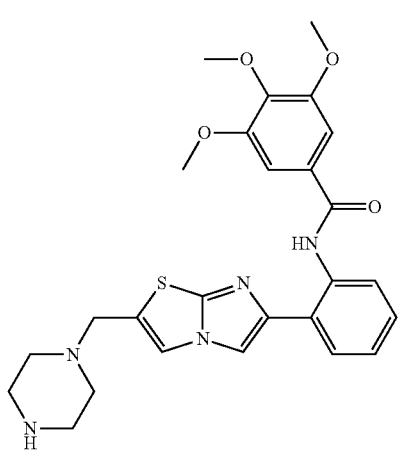
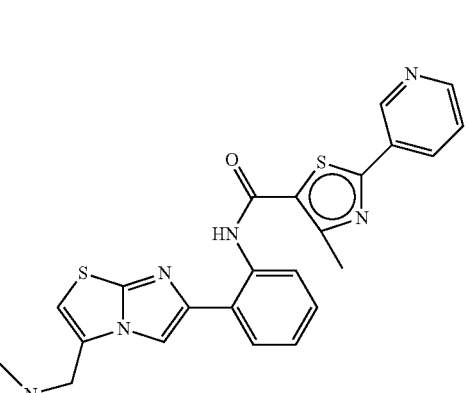
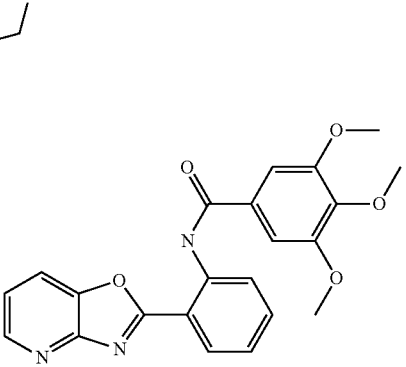

-continued

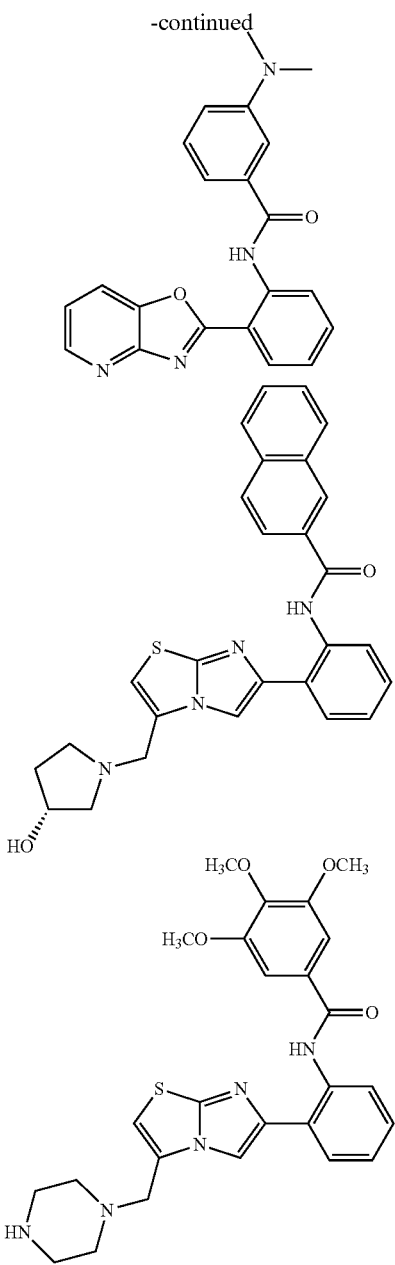

In one embodiment, a sirtuin activator is a stilbene or chalcone compound of formula 1:

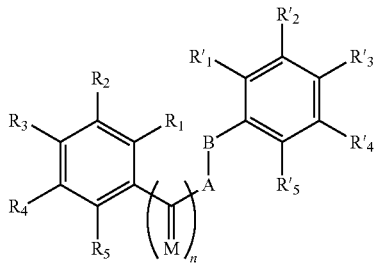

wherein, independently for each occurrence, $R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents O, NR, or S;

A-B represents a bivalent alkyl, alkenyl, alkynyl, amido, sulfonamido, diazo, ether, alkylamino, alkylsulfide, hydroxylamine, or hydrazine group; and n is 0 or 1.

In a further embodiment, a sirtuin activator is a compound of formula 1 and the attendant definitions, wherein n is 0. In a further embodiment, a sirtuin activator is a compound of formula 1 and the attendant definitions, wherein n is 1. In a further embodiment, a sirtuin activator is a compound of formula 1 and the attendant definitions, wherein A-B is ethenyl. In a further embodiment, a sirtuin activator is a compound of formula 1 and the attendant definitions, wherein A-B is —$CH_2CH(Me)CH(Me)CH_2$—. In a further embodiment, a sirtuin activator is a compound of formula 1 and the attendant definitions, wherein M is O. In a further embodiment, the methods comprises a compound of formula 1 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, a sirtuin activator is a compound of formula 1 and the attendant definitions, wherein $R_2$, $R_4$, and $R'_3$ are OH. In a further embodiment, a sirtuin activator is a compound of formula 1 and the attendant definitions, wherein $R_2$, $R_4$, $R'_2$ and $R'_3$ are OH. In a further embodiment, a sirtuin activator is a compound of formula 1 and the attendant definitions, wherein $R_3$, $R_5$, $R'_2$ and $R'_3$ are OH. In a further embodiment, a sirtuin activator is a compound of formula 1 and the attendant definitions, wherein $R_1$, $R_3$, $R_5$, $R'_2$ and $R'_3$ are OH. In a further embodiment, a sirtuin activator is a compound of formula 1 and the attendant definitions, wherein $R_2$ and $R'_2$ are OH; $R_4$ is O-β-D-glucoside; and $R'_3$ is $OCH_3$. In a further embodiment, a sirtuin activator is a compound of formula 1 and the attendant definitions, wherein $R_2$ is OH; $R_4$ is O-β-D-glucoside; and $R'_3$ is $OCH_3$.

In a further embodiment, a sirtuin activator is a compound of formula 1 and the attendant definitions, wherein n is 0; A-B is ethenyl; and $R_1$, $R_2$, $R_3$, $R_4$, $R_5$, $R'_1$, $R'_2$, $R'_3$, $R'_4$, and $R'_5$ are H (trans stilbene). In a further embodiment, a sirtuin activator is a compound of formula 1 and the attendant definitions, wherein n is 1; A-B is ethenyl; M is O; and $R_1$, $R_2$, $R_3$, $R_4$, $R_5$, $R'_1$, $R'_2$, $R'_3$, $R'_4$, and $R'_5$ are H (chalcone). In a further embodiment, a sirtuin activator is a compound of formula 1 and the attendant definitions, wherein n is 0; A-B is ethenyl; $R_2$, $R_4$, and $R'_3$ are OH; and $R_1$, $R_3$, $R_5$, $R'_1$, $R'_2$, $R'_4$, and $R'_5$ are H (resveratrol). In a further embodiment, a sirtuin activator is a compound of formula 1 and the attendant definitions, wherein n is 0; A-B is ethenyl; $R_2$, $R_4$, $R'_2$ and $R'_3$ are OH; and $R_1$, $R_3$, $R_5$, $R'_1$, $R'_4$ and $R'_5$ are H (piceatannol). In a further embodiment, a sirtuin activator is a compound of formula 1 and the attendant definitions, wherein n is 1; A-B is ethenyl; M is O; $R_3$, $R_5$, $R'_2$ and $R'_3$ are OH; and $R_1$, $R_2$, $R_4$, $R'_1$, $R'_4$, and $R'_5$ are H (butein). In a further embodiment, a sirtuin activator is a compound of formula 1 and the attendant definitions, wherein n is 1; A-B is ethenyl; M is O; $R_1$, $R_3$, $R_5$, $R'_2$ and $R'_3$ are OH; and $R_2$, $R_4$, $R'_1$, $R'_4$, and $R'_5$ are H (3,4,2',4',6'-pentahydroxychalcone). In a further embodiment, a sirtuin activator is a compound of formula 1 and the attendant definitions, wherein n is 0; A-B is ethenyl; $R_2$ and $R'_2$ are OH, $R_4$ is O-β-D-glucoside, $R'_3$ is $OCH_3$; and $R_1$, $R_3$, $R_5$, $R'_1$, $R'_4$, and $R'_5$ are H (rhapontin). In a further embodiment, a sirtuin activator is a compound of formula 1 and the attendant definitions, wherein n is 0; A-B is ethenyl; $R_2$ is OH, $R_4$ is O-β-D-glucoside, $R'_3$ is $OCH_3$; and $R_1$, $R_3$, $R_5$, $R'_1$, $R'_2$, $R'_4$, and $R'_5$ are H (deoxyrhapontin). In a further embodiment, a sirtuin activator is a compound of formula 1 and the attendant definitions, wherein n is 0; A-B is —CH$_2$CH(Me)CH(Me)CH$_2$—; R$_2$, R$_3$, R'$_2$, and R'$_3$ are OH; and R$_1$, R$_4$, R$_5$, R'$_1$, R'$_4$, and R'$_5$ are H (NDGA).

In another embodiment, a sirtuin activator is a flavanone compound of formula 2:

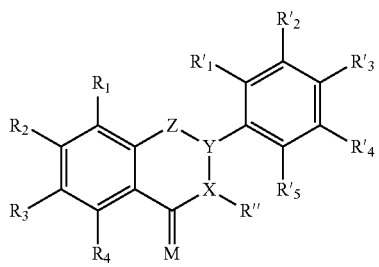

2 wherein, independently for each occurrence,

R$_1$, R$_2$, R$_3$, R$_4$, R'$_1$, R'$_2$, R'$_3$, R'$_4$, R'$_5$, and R" represent H, alkyl, aryl, heteroaryl, aralkyl, alkaryl, heteroaralkyl, halide, NO$_2$, SR, OR, N(R)$_2$, or carboxyl;

R represents H, alkyl, aryl, heteroaryl, or aralkyl;

M represents H$_2$, O, NR, or S;

Z represents CR, O, NR, or S;

X represents CR or N; and

Y represents CR or N.

In a further embodiment, a sirtuin activator is a compound of formula 2 and the attendant definitions, wherein X and Y are both CH. In a further embodiment, a sirtuin activator is a compound of formula 2 and the attendant definitions, wherein M is O. In a further embodiment, a sirtuin activator is a compound of formula 2 and the attendant definitions, wherein M is H$_2$. In a further embodiment, a sirtuin activator is a compound of formula 2 and the attendant definitions, wherein Z is O. In a further embodiment, a sirtuin activator is a compound of formula 2 and the attendant definitions, wherein R" is H. In a further embodiment, a sirtuin activator is a compound of formula 2 and the attendant definitions, wherein R" is OH. In a further embodiment, a sirtuin activator is a compound of formula 2 and the attendant definitions, wherein R" is an alkoxycarbonyl. In a further embodiment, a sirtuin activator is a compound of formula 2 and the attendant definitions, wherein R$_1$ is

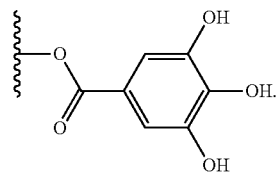 [SMILES: *OC(=O)c1cc(O)c(O)c(O)c1]

In a further embodiment, a sirtuin activator is a compound of formula 2 and the attendant definitions, wherein R$_1$, R$_2$, R$_3$, R$_4$, R'$_1$, R'$_2$, R'$_3$, R'$_4$, R'$_5$ and R" are H. In a further embodiment, a sirtuin activator is a compound of formula 2 and the attendant definitions, wherein R$_2$, R$_4$, and R'$_3$ are OH. In a further embodiment, a sirtuin activator is a compound of formula 2 and the attendant definitions, wherein R$_4$, R'$_2$, R'$_3$, and R" are OH. In a further embodiment, a sirtuin activator is a compound of formula 2 and the attendant definitions, wherein R$_2$, R$_4$, R'$_2$, R'$_3$, and R" are OH. In a further embodiment, a sirtuin activator is a compound of formula 2 and the attendant definitions, wherein R$_2$, R$_4$, R'$_2$, R'$_3$, R'$_4$, and R" are OH.

In a further embodiment, a sirtuin activator is a compound of formula 2 and the attendant definitions, wherein X and Y are CH; M is O; Z and O; R" is H; and R$_1$, R$_2$, R$_3$, R$_4$, R'$_1$, R'$_2$, R'$_3$, R'$_4$, R'$_5$ and R" are H (flavanone). In a further embodiment, a sirtuin activator is a compound of formula 2 and the attendant definitions, wherein X and Y are CH; M is O; Z and O; R" is H; R$_2$, R$_4$, and R'$_3$ are OH; and R$_1$, R$_3$, R'$_1$, R'$_2$, R'$_4$, and R'$_5$ are H (naringenin). In a further embodiment, a sirtuin activator is a compound of formula 2 and the attendant definitions, wherein X and Y are CH; M is O; Z and O; R" is OH; R$_2$, R$_4$, R'$_2$, and R'$_3$ are OH; and R'$_1$, R$_3$, R'$_1$, R'$_4$, and R'$_5$ are H (3,5,7,3',4'-pentahydroxyflavanone). In a further embodiment, a sirtuin activator is a compound of formula 2 and the attendant definitions, wherein X and Y are CH; M is H$_2$; Z and O; R" is OH; R$_2$, R$_4$, R'$_2$, and R'$_3$, are OH; and R$_1$, R$_3$, R'$_1$, R'$_4$ and R'$_5$ are H (epicatechin). In a further embodiment, a sirtuin activator is a compound of formula 2 and the attendant definitions, wherein X and Y are CH; M is H$_2$; Z and O; R" is OH; R$_2$, R$_4$, R'$_2$, R'$_3$, and R'$_4$ are OH; and R$_1$, R$_3$, R'$_1$, and R'$_5$ are H (gallocatechin). In a further embodiment, a sirtuin activator is a compound of formula 2 and the attendant definitions, wherein X and Y are CH; M is H$_2$; Z and O; R" is

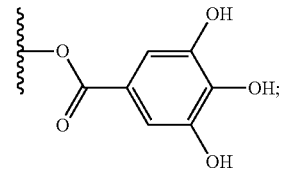 [SMILES: *OC(=O)c1cc(O)c(O)c(O)c1]

R$_2$, R$_4$, R'$_2$, R'$_4$, and R" are OH; and R$_1$, R$_3$, R'$_1$, and R'$_5$ are H (epigallocatechin gallate).

In another embodiment, a sirtuin activator is an isoflavanone compound of formula 3:

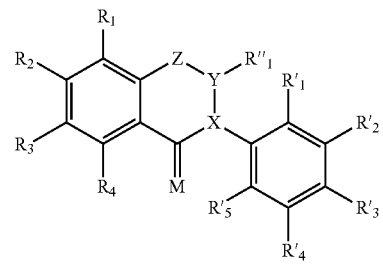

3 wherein, independently for each occurrence,

R$_1$, R$_2$, R$_3$, R$_4$, R'$_1$, R'$_2$, R'$_3$, R'$_4$, R'$_5$, and R"$_1$ represent H, alkyl, aryl, heteroaryl, aralkyl, alkaryl, heteroaralkyl, halide, NO$_2$, SR, OR, N(R)$_2$, or carboxyl;

R represents H, alkyl, aryl, heteroaryl, or aralkyl;

M represents H$_2$, O, NR, or S;

Z represents C(R)$_2$, O, NR, or S;

X represents CR or N; and

Y represents CR or N.

In another embodiment, a sirtuin activator is a flavone compound of formula 4:

4

[Chemical structure of formula 4 showing a bicyclic system with substituents R₁, R₂, R₃, R₄ on one ring, Z, X, M, R″ in the central ring, and R′₁, R′₂, R′₃, R′₄, R′₅ on the phenyl ring]

wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents CR, O, NR, or S; and

X represents CR″ or N, wherein

R″ is H, alkyl, aryl, heteroaryl, alkaryl, heteroaralkyl, halide, $NO_2$, SR, OR, $N(R)_2$, or carboxyl.

In a further embodiment, a sirtuin activator is a compound of formula 4 and the attendant definitions, wherein X is C. In a further embodiment, a sirtuin activator is a compound of formula 4 and the attendant definitions, wherein X is CR. In a further embodiment, a sirtuin activator is a compound of formula 4 and the attendant definitions, wherein Z is O. In a further embodiment, a sirtuin activator is a compound of formula 4 and the attendant definitions, wherein M is O. In a further embodiment, a sirtuin activator is a compound of formula 4 and the attendant definitions, wherein R″ is H. In a further embodiment, a sirtuin activator is a compound of formula 4 and the attendant definitions, wherein R″ is OH. In a further embodiment, a sirtuin activator is a compound of formula 4 and the attendant definitions, wherein $R_1$, $R_2$, $R_3$, $R_4$, $R'_1$, $R'_2$, $R'_3$, $R'_4$, and $R'_5$ are H. In a further embodiment, a sirtuin activator is a compound of formula 4 and the attendant definitions, wherein $R_2$, $R'_2$, and $R'_3$ are OH. In a further embodiment, a sirtuin activator is a compound of formula 4 and the attendant definitions, wherein $R_2$, $R_4$, $R'_2$, $R'_3$, and $R'_4$ are OH. In a further embodiment, a sirtuin activator is a compound of formula 4 and the attendant definitions, wherein $R_2$, $R_4$, $R'_2$, and $R'_3$ are OH. In a further embodiment, a sirtuin activator is a compound of formula 4 and the attendant definitions, wherein $R_3$, $R'_2$, and $R'_3$ are OH. In a further embodiment, a sirtuin activator is a compound of formula 4 and the attendant definitions, wherein $R_2$, $R_4$, $R'_2$, and $R'_3$ are OH. In a further embodiment, a sirtuin activator is a compound of formula 4 and the attendant definitions, wherein $R_2$, $R'_2$, $R'_3$, and $R'_4$ are OH. In a further embodiment, a sirtuin activator is a compound of formula 4 and the attendant definitions, wherein $R_2$, $R_4$, and $R'_3$ are OH. In a further embodiment, a sirtuin activator is a compound of formula 4 and the attendant definitions, wherein $R_2$, $R_3$, $R_4$, and $R'_3$ are OH. In a further embodiment, a sirtuin activator is a compound of formula 4 and the attendant definitions, wherein $R_2$, $R_4$, and $R'_3$ are OH. In a further embodiment, a sirtuin activator is a compound of formula 4 and the attendant definitions, wherein $R_3$, $R'_1$, and $R'_3$ are OH. In a further embodiment, a sirtuin activator is a compound of formula 4 and the attendant definitions, wherein $R_2$ and $R'_3$ are OH. In a further embodiment, a sirtuin activator is a compound of formula 4 and the attendant definitions, wherein $R_1$, $R_2$, $R'_2$, and $R'_3$ are OH. In a further embodiment, a sirtuin activator is a compound of formula 4 and the attendant definitions, wherein $R_3$, $R'_1$, and $R'_2$ are OH. In a further embodiment, a sirtuin activator is a compound of formula 4 and the attendant definitions, wherein $R'_3$ is OH. In a further embodiment, a sirtuin activator is a compound of formula 4 and the attendant definitions, wherein $R_4$ and $R'_3$ are OH. In a further embodiment, a sirtuin activator is a compound of formula 4 and the attendant definitions, wherein $R_2$ and $R_4$ are OH. In a further embodiment, a sirtuin activator is a compound of formula 4 and the attendant definitions, wherein $R_2$, $R_4$, $R'_1$, and $R'_3$ are OH. In a further embodiment, a sirtuin activator is a compound of formula 4 and the attendant definitions, wherein $R_4$ is OH. In a further embodiment, a sirtuin activator is a compound of formula 4 and the attendant definitions, wherein $R_2$, $R_4$, $R'_2$, $R'_3$, and $R'_4$ are OH. In a further embodiment, a sirtuin activator is a compound of formula 4 and the attendant definitions, wherein $R_2$, $R'_2$, $R'_3$, and $R'_4$ are OH. In a further embodiment, a sirtuin activator is a compound of formula 4 and the attendant definitions, wherein $R_1$, $R_2$, $R_4$, $R'_2$, and $R'_3$ are OH.

In a further embodiment, a sirtuin activator is a compound of formula 4 and the attendant definitions, wherein X is CH; Z is O; M is O; and $R_1$, $R_2$, $R_3$, $R_4$, $R'_1$, $R'_2$, $R'_3$, $R'_4$, and $R'_5$ are H (flavone). In a further embodiment, a sirtuin activator is a compound of formula 4 and the attendant definitions, wherein X is COH; Z is O; M is O; $R_2$, $R'_2$, and $R'_3$ are OH; and $R_1$, $R_3$, $R_4$, $R'_1$, $R'_4$, and $R'_5$ are H (fisetin). In a further embodiment, a sirtuin activator is a compound of formula 4 and the attendant definitions, wherein X is CH; Z is O; M is O; $R_2$, $R_4$, $R'_2$, $R'_3$, and $R'_4$ are OH; and $R_1$, $R_3$, $R'_1$, and $R'_5$ are H (5,7,3',4',5'-pentahydroxyflavone). In a further embodiment, a sirtuin activator is a compound of formula 4 and the attendant definitions, wherein X is CH; Z is O; M is O; $R_2$, $R_4$, $R'_2$, and $R'_3$ are OH; and $R_1$, $R_3$, $R'_1$, $R'_4$, and $R'_5$ are H (luteolin). In a further embodiment, a sirtuin activator is a compound of formula 4 and the attendant definitions, wherein X is COH; Z is O; M is O; $R_3$, $R'_2$, and $R'_3$ are OH; and $R_1$, $R_2$, $R_4$, $R'_1$, $R'_4$, and $R'_5$ are H (3,6,3',4'-tetrahydroxyflavone). In a further embodiment, a sirtuin activator is a compound of formula 4 and the attendant definitions, wherein X is COH; Z is O; M is O; $R_2$, $R_4$, $R'_2$, and $R'_3$ are OH; and $R_1$, $R_3$, $R'_1$, $R'_4$, and $R'_5$ are H (quercetin). In a further embodiment, a sirtuin activator is a compound of formula 4 and the attendant definitions, wherein X is CH; Z is O; M is O; $R_2$, $R'_2$, $R'_3$, and $R'_4$ are OH; and $R_1$, $R_3$, $R_4$, $R'_1$, and $R'_5$ are H. In a further embodiment, a sirtuin activator is a compound of formula 4 and the attendant definitions, wherein X is COH; Z is O; M is O; $R_2$, $R_4$, and $R'_3$ are OH; and $R_1$, $R_3$, $R'_1$, $R'_2$, $R'_4$, and $R'_5$ are H. In a further embodiment, a sirtuin activator is a compound of formula 4 and the attendant definitions, wherein X is CH; Z is O; M is O; $R_2$, $R_3$, $R_4$, and $R'_3$ are OH; and $R_1$, $R'_1$, $R'_2$, $R'_4$, and $R'_5$ are further embodiment, a sirtuin activator is a compound of formula 4 and the attendant definitions, wherein X is CH; Z is O; M is O; $R_2$, $R_4$, and $R'_3$ are OH; and $R_1$, $R_3$, $R'_1$, $R'_2$, $R'_4$, and $R'_5$ are H. In a further embodiment, a sirtuin activator is a compound of formula 4 and the attendant definitions, wherein X is COH; Z is O; M is O; $R_3$, $R'_1$, and $R'_3$ are OH; and $R_1$, $R_2$, $R_4$, $R'_2$, $R'_4$, and $R'_5$ are H. In a further embodiment, a sirtuin activator is a compound of formula 4 and the attendant definitions, wherein X is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, a sirtuin activator is a compound of formula 4 and the attendant definitions, wherein X is COH; Z is O; M is O; $R_1$, $R_2$, $R'_2$, and $R'_3$ are OH; and $R_1$, $R_2$, $R_4$, $R'_3$, $R'_4$, and $R'_5$ are H. In a further embodiment, a sirtuin activator is a compound of formula 4 and the attendant definitions, wherein X is COH; Z is O; M is O; $R_3$, $R'_1$, and $R'_2$ are OH; and $R_1$, $R_2$, $R_4$; $R'_3$, $R'_4$, and $R'_5$ are H. In a further embodiment, a sirtuin activator is a compound of formula 4 and the attendant definitions, wherein X is CH; Z is O; M is O; $R'_3$ is OH; and $R_1$, $R_2$, $R_3$, $R_4$, $R'_1$, $R'_2$, $R'_4$, and $R'_5$ are H. In a further embodiment, a sirtuin activator is a compound of formula 4 and the attendant definitions, wherein X is CH; Z is O; M is O; $R_4$ and $R'_3$ are OH; and $R_1$, $R_2$, $R_3$, $R'_1$, $R'_2$, $R'_4$, and $R'_5$ are H. In a further embodiment, a sirtuin activator is a compound of formula 4 and the attendant definitions, wherein X is CH; Z is O; M is O; $R_2$ and $R_4$ are OH; and $R_1$, $R_3$, $R'_1$, $R'_2$, $R'_3$, $R'_4$, and $R'_5$ are H. In a further embodiment, a sirtuin activator is a compound of formula 4 and the attendant definitions, wherein X is COH; Z is O; M is O; $R_2$, $R_4$, $R'_1$, and $R'_3$ are OH; and $R_1$, $R_3$, $R'_2$, $R'_4$, and $R'_5$ are H. In a further embodiment, a sirtuin activator is a compound of formula 4 and the attendant definitions, wherein X is CH; Z is O; M is O; $R_4$ is OH; and $R_1$, $R_2$, $R_3$, $R'_1$, $R'_2$, $R'_3$, $R'_4$, and $R'_5$ are H. In a further embodiment, a sirtuin activator is a compound of formula 4 and the attendant definitions, wherein X is COH; Z is O; M is O; $R_2$, $R_4$, $R'_2$, $R'_3$, and $R'_4$ are OH; and $R_1$, $R_3$, $R'_1$, and $R'_5$, are H. In a further embodiment, a sirtuin activator is a compound of formula 4 and the attendant definitions, wherein X is COH; Z is O; M is O; $R_2$, $R'_2$, $R'_3$, and $R'_4$ are OH; and $R_1$, $R_3$, $R_4$, $R'_1$, and $R'_5$ are H. In a further embodiment, a sirtuin activator is a compound of formula 4 and the attendant definitions, wherein X is COH; Z is O; M is O; $R_1$, $R_2$, $R_4$, $R'_2$, and $R'_3$ are OH; and $R_3$, $R'_1$, $R'_4$, and $R'_5$ are H.

In another embodiment, a sirtuin activator is an isoflavone compound of formula 5:

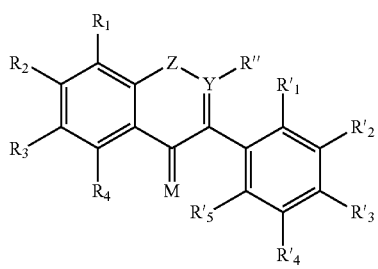

5 wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents $C(R)_2$, O, NR, or S; and

Y represents CR" or N, wherein

R" represents H, alkyl, aryl, heteroaryl, alkaryl, heteroaralkyl, halide, $NO_2$, SR, OR, $N(R)_2$, or carboxyl.

In a further embodiment, a sirtuin activator is a compound of formula 5 and the attendant definitions, wherein Y is CR". In a further embodiment, a sirtuin activator is a compound of formula 5 and the attendant definitions, wherein Y is CH. In a further embodiment, a sirtuin activator is a compound of formula 5 and the attendant definitions, wherein Z is O. In a further embodiment, a sirtuin activator is a compound of formula 5 and the attendant definitions, wherein M is O. In a further embodiment, a sirtuin activator is a compound of formula 5 and the attendant definitions, wherein $R_2$ and $R'_3$ are OH. In a further embodiment, a sirtuin activator is a compound of formula 5 and the attendant definitions, wherein $R_2$, $R_4$, and $R'_3$ are OH.

In a further embodiment, a sirtuin activator is a compound of formula 5 and the attendant definitions, wherein Y is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, a sirtuin activator is a compound of formula 5 and the attendant definitions, wherein Y is CH; Z is O; M is O; $R_2$, $R_4$, and $R'_3$ are OH; and $R_1$, $R_3$, $R'_1$, $R'_2$, $R'_4$, and $R'_5$ are H.

In another embodiment, a sirtuin activator is an anthocyanidin compound of formula 6:

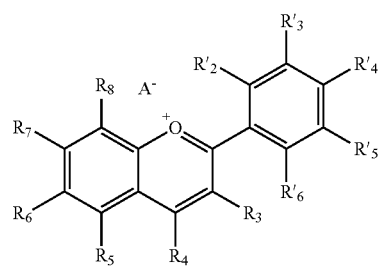

6 wherein, independently for each occurrence, $R_3$, $R_4$, $R_5$, $R_6$, $R_7$, $R_8$, $R'_2$, $R'_3$, $R'_4$, $R'_5$, and $R'_6$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl; and $A^-$ represents an anion selected from the following: $Cl^-$, $Br^-$, or $I^-$.

In a further embodiment, a sirtuin activator is a compound of formula 6 and the attendant definitions, wherein $A^-$ is $Cl^-$. In a further embodiment, a sirtuin activator is a compound of formula 6 and the attendant definitions, wherein $R_3$, $R_5$, $R_7$, and $R'_4$ are OH. In a further embodiment, a sirtuin activator is a compound of formula 6 and the attendant definitions, wherein $R_3$, $R_5$, $R_7$, $R'_3$, and $R'_4$ are OH. In a further embodiment, a sirtuin activator is a compound of formula 6 and the attendant definitions, wherein $R_3$, $R_5$, $R_7$, $R'_3$, $R'_4$, and $R'_5$ are OH.

In a further embodiment, a sirtuin activator is a compound of formula 6 and the attendant definitions, wherein $A^-$ is $Cl^-$; $R_3$, $R_5$, $R_7$, and $R'_4$ are OH; and $R_4$, $R_6$, $R_8$, $R'_2$, $R'_3$, $R'_5$, and $R'_6$ are H. In a further embodiment, a sirtuin activator is a compound of formula 6 and the attendant definitions, wherein $A^-$ is $Cl^-$; $R_3$, $R_5$, $R_7$, $R'_3$, and $R'_4$ are OH; and $R_4$, $R_6$, $R_8$, $R'_2$, $R'_5$, and $R'_6$ are H. In a further embodiment, a sirtuin activator is a compound of formula 6 and the attendant definitions, wherein $A^-$ is $Cl^-$; $R_3$, $R_5$, $R_7$, $R'_3$, $R'_4$, and $R'_5$ are OH; and $R_4$, $R_6$, $R_8$, $R'_2$, and $R'_6$ are H.

In a further embodiment, a sirtuin activator is a stilbene, chalcone, or flavone compound represented by formula 7:

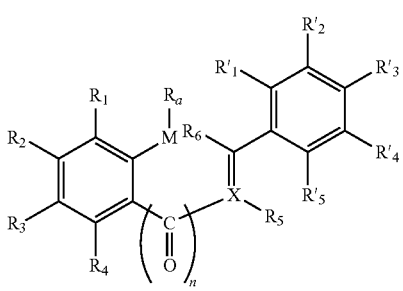

7 wherein, independently for each occurrence,

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

$R_a$ represents H or the two instances of $R_a$ form a bond;
R represents H, alkyl, aryl, heteroaryl, aralkyl; and
n is 0 or 1.

In a further embodiment, a sirtuin activator is an activating compound represented by formula 7 and the attendant definitions, wherein n is 0. In a further embodiment, a sirtuin activator is an activating compound represented by formula 7 and the attendant definitions, wherein n is 1. In a further embodiment, a sirtuin activator is an activating compound represented by formula 7 and the attendant definitions, wherein M is absent. In a further embodiment, a sirtuin activator is an activating compound represented by formula 7 and the attendant definitions, wherein M is O. In a further embodiment, a sirtuin activator is an activating compound represented by formula 7 and the attendant definitions, wherein $R_a$ is H. In a further embodiment, a sirtuin activator is an activating compound represented by formula 7 and the attendant definitions, wherein M is O and the two $R_a$ form a bond.

In a further embodiment, a sirtuin activator is an activating compound represented by formula 7 and the attendant definitions, wherein $R_5$ is H. In a further embodiment, a sirtuin activator is an activating compound represented by formula 7 and the attendant definitions, wherein $R_5$ is OH. In a further embodiment, a sirtuin activator is an activating compound represented by formula 7 and the attendant definitions, wherein $R_1$, $R_3$, and $R'_3$ are OH. In a further embodiment, a sirtuin activator is an activating compound represented by formula 7 and the attendant definitions, wherein $R_2$, $R_4$, $R'_2$, and $R'_3$ are OH. In a further embodiment, a sirtuin activator is an activating compound represented by formula 7 and the attendant definitions, wherein $R_2$, $R'_2$, and $R'_3$ are OH. In a further embodiment, a sirtuin activator is an activating compound represented by formula 7 and the attendant definitions, wherein $R_2$ and $R_4$ are OH.

In a further embodiment, a sirtuin activator is a compound represented by formula 7 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, a sirtuin activator is an activating compound represented by formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, a sirtuin activator is an activating compound represented by formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other sirtuin activators include compounds having a formula selected from the group consisting of formulas 8-25 and 30 set forth below.

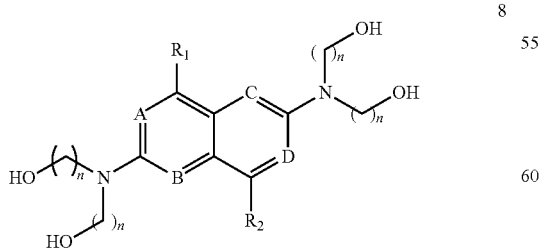

8

$R_1, R_2$ = H, aryl, heterocycle, small alkyl
A, B, C, D = $CR_3$, N
n = 0, 1, 2, 3

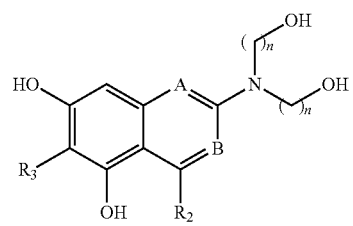

9

$R_1, R_2$ = H, aryl, heterocycle, small alkyl
$R_3$ = H, small alkyl
A, B = $CR_1$, N
n = 0, 1, 2, 3

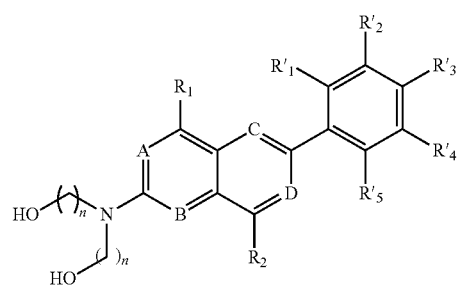

10

$R_1, R_2$ = H, aryl, heterocycle, small alkyl
$R'_1$-$R'_5$ = H, OH
A, B, C, D = $CR_1$, N
n = 0, 1, 2, 3

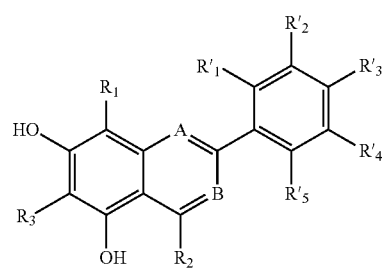

11

$R_1, R_2$ = H, aryl, heterocycle, small alkyl
$R_3$ = H, small alkyl
$R'_1$-$R'_5$ = H, OH
A, B = $CR_1$, N
n = 0, 1, 2, 3

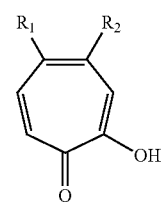

12

$R_1$-$R_2$ = H, alkyl, alkenyl

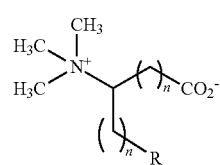

13

R = heterocycle, aryl
n = 0-16

14

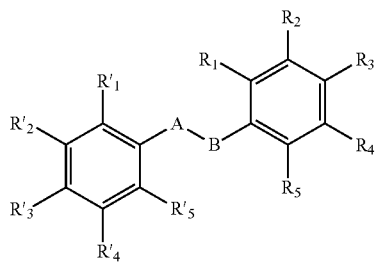

15

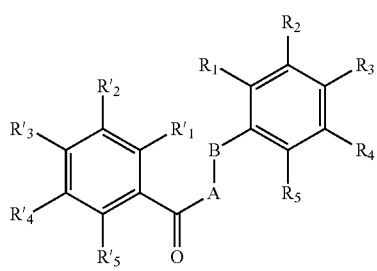

16

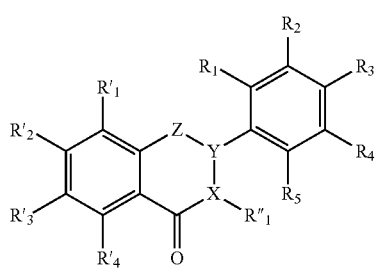

17

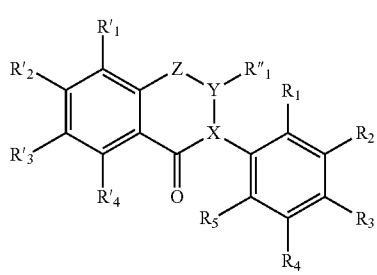

18

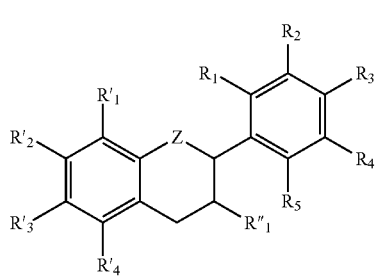

$R_1$ = H, halogen, $NO_2$, SR(R = H, alkyl, aryl), OR(R = H, alkyl, aryl), NRR' (R,R' = alkyl, aryl), alkyl, aryl, carboxy
$R_2$ = H, halogen, $NO_2$, SR(R = H, alkyl, aryl), OR(R = H, alkyl, aryl), NRR' (R,R' = alkyl, aryl), alkyl, aryl, carboxy
$R_3$ = H, halogen, $NO_2$, SR(R = H, alkyl, aryl), OR(R = H, alkyl, aryl), NRR' (R,R' = alkyl, aryl), alkyl, aryl, carboxy
$R_4$ = H, halogen, $NO_2$, SR(R = H, alkyl, aryl), OR(R = H, alkyl, aryl), NRR' (R,R' = alkyl, aryl), alkyl, aryl, carboxy
$R_5$ = H, halogen, $NO_2$, SR(R = H, alkyl, aryl), OR(R = H, alkyl, aryl), NRR' (R,R' = alkyl, aryl), alkyl, aryl, carboxy
$R'_1$ = H, halogen, $NO_2$, SR(R = H, alkyl, aryl), OR(R = H, alkyl, aryl), NRR' (R,R' = alkyl, aryl), alkyl, aryl, carboxy
$R'_2$ = H, halogen, $NO_2$, SR(R = H, alkyl, aryl), OR(R = H, alkyl, aryl), NRR' (R,R' = alkyl, aryl), alkyl, aryl, carboxy
$R'_3$ = H, halogen, $NO_2$, SR(R = H, alkyl, aryl), OR(R = H, alkyl, aryl), NRR' (R,R' = alkyl, aryl), alkyl, aryl, carboxy
$R'_4$ = H, halogen, $NO_2$, SR(R = H, alkyl, aryl), OR(R = H, alkyl, aryl), NRR' (R,R' = alkyl, aryl), alkyl, aryl, carboxy
$R'_5$ = H, halogen, $NO_2$, SR(R = H, alkyl, aryl), OR(R = H, alkyl, aryl), NRR' (R,R' = alkyl, aryl), alkyl, aryl, carboxy
$R''_1$ = H, halogen, $NO_2$, SR(R = H, alkyl, aryl), OR(R = H, alkyl, aryl), NRR' (R,R' = alkyl, aryl), alkyl, aryl, carboxy
A-B = ethene, ethyne, amide, sulfonamide, diazo, alkyl ether, alkyl amine, alkyl sulfide, hydroxyamide, hydrazine
X = CR, N
Y = CR, N
Z = O, S, $C(R)_2$, NR
R = H, alkyl, aryl, aralkyl

19

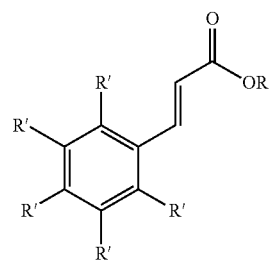

wherein, independently for each occurrence,

R=H, alkyl, aryl, heterocyclyl, heteroaryl, or aralkyl; and

R=H, halogen, $NO_2$, SR, OR, $NR_2$, alkyl, aryl, or carboxy.

20

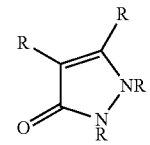

wherein, independently for each occurrence,

R=H, alkyl, aryl, heterocyclyl, heteroaryl, or aralkyl.

21

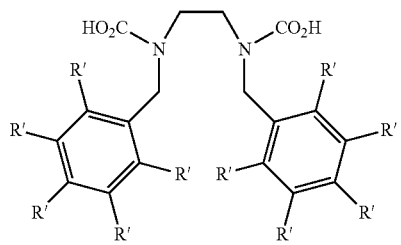

wherein, independently for each occurrence,

R'=H, halogen, $NO_2$, SR, OR, $NR_2$, alkyl, aryl, aralkyl, or carboxy; and

R=H, alkyl, aryl, heterocyclyl, heteroaryl, or aralkyl.

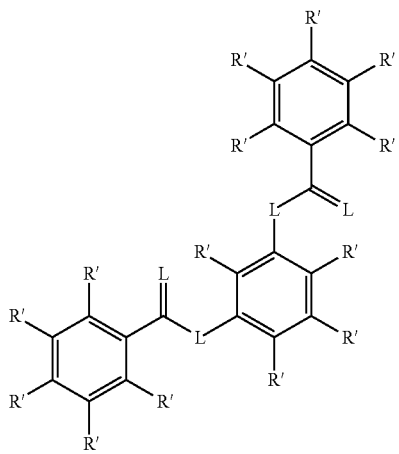

wherein, independently for each occurrence,

L represents CR$_2$, O, NR, or S;

R represents H, alkyl, aryl, aralkyl, or heteroaralkyl; and

R' represents H, halogen, NO$_2$, SR, OR, NR$_2$, alkyl, aryl, aralkyl, or carboxy.

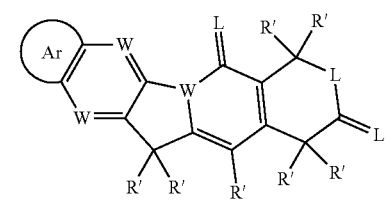

wherein, independently for each occurrence,

L represents CR$_2$, O, NR, or S;

W represents CR or N;

R represents H, alkyl, aryl, aralkyl, or heteroaralkyl;

Ar represents a fused aryl or heteroaryl ring; and

R' represents H, halogen, NO$_2$, SR, OR, NR$_2$, alkyl, aryl, aralkyl, or carboxy.

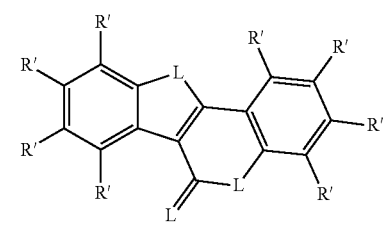

wherein, independently for each occurrence,

L represents CR$_2$, O, NR, or S;

R represents H, alkyl, aryl, aralkyl, or heteroaralkyl; and

R' represents H, halogen, NO$_2$, SR, OR, NR$_2$, alkyl, aryl, aralkyl, or carboxy.

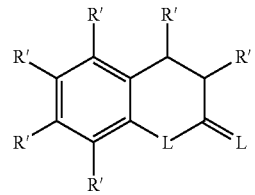

wherein, independently for each occurrence,

L represents CR$_2$, O, NR, or S;

R represents H, alkyl, aryl, aralkyl, or heteroaralkyl; and

R' represents H, halogen, NO$_2$, SR, OR, NR$_2$, alkyl, aryl, aralkyl, or carboxy.

In a further embodiment, a sirtuin activator is a stilbene, chalcone, or flavone compound represented by formula 30:

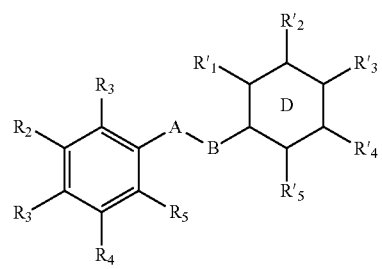

wherein, independently for each occurrence,

D is a phenyl or cyclohexyl group;

R$_1$, R$_2$, R$_3$, R$_4$, R$_5$, R'$_1$, R'$_2$, R'$_3$, R'$_4$, and R'$_5$ represent H, alkyl, aryl, heteroaryl, alkaryl, heteroaralkyl, halide, NO$_2$, SR, OR, N(R)$_2$, carboxyl, azide, ether; or any two adjacent R or R' groups taken together form a fused benzene or cyclohexyl group;

R represents H, alkyl, aryl, or aralkyl; and

A-B represents an ethylene, ethenylene, or imine group; provided that when A-B is ethenylene, D is phenyl, and R'$_3$ is H: R$_3$ is not OH when R$_1$, R$_2$, R$_4$, and R$_5$ are H; and R$_2$ and R$_4$ are not OMe when R$_1$, R$_3$, and R$_5$ are H; and R$_3$ is not OMe when R$_1$, R$_2$, R$_4$, and R$_5$ are H.

In a further embodiment, a sirtuin activator is a compound represented by formula 30 and the attendant definitions, wherein D is a phenyl group.

In a further embodiment, a sirtuin activator is a compound represented by formula 30 and the attendant definitions, wherein A-B is an ethenylene or imine group.

In a further embodiment, a sirtuin activator is a compound represented by formula 30 and the attendant definitions, wherein A-B is an ethenylene group.

In a further embodiment, a sirtuin activator is a compound represented by formula 30 and the attendant definitions, wherein R$_2$ is OH.

In a further embodiment, a sirtuin activator is a compound represented by formula 30 and the attendant definitions, wherein R$_4$ is OH.

In a further embodiment, a sirtuin activator is a compound represented by formula 30 and the attendant definitions, wherein R$_2$ and R$_4$ are OH.

In a further embodiment, a sirtuin activator is a compound represented by formula 30 and the attendant definitions, wherein D is a phenyl group; and A-B is an ethenylene group.

In a further embodiment, a sirtuin activator is a compound represented by formula 30 and the attendant definitions, wherein D is a phenyl group; A-B is an ethenylene group; and $R_2$ and $R_4$ are OH.

In a further embodiment, a sirtuin activator is a compound represented by formula 30 and the attendant definitions, wherein A-B is ethenylene; D is a phenyl ring; $R_2$ and $R_4$ are OH; and $R'_3$ is Cl.

In a further embodiment, a sirtuin activator is a compound represented by formula 30 and the attendant definitions, wherein A-B is ethenylene; D is a phenyl ring; $R_2$ and $R_4$ are OH; and $R'_3$ is OH.

In a further embodiment, a sirtuin activator is a compound represented by formula 30 and the attendant definitions, wherein A-B is ethenylene; D is a phenyl ring; $R_2$ and $R_4$ are OH; and $R'_3$ is H.

In a further embodiment, a sirtuin activator is a compound represented by formula 30 and the attendant definitions, wherein A-B is ethenylene; D is a phenyl ring; $R_2$ and $R_4$ are OH; and $R'_3$ is $CH_2CH_3$.

In a further embodiment, a sirtuin activator is a compound represented by formula 30 and the attendant definitions, wherein A-B is ethenylene; D is a phenyl ring; $R_2$ and $R_4$ are OH; and $R'_3$ is F.

In a further embodiment, a sirtuin activator is a compound represented by formula 30 and the attendant definitions, wherein A-B is ethenylene; D is a phenyl ring; $R_2$ and $R_4$ are OH; and $R'_3$ is Me.

In a further embodiment, a sirtuin activator is a compound represented by formula 30 and the attendant definitions, wherein A-B is ethenylene; D is a phenyl ring; $R_2$ and $R_4$ are OH; and $R'_3$ is an azide.

In a further embodiment, a sirtuin activator is a compound represented by formula 30 and the attendant definitions, wherein A-B is ethenylene; D is a phenyl ring; $R_2$ and $R_4$ are OH; and $R'_3$ is SMe.

In a further embodiment, a sirtuin activator is a compound represented by formula 30 and the attendant definitions, wherein A-B is ethenylene; D is a phenyl ring; $R_2$ and $R_4$ are OH; and $R'_3$ is $NO_2$.

In a further embodiment, a sirtuin activator is a compound represented by formula 30 and the attendant definitions, wherein A-B is ethenylene; D is a phenyl ring; $R_2$ and $R_4$ are OH; and $R'_3$ is $CH(CH_3)_2$.

In a further embodiment, a sirtuin activator is a compound represented by formula 30 and the attendant definitions, wherein A-B is ethenylene; D is a phenyl ring; $R_2$ and $R_4$ are OH; and $R'_3$ is OMe.

In a further embodiment, a sirtuin activator is a compound represented by formula 30 and the attendant definitions, wherein A-B is ethenylene; D is a phenyl ring; $R_2$ and $R_4$ are OH; $R'_2$ is OH; and $R'_3$ is OMe.

In a further embodiment, a sirtuin activator is a compound represented by formula 30 and the attendant definitions, wherein A-B is ethenylene; D is a phenyl ring; $R_2$ is OH; $R_4$ is carboxyl; and $R'_3$ is OH.

In a further embodiment, a sirtuin activator is a compound represented by formula 30 and the attendant definitions, wherein A-B is ethenylene; D is a phenyl ring; $R_2$ and $R_4$ are OH; and $R'_3$ is carboxyl.

In a further embodiment, a sirtuin activator is a compound represented by formula 30 and the attendant definitions, wherein A-B is ethenylene; D is a phenyl ring; $R_2$ and $R_4$ are OH; and $R'_3$ and $R'_4$ taken together form a fused benzene ring.

In a further embodiment, a sirtuin activator is a compound represented by formula 30 and the attendant definitions, wherein A-B is ethenylene; D is a phenyl ring; and $R_4$ is OH.

In a further embodiment, a sirtuin activator is a compound represented by formula 30 and the attendant definitions, wherein A-B is ethenylene; D is a phenyl ring; $R_2$ and $R_4$ are $OCH_2OCH_3$; and $R'_3$ is SMe.

In a further embodiment, a sirtuin activator is a compound represented by formula 30 and the attendant definitions, wherein A-B is ethenylene; D is a phenyl ring; $R_2$ and $R_4$ are OH; and $R'_3$ is carboxyl.

In a further embodiment, a sirtuin activator is a compound represented by formula 30 and the attendant definitions, wherein A-B is ethenylene; D is a cyclohexyl ring; and $R_2$ and $R_4$ are OH.

In a further embodiment, a sirtuin activator is a compound represented by formula 30 and the attendant definitions, wherein A-B is ethenylene; D is a phenyl ring; and $R_3$ and $R_4$ are OMe.

In a further embodiment, a sirtuin activator is a compound represented by formula 30 and the attendant definitions, wherein A-B is ethenylene; D is a phenyl ring; $R_2$ and $R_4$ are OH; and $R'_3$ is OH.

In one embodiment, sirtuin-modulating compounds of the invention are represented by Formula 31:

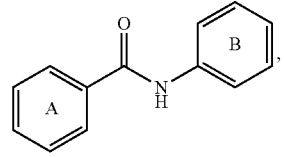

or a salt thereof, where:
Ring A is optionally substituted; and
Ring B is substituted with at least one carboxy or polycyclic aryl group.

In another embodiment, sirtuin-modulating compounds of the invention are represented by Formula 32:

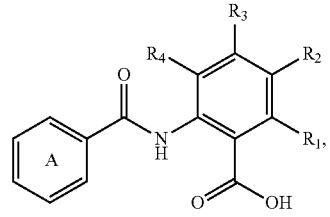

or a salt thereof, where:
Ring A is optionally substituted;
$R_1$, $R_2$, $R_3$ and $R_4$ are independently selected from the group consisting of —H, halogen, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;
$R_5$ and $R_6$ are independently —H, a substituted or unsubstituted alkyl group, a substituted or unsubstituted aryl group or a substituted or unsubstituted heterocyclic group; and
n is 1 or 2.

In certain embodiments, $R_1$, $R_2$, $R_3$ and $R_4$ are independently selected from the group consisting of —H, —$OR_5$ and —$SR_5$, particularly —H and —$OR_5$ (e.g., —H, —OH, —$OCH_3$).

Ring A is preferably substituted. Suitable substituents include halogens (e.g., bromine), acyloxy groups (e.g., acetoxy), aminocarbonyl groups (e.g., arylaminocarbonyl such as substituted, particularly carboxy-substituted, phenylaminocarbonyl groups) and alkoxy (e.g., methoxy, ethoxy) groups.

In yet another aspect, the invention provides novel sirtuin-modulating compounds of Formula (III):

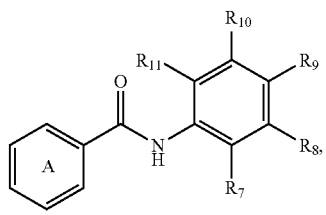

or a salt thereof, where:
Ring A is optionally substituted;
$R_5$ and $R_6$ are independently —H, a substituted or unsubstituted alkyl group, a substituted or unsubstituted aryl group or a substituted or unsubstituted heterocyclic group;
$R_7$, $R_9$, $R_{10}$ and $R_{11}$ are independently selected from the group consisting of —H, halogen, —$R_5$, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;
$R_8$ is a polycyclic aryl group; and
n is 1 or 2.

In certain embodiments, one or more of $R_7$, $R_9$, $R_{10}$ and $R_{11}$ are —H. In particular embodiments, $R_7$, $R_9$, $R_{10}$ and $R_{11}$ are each —H.

In certain embodiments, $R_8$ is a heteroaryl group, such as an oxazolo[4,5-b]pyridyl group. In particular embodiments, $R_8$ is a heteroaryl group and one or more of $R_7$, $R_9$, $R_{10}$ and $R_{11}$ are —H.

Ring A is preferably substituted. Suitable substituents include halogens (e.g., bromine), acyloxy groups (e.g., acetoxy), aminocarbonyl groups (e.g., arylaminocarbonyl, such as substituted, particularly carboxy-substituted, phenylaminocarbonyl groups) and alkoxy (e.g., methoxy, ethoxy) groups, particularly alkoxy groups. In certain embodiments, Ring A is substituted with at least one alkoxy or halo group, particularly methoxy.

In certain embodiments, Ring A is optionally substituted with up to 3 substituents independently selected from ($C_1$-$C_3$ straight or branched alkyl), O—($C_1$-$C_3$ straight or branched alkyl), N($C_1$-$C_3$ straight or branched allyl)$_2$, halo, or a 5 to 6-membered heterocycle.

In certain embodiments, Ring A is not substituted with a nitrile or pyrrolidyl group.

In certain embodiments, $R_8$ is a substituted or unsubstituted bicyclic heteroaryl group, such as a bicyclic heteroaryl group that includes a ring N atom and 1 to 2 additional ring heteroatoms independently selected from N, O or S. Preferably, $R_8$ is attached to the remainder of the compound by a carbon-carbon bond. In certain such embodiments, 2 additional ring heteroatoms are present, and typically at least one of said additional ring heteroatoms is O or S. In certain such embodiments, 2 total ring nitrogen atoms are present (with zero or one O or S present), and the nitrogen atoms are typically each in a different ring. In certain such embodiments, $R_8$ is not substituted with a carbonyl-containing moiety, particularly when $R_8$ is thienopyrimidyl or thienopyridinyl.

In certain such embodiments, $R_8$ is selected from oxazolopyridyl, benzothienyl, benzofuranyl, indolyl, quinoxalinyl, benzothiazolyl, benzooxazolyl, benzimidazolyl, quinolinyl, isoquinolinyl or isoindolyl. In certain such embodiments, $R_8$ is selected from thiazolopyridyl, imidazothiazolyl, benzooxazinonyl, or imidazopyridyl.

Particular examples of $R_8$, where

indicates attachment to the remainder of Formula 33, include:

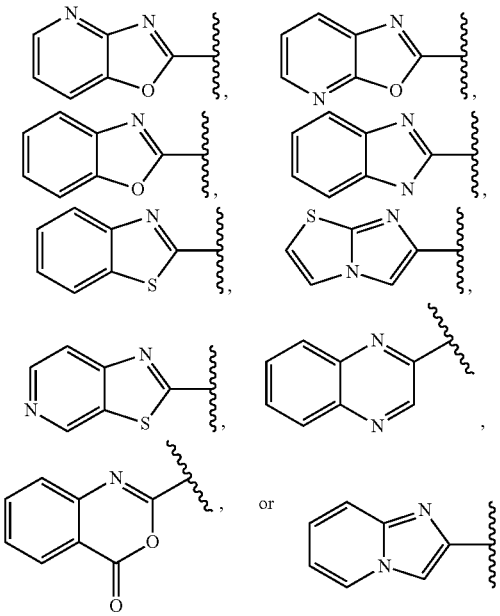

where up to 2 ring carbons not immediately adjacent to the indicated attachment point are independently substituted with O—$C_1$-$C_3$ straight or branched alkyl, $C_1$-$C_3$ straight or branched alkyl or halo, particularly $C_1$-$C_3$ straight or branched alkyl or halo. In certain embodiments, $R_8$ is

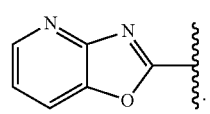 [SMILES: *c1nc2ncccc2o1]

In certain embodiments, $R_8$ is

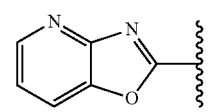 [SMILES: *c1nc2ncccc2o1]

and Ring A is optionally substituted with up to 3 substituents independently selected from ($C_1$-$C_3$ straight or branched alkyl), O—($C_1$-$C_3$ straight or branched allyl), N(C$_1$-C$_3$ straight or branched alkyl)$_2$, halo, or a 5 to 6-membered heterocycle. In certain such embodiments, Ring A is not simultaneously substituted at the 2- and 6-positions with O—(C$_1$-C$_3$ straight or branched alkyl). In certain such embodiments, Ring A is not simultaneously substituted at the 2-, 4- and 6-positions with O—(C$_1$-C$_3$ straight or branched alkyl). In certain such embodiments, Ring A is not simultaneously substituted at the 2-, 3-, and 4-positions with O—(C$_1$-C$_3$ straight or branched alkyl). In certain such embodiments, Ring A is not substituted at the 4-position with a 5 to 6-membered heterocycle. In certain such embodiments, Ring A is not singly substituted at the 3- or 4-position (typically 4-position) with O—(C$_1$-C$_3$ straight or branched alkyl). In certain such embodiments, Ring A is not substituted at the 4-position with O—(C$_1$-C$_3$ straight or branched alkyl) and at the 2- or 3-position with C$_1$-C$_3$ straight or branched alkyl.

In certain embodiments, R$_8$ is

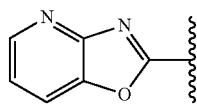

and Ring A is optionally substituted with up to 3 substituents independently selected from (C$_1$-C$_3$ straight or branched alkyl), (C$_1$-C$_3$ straight or branched haloalkyl, where a haloalkyl group is an alkyl group substituted with one or more halogen atoms), O—(C$_1$-C$_3$ straight or branched alkyl), N(C$_1$-C$_3$ straight or branched alkyl)$_2$, halo, or a 5 to 6-membered heterocycle. In certain such embodiments, Ring A is not singly substituted at the 3- or 4-position with O—(C$_1$-C$_3$ straight or branched alkyl). In certain such embodiments, Ring A is not substituted at the 4-position with O—(C$_1$-C$_3$ straight or branched allyl) and at the 2- or 3-position with C$_1$-C$_3$ straight or branched allyl.

In certain embodiments, R$_8$ is

(e.g., where one or both halo is chlorine) and Ring A is optionally substituted with up to 3 substituents independently selected from (C$_1$-C$_3$ straight or branched alkyl), O—(C$_1$-C$_3$ straight or branched alkyl), N(C$_1$-C$_3$ straight or branched alkyl)$_2$, halo, or a 5 to 6-membered heterocycle, but not singly substituted at the 3-position with O—(C$_1$-C$_3$ straight or branched alkyl).

In certain embodiments, such as when R$_8$ has one of the values described above, Ring A is substituted with up to 3 substituents independently selected from chloro, methyl, O-methyl, N(CH$_3$)$_2$ or morpholino. In certain such embodiments, R$_8$ is selected from

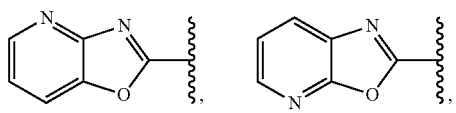

-continued

[structures shown]

where up to 2 ring carbons not immediately adjacent to the indicated attachment point are independently substituted with C$_1$-C$_3$ straight or branched alkyl or halo; each of R$_7$, R$_9$, and R$_{11}$ is —H; and R$_{10}$ is selected from —H, —CH$_2$OH, —CO$_2$H, —CO$_2$CH$_3$, —CH$_2$— piperazinyl, CH$_2$N(CH$_3$)$_2$, —C(O)—NH—(CH$_2$)$_2$—N(CH$_3$)$_2$, or —C(O)-piperazinyl. In certain such embodiments, when R$_8$ is

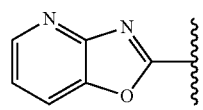 [SMILES: *c1nc2ncccc2o1]

and Ring A is 3-dimethylaminophenyl, none of R$_7$, R$_9$, R$_{10}$ and R$_{11}$ is —CH$_2$—N(CH$_3$)$_2$ or —C(O)—NH—(CH$_2$)$_2$—N(CH$_3$)$_2$, and/or when R$_8$ is

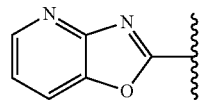 [SMILES: *c1nc2ncccc2o1]

and Ring A is 3,4 dimethoxyphenyl, none of R$_7$, R$_9$, R$_{10}$ and R$_{11}$ is C(O)OCH$_3$ or C(O)OH.

In certain embodiments, such as when R$_8$ has one of the values described above and/or Ring A is optionally substituted as described above, at least one of R$_7$, R$_9$, R$_{10}$ and R$_{11}$ is —H. In certain such embodiments, each of R$_7$, R$_9$, R$_{10}$ and R$_{11}$ is —H.

In certain embodiments, R$_7$, R$_9$, R$_{10}$ or R$_{11}$ is selected from —C(O)OH, —N(CH$_3$)$_2$, —CH$_2$OH, —CH$_2$OCH$_3$, —CH$_2$-piperazinyl, —CH$_2$-methylpiperazinyl, —CH$_2$-pyrrolidyl, —CH$_2$-piperidyl, —CH$_2$-morpholino, —CH$_2$—N(CH$_3$)$_2$, —C(O)—NH—(CH$_2$)$_n$-piperazinyl, —C(O)—NH—(CH$_2$)$_n$-methylpiperazinyl, —C(O)—NH—(CH$_2$)$_n$-pyrrolidyl, —C(O)—NH—(CH$_2$)$_n$-morpholino, —C(O)—NH—(CH$_2$)$_n$-piperidyl, or —C(O)—NH—(CH$_2$)$_n$—N(CH$_3$)$_2$, wherein n is 1 or 2. In certain such embodiments, R$_{10}$ is selected from —C(O)OH, —N(CH$_3$)$_2$, —CH$_2$OH, —CH$_2$OCH$_3$, —CH$_2$-piperazinyl, —CH$_2$— methylpiperazinyl, —CH$_2$-pyrrolidyl, —CH$_2$-piperidyl, —CH$_2$-morpholino, —CH$_2$—N(CH$_3$)$_2$, —C(O)—NH—(CH$_2$)$_n$-piperazinyl, —C(O)—NH—(CH$_2$)$_n$-methylpiperazinyl —C(O)—NH—(CH$_2$)$_n$-Pyrrolidyl, —C(O)—NH—(CH$_2$)$_n$-morpholino, —C(O)—NH—(CH$_2$)$_n$-piperidyl, or —C(O)—NH—(CH$_2$)$_n$—N(CH$_3$)$_2$, wherein n is 1 or 2, and each of R$_7$, R$_9$, and R$_{11}$ is H.

In certain embodiments, Ring A is substituted with a nitrile group or is substituted at the para position with a 5- or 6-membered heterocycle. Typical examples of the heterocycle include pyrrolidyl, piperidinyl and morpholinyl.

In one embodiment, sirtuin-modulating compounds of the invention are represented by Formula 34:

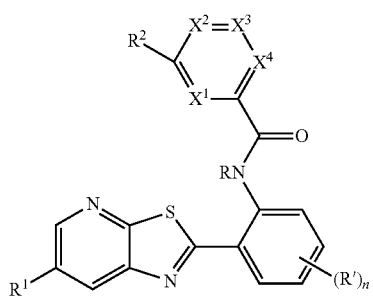

or a salt thereof, wherein:
two of X$^1$ to X$^4$ are selected from —CR*— and —N—;
the other two of X$^1$ to X$^4$ are —CR*—;
R$^1$ is a solubilizing group;
R$^2$ is a phenyl group optionally substituted with a lower alkyl, lower alkoxy, halogen, nitrile or —CF$_3$, or R$^2$ is a 5- to 6-membered heterocycle containing an N heteroatom and, optionally, a second heteroatom selected from N, O or S, wherein said heterocycle is optionally substituted with methyl or a halogen;
R* is independently selected at each occurrence from —H, lower alkyl or halogen;
R is —H or —CH$_3$;
R' is —CH$_3$ or a halogen; and
n is an integer from 0-4.

Typically, R is —H and n is 0, such that compounds of Formula 34 are represented by Formula 35:

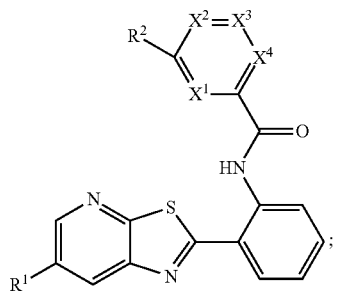

or a salt thereof.

Preferred values in compounds of Formula 34 and 35 are as follows:
two of X$^1$ to X$^4$ are selected from —CR*— and —N—;
the other two of X$^1$ to X$^4$ are —CR*—;
R* is independently selected at each occurrence from —H, lower alkyl or halogen;
R$^1$ is a solubilizing group; and
R$^2$ is selected from phenyl optionally substituted with one or more substituents independently selected from —CN, —F, —Cl and —CF$_3$, and when each of X$^1$ to X$^4$ is —CR*—, R$^2$ is additionally selected from a 5- to 6-membered heterocycle containing an N heteroatom and, optionally, a second heteroatom selected from N, O or S, wherein said heterocycle is optionally substituted with methyl.

In certain embodiments, each of X$^1$ to X$^4$ is —CR*—. In other embodiments, one of X$^1$ to X$^4$ is —N— and the remainder are —CR*—. In certain embodiments, two of X$^1$ to X$^4$ are —N— and the remainder are —CR*—. In certain embodiments, wherein two of X$^1$ to X$^4$ are —N—, X$^1$ and X$^2$ are —N—. In certain embodiments, wherein two of X$^1$ to X$^4$ are —N—, X$^1$ and X$^4$ are —N—. In certain embodiments, when one of X$^1$ to X$^4$ is —N—, X$^1$ is —N—. In certain embodiments, R* is H.

In certain embodiments, such as when each of X$^1$ to X$^4$ is —CR*—, R$^2$ is selected from phenyl, fluorophenyl, difluorophenyl, chlorophenyl, methylthiazolyl, pyrimidinyl, pyridyl and pyrazolyl. In certain such embodiments, R$^2$ is selected from phenyl, fluorophenyl, difluorophenyl, chlorophenyl, 2-methylthiazol-4-yl, pyridyl and pyrazol-1-yl. Preferably, R$^2$ is phenyl or pyridyl.

In certain embodiments, R$^1$ is —CH$_2$—R$^3$ and R$^3$ is a nitrogen-containing heterocycle optionally substituted with one or more substituents selected from C$_1$-C$_4$ alkyl, amino, halogen, methoxy and methoxy-C$_1$-C$_4$-alkyl. In these embodiments, X$^1$ to X$^4$ and R$^2$ can have any of the values described above. In certain such embodiments, R$^2$ is phenyl, pyridyl or 3-fluorophenyl; X$^2$ and X$^3$ are —CR*— and X$^1$ and X$^4$ are independently selected from —CR*— or —N—; or both.

In certain embodiments, R$^1$ is —CH$_2$—R$^3$; and R$^3$ is selected from piperazin-1-yl, 4-(methoxyethyl-piperazin-1-yl, 3,5-dimethylpiperazin-1-yl, morpholin-4-yl, piperidin-1-yl, 4-aminopiperidin-1-yl, pyrrolidin-1-yl, 3-fluoropyrrolidin-1-yl, —NH-(pyrrolidin-3-yl), and 1,4-diaza-bicyclo[2.2.1]heptan-1-yl. In these embodiments, X$^1$ to X$^4$ and R$^2$ can have any of the values described above, but typically R$^2$ is phenyl, pyridyl or 3-fluorophenyl; X$^2$ and X$^3$ are —CH— and X$^1$ and X$^4$ are independently selected from —CH— or —N—; or both.

In certain such embodiments, R$^3$ is selected from 4-(methoxyethyl)-piperazin-1-yl, morpholin-4-yl, piperidin-1-yl and 4-aminopiperidin-1-yl. When R$^3$ has these values, R$^2$ is typically phenyl, 3-fluorophenyl or pyridyl. Also, typically X$^2$ and X$^3$ are —CH— and X$^1$ and X$^4$ are independently selected from —CH— or —N—. In particular embodiments, X$^1$ and X$^4$ are independently selected from —CH— or —N—; X$^2$ and X$^3$ are —CH—; R$^2$ is phenyl, 3-fluorophenyl or pyridyl; and R$^1$ is —CH$_2$—R$^3$ where R$^3$ is selected from 4-(methoxyethyl)-piperazin-1-yl, morpholin-4-yl, piperidin-1-yl and 4-aminopiperidin-1-yl.

In certain embodiment, sirtuin-modulating compounds encompassed by Formula 34 are represented by Formula 36:

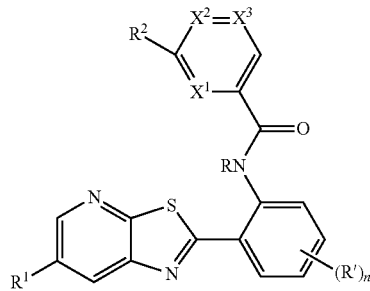

or a salt thereof, wherein:
one of X$^1$ to X$^3$ is selected from —CH— and —N—;
the other two of X$^1$ to X$^3$ are —CH—;
R$^1$ is a solubilizing group;

$R^2$ is a phenyl group optionally substituted with a methyl, halogen or —$CF_3$, or $R^2$ is a 5- to 6-membered heterocycle containing an N heteroatom and, optionally, a second heteroatom selected from N, O or S, wherein said heterocycle is optionally substituted with methyl or a halogen;

R is —H or —$CH_3$;

R' is —$CH_3$ or a halogen; and n is an integer from 0-4.

Typically, R is —H and n is 0, such that compounds of Formula 36 are represented by Formula 37:

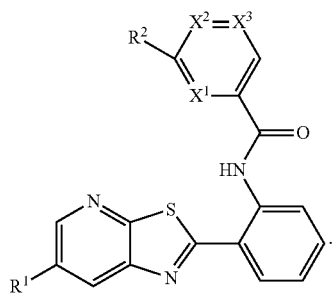

Preferred values in compounds of Formula 36 and 37 are as follows:

one of $X^1$ to $X^3$ is selected from —CH— and —N—;

the other two of $X^1$ to $X^3$ are —CH—;

$R^1$ is a solubilizing group; and $R^2$ is selected from phenyl and fluorophenyl, and, when each of $X^1$ to $X^3$ is —CH—, $R^2$ is additionally selected from a 5- to 6-membered heterocycle containing an N heteroatom and, optionally, a second heteroatom selected from N, O or S, wherein said heterocycle is optionally substituted with methyl.

In certain embodiments, each of $X^1$ to $X^3$ is —CH—. In other embodiments, one of $X^1$ to $X^3$ is —N— and the remainder are —CH—. Typically, when one of $X^1$ to $X^3$ is —N—, $X^1$ is —N—.

In certain embodiments, such as when each of $X^1$ to $X^3$ is —CH—, $R^2$ is selected from phenyl, fluorophenyl, methylthiazolyl, pyrimidinyl, pyridyl and pyrazolyl. In certain such embodiments, $R^2$ is selected from phenyl, fluorophenyl, 2-methylthiazol-4-yl, pyridyl and pyrazol-1-yl. Preferably, $R^2$ is phenyl or pyridyl.

In certain embodiments, $R^1$ is —$CH_2$—$R^3$ and $R^3$ is a nitrogen-containing heterocycle optionally substituted with one or more substituents selected from $C_1$-$C_4$ alkyl, amino, halogen, methoxy and methoxy-$C_1$-$C_4$-alkyl. In these embodiments, $X^1$ to $X^3$ and $R^2$ can have any of the values described above. In certain such embodiments, $R^2$ is phenyl, pyridyl or 3-fluorophenyl; $X^2$ and $X^3$ are —CH— and $X^1$ is —CH— or —N—; or both.

In certain embodiments, $R^1$ is —$CH_2$—$R^3$; and $R^3$ is selected from piperazin-1-yl, 4-(methoxyethyl-piperazin-1-yl, 3,5-dimethylpiperazin-1-yl, morpholin-4-yl, piperidin-1-yl, 4-aminopiperidin-1-yl, pyrrolidin-1-yl, 3-fluoropyrrolidin-1-yl, —NH-(pyrrolidin-3-yl), and 1,4-diaza-bicyclo[2.2.1]heptan-1-yl. In these embodiments, $X^1$ to $X^3$ and $R^2$ can have any of the values described above, but typically $R^2$ is phenyl, pyridyl or 3-fluorophenyl; $X^2$ and $X^3$ are —CH— and $X^1$ is —CH— or —N—; or both.

In certain such embodiments, $R^3$ is selected from 4-(methoxyethyl)-piperazin-1-yl, morpholin-4-yl, piperidin-1-yl and 4-aminopiperidin-1-yl. When $R^3$ has these values, $R^2$ is typically phenyl, 3-fluorophenyl or pyridyl. Also, typically $X^2$ and $X^3$ are —CH— and $X^1$ is —CH— or —N—. In particular embodiments, $X^1$ is —CH— or —N—; $X^2$ and $X^3$ are —CH—; $R^2$ is phenyl, 3-fluorophenyl or pyridyl; and $R^1$ is —$CH_2$—$R^3$ where $R^3$ is selected from 4-(methoxyethyl)-piperazin-1-yl, morpholin-4-yl, piperidin-1-yl and 4-aminopiperidin-1-yl.

In another embodiment, sirtuin-modulating compounds of the invention are represented by Formula 38:

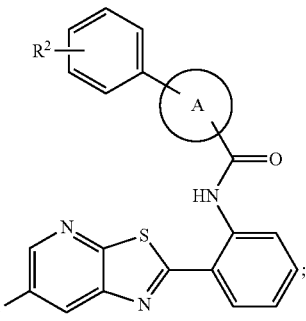

or a salt thereof, wherein:

ring A is selected from:

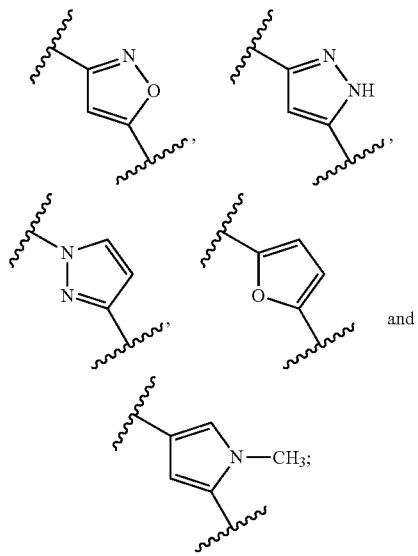

$R^1$ is a solubilizing group; and $R^\#$ is a —H or —O—$CH_3$.

In yet another embodiment, sirtuin-modulating compounds of the invention are represented by Formula 39:

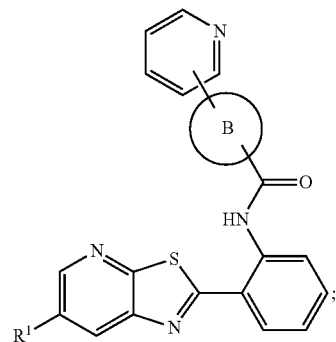

or a salt thereof, wherein:
ring B is selected from:

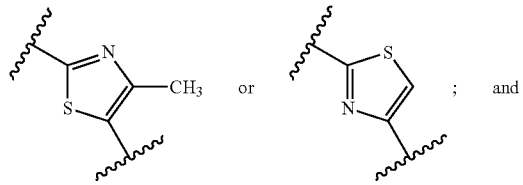

$R^1$ is a solubilizing group.

In some embodiments, a sirtuin pathway activating compound is any compound described in U.S. Pat. Nos. 7,829,556, 7,855,289, 7,893,086, 8,044,198, 8,088,928, and 8,093,401, which are each incorporated herein by reference in their entirety.

In some embodiments, a sirtuin activating compound is represented by

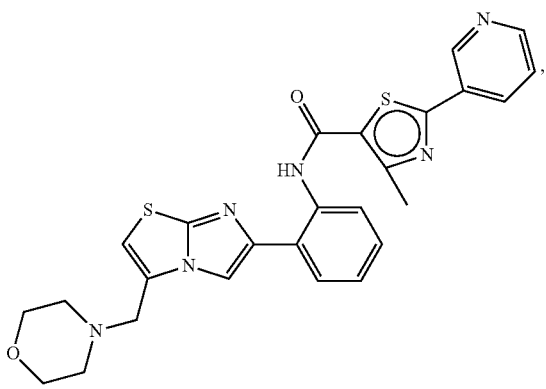

or a salt thereof.

In some embodiments, a sirtuin-pathway activating compound is a compound of the formula:

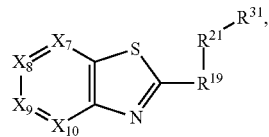

or a salt thereof, wherein:
each of $X_7$, $X_8$, $X_9$ and $X_{10}$ is independently selected from N, $CR^{20}$, or $CR_1'$, wherein:
each $R^{20}$ is independently selected from H or a solubilizing group;
each $R_1'$ is independently selected from H or optionally substituted $C_1$-$C_3$ straight or branched alkyl, wherein when $R_1'$ is substituted, $R_1'$ is substituted with one or more of —OH, halogen, —$OR^a$, —O—$COR^a$, —$COR^a$, —C(O)$R^a$, —CN, —$NO_2$, —COOH, —$COOR^a$, —$OCO_2R^a$, —C(O)$NR^aR^b$, —OC(O)$NR^aR^b$, —$SO_3H$, —$NH_2$, —$NHR^a$, —N($R^aR^b$), —$COOR^a$, —CHO, —$CONH_2$, —$CONHR^a$, —CON($R^aR^b$), —$NHCOR^a$, —$NRCOR^a$, —$NHCONH_2$, —$NHCONR^aH$, —$NHCON(R^aR^b)$, —$NR^cCONH_2$, —$NR^c$-CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$—SO$_2$NHR$_a$, —SO$_2$NR$^a$R$^b$, —CH=CHR$^a$, —CH=CR$^a$R$^b$, —CR$^c$=CR$^a$R$^b$, CR$^c$=CHR$^a$, —CR$^c$=CR$^a$R$^b$, —CCR$^a$, —SH, —SO$_k$R$^a$, —S(O)$_k$OR$^a$ and —NH—C(=NH)—NH$_2$, wherein
k is 0, 1 or 2;
$R^a$-$R^d$ are each independently an aliphatic, substituted aliphatic, benzyl, substituted benzyl, aromatic or substituted aromatic group; and
—NR$^a$R$^b$, taken together, can also form a substituted or unsubstituted non-aromatic heterocyclic group;
wherein a non-aromatic heterocyclic group, benzylic group or aryl group can also have an aliphatic or substituted aliphatic group as a substituent; a substituted aliphatic group can also have a non-aromatic heterocyclic ring, a substituted non-aromatic heterocyclic ring, benzyl, substituted benzyl, aryl or substituted aryl group as a substituent; and a substituted aliphatic, non-aromatic heterocyclic group, substituted aryl, or substituted benzyl group can have more than one substituent;
one of $X_7$, $X_8$, $X_9$ and $X_{10}$ is N and the others are selected from $CR^{20}$ or $CR_1'$; and
zero to one $R^{20}$ is a solubilizing group;
$R^{19}$ is selected from:

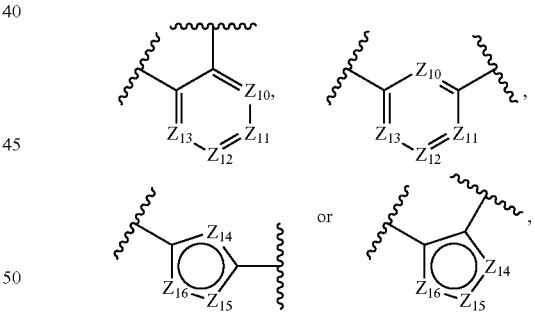

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$,
wherein:
zero to two of $Z_{10}$, $Z_{11}$, $Z_{12}$ and $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or 0;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and $R^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R$_1$'—, —NR$_1$'—C(O)—CR$_1$'R$_1$'—NR$_1$'—, —NR$_1$'—C(=NR$_1$')—NR$_1$'—, —C(O)—NR$_1$'—, —C(O)—NR$_1$'—S(O)$_2$—, —NR$_1$'—, —CR$_1$'R$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—O—, —NR$_1$'—C(O)—CR$_1$'R$_1$'—CR$_1$'R$_1$'—O—, —NR$_1$'—S(O)$_2$—CR$_1$'R$_1$'—, —NR$_1$'—S(O)$_2$—CR$_1$'R$_1$'—CR$_1$'R$_1$'—, —NR$_1$'—C(O)—CR$_1$'R$_1$'—CR$_1$'R$_1$'—, —NR$_1$'—C(S)—NR$_1$'—CR$_1$'R$_1$'—CR$_1$'R$_1$'—, —NR$_1$'—C(O)—O— or —NR$_1$'—C(O)—CR$_1$'R$_1$'—; and $R^{31}$ is selected from an optionally substituted monocyclic or bicyclic aryl, or an optionally substituted monocyclic or bicyclic heteroaryl, with the proviso that:

when $X_7$ is N, $R^{19}$ is

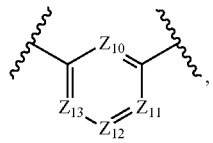

and each of $Z_{10}$, $Z_{11}$, $Z_{12}$ and $Z_{13}$ is independently selected from CR$^{20}$ or CR$_1$', then:
a) at least one of $X_8$, $X_9$ and $X_{10}$ is C—(C$_1$-C$_3$ straight or branched alkyl) or C-(solubilizing group); or
b) at least one of $Z_{10}$, $Z_{11}$, $Z_{12}$ and $Z_{13}$ is CR$^{20}$, wherein $R^{20}$ is a solubilizing group.

In some embodiments, a sirtuin-pathway activating compound is a compound of the formula:

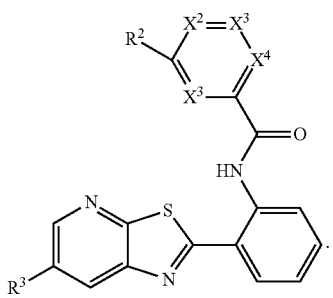

or a salt thereof, wherein:
two of $X^1$ to $X^4$ are selected from —CR*— and —N—;
the other two of $X^1$ to $X^4$ are —CR*—;
R* is independently selected at each occurrence from —H, lower alkyl or halogen;
$R^1$ is a solubilizing group; and
$R^2$ is selected from phenyl optionally substituted with one or more substituents independently selected from —CN, —F, —Cl and —CF$_3$, and when each of $X^1$ to $X^4$ is —CR*—, $R^2$ is additionally selected from a 5- to 6-membered heterocycle containing an N heteroatom and, optionally, a second heteroatom selected from N, O or S, wherein said heterocycle is optionally substituted with methyl.

In some embodiments, a sirtuin-pathway activating compound is a compound of the formula:

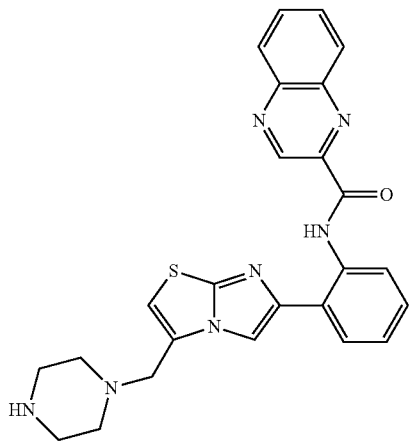 [SMILES: O=C(Nc1ccccc1-c1cn2c(CN3CCNCC3)csc2n1)c1cnc2ccccc2n1]

or a salt thereof.

In some embodiments, a sirtuin-pathway activating compound is a compound of the formula:

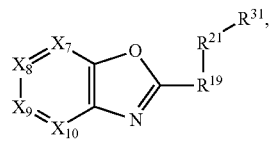

or a salt thereof, wherein:
each of $X_7$, $X_8$, $X_9$ and $X_{10}$ is independently selected from N, CR$^{20}$, and CR$_1$', wherein:
each $R^{20}$ is independently selected from H and a solubilizing group;
each $R_1$' is independently selected from H and optionally substituted C$_1$-C$_3$ straight or branched alkyl, wherein when $R_1$' is substituted, $R_1$' is substituted with one or more of —OH, halogen, —OR$^a$, —O—COR$^a$, —COR$^a$, —C(O)R$^a$, —CN, —NO$_2$, —COOH, —COOR$^a$, —OCO$_2$R$^a$, —C(O)NR$^a$R$^b$, —OC(O)NR$^a$R$^b$, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —SO$_2$NH$_2$, —SO$_2$NHR$^a$, —SO$_2$NR$^a$R$^b$, —CH=CHR$^a$, —CH=CR$^a$R$_b$, —CR$^c$=CR$^a$R$^b$, CR$^c$=CHR$^a$, —CR$^c$=CR$^a$R$^b$, —CCR$^a$, —SH, —SO$_k$R$^a$, —S(O)$_k$OR$^a$ and —NH—C(=NH)—NH$_2$, wherein k is 0, 1 or 2;

$R^a$-$R^d$ are each independently an aliphatic, substituted aliphatic, benzyl, substituted benzyl, aromatic or substituted aromatic group; and —NR$^a$R$^b$, taken together, can also form a substituted or unsubstituted non-aromatic heterocyclic group;

wherein a non-aromatic heterocyclic group, benzylic group or aryl group can also have an aliphatic or substituted aliphatic group as a substituent; a substituted aliphatic group can also have a non-aromatic heterocyclic ring, a substituted non-aromatic heterocyclic ring, benzyl, substituted benzyl, aryl or substituted aryl group as a substituent; and a substituted aliphatic, non-aromatic heterocyclic group, substituted aryl, or substituted benzyl group can have more than one substituent;

one of $X_7$, $X_8$, $X_9$ and $X_{10}$ is N and the others are selected from $CR^{20}$ and $CR_1'$; and zero to one $R^{20}$ is a solubilizing group;

$R^{19}$ is selected from:

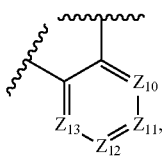

wherein:

each $Z_{10}$, $Z_{11}$, $Z_{12}$ and $Z_{13}$ is independently selected from $CR^{20}$ and $CR_1'$;

wherein:

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, and —C(O)—$NR_1'$ and $R^{31}$ is selected from an optionally substituted monocyclic or bicyclic aryl, and an optionally substituted monocyclic or bicyclic heteroaryl, with the proviso that:

said compound is not:

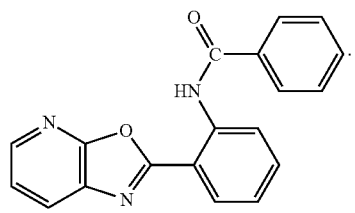 [SMILES: O=C(Nc1ccccc1-c1nc2cccnc2o1)c1ccccc1]

In some embodiments, a sirtuin-pathway activating compound is a compound of the formula:

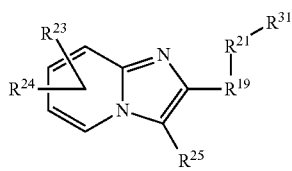

or a salt thereof, wherein:

each of $R^{23}$ and $R^{24}$ is independently selected from H, —$CH_3$ and a solubilizing group;

$R^{25}$ is selected from H and a solubilizing group; and $R^{19}$ is:

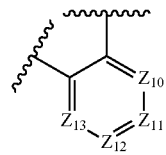

wherein:

each $Z_{10}$, $Z_{11}$, $Z_{12}$ and $Z_{13}$ is independently selected from $CR^{20}$ and $CR_1''$;

wherein:

zero to one $R^{20}$ is a solubilizing group; and zero to one $R_1''$ is an optionally substituted $C_1$-$C_3$ straight or branched alkyl;

each $R^{20}$ is independently selected from H and a solubilizing group;

$R^{21}$ is selected from —$NR_1'$—C(O)— —C(O)—$NR_1'$; and each $R_1'$ is independently selected from H and optionally substituted $C_1$-$C_3$ straight or branched alkyl, wherein when $R_1'$ and/or $R_1''$ is substituted, $R_1'$ and/or $R_1''$ is substituted with one or more of —OH, halogen, —$OR^a$, —O—$COR^a$, —$COR^a$, —$C(O)R^a$, —CN, —$NO_2$, —COOH, —$COOR^a$, —$OCO_2R^a$, —$C(O)NR^aR^b$, —$OC(O)NR^aR^b$, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —NHCON$(R^aR^b)$, —$NR^cCONH_2$, —$NR^cCONR^aH$, —$NR^cCON(R^aR^b)$, —$C(=NH)$—$NH_2$, —$C(=NH)$—$NHR^a$, —$C(=NH)$—$N(R^aR^b)$, —$C(=NR^c)$—$NH_2$, —$C(=NR^c)$—$NHR^a$, —$C(=NR^c)$—$N(R^aR^b)$, —NH—C$(=NH)$—$NHR^a$, —NH—C$(=NH)$—$N(R^aR^b)$, —NH—C$(=NR^c)$—$NH_2$, —NH—C$(=NR^c)$—$NHR^a$, —NH—C$(=NR^c)$—$N(R^aR^b)$, —$NR^d$—C$(=NH)$—$NH_2$, —$NR^d$—C$(=NH)$—$NHR^a$, —$NR^d$—C$(=NH)$—$N(R^aR^b)$, —$NR^d$—C$(=NR^c)$—$NH_2$, —$NR^d$—C$(=NR^c)$—$NHR^a$, —$NR^d$—C$(=NR^c)$—$N(R^aR^b)$, —$NHNH_2$, —$NHNHR^a$, —$SO_2NH_2$, —$SO_2NHR_a$, —$SO_2NR^aR^b$, —CH=$CHR^a$, —CH=$CR^aR^b$, —$CR^c$=$CR^aR^b$, $CR^c$=$CHR^a$, —$CR^c$=$CR^aR^b$, —$CCR^a$, —SH, —$SO_kR^a$, —$S(O)_kOR^a$ and —NH—C$(=NH)$—$NH_2$, wherein k is 0, 1 or 2;

$R^a$-$R^d$ are each independently an aliphatic, substituted aliphatic, benzyl, substituted benzyl, aromatic or substituted aromatic group; and —$NR^aR^b$, taken together, can also form a substituted or unsubstituted non-aromatic heterocyclic group;

wherein a non-aromatic heterocyclic group, benzylic group or aryl group can also have an aliphatic or substituted aliphatic group as a substituent; a substituted aliphatic group can also have a non-aromatic heterocyclic ring, a substituted non-aromatic heterocyclic ring, benzyl, substituted benzyl, aryl or substituted aryl group as a substituent; and a substituted aliphatic, non-aromatic heterocyclic group, substituted aryl, or substituted benzyl group can have more than one substituent; and $R^{31}$ is selected from an optionally substituted monocyclic or bicyclic aryl, and an optionally substituted monocyclic or bicyclic heteroaryl, with the proviso that $R^{31}$ is not 2,4-dimethoxyphenyl.

In various other embodiments, compositions are formulated such that they do not contain (or exclude) one or more of the following ingredients: caffeine, green tea extract or extracts from guarana seed or guarana plants.

In other embodiments, the sirtuin-pathway activator or AMPK pathway activator can be irisin, quinic acid, cinnamic acid, ferulic acid, fucoxanthin, a biguanide (such as metformin), rosiglitazone, or any analog thereof. Alternatively the sirtuin-pathway activator or AMPK pathway activator can be isoflavones, pyroloquinoline (PQQ), quercetin, L-carnitine, lipoic acid, coenzyme Q10, pyruvate, 5-aminoimidazole-4-carboxamide ribotide (ALCAR), bezfibrate, oltipraz, and/or genistein. In some embodiments, the sirtuin pathway activator is a PDE inhibitor.

In some embodiments, the composition can comprise combinations of metformin, resveratrol, and a branched chain amino acid or metabolite thereof. For example, a composition can comprise metformin, resveratrol, and HMB or the composition can comprise metformin, resveratrol, and leucine. Combinations of metformin, resveratrol, and a branched chain amino acid can cause an increase in fatty acid oxidation of over 700, 800, 900, 1000, 1200, 1400, 1600, or 1800%.

In some embodiments, the composition can comprise synergistic combinations of sirtuin pathway activators. For example, a composition can comprise synergistic amounts of metformin and a PDE inhibitor. In some embodiments, the composition comprises metformin and caffeine.

In some embodiments, the sirtuin-pathway activator can be an agent that stimulates the expression of the Fndc5, PGC1-α, or UCP1. The expression can be measured in terms of the gene or protein expression level. Alternatively, the sirtuin pathway activator can be irisin. Methods for increasing the level of irisin are described in Boström et al., "A PGC1-α-dependent myokine that drives brown-fat-like development of white fat and thermogenesis," Nature, Jan. 11, 2012.

In some embodiments, the activator is a flavones or chalcone. In one embodiment, exemplary sirtuin activators are those described in Howitz et al. (2003) Nature 425: 191 and include, for example, resveratrol (3,5,4'-Trihydroxy-trans-stilbene), butein (3,4,2',4'-Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahyddroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4, 2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5, 7,3',4'); 5,7,3',4',5'-pentahydroxyflavone; Luteolin (5,7,3',4'-Tetrahydroxyflavone); 3,6,3',4'-Tetrahydroxyflavone; 7,3',4', 5'-Tetrahydroxyflavone; Kaempferol (3,5,7,4'-Tetrahydroxyflavone); 6-Hydroxyapigenin (5,6,7,4'-Tetrahydoxyflavone); Scutellarein); Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl) ethylenediamine-N,N'-diacetic acid-H2O); Ambroxol (trans-4-(2-Amino-3,5-dibromobenzylamino) cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl). Analogs and derivatives thereof can also be used.

The subject application provides compositions useful for inducing an increase in fatty acid oxidation and mitochondrial biogenesis in a subject. Such compositions contain: HMB in combination with resveratrol; leucine in combination with resveratrol; both leucine and HMB in combination with resveratrol; KIC in combination with resveratrol; both KIC and HMB in combination with resveratrol; both KIC and leucine in combination with resveratrol; or KIC, HMB and leucine in combination with resveratrol.

Phosphodiesterase Inhibitors

In some embodiments, the sirtuin pathway activator modulates the activity of phosphodiesterase (PDE). In some embodiments, the sirtuin pathway activator is a PDE inhibitor, such as a non-specific PDE inhibitor. PDE inhibitors can be naturally occurring or non-naturally occurring (e.g. manufactured), and may be provided in the form of a natural source comprising the PDE inhibitor, or an extract thereof (e.g. purified). Examples of non-specific PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2, 6-dione), aminophylline, paraxanthine, and salts, derivatives, metabolites, catabolites, anabolites, precursors, and analogs thereof. Non-limiting examples of natural sources of PDE inhibitors include coffee, tea, guarana, yerba mate, cocoa, and chocolate (e.g. dark chocolate).

In some embodiments, a PDE inhibitor is administered in place of or in addition to resveratrol or other sirtuin pathway activator. In some embodiments, compositions comprising one or more components described herein comprise a PDE inhibitor in place of or in addition to resveratrol or other sirtuin pathway activator. Typically, a PDE inhibitor is provided in an amount that is synergistic with one or more other components of a composition or method of treatment.

Branched Chain Amino Acids

The invention provides for compositions that include branched chain amino acids. Branched chain amino acids can have aliphatic side chains with a branch carbon atom that is bound to two or more other atoms. The other atoms may be carbon atoms. Examples of branched chain amino acids include leucine, isoleucine, and valine. Branched chain amino acids may also include other compounds, such as 4-hydroxyisoleucine. In some embodiments, the compositions may be substantially free of one or more, or all of non-branched chain amino acids. For example, the compositions can be free of alanine, arginine, asparagine, aspartic acid, cysteine, glutamic acid, glutamine, glycine, histidine, lysine, methionine, phenylalanine, proline, serine, threonine, tryptophan, and/or tyrosine. In some embodiments, the compositions may be substantially free of isoleucine and/or valine.

Without being limited to theory, ingestion of branched chain amino acids, such as leucine, can stimulate tissue protein synthesis via both mTOR-dependent and -independent pathways, as well as to exert an antiproteolytic effect. These effects predominate in muscle, but also can manifest in other tissues, including adipose tissue. Given the energetic cost of protein synthesis and turnover, leucine may increase fatty acid oxidation and net energy utilization and attenuate adiposity. Indeed, leucine has been reported to exert a thermogenic effect and to augment weight and adipose tissue loss during energy restriction. Also, leucine and leucine-rich diets can favorably modulate inflammatory cytokine patterns in adipocytes and mice.

In some embodiments, any of the compositions described herein can include salts, derivatives, metabolites, catabolites, anabolites, precursors, and analogs of any of the branched chain amino acids. For example, the metabolites of branched chain amino acids can include hydroxymethylbutyrate (HMB), α-hydroxyisocaproic acid, and keto-isocaproic acid (KIC), keto isovalerate, and keto isocaproate. Non-limiting exemplary anabolites of branched chain amino acids can include glutamate, glutamine, threonine, α-ketobytyrate, α-aceto-α-hydroxy butyrate, α,β-dihydroxy-β-methylvalerate, α-keto-β-methylvalerate, α,β-dihydroxy isovalerate, and α-keto isovalerate.

In certain embodiments of the invention, any of the compositions disclosed herein can be formulated such that they do not contain (or exclude) one or more amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. The compositions can be substantially free of any non-branched chain amino acids. The mass or molar amount of a non-branched chain amino acid can be less than 0.01, 0.1, 0.5, 1, 2, or 5% of the total composition.

Vitamin B6

Without being limited to any particular theory or mode of action, elevations in the active B6 metabolite (pyridoxal phosphate) can reduce the tone and activity of the adipocyte calcium channel. Intracellular free Ca2+ is a primary regulator of adipocyte fatty acid synthase expression and activity, which can result in a suppression of both the expression and activity of fatty acid synthase, which in turn is one of the rate limiting steps in neutral lipid synthesis in adipocytes.

As used herein, vitamin B6 includes its different forms, including pyridoxine, pyridoxine 5'-phosphate, pyridoxal, pyridoxal phosphate, pyridoxal 5'-phosphate, pyridoxamine, pyridoxamine 5'-phosphate. In other embodiments, vitamin B6 can also include 4-pyridoxic acid, which is a catabolite of the above forms of vitamin B6 that is excreted. The compositions described herein can include any one or more of these forms of vitamin B6.

The active form of vitamin B6 in the body is pyridoxal 5-phosphate, which is a coenzyme for all transamination and some decarboxylation and deamination reactions. Furthermore, pyridoxal 5-phosphate is required as a coenzyme for all transamination reactions which occur in the body (Peterson D L, Martinez-Carrion M. The mechanism of transamination. Function of the histidyl residue at the active site of supernatant aspartate transaminase. J Biol Chem. 1970 Feb. 25; 245(4):806-13).

In some embodiments, any of the compositions described herein can include salts, derivatives, metabolites, catabolites, anabolites, precursors, and analogs of any of the forms of vitamin B6. Exemplary catabolites of vitamin B6 include 2-methyl-3-hydroxy-5-formylpyridine-4-carboxylate and 3-hydroxy-2-methylpyridine-4,5,-dicarboxylate. Exemplary analogs of vitamin B6 are described in U.S. Pat. Nos. 7,230,009, and 6,369,042. Exemplary precursors of vitamin B6 are described in U.S. Pat. No. 7,495,101.

Pharmaceutically Active Agents

The combination compositions can further include one or more pharmaceutically active agents. Examples of therapeutically active agents include ibuprofen, aldoril, and gemfebrozil, verapamil, maxzide, diclofenac and metrolol, maproltiline, triazolam and minoxidil. For example, the combination compositions can comprise a pharmaceutically active anti-diabetic agent, weight loss agent, or calcium regulation agent. U.S. Pat. No. 7,109,198 and U.S. Patent Application No. 20090142336 describe a variety of pharmaceutically active agents or therapeutically active agents suitable for inclusion in a combination composition described herein. Examples of anti-diabetic agents include biguanides (such as metformin), thiazoladinediones and meglitinides (such as repaglinide, pioglitazone, and rosiglitazone), alpha glucosidease inhibitors (such as acarbose), sulfonylureas (such as tolbutamide, acetohexamide, tolazamide, chlorpropamide, glipizide, glyburide, glimepiride, gliclazide), incretins, ergot alkaloids (such as bromocriptine), and DPP inhibitors (such as sitagliptin, vildagliptin, saxagliptin, lingliptin, dutogliptin, gemigliptin, alogliptin, and berberine). The anti-diabetic agent can be an oral anti-diabetic agent. The anti-diabetic agent can also be injectable anti-diabetic drugs, including insulin, amylin analogues (such as pramlintide), and inretin mimetics (such as exenatide and liraglutide). Examples of anti-obesity therapeutic agents include lipase inhibitors (such as Orlistat), dopaminergic, noradrenergic, and serotoninergic compounds, cannabinoid receptor antagonists (such as rimonabant), exenatide, pramlintide, and CNS agents (such as topimerate). These examples are provided for discussion purposes only, and are intended to demonstrate the broad scope of applicability of the invention to a wide variety of drugs. It is not meant to limit the scope of the invention in any way.

In some embodiments, one or more components described herein, such as resveratrol, leucine, HMB, and KIC can be combined with two or more pharmaceutically active agents. For example, a sirtuin pathway activator can be combined with glipizide and metformin, glyburide and metformin, pioglitazone and glimepiride, pioglitazone and metformin, repaglinide and metformin, rosiglitazone and glimepiride, rosiglitazone and metformin, or sitagliptin and metformin.

The amount of pharmaceutical agent, or any other component used in a combination composition described herein, can be used in an amount that is sub-therapeutic. In some embodiments, using sub-therapeutic amounts of an agent or component can reduce the side-effects of the agent. Use of sub-therapeutic amounts can still be effective, particularly when used in synergy with other agents or components.

A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of metformin hydrochloride, the physician suggested starting dose is 1000 mg daily, with subject specific dosing having a range of 500 mg to a maximum of 2500 mg daily (metformin hydrochloride extended-release tablets label www.accessdatafda.gov/drugsatfda_docs/label/2008/021574s0101bl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg. In some embodiments, the dosing can be recommended by a healthcare provider including, but not limited to a patient's physician, nurse, nutritionist, pharmacist, or other health care professional. A health care professional may include a person or entity that is associated with the health care system. Examples of health care professionals may include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

Dosing Amounts

In some embodiments, a composition comprises an amount of a sirtuin pathway activator, such as a a polyphenol (e.g. resveratrol). The amount of sirtuin pathway activator may be a subtheratpeutic amount, and/or an amount that is synergistic with one or more other compounds in the composition or one or more other compounds administered simultaneously or in close temporal proximity with the composition. In some embodiments, the sirtuin pathway activator is administered in a low dose, a medium dose, or a high dose, which describes the relationship between two doses, and generally do not define any particular dose range. For example, a daily low dose of resveratrol may comprise about, less than about, or more than about 0.5 mg/kg, 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more; a daily medium dose of resveratrol may comprise about, less than about, or more than about 20 mg/kg, 25 mg/kg, 50 mg/kg, 75 mg/kg, 100 mg/kg, 125 mg/kg, 150 mg/kg, 175 mg/kg, 200 mg/kg, 250 mg/kg, or more; and a daily high dose of resveratrol may comprise about, less than about, or more than about 150 mg/kg, 175 mg/kg, 200 mg/kg, 225 mg/kg, 250 mg/kg, 300 mg/kg, 350 mg/kg, 400 mg/kg, or more.

In some embodiments of the invention, the following amounts of leucine, HMB, KIC, vitamin D, vitamin K2, and/or resveratrol are to be administered to a subject: leucine about, less than about, or more than about 0.5-3.0 g/day (e.g. 0.5, 0.75, 1, 1.25, 1.5, 1.75, 2, 2.5, 3, or more g/day); HMB about, less than about, or more than about 0.20-3.0 g/day (e.g. 0.2, 0.4, 0.5, 0.75, 1, 1.5, 2, 2.5, 3, or more g/day); KIC about, less than about, or more than about 0.2-3.0 g/day (e.g. 0.2, 0.4, 0.5, 0.75, 1, 1.25, 1.5, 1.75, 2, 2.5, 3, or more g/day); vitamin D about, less than about, or more than about 2.5-25 µg/day (e.g. 2.5, 5, 7.5, 10, 12.5, 15, 17.5, 20, 25, or more µg/day); vitamin K2 about, less than about, or more than about 5-200 µg/day (e.g. 5, 10, 25, 50, 75, 100, 150, 200, or more µg/day); and/or resveratrol about, less than about, or more than about 10-500 mg/day (e.g. 10, 25, 50, 51, 75, 100, 150, 200, 250, 300, 350, 400, 450, 500, or more mg/day). Thus, one embodiment provides a composition comprising leucine in an amount of about 0.75 to about 3.0 g (0.75 to 3.0 g) and resveratrol in an amount between about 50 and about 500 mg (or 50 to 500 mg). Another embodiment provides a composition comprising HMB in an amount of 0.40-3.0 g (or 0.40 to 3.0 g) and resveratrol in an amount between 50-500 mg (or 50 to 500 mg). Another embodiment provides for a composition comprising leucine in an amount of about 0.75-about 3.0 g (or 0.75 to 3.0 g), HMB in an amount of about 0.40 and about 3.0 g (or 0.40 to 3.0 g) and resveratrol in an amount between about 50 and about 500 mg (or 50 to 500 mg). In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or other sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Another aspect of the invention provides compositions comprising synergizing amounts of resveratrol and leucine; resveratrol and HMB; resveratrol, leucine and HMB; resveratrol and KIC; resveratrol, KIC and leucine; resveratrol, KIC, and HMB; or resveratrol, KIC, leucine and HMB. In some embodiments, a synergizing amount of resveratrol is an amount of at least 35 mg of resveratrol and no more than 500 (or about 500) mg resveratrol (e.g. 35, 50, 75, 100, 150, 200, 250, 300, 350, 400, 450, or 500 mg resveratrol) in combination with leucine and/or HMB. Synergizing amounts of leucine and/or KIC in a composition containing leucine and/or KIC and resveratrol can range from about, less than about, or more than about 0.50 to 3.0 g (or about 0.50 to about 3.0 g; e.g. 0.5, 0.75, 1, 1.5, 2, 2.5, 3 or more grams) or 0.75 to 3.0 g (or about 0.75 to 3.0 g; e.g. 0.75, 1, 1.25, 1.5, 1.75, 2, 2.5, 3 or more grams). Synergizing amounts of HMB provided in a composition containing HMB and resveratrol contains HMB in an amount of about, less than about, or more than about 0.20-3.0 g (or about 0.20 to about 3.0 g; e.g. 0.2, 0.4, 0.5, 0.75, 1, 1.5, 2, 2.5, 3, or more grams). In some embodiments, where combinations of leucine and KIC are used in a composition, the total amount of leucine and KIC is less than, or equal to, 3.0 g (or less than about 3.0 g; e.g. less than about 0.7, 0.75, 1, 1.5, 2, 2.5, 3 grams) and at least (or at least about) 0.70 g (e.g. at least about 0.7, 0.75, 1, 1.5, 2, 2.5, 3 grams). In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or other sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Another embodiment provides for a composition containing synergizing amounts of HMB, leucine and resveratrol. In such compositions, the total amount of leucine and HMB within the composition can be less than 3.0 g (or less than about 3.0 g; e.g. less than about 0.7, 0.75, 1, 1.5, 2, 2.5, 3 grams) and at least 0.70 g (or at least about 0.70 g; e.g. at least about 0.7, 0.75, 1, 1.5, 2, 2.5, 3 grams). Compositions containing both leucine and HMB can contain amounts of leucine and HMB that total about, less than about, or more than about 0.70 g to 3.0 g (about 0.70 g to about 3.0 g; e.g. 0.7, 1, 1.25, 1.5, 1.75, 2, 2.5, 3, or more grams), 0.75 g to 3.0 g (about 0.75 g to about 3.0 g), or 1.0 g to 3.0 g (about 1.0 g to about 3.0 g) within the composition and resveratrol in synergizing amounts (at least 35 mg of resveratrol and no more than 500 (or about 500) mg resveratrol (e.g. about, less than about, or more than about 35, 50, 75, 100, 150, 200, 250, 300, 350, 400, 450, or 500 mg resveratrol) or an amount of resveratrol between 50 and 500 mg (or about 50 to about 500 mg). In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Yet another embodiment provides for a composition containing synergizing amounts of HMB, leucine, KIC and resveratrol. In such compositions, the total amount of leucine, KIC and HMB within the composition can be less than 3.0 g (or less than about 3.0 g; e.g. less than about 0.7, 0.75, 1, 1.5, 2, 2.5, 3 grams) and at least 0.70 g (or at least about 0.70 g; e.g. at least about 0.7, 0.75, 1, 1.5, 2, 2.5, 3 grams). Thus, compositions containing leucine, KIC and HMB can contain amounts of leucine, KIC and HMB that total about, less than about, or more than about 0.70 g to 3.0 g (about 0.70 g to about 3.0 g; e.g. 0.7, 0.75, 1, 1.5, 2, 2.5, 3 grams), 0.75 g to 3.0 g (about 0.75 g to about 3.0 g), or 1.0 g to 3.0 g (about 1.0 g to about 3.0 g) within the composition and resveratrol in synergizing amounts (at least 35 mg of resveratrol and no more than 500 (or about 500) mg resveratrol (e.g. about, less than about, or more than about 35, 50, 75, 100, 150, 200, 250, 300, 350, 400, 450, or 500 mg resveratrol) or an amount of resveratrol between 50 and 500 mg (or about 50 to about 500 mg). In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Still other embodiments provide compositions comprising: a) about, less than about, or more than about 50 to 100 mg resveratrol (e.g. 50, 60, 70, 80, 90, 100, or more mg) and about, less than about, or more than about 400 mg to 500 mg HMB (e.g. 400, 425, 450, 475, 500, or more mg); b) about, less than about, or more than about 50 to 100 mg resveratrol (e.g. 50, 60, 70, 80, 90, 100, or more mg) and about, less than about, or more than about 750 mg to 1250 mg leucine (e.g. 750, 850, 950, 1050, 1150, 1250 or more mg); c) about, less than about, or more than about 50 to 100 mg resveratrol (e.g. 50, 60, 70, 80, 90, 100, or more mg) and about, less than about, or more than about 750 mg to 1250 mg KIC (e.g. 750, 850, 950, 1050, 1150, 1250 or more mg); or d) about, less than about, or more than about 50 mg to about 100 mg resveratrol (e.g. 50, 60, 70, 80, 90, 100, or more mg) and: i) a combination of HMB and KIC in an amount of about 400 mg and about 1250 mg (e.g. 400, 500, 600, 700, 800, 900, 1000, 1100, 1250, or more mg); ii) a combination of HMB and leucine in an amount of about 400 mg and about 1250 mg (e.g. 400, 500, 600, 700, 800, 900, 1000, 1100, 1250, or more mg); iii) a combination of KIC and leucine in an amount of about 400 mg and about 1250 mg (e.g. 400, 500, 600, 700, 800, 900, 1000, 1100, 1250, or more mg); or iv) a combination of HMB, KIC and leucine in an amount of about 400 mg and about 1250 mg (e.g. 400, 500, 600, 700, 800, 900, 1000, 1100, 1250, or more mg). In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

In some embodiments a unit dosage can comprise resveratrol in combination with one or more other components. In some embodiments, a unit dosage comprises one or more of: about, less than about, or more than about 50, 100, 200, 300, 400, 500 or more mg of HMB; about, less than about, or more than about 10, 20, 30, 40, 50, 75, 100, or more mg resveratrol; about, less than about, or more than about 2.5, 5, 7.5, 10, 12.5, 15, 17.5, 20, or more mg of vitamin B6; about, less than about, or more than about 2.5, 5, 7.5, 10, 12.5, 15, 17.5, 20, 25, or more µg of vitamin D; about, less than about, or more than about 5, 10, 25, 50, 75, 100, 150, 200, or more µg of vitamin K2; and about, less than about, or more than about 400, 500, 600, 700, 800, 900, 1000, 1100, 1250, 1500, or more mg of leucine. A unit dosage can comprise about, less than about, or more than about 500 mg beta hydroxyl, beta methyl butyrate and about, less than about, or more than about 50 mg resveratrol. A unit dosage can comprise about, less than about, or more than about 500 mg beta hydroxy, beta methyl butyrate; and about, less than about, or more than about 50 mg resveratrol; and about, less than about, or more than about 15 mg vitamin B6. A unit dosage can comprise about, less than about, or more than about 1.125 g leucine and about, less than about, or more than about 50 mg resveratrol. A unit dosage can comprise about, less than about, or more than about 1.125 g leucine, 50 mg resveratrol and 15 mg vitamin B6. A unit dosage can comprise about, less than about, or more than about 750 mg leucine, 35 mg resveratrol and 10 mg vitamin B6. A unit dosage may comprise about 500 mg HMB, 51 mg resveratrol (98%), 12.5 µg of vitamin D, and 50 µg of vitamin K2. In some embodiments, a composition further comprises a PDE inhibitor in a synergizing amount. In some embodiments, a composition further comprises a sirtuin pathway activator in a synergizing amount. In some embodiments, resveratrol is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

In some embodiments a unit dosage can comprise chlorogenic acid (e.g. about, less than about, or more than about 25, 50, 75, 100, 150, 200, or mg) in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 100 mg chlorogenic acid. A unit dosage can comprise 500 mg beta hydroxy, beta methyl butyrate (e.g. 50, 100, 200, 300, 400, 500 or more mg); and 100 mg chlorogenic acid; and 15 mg vitamin B6. A unit dosage can comprise 1.125 g leucine (e.g. 400, 500, 600, 700, 800, 900, 1000, 1100, 1250, or more mg) and 100 mg chlorogenic acid. A unit dosage can comprise 1.125 g leucine (e.g. 400, 500, 600, 700, 800, 900, 1000, 1100, 1250, or more mg); 100 mg chlorogenic acid; and 15 mg vitamin B6 (e.g. 2.5, 5, 7.5, 10, 12.5, 15, 17.5, 20, or more mg). A unit dosage can comprise 750 mg leucine, 75 mg chlorogenic acid and 10 mg vitamin B6.

In some embodiments a unit dosage can comprise quinic acid in about, less than about, or more than about the indicated amounts (e.g. 10, 15, 20, 25, 30, 40, 50, or more mg), in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 25 mg quinic acid. A unit dosage can comprise 500 mg beta hydroxy, beta methyl butyrate (e.g. 50, 100, 200, 300, 400, 500 or more mg), 25 mg quinic acid and 15 mg vitamin B6 (e.g. 2.5, 5, 7.5, 10, 12.5, 15, 17.5, 20, or more mg). A unit dosage can comprise 1.125 g leucine (e.g. 400, 500, 600, 700, 800, 900, 1000, 1100, 1250, or more mg) and 25 mg quinic acid. A unit dosage can comprise 1.125 g leucine (e.g. 400, 500, 600, 700, 800, 900, 1000, 1100, 1250, or more mg), 25 mg quinic acid and 15 mg vitamin B6 (e.g. 2.5, 5, 7.5, 10, 12.5, 15, 17.5, 20, or more mg). A unit dosage can comprise 750 mg leucine, 15 mg quinic acid and 10 mg vitamin B6.

In some embodiments a unit dosage can comprise fucoxanthin in about, less than about, or more than about the indicated amounts (e.g. 0.5, 0.75, 1, 1.25, 1.5, 1.75, 2, 2.25, 2.5, 3, 5, or more mg) in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 2.5 mg fucoxanthin. A unit dosage can comprise 500 mg beta hydroxy, beta methyl butyrate (e.g. 50, 100, 200, 300, 400, 500 or more mg), 2.5 mg fucoxanthin and 15 mg vitamin B6 (e.g. 2.5, 5, 7.5, 10, 12.5, 15, 17.5, 20, or more mg). A unit dosage can comprise 1.125 g leucine (e.g. 400, 500, 600, 700, 800, 900, 1000, 1250, or more mg) and 2.5 mg fucoxanthin. A unit dosage can comprise 1.125 g leucine (e.g. 400, 500, 600, 700, 800, 900, 1000, 1100, 1250, or more mg), 2.5 mg fucoxanthin and 15 mg vitamin B6 (e.g. 2.5, 5, 7.5, 10, 12.5, 15, 17.5, 20, or more mg). A unit dosage can comprise 750 mg leucine, 1.5 mg fucoxanthin and 10 mg vitamin B6.

In some embodiments, a composition comprises an amount of an antidiabetic agent, such as a biguanide (e.g. metformin). The amount of antidiabetic agent may be a subtherapeutic amount, and/or an amount that is synergistic with one or more other compounds in the composition or one or more other compounds administered simultaneously or in close temporal proximity with the composition. In some embodiments, the antidiabetic agent is administered in a very low dose, a low dose, a medium dose, or a high dose, which describes the relationship between two doses, and generally do not define any particular dose range. For example, a daily very low dose of metformin may comprise about, less than about, or more than about 5 mg/kg, 10 mg/kg, 25 mg/kg, 50 mg/kg, 75 mg/kg, 100 mg/kg, or more; a daily low dose of metformin may comprise about, less than about, or more than about 75 mg/kg, 100 mg/kg, 150 mg/kg, 175 mg/kg, 200 mg/kg, or more; a daily medium dose of metformin may comprise about, less than about, or more than about 150 mg/kg, 175 mg/kg, 200 mg/kg, 250 mg/kg, 300; and a daily high dose of metformin may comprise about, less than about, or more than about 200 mg/kg, 250 mg/kg, 300 mg/kg, 350 mg/kg, 400 mg/kg, 500 mg/kg, 700 mg/kg, or more.

In some embodiments a unit dosage can comprise metformin in about, less than about, or more than about the indicated amounts (e.g. 25, 50, 100, 150, 200, 250, 300, 400, 500, or more mg) in combination with one or more other components in about, less than about, or more than about the indicated amounts (such as 10, 20, 30, 40, 50, 75, 100, or more mg of resveratrol; 50, 100, 200, 300, 400, 500 or more mg HMB; and/or 400, 500, 600, 700, 800, 900, 1000, 1100, 1250, or more mg of leucine). A unit dosage can comprise about, less than about or more than about 50 mg metformin, 500 mg beta hydroxy, beta methyl butyrate and 50 mg resveratrol. A unit dosage can comprise about, less than about or more than about 50 mg metformin, 1.125 g leucine and 50 mg resveratrol. A unit dosage can comprise about, less than about or more than about 100 mg metformin, 500 mg beta hydroxy, beta methyl butyrate and 50 mg resveratrol. A unit dosage can comprise about, less than about or more than about 100 mg metformin, 1.125 g leucine and 50 mg resveratrol. A unit dosage can comprise about, less than about or more than about 250 mg metformin, 500 mg beta hydroxy, beta methyl butyrate and 50 mg resveratrol. A unit dosage can comprise about, less than about or more than about 250 mg metformin, 1.125 g leucine and 50 mg resveratrol. In some embodiments, a composition further comprises a PDE inhibitor in a synergizing amount. In some embodiments, a metformin composition further comprises a sirtuin pathway activator in a synergizing amount. In some embodiments, resveratrol in an example composition is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

In some embodiments of the invention, the combination compositions can have a specified ratio of branched chain amino acids and/or metabolites thereof to a sirtuin pathway activator. The specified ratio can provide for effective and/or synergistic regulation of energy metabolism. For example, the specified ratio can cause a decrease in weight gain of a subject, a decrease in visceral adipose volume of a subject, an increase in fat oxidation of a subject, an increase in insulin sensitivity of a subject, an increase of glucose uptake in muscle of a subject, a decrease in inflammation markers, an increase in vasodilatation, and/or an increase in body temperature. Such beneficial effects can result from, in part, an increase in mitochondrial biogenesis, or a variety of other changes in the energy metabolism pathway. The ratio of branched chain amino acids and/or metabolites thereof to a sirtuin pathway activator can be a mass ratio, a molar ratio, or a volume ratio.

In some embodiments, the molar ratio of (a) branched chain amino acids and/or metabolites thereof to (b) a sirtuin pathway activator is about or greater than about 20, 25, 30, 35, 40, 45, 50, 55, 60, 65, 70, 75, 80, 85, 90, 100, 120, or 150. In other embodiments, the molar ratio of one or more branched chain amino acids and/or metabolites thereof to sirtuin pathway activator contained in the subject compositions is about or greater than about 20, 30, 40, 50, 60, 70, 80, 90, 95, 90, 95, 100, 105, 110, 120, 130, 140, 150, 160, 170, 180, 190, 200, 220, 250, 300, 350, 400, or 500. In some embodiments, the molar ratio of component (a) to (b) in said composition is greater than about 20, 40, 60, 80, 100, 120, or 150. In some embodiments, the molar ratio of component (a) to (b) in said composition is greater than about 80, 100, 120, or 150. In some embodiments, the molar ratio of component (a) to (b) in said composition is greater than about 80, 100, 120, or 150. In some embodiments, the molar ratio of component (a) to (b) in said composition is greater than about 200, 250, or 300. In some embodiments, the molar ratio of component (a) to (b) in said composition is greater than about 40, 150, 250, or 500.

In some embodiments, the molar or mass ratios are circulating molar or mass ratios achieved after administration one or more compositions to a subject. The compositions can be a combination composition described herein. The molar ratio of a combination composition in a dosing form can be adjusted to achieve a desired circulating molar ratio. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the circulating molar ratio of leucine to resveratrol (or sirtuin pathway activator) is about or greater than about 1000, 1500, 2000, 2500, 3000, 3500, 4000, 10000, 50000, or more. In some embodiments, the mass ratio of leucine to resveratrol is about or greater than about 750, 1000, 1200, 1500, 1700, 2000, or 2500.

The circulating molar ratio of HMB to resveratrol (or sirtuin pathway activator) can be about or greater than about 3, 5, 10, 15, 20, 25, 30, 35, 40, 50, 60, 75, 100, 250, 500, or more. In some embodiments, the mass ratio of HMB to resveratrol is about or greater than about 1, 3, 6, 9, 12, 15, 20, or 25.

In some embodiments, the circulating mass ratio of HMB to resveratrol (or sirtuin pathway activator) is about or greater than about 100, 120, 140, 160, 180, 200, 220, or 250. In some embodiments, the mass ratio of HMB to resveratrol is about or greater than about 400, 600, 800, 1000, 1200, or 1400.

In some embodiments, the circulating molar ratio of HMB to chlorogenic acid is about or greater than about 5, 10, 20, or 40. In some embodiments, the molar ratio of leucine to chlorogenic acid is about or greater than about 500, 1000, 2000, or 4000.

In some embodiments, the circulating molar ratio of HMB to caffeic acid is about or greater than about 2, 5, 10, or 20.

In some embodiments, the molar ratio of leucine to caffeic acid is about or greater than about 200, 500, 1000, or 2000.

In some embodiments, the circulating molar ratio of HMB to quinic acid is about or greater than about 5, 10, 20, or 40. In some embodiments, the molar ratio of leucine to quinic acid is about or greater than about 500, 1000, 2000, or 4000.

In some embodiments, the circulating molar ratio of HMB to cinnamic acid is about or greater than about 5, 10, 20, or 40. In some embodiments, the molar ratio of leucine to cinnamic acid is about or greater than about 500, 1000, 2000, or 4000.

In some embodiments, the circulating molar ratio of HMB to ferulic acid is about or greater than about 5, 10, 20, or 40. In some embodiments, the molar ratio of leucine to ferulic acid is about or greater than about 500, 1000, 2000, or 4000.

In some embodiments, the circulating molar ratio of HMB to piceatannol is about or greater than about 2000, 5000, 10000, or 20000. In some embodiments, the molar ratio of leucine to piceatannol is about or greater than about 200000, 500000, 1000000, or 2000000.

In some embodiments, the circulating molar ratio of HMB to ellagic acid is about or greater than about 0.05, 0.1, 0.2, or 0.4. In some embodiments, the molar ratio of leucine to ellagic acid is about or greater than about 5, 10, 20, or 40.

In some embodiments, the circulating molar ratio of HMB to epigallocatechin gallate is about or greater than about 2, 5, 10, or 20. In some embodiments, the molar ratio of leucine to epigallocatechin gallate is about or greater than about 200, 500, 1000, or 2000.

In some embodiments, the circulating molar ratio of HMB to fucoxanthin is about or greater than about 20, 50, 100, or 200. In some embodiments, the molar ratio of leucine to fucoxanthin is about or greater than about 2000, 5000, 10000, or 20000.

In some embodiments, the circulating mass ratio of HMB to grape seed extract is about or greater than about 0.3, 0.6, 1.2, or 2.4. In some embodiments, the mass ratio of leucine to grape seed extract is about or greater than about 30, 65, 130, or 260.

In some embodiments, the circulating molar ratio of HMB to metformin is about or greater than about 0.02, 0.05, 0.1, or 0.2. In some embodiments, the molar ratio of leucine to metformin is about or greater than about 2, 5, 10, or 20

In some embodiments, the circulating molar ratio of HMB to rosiglitazone is about or greater than about 10, 25, 50, or 100. In some embodiments, the molar ratio of leucine to rosiglitazone is about or greater than about 1000, 2500, 5000, or 10000.

Dosing Forms

The compositions described herein can be compounded into a variety of different dosage forms. It can be used orally as a tablet, chewable tablet, caplets, capsule, soft gelatin capsules, lozenges or solution. It can also be used as a nasal spray or for injection when in its solution form. In some embodiments, the composition may be a liquid composition suitable for oral consumption. Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The liquid forms, in which the formulations disclosed herein may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

A subject can be treated by combination of an injectable composition and an orally ingested composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions of this invention is conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

This invention further encompasses anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time. Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 4, 6, 8, 12, 16, 20, or 24 hours. The release of the one or more components can be at a constant or changing rate.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the one or more cofactors may be provided so that it reaches its maximum concentration at a rate that is significantly reduced over an immediate release dosage form. The compositions of the present invention may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors may have different cofactors released at different rates or at different times. For example, there can be additional layers of cofactors interspersed with eneteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In some embodiments, liquid food carriers, such as in the form of beverages, such as supplemented juices, coffees, teas, sodas, flavored waters, and the like can be used. For example, the beverage can comprise the formulation as well as a liquid component, such as various deodorant or natural carbohydrates present in conventional beverages. Examples of natural carbohydrates include, but are not limited to, monosaccharides such as, glucose and fructose; disaccharides such as maltose and sucrose; conventional sugars, such as dextrin and cyclodextrin; and sugar alcohols, such as xylitol and erythritol. Natural deodorant such as taumatin, *stevia* extract, levaudioside A, glycyrrhizin, and synthetic deodorant such as saccharin and aspartame may also be used. Agents such as flavoring agents, coloring agents, and others can also be used. For example, pectic acid and the salt thereof, alginic acid and the salt thereof, organic acid, protective colloidal adhesive, pH controlling agent, stabilizer, a preservative, glycerin, alcohol, or carbonizing agents can also be used. Fruit and vegetables can also be used in preparing foods or beverages comprising the formulations discussed herein.

Alternatively, the compositions can be a snack bar supplemented with any of the compositions described herein. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like.

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, ⅐, ⅛, ⅑, ⅒. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 550 mg leucine. In some embodiments, a unit dose comprises about, less than about, or more than about 200 mg of one or more leucine metabolites. In some embodiments, a unit dose (e.g. a unit dose comprising leucine) is administered as two unit doses two times per day. In some embodiments, a unit dose (e.g. a unit dose comprising one or more leucine metabolites, such as HMB) is administered as one unit dose two timer per day.

Compositions disclosed herein can further comprise a flavorant and can be a solid, liquid, gel or emulsion.

Methods

The subject application provides methods of increasing sirtuin pathway output (including AMPK, a signaling molecule in the sirtuin pathway) in a subject. As described herein, the output of the sirtuin pathway can be characterized at the molecular level or by a resulting physiological effect. In some embodiments, the invention provides for methods of increasing fatty acid oxidation in a subject comprising the administration of a composition as disclosed herein to the subject. In various embodiments of the invention, a composition is administered to the subject in an amount that delivers synergizing amounts of one or more branched amino acids and a polyphenol sufficient to increase fatty acid oxidation within the cells of the subject.

The methods described herein can be useful for a variety of applications. These applications include (a) an increase in sirtuin-pathway output, (b) an increase in mitochondrial biogenesis, (c) an increase in the formation of new mitochondria, (d) an increase in mitochondrial functions, (e) an increase in fatty acid oxidation, (f) an increase in heat generation, (g) an increase in insulin sensitivity, (h) an increase in glucose uptake, (i) an increase in vasodilation, (j) a decrease in weight, (k) a decrease in adipose volume, (l) a decrease in inflammatory response or markers in a subject, and (m) an increase in irisin production. Any of these applications can be achieved by administering one or more compositions described herein.

Accordingly, the invention provides a method for administering a composition comprising (a) one or more types of branched amino acids and/or metabolites thereof and (b) a sirtuin-pathway activator present in a sub-therapeutic amount, wherein the composition is synergistically effective in increasing the sirtuin-pathway output by at least about 5 fold as compared to that of component (b) when it is being used alone.

The output of the pathways can be measured using one or more methods, disclosed herein and/or known in the art. For example, fatty acid oxidation can be determined by measuring oxygen consumption, or $^3$H-labeled palmitate oxidation. Mitochondrial biogenesis can be measured using a mitochondrial probe by using fluorescence. AMPK activity can be determined by measuring AMPK phosphorylation via an ELISA assay or by Western blot. Sirt1 activity can be determined by measuring deacetylation of a substrate, which can be detected using a fluorophore.

An increase in sirt1, sirt2, or sirt3 is observed by applying a corresponding substrate in a deacylation assay conducted in vitro. The substrate for measuring SIRT1 activity can be any substrate known in the art (for example a peptide containing amino acids 379-382 of human p53 (Arg-His-Lys-Lys[Ac]). The substrate for measuring SIRT3 activity can be any substrate known in the art (for example a peptide containing amino acids 317-320 of human p53 (Gln-Pro-Lys-Lys[Ac])). In some instances, the increase in sirt activity in one or more assays conducted in the presence of one or more combination compositions described herein results in an activity increase of at least about 1, 2, 3, 5, or 10 fold, as compared to the activity measured in the presence of only one component of the combination compositions. For example, the use of a combination composition comprising (a) a sirtuin pathway activator (such as resveratrol) and (b) a branched chain amino acid or metabolite thereof (such as HMB) results in an increase in sirt3 activity by at least about 5 fold as compared to the activity measured in the presence of (a) or (b) alone. Also, the use of a combination composition comprising resveratrol and leucine results in an increase in sirt1 activity that is 1.5, 2, 5 or 10 fold greater than the activity measured in the presence of only resveratrol or leucine.

The invention provides a method for administering a composition comprising: (a) one or more types of branched amino acids and/or metabolites thereof, and (b) a sirtuin-pathway activator, wherein molar ratio of component (a) to (b) in said composition is greater than about 20, and wherein the composition when administered to a subject in need thereof synergistically enhances mitochondrial biogenesis as measured by a decrease in weight gain of a subject, a decrease in visceral adipose volume of a subject, an increase in fat oxidation of a subject, an increase in insulin sensitivity of a subject, an increase of glucose uptake in muscle of a subject, a decrease in inflammation markers, an increase in vasodilatation, and/or an increase in body temperature.

The invention provides a method for administering a composition comprising: a unit dosage suitable for oral ingestion, said unit dosage comprising: (a) one or more types of branched amino acids and/or metabolites thereof, and (b) a substantially homogeneous population of polyphenol molecules, and wherein the unit dosage is effective in inducing a decrease in weight gain of a subject, a decrease in visceral adipose volume of a subject, an increase in fat oxidation of a subject, an increase in insulin sensitivity of a subject, an increase of glucose uptake in muscle of a subject, an increase in vasodilatation, and/or an increase in body temperature.

The invention provides a method for administering a food composition comprising: (a) one or more types of branched amino acids and/or metabolites thereof; (b) a sirtuin pathway activator, wherein (a) and (b) are present in an amount that synergistically effect a decrease in weight gain of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature; and (c) a food carrier.

The invention provides a method for administering a composition comprising: a synergistically effective amount of (a) one or more types of branched amino acids and/or metabolites thereof; and (b) a sirtuin-pathway activator, wherein the composition is substantially free of non-branched amino acids, wherein the combination when administered to a subject in need thereof enhances mitochondrial biogenesis to a greater degree as compared to administering to a subject component (a) or component (b) alone, and wherein the enhanced mitochondrial biogenesis is measured by a decrease in weight of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature.

The invention provides a method for administering a composition comprising: a synergistically effective amount of (a) one or more types of branched amino acids and/or metabolites thereof; and (b) a sirtuin-pathway activator, wherein the composition is substantially free of non-branched amino acids, wherein the combination when administered to a subject in need thereof enhances mitochondrial biogenesis to a greater degree as compared to administering to a subject component (a) or component (b) alone, and wherein the enhanced mitochondrial biogenesis is measured by a decrease in weight of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature.

The invention provides a method for administering a composition comprising: (a) one or more types of branched amino acids and/or metabolites thereof, and (b) a signaling molecule downstream of PGC1α in a sirtuin-signaling pathway.

The invention provides for a method of enhancing fat oxidation in a subject in need thereof comprising administering to the subject any of the compositions described herein over a time period, wherein the fat oxidation in the subject is increased over the time period. The fat oxidation can be increased by about or greater than about 5, 10, 15, 20, 50, 100, 200, or 500%.

The invention provides for a method of reducing an inflammatory response in a subject in need thereof comprising administering to the subject a composition any of the compositions described herein over a time period, wherein the inflammatory response in the subject is reduced over the time period. The inflammatory response can be decreased by about or greater than about 5, 10, 15, 20, 50, or 100%.

Inflammatory marker and cytokine levels, including but not limited to IL-6, adiponectin, TNF-α and CRP levels in plasma can determined by immune assays, such as ELISA (Assay Designs, Ann Arbor, Mich.; Linco Research, St. Charles, Mo.; and Bioscience, San Diego, Calif.).

The invention provides for a method of increasing or maintaining body temperature in a subject comprising administering to the subject a composition any of the compositions described herein over a time period, wherein the body temperature in the subject is increased over the time period. The body temperature can be increased by about or greater than about 1, 2, 3, 4, 5, 10, 15, or 20%.

The invention provides for a method of inducing vasodilatation comprising administering to the subject a composition of any of the compositions described herein over a time period, wherein the vasodilation in the subject is induced over the time period. The vasodilation of blood vessels can be increased by about or greater than about 1, 2, 3, 5, 10, 20, 50, or 100%. The vasodilation can be measured by optically, by measuring vasorestriction, or by a variety of other techniques. These techniques include the invasive forearm technique, the brachial artery ultrasound technique, and pulse wave analysis. Methods for measuring vasodilation are described in Lind et al., "Evaluation of four different methods to measure endothelium-dependent vasodilation in the human peripheral circulation," Clinical Science 2002, 102, 561-567.

The invention provides for a method of increasing irisin production, comprising administering to the subject any of the compositions described herein, wherein irisin production in the subject increases over a time period. In some embodiments, the increase in irisin production (or in an indicator providing evidence thereof) is an increase of about, or more than about 5%, 10%, 20%, 30%, 40%, 50%, 60%, 70%, 80%, 90%, 100%, 125%, 150%, 175%, 200%, or more. In some embodiments, the increase in irisin production (or in an indicator providing evidence thereof) is an increase of about, or more than about 1-fold, 3-fold, 5-fold, 6-fold, 8-fold, 10-fold, 15-fold, 20-fold, 50-fold, or more. In some embodiments, the increase in irisin production is evidenced by an increase in FNDC5 expression (e.g. as measured from mRNA and/or protein level). In some embodiments, the increase in irisin production is evidenced by an increase in one or more indicia of fat cell browning (e.g. fatty acid oxidation, and/or an increase in expression of one or more brown fat selective genes in adipose tissue). Non-limiting examples of brown fat selective genes include Ucp1, Cidea, Prdm16, and Ndufs. In some embodiments, the increase in irisin production is evidenced by increased secretion of irisin from the cell (e.g. as measured from media in which the cell is cultured, or from circulating plasma in a subject). Increases in gene levels can be measured directly (e.g. changes in mRNA or protein levels) or indirectly (changes in effects associated with expression increase, such as an increased expression of a downstream gene). Methods for detecting changes in gene expression level are known in the art, and include, without limitation, methods for the detection of mRNA (e.g. RT-PCR, Northern blot, and microarray hybridization), detection of protein products (e.g. Western blot, and ELISA), a detection of one or more activities of the translated protein (e.g. enzyme activity assays).

The invention provides for a method of treating diabetes, comprising administering to the subject any of the compositions described herein over a time period, wherein the insulin sensitivity in the subject is increased over the time period. Insulin sensitivity can be increased by about or greater than about 1, 2, 3, 5, 10, 20, 50, 100, or 200%. In some embodiments, a branched chain amino acid (or a metabolite thereof) and/or a sirtuin pathway activator are administered in an amount that reduces the therapeutically effective dose of metformin for a subject. In some embodiments, the therapeutically effective dose of metformin is reduced by about or more than about 50%, 60%, 70%, 80%, 90%, 95%, 97.5%, 99.9%, 99.99%, or more. In some embodiments, administration of compositions of the invention reduces body fat (e.g. visceral fat) by about or more than about 5%, 10%, 15%, 20%, 25%, 50%, or more.

Insulin sensitivity can be measured using a variety of techniques, including $HOMA_{IR}$. $HOMA_{IR}$, which is the homeostasis model assessment of insulin resistance can be used as a screening index of changes in insulin sensitivity. $HOMA_{IR}$ can be calculated via standard formula from fasting plasma insulin and glucose as follows: $HOMA_{IR}$=[Insulin (uU/mL)×glucose (mM)]/22.5.

In some embodiments, insulin signaling can also be measured. Insulin signaling can be measured by measuring total and phosphorylated Akt, GSK-3β, IGF-1R, IR, IRS-1, p70S6K and PRAS40 in tissue lysates via the Luminex Kits "Akt Pathway Total 7-Plex Panel" (Cat# LH00002) and "Akt Pathway Phospho 7-Plex Panel" (Cat# LHO0001) from Invitrogen Life Science.

The subject application also provides methods of increasing mitochondrial biogenesis in a subject comprising the administration of a composition disclosed herein to a subject. In various embodiments of the invention, a composition is administered to the subject in an amount that delivers synergizing amounts of HMB and resveratrol sufficient to increase mitochondrial biogenesis within the cells of the subject. Another embodiment provides for the administration of a composition comprising synergizing amounts of leucine and resveratrol to the subject in an amount sufficient to increase mitochondrial biogenesis within the cells of the subject. Yet other embodiments provide for the administration of a composition comprising synergizing amounts of leucine, HMB and resveratrol to a subject in an amount sufficient to increase mitochondrial biogenesis in the subject. Mitochondrial biogenesis and fat oxidation may be induced in various cells, including muscle cells and adipocytes.

Another aspect of the invention provides methods of reducing weight gain or reducing adipose volume in a subject comprising the administration of compositions disclosed herein. Body weight can be measured with a calibrated scale and height measured with a wall-mounted stadiometer, and body mass index can be calculated via standard equation (kg/m$^2$). Fat mass can be assessed via dual-energy X-ray absorptiometry at baseline, and 12 and 24 weeks. A LUNAR Prodigy dual-energy X-ray absorptiometry system (GE Healthcare, Madison, Wis.), or any other X-ray absorptiometry system known in the art, can be maintained and calibrated for use. A spine phantom can be assessed every day to determine whether any drift in the machine occurred, followed by a daily calibration block.

In this aspect of the invention, a composition is administered to the subject in an amount that delivers synergizing amounts of HMB and resveratrol sufficient to reduce weight gain in a subject. Another embodiment provides for the administration of a composition comprising synergizing amounts of leucine and resveratrol to the subject in an amount sufficient to reduce weight gain in the subject. Yet other embodiments provide for the administration of a composition comprising synergizing amounts of leucine, HMB and resveratrol to a subject in an amount sufficient to reduce weight gain in the subject.

Administration of compositions disclosed herein that increase SIRT1 and SIRT3 activity may be useful in any subject in need of metabolic activation of adipocytes or one or more of their muscles, e.g., skeletal muscle, smooth muscle or cardiac muscle or muscle cells thereof. A subject may be a subject having cachexia or muscle wasting. Increasing SIRT3 activity may also be used to increase or maintain body temperature, e.g., in hypothermic subjects and increasing SIRT1 activity is beneficial for treating diabetes (type 2 diabetes) and impaired glucose tolerance and reducing inflammatory responses in a subject.

Increasing SIRT3 activity may also be used for treating or preventing cardiovascular diseases, reducing blood pressure by vasodilation, increasing cardiovascular health, and increasing the contractile function of vascular tissues, e.g., blood vessels and arteries (e.g., by affecting smooth muscles). Generally, activation of SIRT3 may be used to stimulate the metabolism of adipocytes or any type of muscle, e.g., muscles of the gut or digestive system, or the urinary tract, and thereby may be used to control gut motility, e.g., constipation, and incontinence. SIRT3 activation may also be useful in erectile dysfunction. It may also be used to stimulate sperm motility, e.g., and be used as a fertility drug. Other embodiments in which it would be useful to increase SIRT3 include repair of muscle, such as after a surgery or an accident, increase of muscle mass; and increase of athletic performance.

Thus the invention provides methods in which beneficial effects are produced by contacting one or more muscle cells with an agent that increases the protein or activity level of SIRT3 in the cell. These methods effectively facilitate, increase or stimulate one or more of the following: mimic the benefits of calorie restriction or exercise in the muscle cell, increase mitochondrial biogenesis or metabolism, increase mitochondrial activity and/or endurance in the muscle cell, sensitize the muscle cell to glucose uptake, increase fatty acid oxidation in the muscle cell, decrease reactive oxygen species (ROS) in the muscle cell, increase PGC-1α and/or UCP3 and/or GLUT4 expression in the muscle cell, and activate AMP activated protein kinase (AMPK) in the muscle cell. Various types of muscle cells can be contacted in accordance with the invention. In some embodiments, the muscle cell is a skeletal muscle cell. In certain embodiments, the muscle cell is a cell of a slow-twitch muscle, such as a soleus muscle cell.

Resting metabolic rate (RMR)/Substrate Oxidation is measured by indirect calorimetry using the open circuit technique between the hours of 6 AM and 10 AM after a 12-hour fast and 48-hour abstention from exercise utilizing a SensorMedics Vmax 29n metabolic cart (Sensor Medics, Anaheim, Calif.). Following a urinary void, the participant rests quietly for 30 minutes in an isolated room with temperature controlled (21-24° C.) environment. The subject is then placed in a ventilated hood for a minimum of 30 minutes, until steady state is achieved. Criteria for a valid measurement can be a minimum of 15 minutes of steady state, with steady state determined as less than 10% fluctuation in minute ventilation and oxygen consumption and less than 5% fluctuation in respiratory quotient. Metabolic rate is calculated using the Weir equation, RQ is calculated as $CO_2$ production/$O_2$ consumption, and substrate oxidation is calculated from RQ after correction for urinary nitrogen losses.

Glucose uptake can be measured using in vivo or in vitro techniques. For example, glucose uptake can be measured in vivo using a PET scan in conjunction with labeled glucose or glucose analog. Measurements of glucose uptake can be quantified from the PET scan or by any other technique known in the art. In some embodiments, the glucose uptake can be measured by quantitation of exogenously administered 18-F-deoxyglucose uptake via PET.

ROS/Oxidative Stress can be measured by drawing blood into EDTA-treated tubes, centrifuging to separate plasma, and aliquoting samples for individual assays. Plasma can be maintained at −80° C. under nitrogen to prevent oxidative changes prior to measurements. Plasma malonaldehyde (MDA) can be measured using a fluorometric assay, and plasma 8-isoprostane $F_{2\alpha}$ was measured by ELISA (Assay Designs, Ann Arbor, Mich.).

Another embodiment provides for the administration of a composition comprising synergizing amounts of leucine and resveratrol to the subject in an amount sufficient to increase fatty acid oxidation within the cells of the subject. Yet other embodiments provide for the administration of a composition comprising synergizing amounts of leucine, HMB and resveratrol to a subject in an amount sufficient to increase fatty acid oxidation in the subject.

The compositions can be administered to a subject orally or by any other methods. Methods of oral administration include administering the composition as a liquid, a solid, or a semi-solid that can be taken in the form of a dietary supplement or a food stuff.

The compositions can be administered periodically. For example, the compositions can be administered one, two, three, four times a day, or even more frequent. The subject can be administered every 1, 2, 3, 4, 5, 6 or 7 days. In some embodiments, the compositions are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 5 years or even longer. In some embodiments of the invention, the dosages that are administered to a subject can change or remain constant over the period of treatment. For example, the daily dosing amounts can increase or decrease over the period of administration.

The length of the period of administration and/or the dosing amounts can be determined by a physician, a nutritionist, or any other type of clinician. The physician, nutritionist, or clinician can observe the subject's response to the administered compositions and adjust the dosing based on the subject's performance. For example, dosing for subjects that show reduced effects in energy regulation can be increased to achieve desired results.

In some embodiments, the compositions administered to a subject can be optimized for a given subject. For example, the ratio of branched chain amino acids to a sirtuin pathway activator or the particular components in a combination composition can be adjusted. The ratio and/or particular components can be selected after evaluation of the subject after being administered one or more compositions with varying ratios of branched chain amino acids to a sirtuin pathway activator or varying combination composition components.

Another aspect of the invention provides for achieving desired effects in one or more subjects after administration of a combination composition described herein for a specified time period.

After a period of 6 weeks of administration of the composition, a combination composition comprising (a) a dosing level of resveratrol and a dosing level of HMB or (b) a dosing level of resveratrol and a dosing level of leucine can reduce weight gain in the one or more subjects by at least about 10, 15, 20, or 20.5%. The p-value can be less than 0.05 (e.g. less than about 0.05, 0.03, 0.02, 0.01, 0.001, 0.0001, or lower). The one or more subjects treated with the same dosing level of one of the components (resveratrol, leucine, or HMB) may have insignificant weight reduction, or a weight reduction that is less than about 0, 5, or 10%.

After a period of 2 weeks of administration, a composition comprising (a) a dosing level of resveratrol and a dosing level of HMB or (b) a dosing level of resveratrol and a dosing level of leucine can increase whole body fat oxidation in the one or more subjects by at least about 10, 15, or 20%. The p-value can be less than 0.05 (e.g. less than about 0.05, 0.03, 0.02, 0.01, 0.001, 0.0001, or lower). The increase in whole body fat oxidation can be sustained while the subjects are administered the composition, or for a period of at least 2, 4, 6, 10, 13, 26, or 52 weeks. The one or more subjects treated with the same dosing level of one of the components (resveratrol, leucine, or HMB) may have insignificant increase in whole body fat oxidation, or an increase in whole body fat oxidation that is less than about 0, 5, or 10%.

After a period of 2 weeks of administration, a composition comprising (a) a dosing level of resveratrol and a dosing level of HMB or (b) a dosing level of resveratrol and a dosing level of leucine can increase the thermic effect of food in the one or more subjects by at least about 10, 15, 17, or 20%. The p-value can be less than 0.05 (e.g. less than about 0.05, 0.03, 0.02, 0.01, 0.001, 0.0001, or lower). The increase in the thermic effect of food can be sustained while the subjects are administered the composition, or for a period of at least 2, 4, 6, 10, 13, 26, or 52 weeks. The one or more subjects treated with the same dosing level of one of the components (resveratrol, leucine, or HMB) may have insignificant increase the thermic effect of food, or an increase the thermic effect of food that is less than about 0, 5, or 10%.

After a period of 2 weeks of administration, a composition comprising (a) a dosing level of resveratrol and a dosing level of HMB or (b) a dosing level of resveratrol and a dosing level of leucine can increase total energy expenditure in the one or more subjects by at least about 10, 15, 17, or 20%. The p-value can be less than 0.05 (e.g. less than about 0.05, 0.03, 0.02, 0.01, 0.001, 0.0001, or lower). The increase total energy expenditure can be sustained while the subjects are administered the composition, or for a period of at least 2, 4, 6, 10, 13, 26, or 52 weeks. The one or more subjects treated with the same dosing level of one of the components (resveratrol, leucine, or HMB) may have insignificant increase total energy expenditure, or an increase total energy expenditure that is less than about 0, 5, or 10%.

The administration of a composition described herein, such as a combination composition, to a subject can allow for the regulation or maintenance of the subject's energy metabolism. The regulation or maintenance of energy metabolism can allow for a subject to experience a number of beneficial effects. These beneficial effects include a reduction in weight, a reduction in adipose tissue, an increase in fatty acid oxidation, an increase in browning of adipose tissue (as indicated by one or more indicia of fat cell browning), an increase in insulin sensitivity, a decrease in oxidative stress, and/or a decrease in inflammation. Compared to a baseline prior to treatment, these effects can result in an improvement of about or greater than about 5%, 10%, 15%, 20%, 30%, 40%, 50%, 75%, or more. In some embodiments, compared to a baseline prior to treatment, these effects can result in an improvement of about or greater than about 100%, 125%, 150%, 200%, 250%, 300%, 400%, 500%, or more. Alternatively, administration of a composition described herein can allow for maintenance of the subject's weight, amount of adipose tissue, amount of fatty acid oxidation, level of insulin sensitivity, oxidative stress level, and/or level of inflammation. These amounts and/or levels can be maintained within about 0%, 1%, 5%, or 10% of the amounts and/or levels at the initiation of administration.

The invention provides for a method of treating subjects, comprising identifying a pool of subjects amenable to treatment. The identifying step can include one or more screening tests or assays. For example, subjects that are identified as diabetic or that have above average or significantly greater than average body mass indices and/or weight can be selected for treatment. The identifying step can include a genetic test that identifies one or more genetic variants that suggest that the subject is amenable to treatment. The identified subjects can then be treated with one or more compositions described herein. For example, they may be treated with a combination composition comprising a sirtuin pathway activator and a branched-chain amino acid.

The invention also provides for methods of manufacturing the compositions described herein. In some embodiments, the manufacture of a composition described herein comprises mixing or combining two or more components. These components can include a sirtuin or AMPK pathway activator (such as a polyphenol or polyphenol precursor like resveratrol, chlorogenic acid, caffeic acid, cinnamic acid, ferulic acid, EGCG, piceatannol, or grape seed extract, or another agent like quinic acid, fucoxanthin, or a PDE inhibitor), branched chain amino acids or metabolites thereof (such as leucine, valine, isoleucine, HMB, or KIC), and/or an anti-diabetic (such as metformin). In some embodiments, the sirtuin activator is a polyphenol. In other embodiments, the sirtuin activator is a polyphenol precursor. The amount or ratio of components can be that as described herein. For example, the mass ratio of leucine combined with resveratrol can be greater than about 80.

In some embodiments, the compositions can be combined or mixed with a pharmaceutically active agent, a carrier, and/or an excipient. Examples of such components are described herein. The combined compositions can be formed into a unit dosage as tablets, capsules, gel capsules, slow-release tablets, or the like.

In some embodiments, the composition is prepared such that a solid composition containing a substantially homogeneous mixture of the one or more components is achieved, such that the one or more components are dispersed evenly throughout the composition so that the composition may be readily subdivided into equally effective unit dosage forms such as tablets, pills and capsules.

Kits

The invention also provides kits. The kits include one or more compositions described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

EXAMPLES

Example 1—Effects of Leucine, KIC and HMB Alone, or in Combination with Resveratrol on Mitochondrial Biogenesis The experiment shows that Leucine stimulates muscle protein synthesis via a partially mTOR-independent mechanism. We have shown that catabolic systems are also stimulated to fuel this process, resulting in increased mitochondrial biogenesis and fatty acid oxidation (FAO). To address the mechanism of this effect, we first determined its mTOR-dependence by assessing leucine stimulation of FAO in the presence and absence of 20 nM rapamycin; although rapamycin inhibited FAO in c2c12 myotubes, the degree of leucine stimulation was preserved (~50%, p<0.03; FIG. 1).

Figure 2:
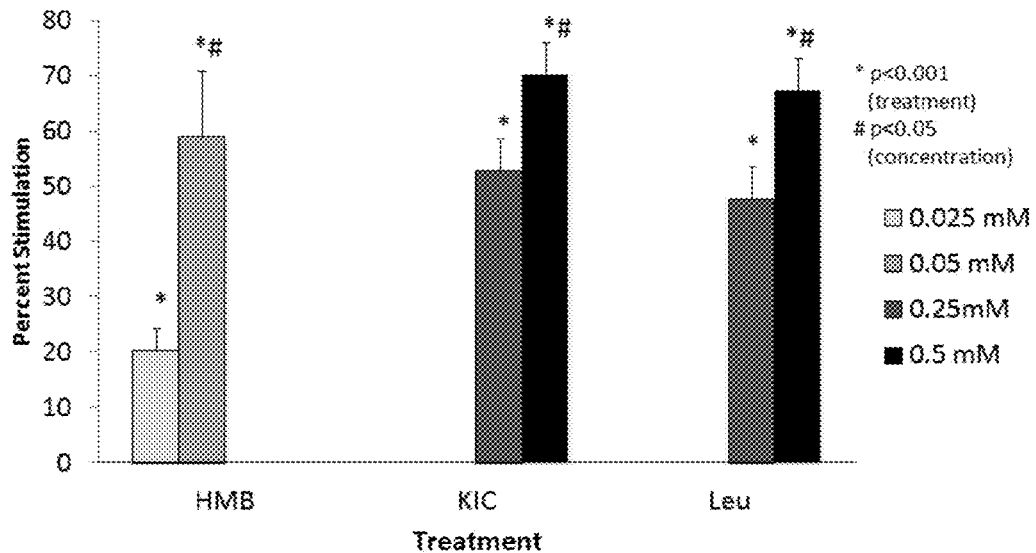
FIG. 2 depicts a graph showing the effects of HMB, KIC, and leucine on fatty acid oxidation.

We next investigated the role of intact leucine (0-0.5 mM) vs. its metabolites, α-ketoisocaproic acid (KIC)(0-0.5 mM) and HMB (0-50 μM). All three compounds induced comparable increases in FAO (~60-70%, p<0.001; FIG. 2). Both leucine and HMB increased myotube mitochondrial biogenesis (assessed fluorometrically via NAO binding) by ~50%, (p<0.005, FIG. 3). Consistent with this, HMB and leucine both stimulated expression of mitochondrial regulatory (PGC-1α and NRF-1) and component (UCP3) genes (p<0.01, FIG. 4). These data demonstrate that leucine stimulates mitochondrial biogenesis and fatty acid oxidation independently of mTOR and that these effects appear to be mediated by its metabolite, e.g., HMB.

Example 2—Stimulation of SIRT1 and SIRT 3

Figure 5:
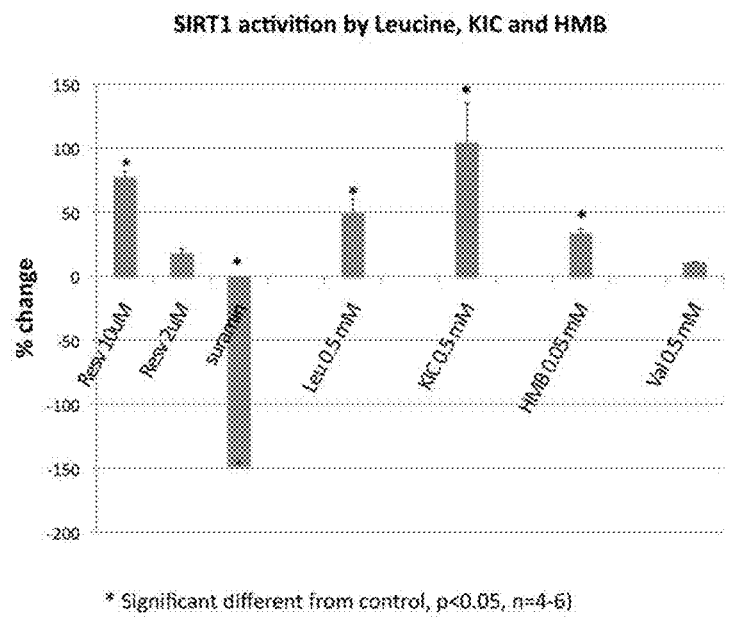
FIG. 5 depicts a graph showing the effects of resveratrol, suramin, leucine, KIC, HMB, and leucine on SIRT1 activation.

The effects of leucine, KIC and HMB on activation of SIRT1 were assessed in the presence and absence of resveratrol in a cell-free system. SIRT1 activity was measured by using the SIRT1 Fluorimetric Drug Discovery Kit (BML-AK555, ENZO Life Sciences International, Inc. PA, USA). In this assay, SIRT1 activity is assessed by the degree of deacetylation of a standardized substrate containing an acetylated lysine side chain. The substrate utilized is a peptide containing amino acids 379-382 of human p53 (Arg-His-Lys-Lys[Ac]), an established target of SIRT1 activity; SIRT1 activity is directly proportional to the degree of deacetylation of Lys-382. Samples were incubated with peptide substrate (25 μM), and NAD$^+$ (500 μM) in a phosphate-buffered saline solution at 37° C. on a horizontal shaker for 45 minutes. The reaction was stopped with the addition of 2 mM nicotinamide and a developing solution that binds to the deacetylated lysine to form a fluorophore. Following 10 minutes incubation at 37° C., fluorescence was read in a plate-reading fluorometer at an excitation wavelength of 360 nm and an emission wavelength of 450 nm. Resveratrol (100 mM) served as a SIRT1 activator (positive control) and suramin sodium (25 mM) as a SIRT1 inhibitor (negative control). A standard curve was constructed using deacetylated substrate (0-10 μM). Leucine, KIC and HMB all significantly increased SIRT1 activity in a dose-responsive manner, while valine (a branched chain amino acid control) exerted no significant effect. FIG. 5 demonstrates the effects of leucine and its' metabolites on SIRT1 activity at the physiological concentrations of each compound found after a leucine-rich meal. As shown in the figure, these effects are quantitatively comparable (and not significantly different from) to those exerted by a low dose of resveratrol (e.g. 10 µM).

Figure 6:
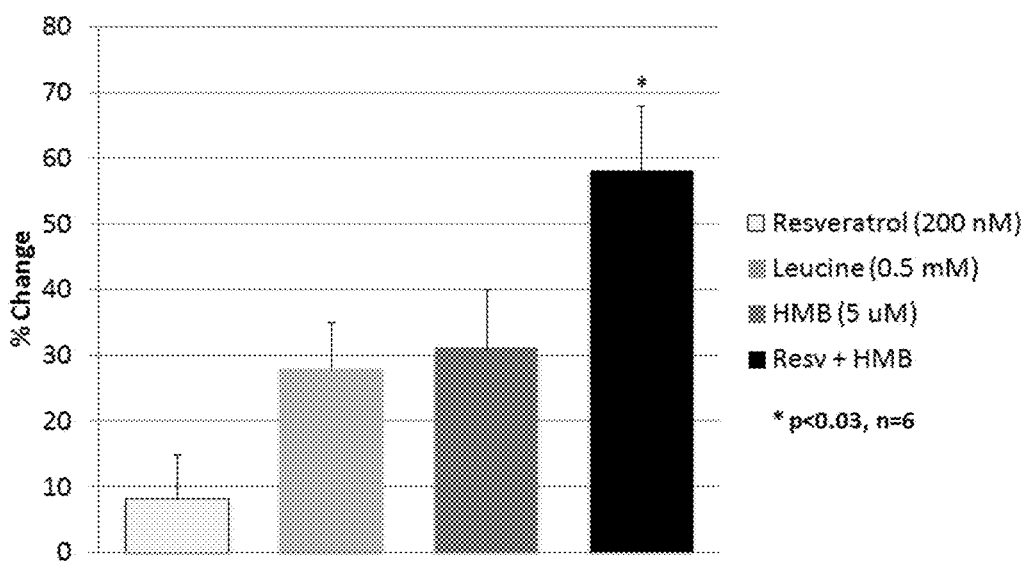
FIG. 6 depicts a graph showing the effects of resveratrol, leucine, HMB, and a combination composition of HMB and Resveratrol on activation of Sirt3.

For assaying SIRT3 activity, adipocytes (3T3-L1) were grown to confluence, differentiated and incubated with leucine (0.5 mM), HMB (5 uM), resveratrol (200 nM), HMB (5 uM)+resveratrol (200 nM) or vehicle for 4 hours. Mitochondrial protein was then isolated from the cells, and Sirt3 activity was assessed by fluorometric measurement of deacetylation of a Sirt3 substrate, similar to the methodology described above for Sirt1. The Sirt3 substrate was a peptide containing amino acids 317-320 of human p53 (Gln-Pro-Lys-Lys[Ac]). Resveratrol, leucine and HMB exerted no significant independent effect on Sirt3 activity. However, combining resveratrol (200 nM) with HMB (5 uM) resulted in a 58% increase in Sirt3 activity ($p<0.03$, FIG. 6).

Figure 7:
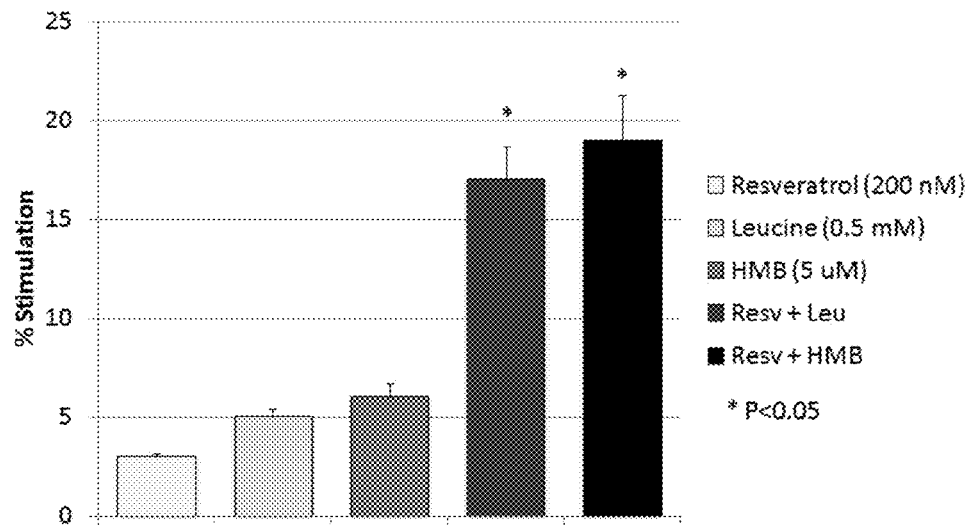
FIG. 7 depicts a graph showing synergistic effects of leucine and HMB with resveratrol on fatty acid oxidation under low glucose conditions.
Figure 8:
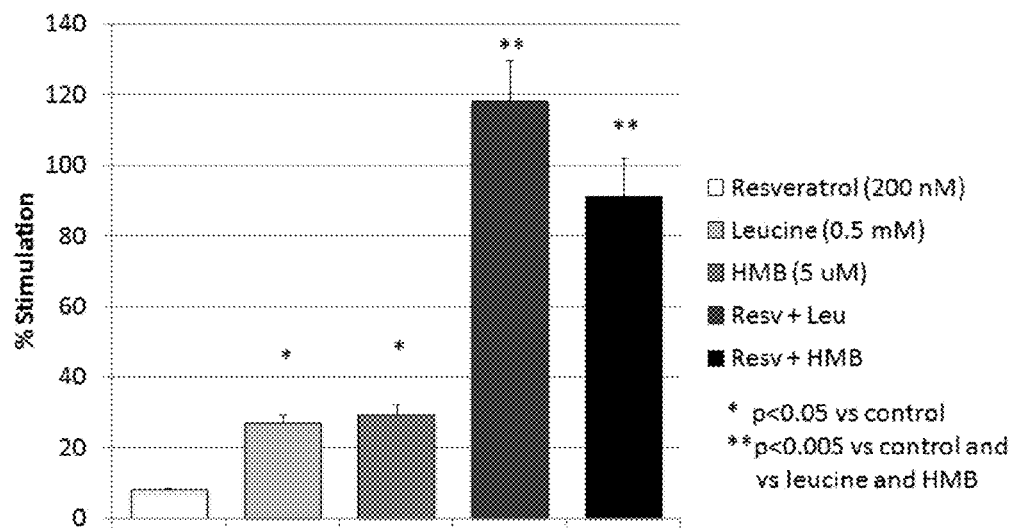
FIG. 8 depicts a graph showing synergistic effects of leucine and HMB with resveratrol on fatty acid oxidation under high glucose conditions.

Example 3—Leucine and HMB Synergize with Resveratrol to Stimulate Fatty Acid Oxidation Adipocytes (3T3-L1) were grown to confluence, differentiated and incubated with leucine (0.5 mM), HMB (5 uM), resveratrol (200 nM), HMB (5 uM)+resveratrol (200 nM) or vehicle for 4 hours in the presence of low (5 mM) or high (25 mM) glucose and fatty acid oxidation was measured using $^3$H-palmitate. In the presence of low glucose, only the combination treatments (200 nM resveratrol+5 uM HMB; 200 nM resveratrol+0.5 mM leucine) stimulated modest increases in fatty acid oxidation (18%, $p<0.05$), while the individual components exerted no independent effect (FIG. 7). High glucose medium reduced fatty acid oxidation by 46% ($p<0.05$). The low dose of resveratrol used exerted no effect on fatty acid oxidation under high glucose conditions, while the leucine and HMB exerted modest, but significant, effects (27% and 29%, respectively, $p<0.05$ vs. control, FIG. 8). In contrast, the leucine-resveratrol and HMB-resveratrol combinations each exerted a markedly greater effect (118% and 91% stimulation, respectively; $p<0.005$ vs. control and vs. the independent effects of leucine, HMB and resveratrol; FIG. 8). These data demonstrate synergy between resveratrol and leucine or its metabolite, HMB, in stimulation of fat oxidation and promotion of a more oxidative phenotype under conditions that model hyperglycemia.

Fatty acid oxidation was measured using $^3$H-labeled palmitate oxidation, with the $^3$H label trapped as water as a result of the fat oxidation. The $^3$H was then measured via scintillation counter.

Example 4—Weight Gain, Fat Oxidation, Insulin Sensitivity, and Inflammatory Stress in Animals Treated with Resveratrol and Leucine or HMB Six week old male c57/BL6 mice were fed a high-fat diet with fat increased to 45% of energy (Research Diets D12451) for 6 weeks to induce obesity. At the end of this obesity induction period, animals were randomly divided into the following seven different diet treatment groups with 10 animals per group (overall 70 animals) and maintained on these diets for 6 weeks:

Group 1 (labeled "control group"): high-fat diet only (same as in obesity induction period (Research Diets D12451)).

This diet was modified for groups 2 to 7 in the following way:

Group 2 (labeled "low dose resveratrol"): high-fat diet mixed with 12.5 mg resveratrol/kg diet.

Group 3 (labeled "high dose resveratrol"): high-fat diet mixed with 225 mg resveratrol/kg diet.

Group 4 (labeled "low dose HMB"): high-fat diet mixed with 2 g of the calcium salt of hydroxymethylbutyrate, a naturally occurring metabolite of leucine (CaHMB).

Group 5 (labeled "low dose resveratrol plus low dose CaHMB"): high fat-diet mixed with 12.5 mg of resveratrol/kg diet and 2 g CaHMB/kg diet.

Group 6 (labeled "low dose resveratrol plus high dose HMB"): high fat-diet mixed with 12.5 mg of resveratrol/kg diet and 10 g CaHMB/kg diet.

Group 7 (labeled "low dose resveratrol plus leucine"): high fat-diet mixed with 12.5 mg of resveratrol/kg diet and leucine increased to 200% of its normal level (from 1.21 to 2.42% by weight) of the control diet The animals were housed in polypropylene cages at a room temperature of 22±2° C. and regime of 12 h light/dark cycle. The animals had free access to water and their experimental food throughout the experiment. At the of the treatment period (6 weeks) all animals were humanely euthanized, and blood and tissues collected for further experiments.

Oxygen consumption/substrate utilization: at the end of the obesity induction period (day 0 of treatment group) and at 2 weeks and 6 weeks of treatment, oxygen consumption and substrate utilization was measured via metabolic chambers using the Comprehensive Lab Animal Monitoring Systems (CLAMS, Columbus Instruments, Columbus, Ohio) in subgroups of each treatment group. Each animal was placed in individual cages without bedding that allow automated, non-invasive data collection. Each cage is an indirect open circuit calorimeter that provides measurement of oxygen consumption, carbon dioxide production, and concurrent measurement of food intake. All mice were acclimatized to the chambers for 24 hours prior to the experiment and maintained under the regular 12:12 light:dark cycle with free access to water and food. All experiments were started in the morning and data were collected for 24 hours. Each chamber was passed with 0.61 of air/min and was sampled for 2 min at 32-minute intervals. Exhaust $O_2$ and $CO_2$ content from each chamber was compared with ambient $O_2$ and $CO_2$ content. Food consumption was measured by electronic scales.

MicroPET/CT (glucose and palmitate uptake): at the end of the treatment period (6 weeks of treatment) subgroups of each treatment diet group (5 animals/group, 35 animals total) were used to measure whole body glucose and palmitate uptake via PET/CT Imaging. To visualize these compounds using microPET imaging, the glucose or palmitate was labeled with fluorine-18 (108 mins half life) or carbon-11 (20 mins half life), respectively. Each mouse was fasted for 4 hours, then anesthetized using 1-3% isoflurane delivered by nose cone or in a mouse-sized induction chamber purpose-built for small animal imaging protocols. While under anesthesia the mice were injected iv with <2 mCi of each tracer, then be left for a period of time (minutes to up ~1 hour) to allow the uptake of the tracer. During the scan, mice were kept warm using a thermostatically controlled heated bed and were treated with ophthalmic ointment prior to scanning. Following the live scan the mice were returned to their cage and revived. Mice were monitored constantly during this time. Following live data acquisition the mice were sacrificed by isoflurane overdose and organs harvested for further experiments.

RNA extraction: The Ambion ToTALLY RNA isolation kit (Ambion, Inc., Austin, Tex., USA) was used to extract total RNA from tissue according to the manufacturer's instruction. The concentration, purity and quality of the isolated RNA will be assessed by measuring the 260/280 ratio (1.8-2.0) and 260/230 ratio (close to 2.0) by using the ND-1000 Spectrophotometer (NanoDrop Technologies Inc., Del. USA). Biomarkers of the sirtuin-pathway, cytokines, and inflammatory markers (including but not limited to C-reactive protein, IL-6, MCP-1, and adiponectin molecules) can be assessed at the RNA level.

Gene Expression: Expression of 18S, Sirt1, Sirt3, PGC1-α, cytochrome c oxidase subunit VIIc1 (COX 7), mitochondrial NADH dehydrogenase, nuclear respiratory factor 1 (NRF1), uncoupling protein (UCP2 (adipocyte)/UCP3 (myocyte), p53, AMPK, Akt/PKB, and GLUT4 is measured via quantitative real-time PCR using an ABI 7300 Real-Time PCR system (Applied Biosystems, Branchburg, N.J.) with a TaqMan® core reagent kit. All primers and probe sets can be obtained from Applied Biosystems TaqMan® Assays-on-Demand and utilized accordingly to manufacturer's instructions. Pooled RNA from each cell type are serial-diluted in the range of 0.0156-50 ng and were used to establish a standard curve; total RNA for each unknown sample is also diluted in this range. RT-PCR reactions are performed according to the instructions of the ABI Real-Time PCR system and TaqMan Real Time PCR Core Kit. Expression of each gene of interest is then normalized using the corresponding 18S quantitation.

SIRT1 Activity: SIRT1 activity was measured by using the SIRT1 Fluorimetric Drug Discovery Kit (BML-AK555, ENZO Life Sciences International, Inc. PA, USA). In this assay, SIRT1 activity is assessed by the degree of deacetylation of a standardized substrate containing an acetylated lysine side chain. The substrate utilized is a peptide containing amino acids 379-382 of human p53 (Arg-His-Lys-Lys[Ac]), an established target of SIRT1 activity; SIRT1 activity is directly proportional to the degree of deacetylation of Lys-382. Samples were incubated with peptide substrate (25 μM), and $NAD^+$ (500 μM) in a phosphate-buffered saline solution at 37° C. on a horizontal shaker for 45 minutes. The reaction was stopped with the addition of 2 mM nicotinamide and a developing solution that binds to the deacetylated lysine to form a fluorophore. Following 10 minutes incubation at 37° C., fluorescence was read in a plate-reading fluorometer at an excitation wavelength of 360 nm and an emission wavelength of 450 nm. Resveratrol (100 mM) served as a SIRT1 activator and suramin sodium (25 mM) as a SIRT1 inhibitor; wells including each were utilized as positive and negative controls in each set of reactions. A standard curve was constructed using deacetylated substrate (0-10 μM). Data was normalized to cellular protein concentration measured via BCA-assay.

Western blot analysis: Tissue samples (adipose and muscle) is homogenized in ice-cold RIPA lysis buffer containing 150 mM sodium chloride, 1.0% Triton X-100, 0.5% sodium deoxycholate, 0.1% SDS and 50 mM Tris (pH 8.0), aprotinin (1 μg/ml), Leupeptin (10 μg/ml), Pepstatin A (1 μg/ml), 1 mM PMSF, 5 mM EDTA, 1 mM EGTA, 10 mM NaF, 1 mM Na Orthovanadate with an electric homogenizer, then maintained on constant agitation for 2 hours at 4° C. and centrifuged at 4,000 g for 30 min at 4° C. Aliquots of supernatants (containing 15-25 μg of total protein) is treated with 2× Laemmli sample buffer containing 100 mM dithiothreitol and run on 10% (for or 15% SDS-PAGE (for Sirt3). The resolved proteins is transferred to PVDF membrane and blocked in 5% nonfat dry milk in Tris-buffered saline containing 0.1% Tween 10, pH 7.5. After membranes are blocked, the membranes are rinsed in TBST, incubated overnight with appropriate antibody, rinsed in TBST, and incubated for 120 min with horseradish peroxidase-conjugated anti-rabbit IgG. Antibody-bound protein is visualized with enhanced chemiluminescence (ECL, Amersham).

The following antibodies are used: Anti-Sirt3 antibody (Cell Signaling Technology, Beverly, Mass.), Anti-Idh2 (Isocitrate dehydrogenase 2) (Santa Cruz, Calif.), Anti-COX antibody (Santa Cruz).

Low doses of resveratrol and HMB exerted no significant independent effect on body weight, weight gain, visceral adipose tissue mass, fat oxidation, respiratory exchange ratio (RER), or heat production, while the high dose of resveratrol significantly increased both heat production and skeletal muscle fat oxidation and decreased RER, indicating a whole-body shift towards fat oxidation (table 1); however, high dose resveratrol exerted no significant effect on body weight, weight gain, or visceral adipose tissue mass. In contrast with the lack of independent effects of a low dose of resveratrol or HMB, combining a low dose of resveratrol with either HMB or leucine resulted in significant reductions in body weight, weight gain, visceral adipose tissue mass, fat oxidation and heat production, and an associated decrease in RER (table 1).

TABLE 1

Effects of resveratrol, leucine and HMB on body weight, weight gain, adiposity and fat oxidation in diet-induced obese mice.[1]

|  | Control | Low Resveratrol[2] | High Resveratrol[3] | Low HMB[4] | Low Resv/ Low HMB | Low Resv/ High HMB[5] | Low Resv/ Leucine[6] | P value |
|---|---|---|---|---|---|---|---|---|
| Weight (g) | 40.5 ± 0.5[a] | 40.8 ± 2.5[a] | 38.7 ± 1.2[a] | 40.3 ± 2.1[a] | 36.2 ± 3.2[b] | 34.4 ± 1.1[b] | 38.3 ± 2.3[b] | P < 0.05 |
| Weight gain (g) | 22.4 ± 1.1[a] | 20.9 ± 1.5[a] | 22.3 ± 2.4[a] | 22.5 ± 1.2 | 18.2 ± 1.2[b] | 19.2 ± 1.0[b] | 19.2 ± 1.6[b] | p < 0.01 |

TABLE 1-continued

Effects of resveratrol, leucine and HMB on body weight, weight gain, adiposity and fat oxidation in diet-induced obese mice.[1]

| | Control | Low Resveratrol[2] | High Resveratrol[3] | Low HMB[4] | Low Resv/ Low HMB | Low Resv/ High HMB[5] | Low Resv/ Leucine[6] | P value |
|---|---|---|---|---|---|---|---|---|
| Visceral Adipose Volume (mm$^3$) | 6556 ± 143 | 6551 ± 575$^a$ | 6031 ± 323$^a$ | 6184 ± 460$^a$ | 5302 ± 324$^b$ | 4879 ± 243$^b$ | 4259 ± 321$^b$ | p < 0.01 |
| Fat oxidation (PET palmitate uptake; Muscle SUV) | 1.34 ± 0.15$^a$ | 1.51 ± 0.44$^a$ | 2.29 ± 0.11$^b$ | 1.90 ± 0.29$^a$ | 2.09 ± 0.30$^b$ | 1.97 ± 0.28$^b$ | 1.76 ± 0.09$^{a,b}$ | P < 0.05 |
| Respiratory Exchange Ratio (24 hr RER) | 0.850 ± 0.008$^a$ | 0.847 ± 0.008$^a$ | 0.825 ± 0.007$^b$ | 0.844 ± 0.012$^a$ | 0.815 ± 007$^b$ | 0.8818 ± 0.09$^b$ | 0.811 ± 0.010$^b$ | P < 0.01 |
| Heat Production | 0.521 ± 0.015$^a$ | 0.517 ± 0.014$^a$ | 0.552 ± 0.015$^b$ | 0.526 ± 0.011$^a$ | 0.544 ± 0.010$^b$ | 0.547 ± 0.009$^b$ | 0.550 ± 0.012$^b$ | P < 0.05 |

[1] non-matching letter superscripts in each row denote significant differences at the indicated p value
[2] Low resveratrol: 12.5 mg resveratrol/kg diet
[3] High resveratrol: 225 mg resveratrol/kg diet
[4] Low HMB: 2 g hydroxymethylbutyrate (calcium salt)
[5] Leucine: Leucine increased two-fold, from 1.21% in other diets to 2.42%

Figure 9:
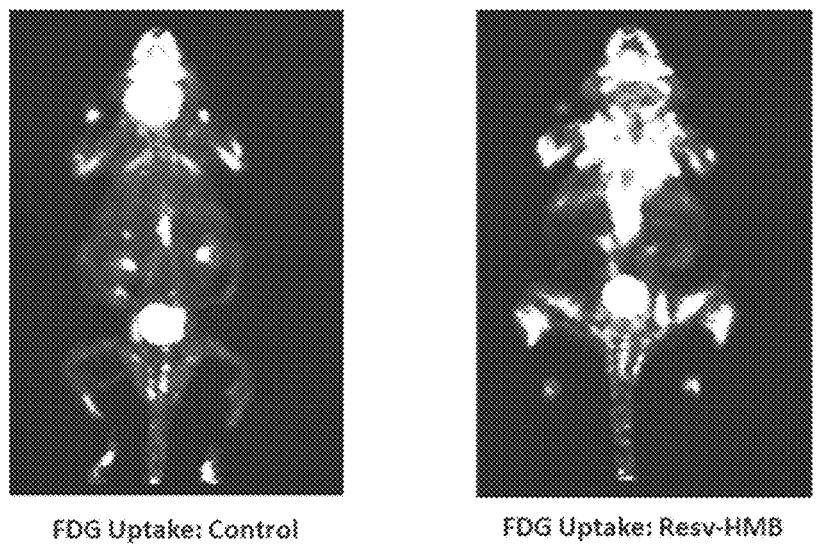
FIG. 9 depicts two FDG-PET images showing the synergistic effects of resveratrol and HMB on glucose uptake using FDG-PET scanning analysis.

Table 2 shows the effects of the dietary treatments on indices of insulin sensitivity. None of the treatments exerted any effect on plasma glucose. Neither resveratrol at either dose nor HMB exerted any significant effect on plasma insulin or on muscle glucose uptake. However, the combination of a low dose of resveratrol with either HMB or leucine resulted in significant, marked decreases in plasma insulin. This reduction in insulin with no change in plasma glucose reflects significant improvements in muscle and whole-body insulin sensitivity, as demonstrated by significant and substantial decreases in HOMA$_{IR}$ (homeostatic assessment of insulin resistance) and corresponding increases in skeletal muscle $^{18}$F-deoxyglucose uptake (table 2 and FIG. 9).

TABLE 2

Effects of resveratrol, leucine and HMB on indices of insulin sensitivity in diet-induced obese mice.[1]

| | Control | Low Resveratrol[2] | High Resveratrol[3] | Low HMB[4] | Low Resv/ Low HMB | Low Resv/ High HMB[5] | Low Resv/ Leucine[6] | P value |
|---|---|---|---|---|---|---|---|---|
| Glucose (mM) | 4.97 ± 0.60$^a$ | 5.14 ± 0.85$^a$ | 5.14 ± 0.75$^a$ | 4.28 ± 0.49$^a$ | 4.67 ± 0.49$^a$ | 4.33 ± 0.41$^a$ | 5.05 ± 0.92$^a$ | NS |
| Insulin (μU/mL) | 12.5 ± 3.4$^a$ | 10.4 ± 1.6$^a$ | 10.1 ± 2.7$^a$ | 8.3 ± 1.1$^a$ | 5.8 ± 0.7$^b$ | 3.9 ± 1.2$^b$ | 5.5 ± 1.4$^b$ | P < 0.005 |
| HOMA$_{IR}$ | 2.61 ± 0.82$^a$ | 2.41 ± 0.66$^a$ | 0.59 ± 0.26$^b$ | 1.93 ± 0.32$^a$ | 1.18 ± 0.25$^c$ | 0.87 ± 0.31$^b$ | 1.14 ± 0.37$^c$ | P < 0.01 |
| Muscle Glucose Uptake ($^{18}$F-deoxyglucose SUV) | 3.64 ± 0.88$^a$ | 3.63 ± 1.29$^a$ | 3.87 ± 0.32$^a$ | 2.99 ± 0.42$^a$ | 5.90 ± 0.41$^b$ | 5.93 ± 1.63$^b$ | 5.68 ± 0.75$^b$ | P < 0.02 |

[1] non-matching letter superscripts in each row denote significant differences at the indicated p value
[2] Low resveratrol: 12.5 mg resveratrol/kg diet
[3] High resveratrol: 225 mg resveratrol/kg diet
[4] Low HMB: 2 g hydroxymethylbutyrate (calcium salt)
[5] Leucine: Leucine increased two-fold, from 1.21% in other diets to 2.42%

Figure 10:
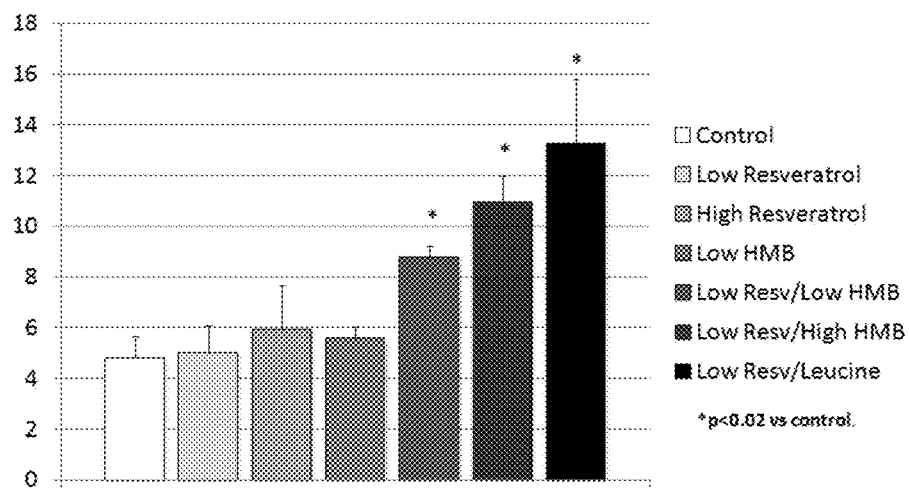
FIG. 10 depicts a graph showing the effects of resveratrol, leucine, and HMB on adipose tissue SIRT1 activity in diet-induced obese mice.

FIG. 10 shows the effects of dietary treatments on adipose tissue Sirt1 activity. Neither resveratrol nor HMB exerted significant independent effects on Sirt1 activity, although high dose resveratrol exhibited a non-significant trend towards an increase. In contrast, combining a low dose of resveratrol with either HMB or leucine resulted in ~two-fold increases in tissue Sirt1 activity. Such sirtuin activation would be anticipated to reduce inflammatory response. Consistent with this concept, the high dose of resveratrol significantly reduced circulating IL-6, while the combination of a low dose of resveratrol (which exerted no independent effect) with HMB resulted in a markedly greater lowering of IL-6 (table 3). Similarly, while neither HMB nor a low dose of resveratrol exerted any effect on MCP-1 or c-reactive protein, the combination of a low dose of resveratrol with either HMB or leucine resulted in significant decreases in both inflammatory biomarkers. Moreover, the anti-inflammatory cytokine adiponectin was increased in response to a low dose of resveratrol in combination with either HMB or leucine, while the individual components at these doses exerted no significant effect (table 3).

ate synergistic effects with leucine, HMB, or sub-therapeutic doses of other compounds. These experiments were conducted in fully differentiated adipocytes (3T3-L1) and myotubes (C2C12). To evaluate the impact of these combinations on cross-talk between adipose and muscle tissues, adipocytes were treated for 48 hours, the medium collected (conditioned media, CM) and then exposed to myotubes; similar experiments were conducted with myotubes treated, CM collected, and exposed to adipocytes. Following assessment of fatty acid oxidation, Sirt1 activity, AMPK activity, mitochondrial biogenesis and glucose utilization (measured as glucose-induced extracellular acidification in the absence of fatty acids in the media) were assessed for lead combinations and appropriate controls.

Cell Culture: C2C12 and 3T3-L1 preadipocytes (American Type Culture Collection) were plated at a density of 8000 cells/cm$^2$ (10 cm$^2$ dish) and grown in Dulbecco's modified eagle's medium (DMEM) containing 10% fetal bovine serum (FBS), and antibiotics (growth medium) at 37° C. in 5% $CO_2$. Confluent 3T3-L1 preadipocytes were induced to differentiate with a standard differentiation

TABLE 3

Effects of resveratrol, leucine and HMB on inflammatory biomarkers in diet-induced obese mice.[1]

|  | Control | Low Resveratrol[2] | High Resveratrol[3] | Low HMB[4] | Low Resv/ Low HMB | Low Resv/ High HMB[5] | Low Resv/ Leucine[6] | P value |
|---|---|---|---|---|---|---|---|---|
| C-reactive protein (ng/mL) | 95.6 ± 9.6$^a$ | 134.8 ± 8.5$^a$ | 123.9 ± 35.3$^a$ | 98.6 ± 5.1 | 67.4 ± 12.2$^b$ | 58.3 ± 12.4$^b$ | 55.9 ± 17.7$^b$ | P < 0.01 |
| IL-6 (pg/mL) | 29.0 ± 6.4$^a$ | 23.2 ± 2.9$^a$ | 14.1 ± 1.3$^b$ | 19.9 ± 3.1$^a$ | 6.9 ± 1.2$^c$ | 4.5 ± 2.6$^c$ | 11.2 ± 4.1$^b$ | P < 0.005 |
| MCP-1 (pg/mL) | 115.8 ± 19.7$^a$ | 104.4 ± 16.5$^a$ | 27.3 ± 6.8$^b$ | 116.8 ± 9.3$^a$ | 24.2 ± 6.2$^b$ | 15.2 ± 3.7$^b$ | 34.9 ± 5.9$^b$ | P < 0.001 |
| Adiponectin (ng/mL) | 11.0 ± 0.9$^a$ | 12.4 ± 1.1 | 14.8 ± 1.8$^b$ | 11.1 ± 1.6$^a$ | 14.1 ± 0.8$^b$ | 16.3 ± 3.0$^b$ | 14.5 ± 1.0$^b$ | P < 0.03 |

[1]non-matching letter superscripts in each row denote significant differences at the indicated p value
[2]Low resveratrol: 12.5 mg resveratrol/kg diet
[3]High resveratrol: 225 mg resveratrol/kg diet
[4]Low HMB: 2 g hydroxymethylbutyrate (calcium salt)
[5]Leucine: Leucine increased two-fold, from 1.21% in other diets to 2.42%

Collectively, these data demonstrate synergy between low doses of resveratrol and leucine or its metabolite HMB in activating Sirt1 and Sirt1-dependent outcomes. These include increased fat oxidation and attenuation of adiposity and obesity, augmentation of insulin sensitivity and reversal of insulin resistance, and attenuation of systemic inflammatory stress.

Example 5—Synergistic Effects of Polyphenols and Related Compounds on Sirtuin Activation and Downstream Pathways All compounds were tested for potential to independently or synergistically modulate sirtuin signaling either by direct stimulation or indirect via upstream signaling via AMPK. A key outcome of Sirt1 signaling is stimulation of PGC1-α and subsequent stimulation of mitochondrial biogenesis and fatty acid oxidation. Accordingly, fatty acid oxidation, measured as palmitate-induced oxygen consumption as described below, was utilized as a sensitive first level of screening for aerobic mitochondrial metabolism. A dose-response curve for fatty acid oxidation was established for each compound studied, and a "sub-therapeutic dose" was defined as the highest dose that exerted no effect in this system. This dose, typically found to be in the 200-1000 nM range for most compounds studied, was then used to evalumedium consisting of DMEM medium supplemented with 10% FBS, 250 nM dexamethasone, 0.5 mM 3-Isobutyl-1-methylxanthine (IBMX) and 1% penicillin-streptomycin. Preadipocytes were maintained in this differentiation medium for 3 days and subsequently cultured in growth medium. Cultures were re-fed every 2-3 days to allow >90% cells to reach fully differentiation before conducting chemical treatment. For differentiation of C2C12 cells, cells were grown to 100% confluence, transferred to differentiation medium (DMEM with 2% horse serum and 1% penicillin-streptomycin), and fed with fresh differentiation medium every day until myotubes were fully formed (3 days).

Measurements:

Fatty acid oxidation: Cellular oxygen consumption was measured using a Seahorse Bioscience XF24 analyzer (Seahorse Bioscience, Billerica, Mass.) in 24-well plates at 37° C., as described by Feige et al. (Feige J, Lagouge M, Canto C, Strehle A, Houten S M, Milne J C, Lambert P D, Mataki C, Elliott P J, Auwerx J. Specific SIRT1 activation mimics low energy levels and protects against diet-induced metabolic disorders by enhancing fat oxidation. Cell Metabolism 2008; 8:347-358) with slight modifications. Cells were seeded at 40,000 cells per well, differentiated as described above, treated for 24 hours with the indicated treatments, washed twice with non-buffered carbonate-free pH 7.4 low glucose (2.5 mM) DMEM containing carnitine (0.5 mM), equilibrated with 550 µL of the same media in a non-$CO_2$ incubator for 45 minutes, and then inserted into the instrument for 15 minutes of further equilibration, followed by $O_2$ consumption measurement. Three successive baseline measures at five-minute intervals were taken prior to injection of palmitate (200 µM final concentration). Four successive 5-minute measurements of $O_2$ consumption were then conducted, followed by 10 minute re-equilibration and another 3-4 5-minute measurements. This measurement pattern was then repeated over a 4-6 hour period. Data for each sample were normalized to the pre-palmitate injection baseline for that sample and expressed as % change from that baseline. Pre-palmitate injection values were 371±14 pmol $O_2$/minute for myotubes and 193±11 pmol $O_2$/minute for adipocytes. The area under of the curve of $O_2$ consumption change from baseline for each sample was then calculated and used for subsequent analysis.

Glucose Utilization: In the absence of a fatty acid source and oxidative metabolism, glycolysis and subsequent lactate production results in extracellular acidification, which was also measured using a Seahorse Bioscience XF24 analyzer. Cells were prepared and equilibrated similar to the methods described above for fatty acid oxidation, with the exclusion of carnitine from the medium. Following instrument equilibration and three baseline measurements, glucose was injected to a final concentration of 10 mM in each well. Measurements were taken as described above utilizing the sensors for extracellular acidification rather than $O_2$ consumption. Insulin (final concentration of 5 nM) was added to some wells as a positive control. Data for each sample were normalized to the pre-glucose injection baseline for that sample and expressed as % change from that baseline. The area under of the curve of extracellular acidification change from baseline for each sample was then calculated and used for subsequent analysis.

Mitochondrial biogenesis: Mitochondrial biogenesis was assessed as change in mitochondrial mass, as described by Sun et al. (Sun X and Zemel M B (2009) Leucine modulation of mitochondrial mass and oxygen consumption in skeletal muscle cells and adipocytes. Nutrition and Metabolism 6:26 (doi:10.1.1186/1743-707S-6-26)). The mitochondrial probe NAO (Invitrogen, Carlsbad, Calif.) was used to analyze mitochondrial mass by fluorescence (excitation 485 nm and emission 520 nm). and quantitative data were obtained with a fluorescence microplate reader (Synergy HT, BioTek Instruments, Winooski, Vt.). The intensity of fluorescence was expressed as arbitrary units per µg protein and normalized to control values within each assay.

AMPK Activity: AMP-activated protein kinase (AMPK) was measured using a commercial kit (CycLex AMPK Kinase Assay Kit, CycLex Co, Ltd, Nagano, Japan). The assay is based upon AMPK phosphorylation of IRS-1 S789. Phosphorylated IRS-1 S789 is then detected by an anti-phospho-mouse IRS-1 S789 monoclonal antibody, which is then bound to horseradish peroxidase conjugated anti-mouse IgG which catalyzes a chromogenic reaction with tetramethylbenzidine. Color formation is proportional to AMPK activity and was measured in 96-well ELISA plates at dual wavelengths (450/540 nm) using a microplate reader (Synergy HT, BioTek Instruments, Winooski, Vt.). These values are expressed as fluorescent units/mg protein and normalized to control values within each assay.

Sirt1 activity: SIRT1 activity was measured by using the SIRT1 Fluorimetric Drug Discovery Kit (BML-AK555, ENZO Life Sciences International, Inc. PA, USA). The assay measures SIRT1 activity by the degree of deacetylation of a standardized substrate containing an acetylated lysine side chain. The substrate utilized is a peptide containing amino acids 379-382 of human p53 (Arg-His-Lys-Lys[Ac]), an established target of SIRT1 activity; SIRT1 activity is directly proportional to the degree of deacetylation of Lys-382. Samples were incubated with peptide substrate (25 µM), and $NAD^+$ (500 µM) in a phosphate-buffered saline solution at 37° C. on a horizontal shaker for 45 minutes. The reaction was stopped with the addition of 2 mM nicotinamide and a developing solution that binds to the deacetylated lysine to form a fluorophore. Following 10 minutes incubation at 37° C., fluorescence was read in a plate-reading fluorometer (Synergy HT, BioTek Instruments, Winooski, Vt.) at an excitation wavelength of 360 nm and an emission wavelength of 450 nm. Resveratrol (100 mM) served as a SIRT1 activator (positive control) and suramin sodium (25 mM) as a SIRT1 inhibitor (negative control). A standard curve was constructed using deacetylated substrate (0-10 µM).

Statistics: Data were analyzed via one-way analysis of variance and least significant difference test was used to separate significantly different group means Results:

Resveratrol-Leucine and Resveratrol-HMB: Leucine (0.5 mM) and HMB (5 µM) stimulated Sirt1 activity and fatty acid oxidation by 30-50%, similar to the effects of 10 µM resveratrol, while lower levels of resveratrol (here 200 nM) exerted no effect; leucine, HMB and a low dose of resveratrol exerted no independent effects on Sirt3. However, the combination of either leucine or HMB with 200 nM resveratrol resulted in a ~90% stimulation of Sirt1, a ~60% stimulation of both Sirt3 and 91%-118% increases in fatty acid oxidation (p<0.005).

The concentrations of leucine and HMB in all experiments described below are 0.5 mM (leucine) and 5 µM (HMB). Each of the compounds studied in combination with leucine or HMB were studied at concentrations that exerted no independent effect on the variables under study in order to assess potential synergies. These concentrations are defined for each compound below.

Chlorogenic acid: Chlorogenic acid is a naturally occurring polyphenol described as a hydroxycinnamic acid; it is an ester of caffeic acid and L-quinic acid (evaluated below). Chlorogenic acid dose-response curves indicate concentrations of 500 nM or below exert no effect; accordingly, this was the concentration used in synergy experiments.

Figure 3:
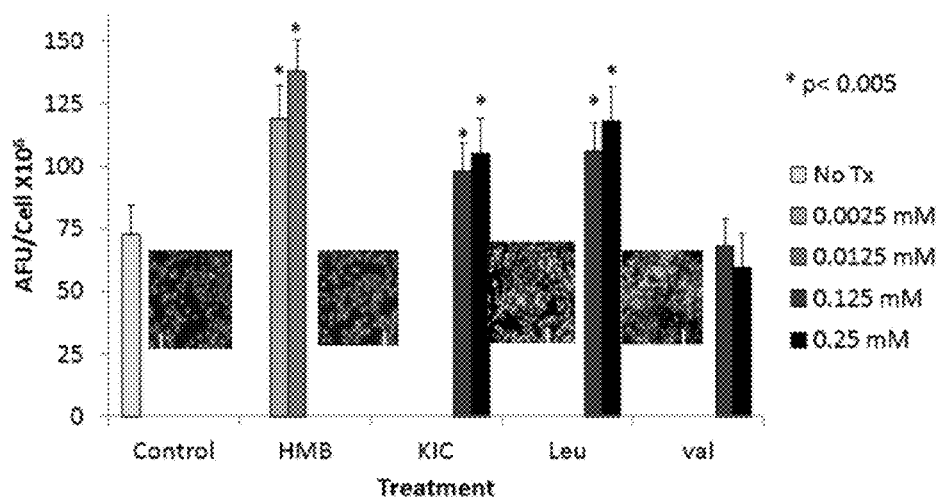
FIG. 3 depicts a graph showing the effects of HMB, KIC, leucine, and valine on mitochondrial biogenesis.
Figure 4:
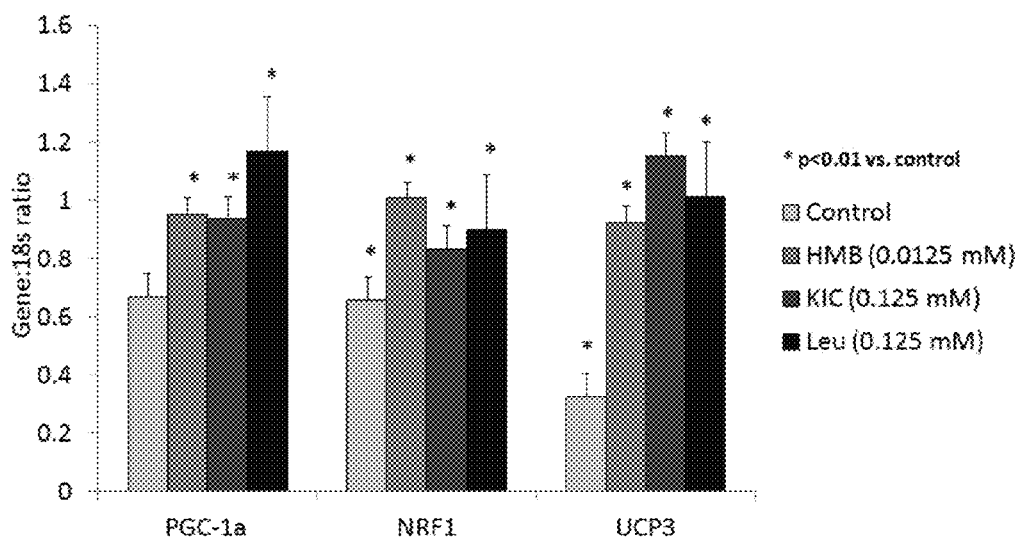
FIG. 4 depicts a graph showing the effects of HMB, KIC, and leucine on the expression of mitochondrial regulatory and component genes.
Figure 12:
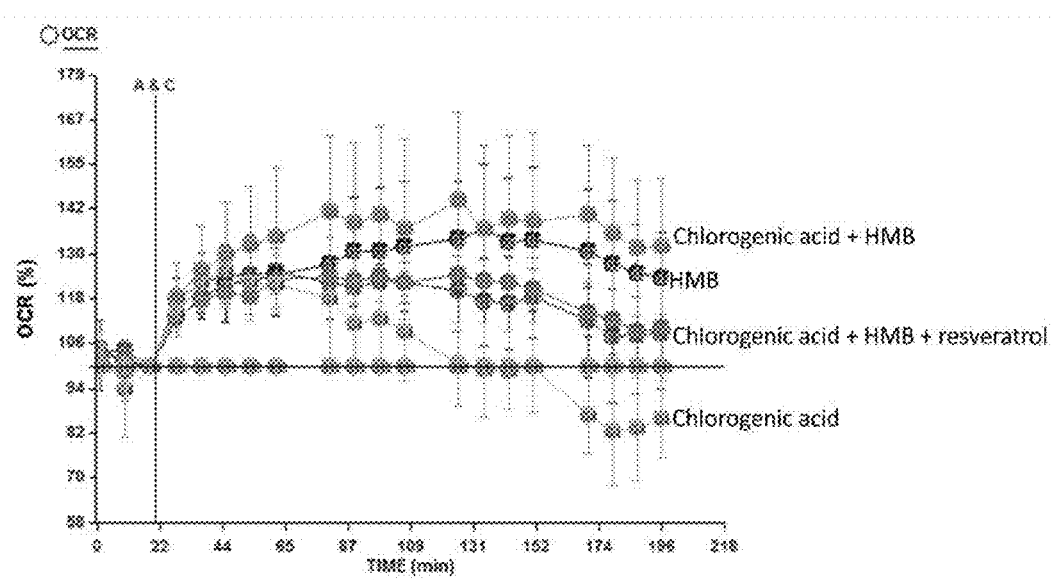
FIG. 12 depicts a graph showing interactive effects of chlorogenic acid (500 nM) with HMB (5 μM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 13:
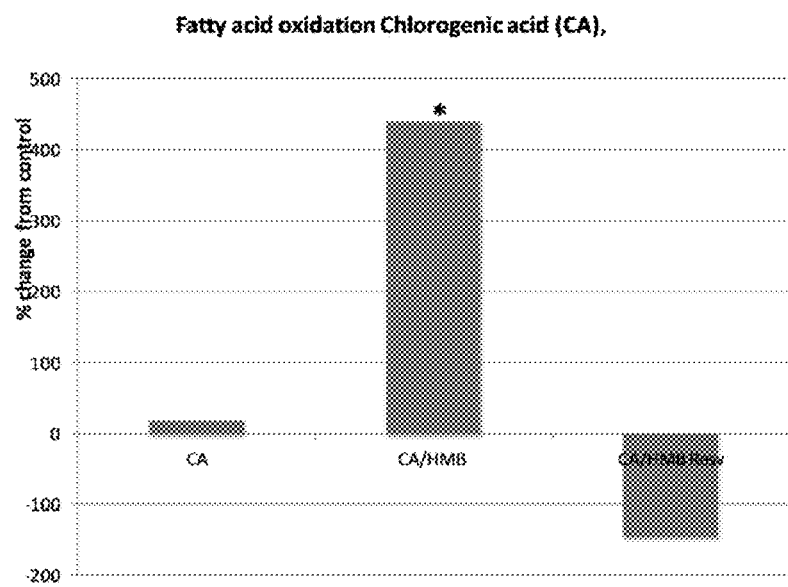
FIG. 13 depicts a graph showing interactive effects of chlorogenic acid (500 nM) and HMB (5 μM) on fatty acid oxidation (data expressed as % change from control value. *p=0.05)

FIG. 12 shows the effects of the chlorogenic acid combinations in myotubes, and significant quantitative data are summarized in FIG. 3. Chlorogenic acid (500 nM)/HMB elicited a 42% increase in fatty acid oxidation with 6 hour treatment (p=0.003) and 441% over 24 hours (p=0.05) in skeletal muscle cells (myotubes), while no significant effect was observed in adipocytes. Notably, adding resveratrol (200 nM) attenuated or eliminated these effects, suggesting potential competition for a common site of action (FIG. 13).

Figure 14:
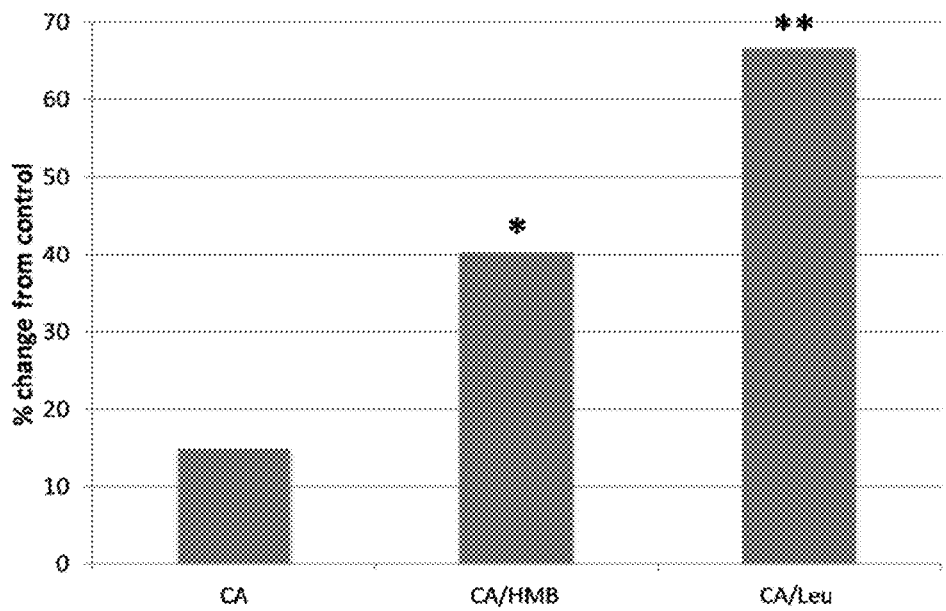
FIG. 14 depicts a graph showing interactive effects of chlorogenic acid (500 nM) with HMB (5 μM) and leucine (0.5 mM) on Sirt1 activity in 3T3-L1 adipocytes (data expressed as % change from control value; *p=0.005; **p=0.0001).

The chlorogenic acid/HMB combination stimulated adipocyte Sirt1 activity 40% (p=0.005) while the chlorogenic acid/leucine combination stimulated Sirt1 by 67% (p=0.0001) (FIG. 14) and more modestly stimulated AMPK activity (30-35%, NS: p=0.078). In contrast to myotubes, the chlorogenic acid/HMB and chlorogenic acid/leucine combinations exerted no direct effect on adipocyte fatty acid oxidation; however, adipocyte conditioned media experiments demonstrated that treatment of adipocytes with these combinations for 48 hours resulted in conditioned media that stimulated myotube fatty acid oxidation by 76% (p=0.013).

Figure 15:
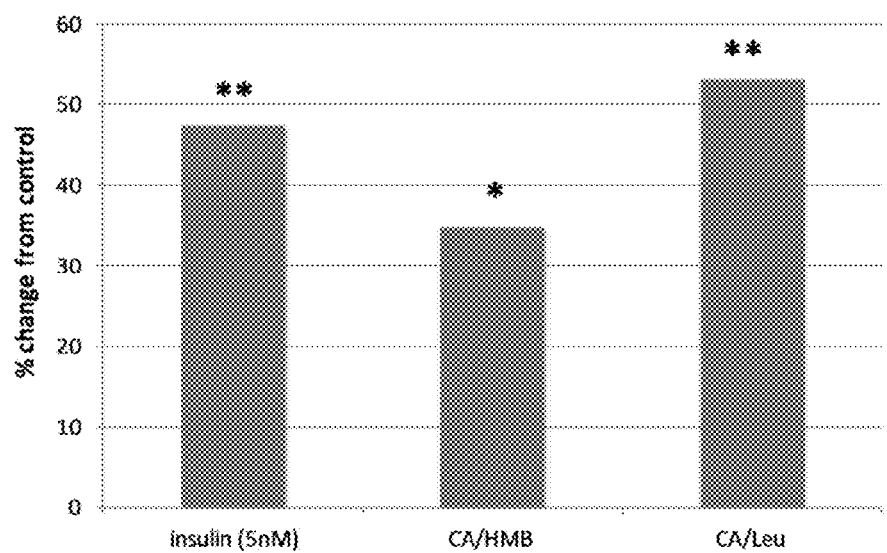
FIG. 15 depicts a graph showing interactive effects of chlorogenic acid (500 nM) with HMB (5 μM) and leucine (0.5 mM) on glucose utilization (*p=0.045; **p=0.007). Glucose utilization was measured as extracellular acidification response to glucose injection. Response to insulin (5 nM) is included for reference.

Both chlorogenic acid-leucine and chlorogenic acid-HMB exerted significant effects on glucose utilization as measured by extracellular acidification responses to glucose addition (chlorogenic acid-leucine: 53%, p=0.007; chlorogenic acid-HMB: 35%, p=0.045; FIG. 15).

Caffeic Acid: Caffeic acid is another naturally occurring phenolic compound described as another hydroxycinnamic acid. Caffeic acid dose-response curves indicate concentrations of 1 µM or below exert no effect; accordingly, this was the concentration used in synergy experiments.

Figure 16:
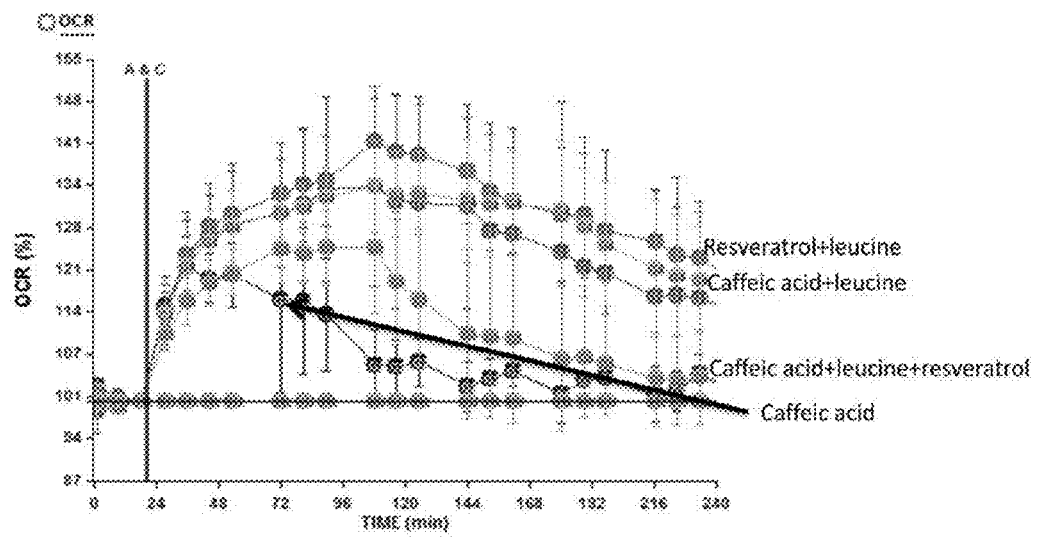
FIG. 16 depicts a graph showing interactive effects of caffeic acid (1 μM) with leucine (0.5 mM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 17:
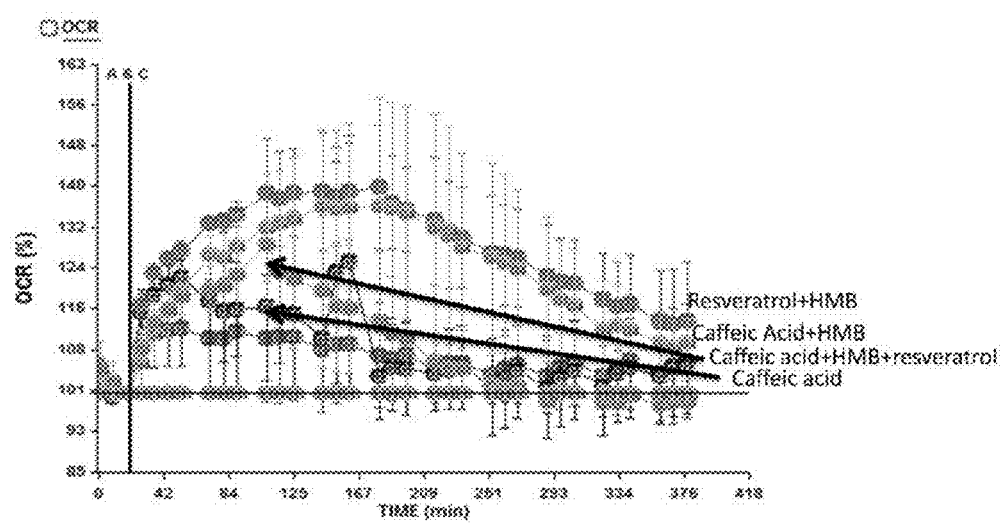
FIG. 17 depicts a graph showing interactive effects of caffeic acid (1 μM) with HMB (5 μM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 18:
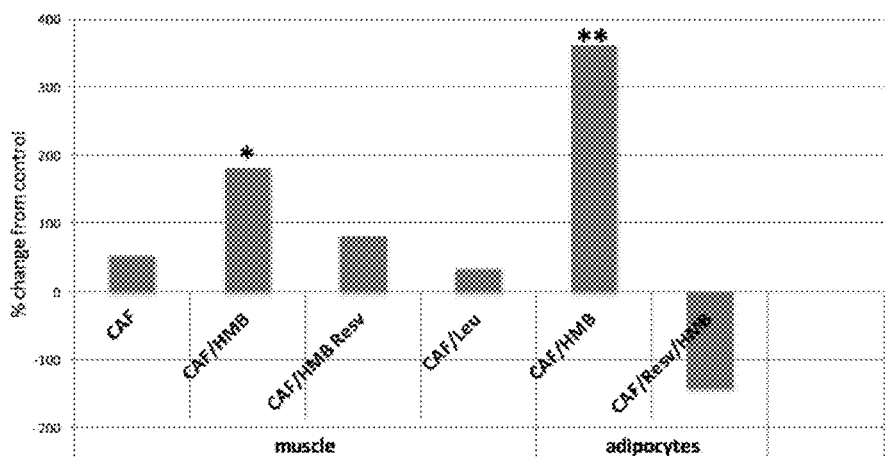
FIG. 18 depicts a graph showing interactive effects of caffeic acid (1 μM), HMB (5 μM), leucine (0.5 mM) and resveratrol (200 nM) on fatty acid oxidation in C2C12 myotubes and 3T3-L1 adipocytes (data expressed as % change from control value;*p=0.05; **p=0.016).

FIGS. 16 and 17 show the effects of the caffeic acid combinations in myotubes, and the quantitative data is summarized in FIG. 18. The caffeic acid-leucine combination exerted a modest, non-statistically significant increase in myotube fatty acid oxidation (35%), while the caffeic acid-HMB combination exerted significant effects on fatty acid oxidation in both adipocytes (361%, p=0.05) and myotubes (182%, p=0.016). These effects were inhibited by the addition of 200 nM resveratrol, suggesting competition, similar to that seen with chlorogenic acid (FIG. 17).

Quinic Acid: Quinic acid is a naturally occurring polyol found in coffee beans and some other plant products. Although not a polyphenol, it is evaluated here because it is a component of chlorogenic acid and may be produced via hydrolysis of chlorogenic acid. Quinic acid dose-response curves indicate concentrations of 500 nM or below exert no effect; accordingly, this was the concentration used in synergy experiments.

Figure 19:
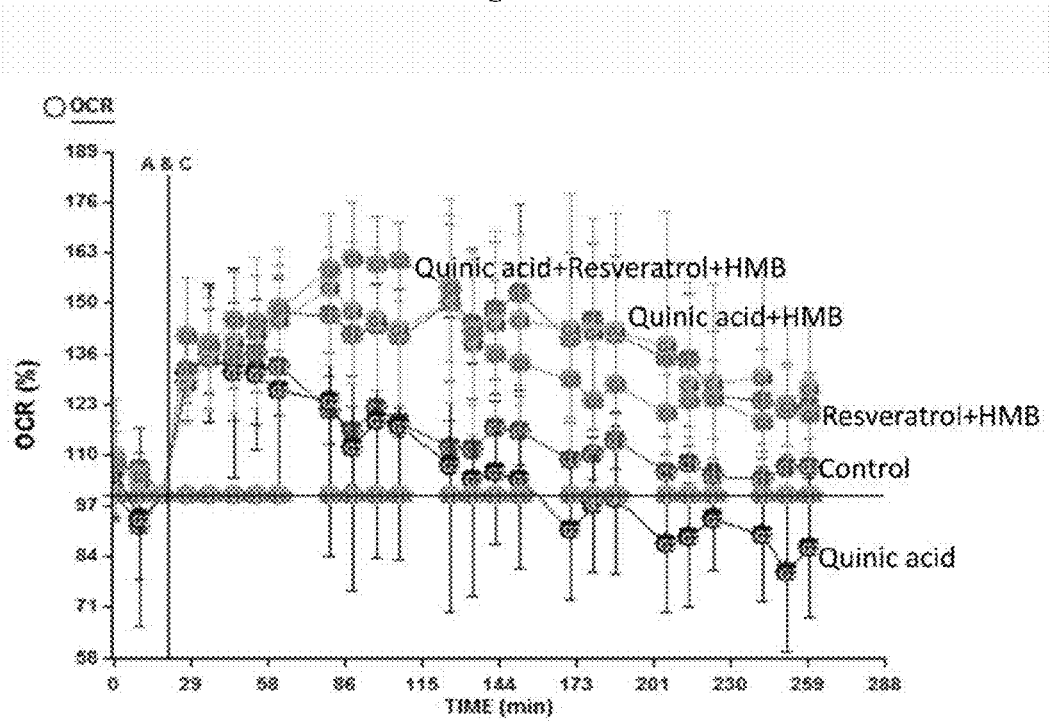
FIG. 19 depicts a graph showing interactive effects of quinic acid (500 nM) with HMB (5 μM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 20:
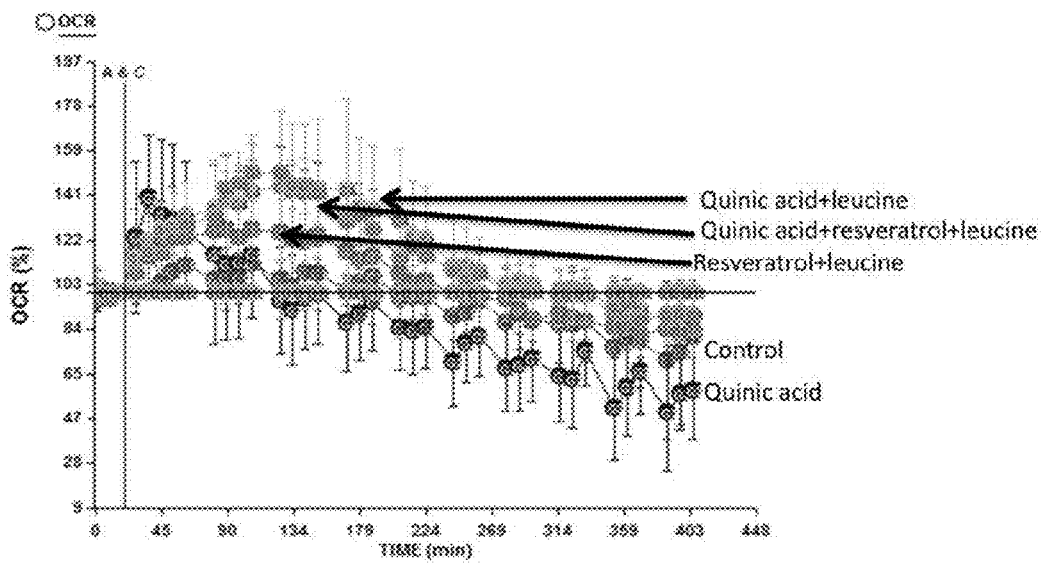
FIG. 20 depicts a graph showing interactive effects of quinic acid (500 nM) with leucine (0.5 mM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 21:
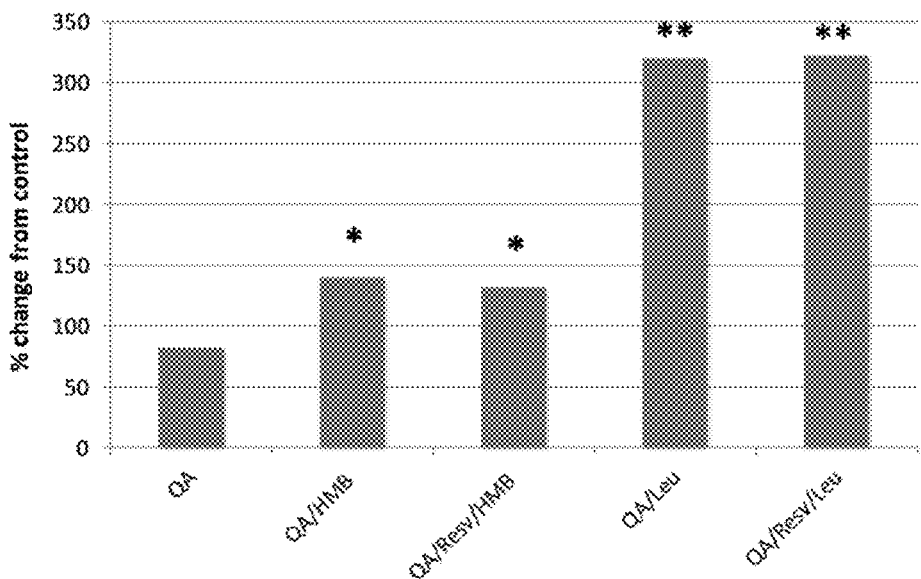
FIG. 21 depicts a graph showing interactive effects of quinic acid (500 nM), HMB (5 μM), leucine (0.5 mM) and resveratrol (200 nM) on fatty acid oxidation in C2C12 myotubes and 3T3-L1 adipocytes (data expressed as % change from control value; *p=0.05; **p=0.012).
Figure 22:
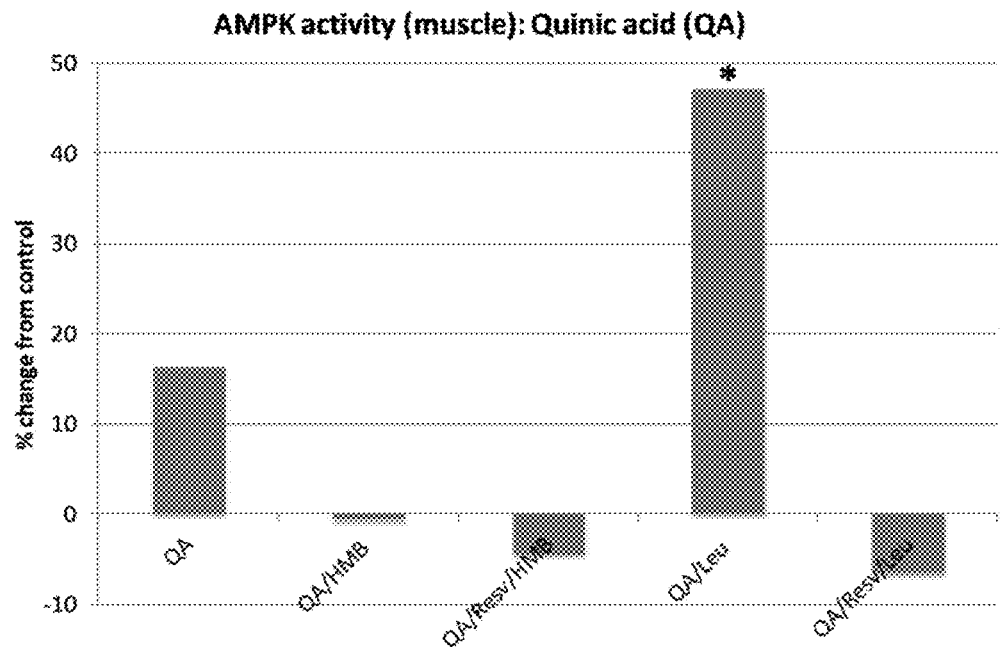
FIG. 22 depicts a graph showing interactive effects of quinic acid (500 nM), HMB (5 μM), leucine (0.5 mM) and resveratrol (200 nM) on AMPK activity (data expressed as % change from control value; *p=0.0001).
Figure 23:
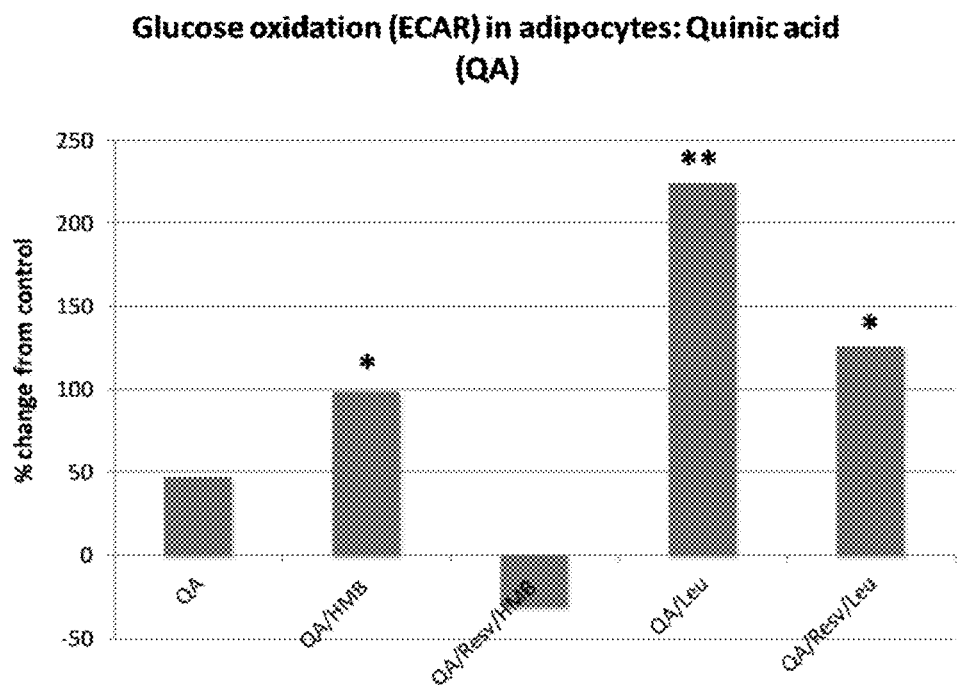
FIG. 23 depicts a graph showing interactive effects of quinic acid (500 nM), HMB (5 μM), leucine (0.5 mM) and resveratrol (200 nM) on glucose utilization. Glucose utilization was measured as extracellular acidification response to glucose injection (*p=0.05; **p=0.0003).

FIGS. 19 and 20 show the effects of the quinic acid combinations in adipocytes, and the quantitative data is summarized in FIG. 21. Quinic acid-HMB and quinic acid-leucine combinations produced robust increases in adipocyte fatty acid oxidation (141% for the quinic acid-HMB combination, p=0.05; 320% for the quinic acid-leucine combination, p=0.012; FIG. 21) and more modest increases in myotubes (~30%, p=0.03). Unlike chlorogenic acid and caffeic acid, addition of resveratrol (200 nM) did not attenuate these effects. The quinic acid combinations appear not to exert their effects directly on Sirt1, as there was no short-term effect on Sirt1 activity, and instead acts upstream with a significant increase in AMPK activity (47%, p<0.0001; FIG. 22). Both the quinic acid-leucine and quinic acid-HMB combinations exerted significant effects on glucose utilization as measured by extracellular acidification responses to glucose addition in both adipocytes and myotubes (quinic acid-HMB, 99%, p=0.05; quinic acid-leucine, 224%, p=0.0003; FIG. 23).

Other Polyols: As noted above, quinic acid was evaluated as a hydrolysis product of chlorogenic acid. To determine if the robust effects of quinic acid reflected the effects of a unique molecule (quinic acid) or polyols as a class of compounds, other polyols were evaluated, as follows. These data suggest that effects of quinic acid are not readily extrapolated to other polyols.

Sorbitol is a sugar alcohol analogue of glucose. Sorbitol dose-response curves indicate concentrations of 500 nM or below exert no effect; accordingly, this was the concentration used in synergy experiments. Addition of this level of sorbitol to either HMB or leucine resulted in stimulation of myotube fatty acid oxidation (44-70%, p=0.023). However, these effects are not significantly different from the independent effects of leucine and HMB in the absence of sorbitol, indicating no synergy.

Myo-inositol is a polyol metabolite of glucose. Myo-inositol dose-response curves indicate concentrations of 100 nM or below exert no effect; accordingly, this was the concentration used in synergy experiments. Combining 100 nM myo-inositol with leucine or HMB produced 60% increase in fat oxidation, comparable to the independent effects of leucine and HMB in the absence of myo-inositol, indicating no synergy.

Maltitol is a disaccharide made by hydrogenation of maltose. Maltitol dose-response curves indicate concentrations of 100 nM or below exert no effect; accordingly, this was the concentration used in synergy experiments. However, no synergy was noted.

Cinnamic Acid: Cinnamic acid is a naturally occurring phenolic found in cinnamon oil. It bears strong structural homology to both caffeic acid and chlorogenic acid. Cinnamic acid dose-response curves indicate concentrations of 500 nM or below exert no effect; accordingly, this was the concentration used in synergy experiments.

Figure 24:
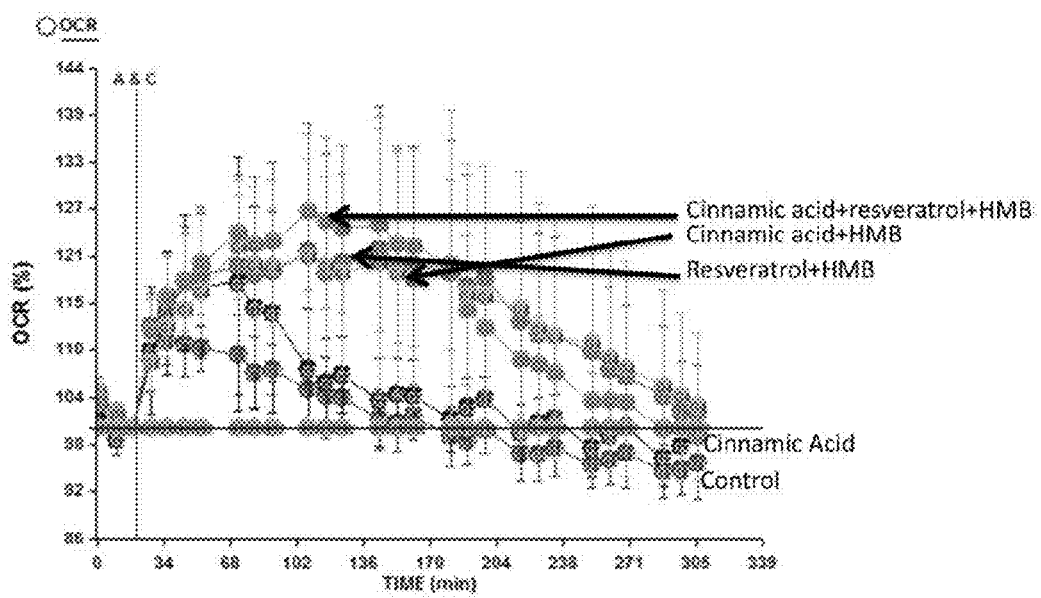
FIG. 24 depicts a graph showing interactive effects of cinnamic acid (500 nM) with HMB (5 μM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 25:
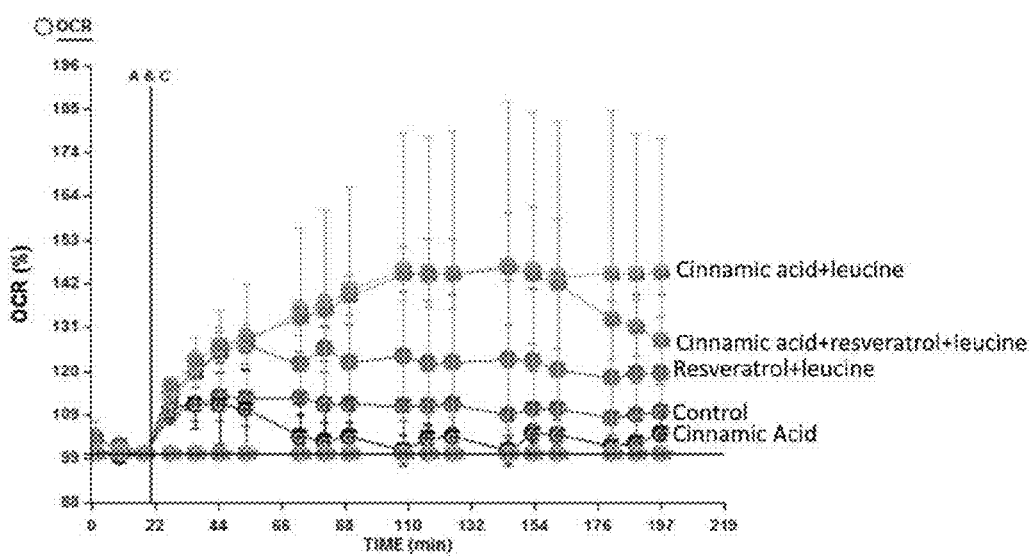
FIG. 25 depicts a graph showing interactive effects of cinnamic acid (500 nM) with leucine (0.5 mM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 26:
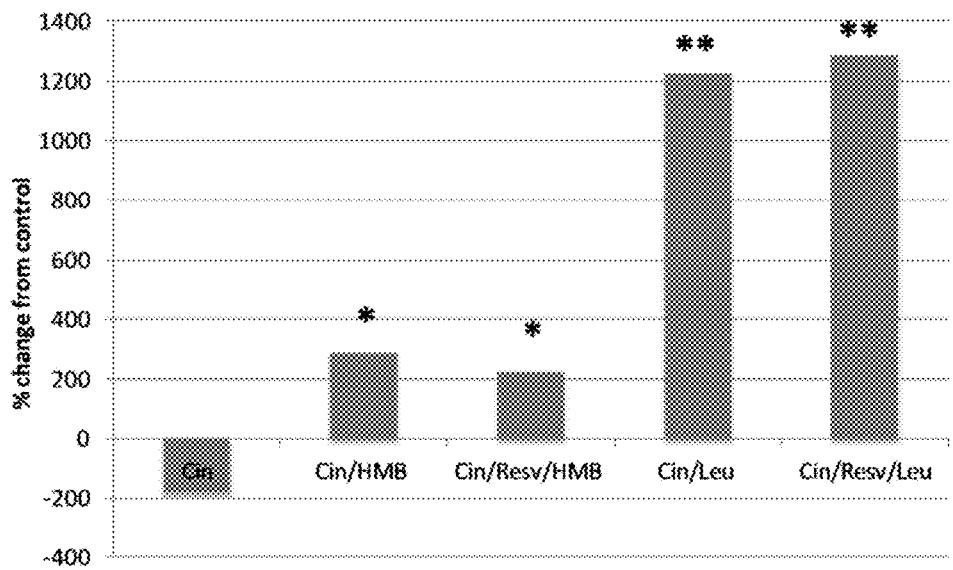
FIG. 26 depicts a graph showing interactive effects of cinnamic acid (500 nM) with HMB (5 μM), leucine (0.5 mM) and resveratrol (200 nM) on fatty acid oxidation in 3T3-L1 adipocytes (data expressed as % change from control value; *p=0.004; **p=0.006).
Figure 27:
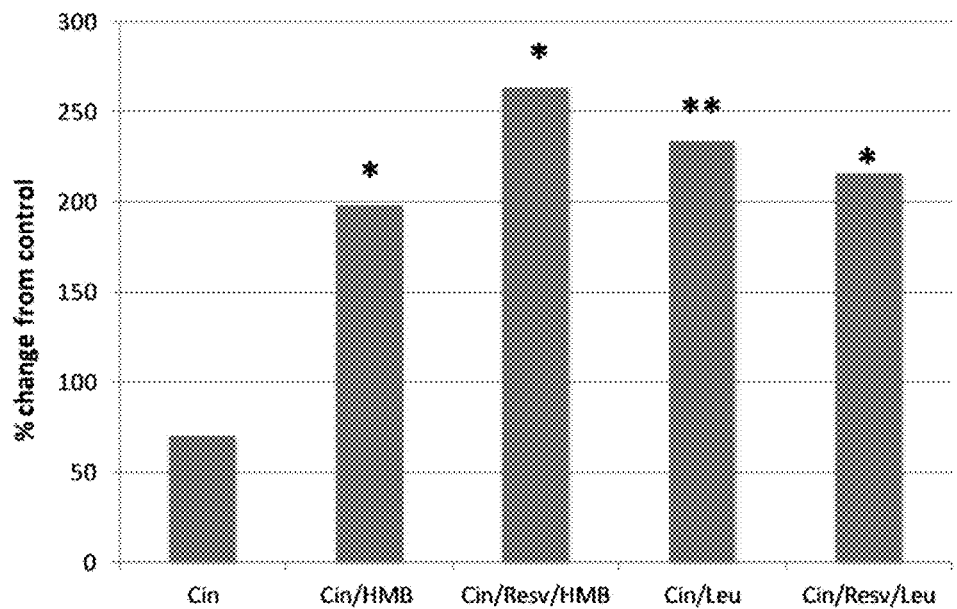
FIG. 27 depicts a graph showing interactive effects of cinnamic acid (500 nM) with HMB (5 μM), leucine (0.5 mM) and resveratrol (200 nM) on fatty acid oxidation in C2C12 myotubes (data expressed as % change from control value; *p=0.02; **p=0.05).
Figure 28:
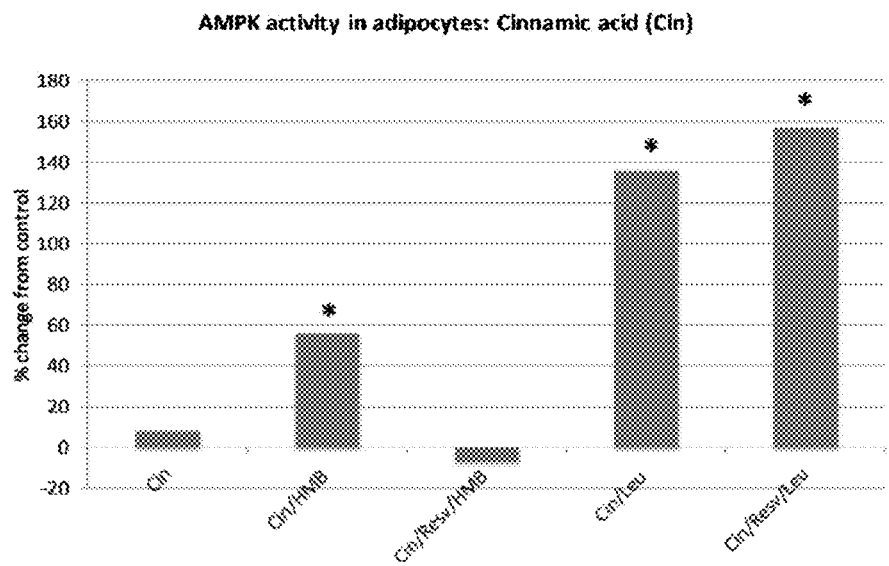
FIG. 28 depicts a graph showing interactive effects of cinnamic acid (500 nM) with HMB (5 μM), leucine (0.5 mM) and resveratrol (200 nM) on AMPK activity (data expressed as % change from control value; *p=0.0001).

The cinnamic acid combinations exerted robust effects in both adipocytes and myotubes. FIGS. 24 and 25 show the effects of the cinnamic acid combinations in myotubes, and the quantitative data for adipocytes and myotubes is summarized in FIGS. 26 and 27, respectively. Cinnamic acid-HMB and cinnamic acid-leucine combinations increased adipocyte fatty acid oxidation by 290% (p=0.004) and 1227% (p=0.006), respectively (FIG. 26). In myotubes, the same combinations increased fatty acid oxidation by 199% (p=0.02) and 234% (p=0.05) (FIG. 27). Further, treatment of adipocytes with these cinnamic acid combinations to produce adipocyte conditioned media which was then applied to myotubes resulted in a 273% increase in myotube fatty acid oxidation (p=0.0002). As with quinic acid, these effects were not attenuated by the addition of 200 nM resveratrol and there was no short-term effect on Sirt1 activity. Instead, the primary effect of these combinations appears to be AMPK-mediated, with Sirt1 effects occurring downstream over a longer period of time, as the combinations resulted in 136-157% increases in AMPK activity (p=0.0001; FIG. 28).

Figure 29:
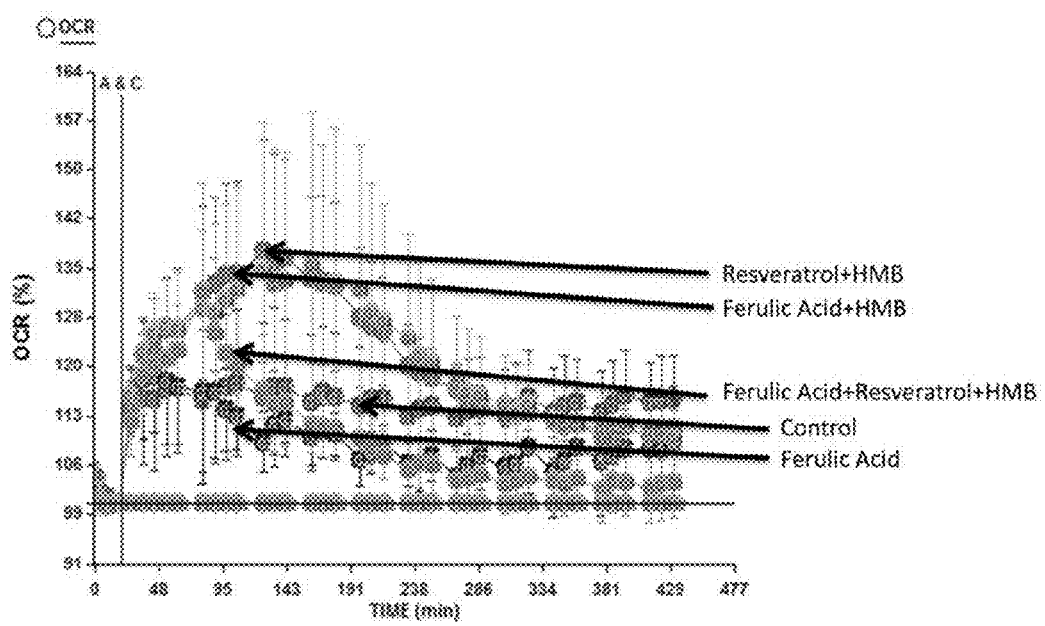
FIG. 29 depicts a graph showing interactive effects of ferulic acid (500 nM) with HMB (5 μM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 30:
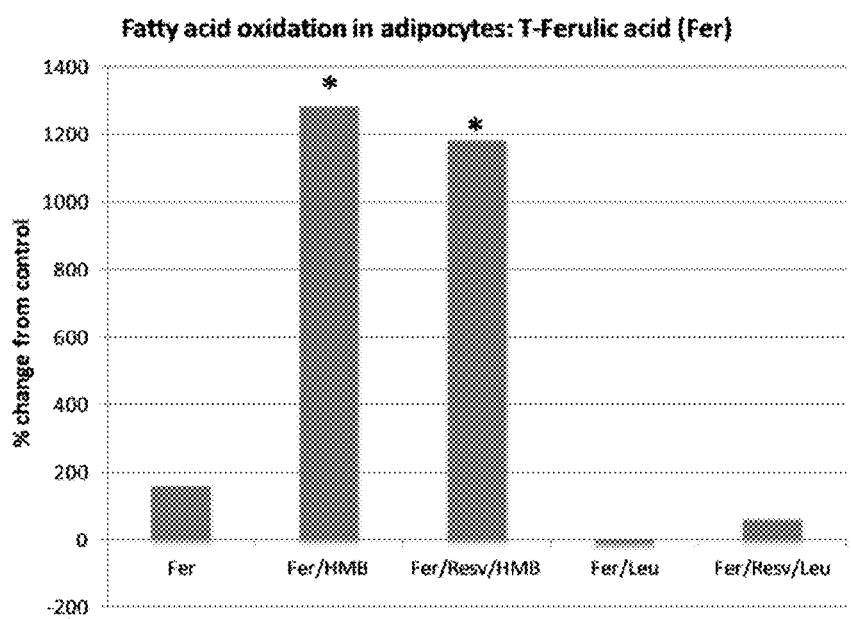
FIG. 30 depicts a graph showing interactive effects of ferulic acid (500 nM) with HMB (5 μM), leucine (0.5 mM) and resveratrol (200 nM) on fatty acid oxidation in 3T3-L1 adipocytes (data expressed as % change from control value; *p=0.018)
Figure 31:
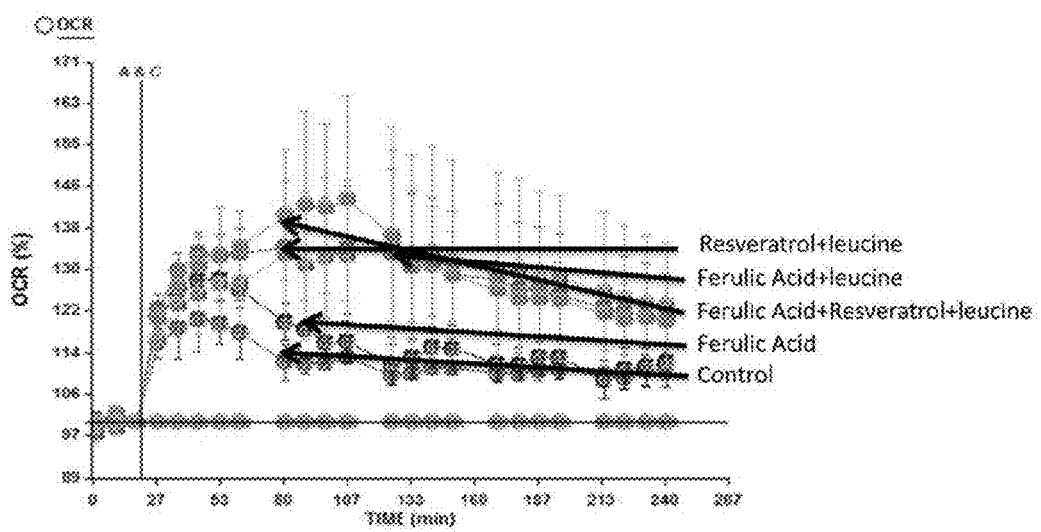
FIG. 31 depicts a graph showing interactive effects of ferulic acid (500 nM) with leucine (0.5 mM) and resveratrol (200 nM) on fatty acid oxidation in C2C12 myotubes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 32:
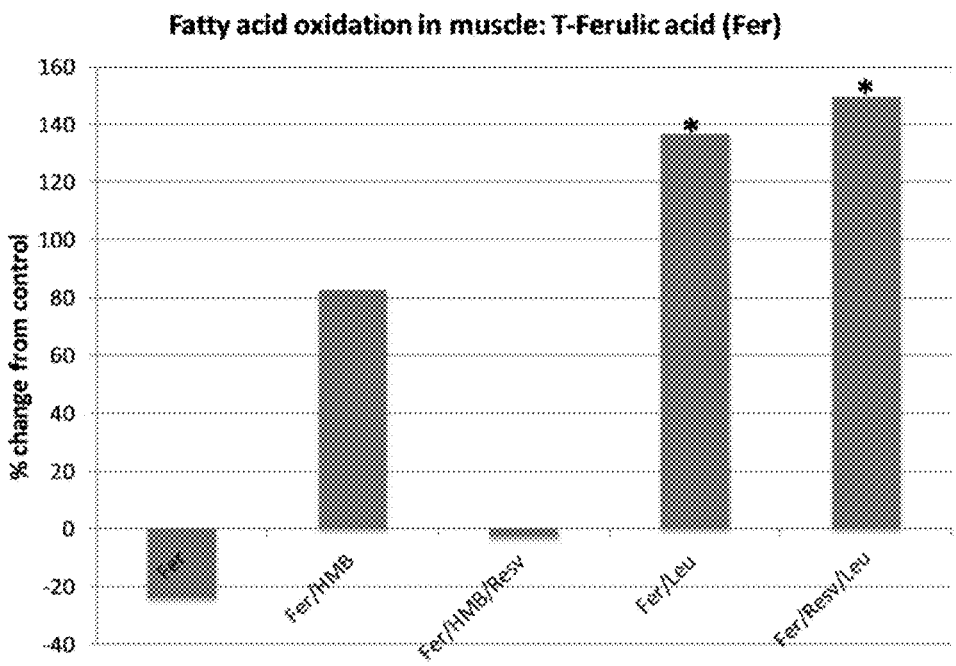
FIG. 32 depicts a graph showing interactive effects of ferulic acid (500 nM) with HMB (5 μM), leucine (0.5 mM) and resveratrol (200 nM) on fatty acid oxidation in 3T3-L1 adipocytes (data expressed as % change from control value; *p=0.034).
Figure 33:
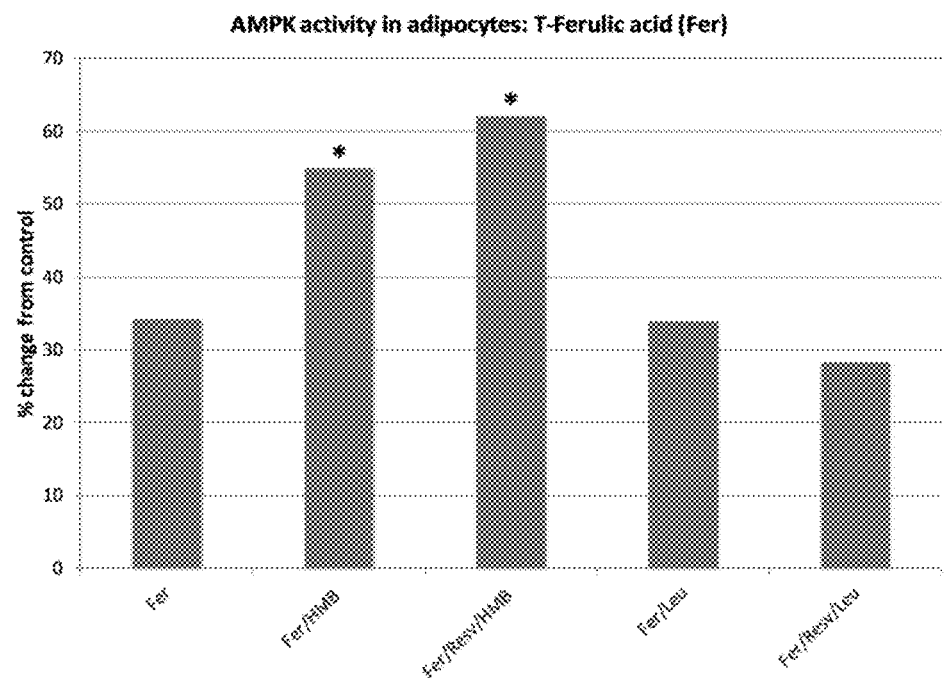
FIG. 33 depicts a graph showing interactive effects of ferulic acid (500 nM) with HMB (5 μM), leucine (0.5 mM) and resveratrol (200 nM) on AMPK activity (data expressed as % change from control value; *p=0.05).

Ferulic acid: Ferulic acid is another hydroxycinnamic acid. Ferulic acid is naturally occurring in coffee and apples, as well as some other fruits, legumes and grains. Ferulic acid dose-response curves indicate concentrations of 500 nM or below exert no effect; accordingly, this was the concentration used in synergy experiments. Ferulic acid combinations exerted strong effects on fatty acid oxidation. The ferulic acid-HMB combination increased fatty acid oxidation by 1281% (p=0.018) in adipocytes (FIGS. 29 and 30) and by 82% in myotubes (p=0.05) (FIGS. 31 and 32). However, the ferulic acid-leucine combination exerted no significant effect in adipocytes (FIG. 30), but increased fatty acid oxidation by 137% in myotubes (p=0.034; FIG. 32). Similar to cinnamic acid, the effects of the ferulic acid-HMB combination in adipocytes and the ferulic acid-leucine combination in myocytes were not attenuated by the addition of resveratrol and there was no short-term direct effect on Sirt1 activity, but there was a significant stimulation of AMPK activity (55-62%, p=0.05; FIG. 33).

Figure 34:
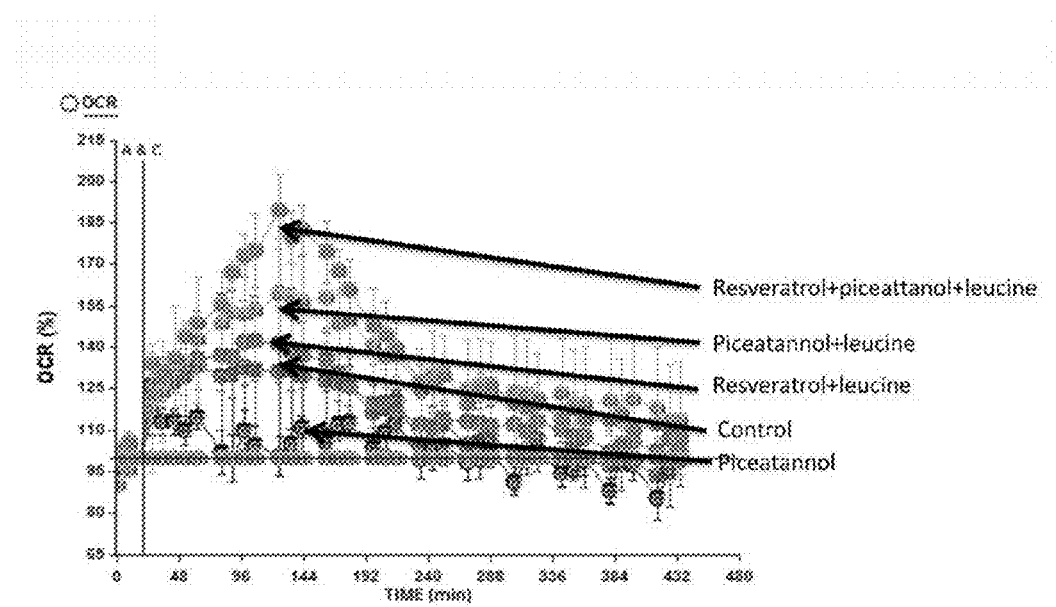
FIG. 34 depicts a graph showing interactive effects of piceatannol (1 nM) with leucine (0.5 mM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 35:
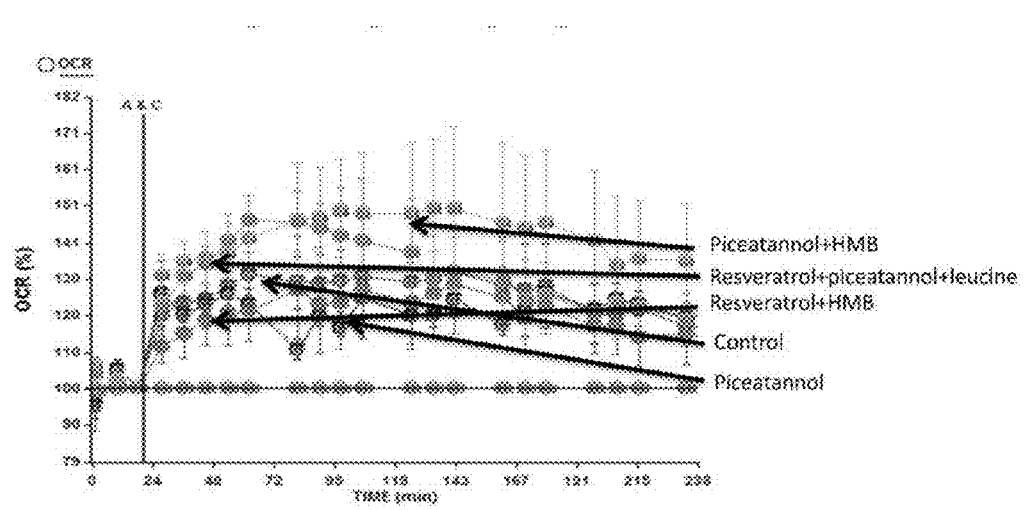
FIG. 35 depicts a graph showing interactive effects of piceatannol (1 nM) with HMB (5 μM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 36:
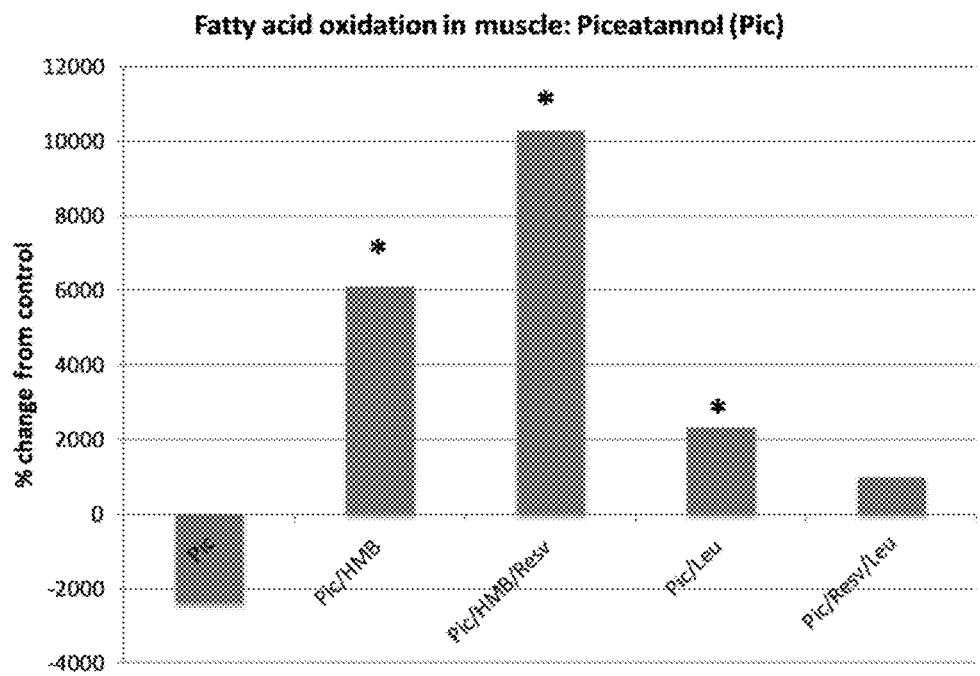
FIG. 36 depicts a graph showing interactive effects of piceatannol (1 nM) with HMB (5 μM), leucine (0.5 mM) and resveratrol (200 nM) on fatty acid oxidation in C2C12 myotubes (data expressed as % change from control value; *p=0.039).

Piceatannol: Piceatannol is a polyphenol classified as a stilbene. It is a metabolite of resveratrol and is naturally occurring in red wine. Piceatannol dose-response curves indicate concentrations of 1 nM or below exert no effect; accordingly, this was the concentration used in synergy experiments. To date, only fatty acid oxidation experiments have been conducted (FIGS. 34-36). Data from these experiments demonstrate significant effects of both combinations in both adipocytes and myotubes. The piceatannol-leucine combination elicited a 73% increase in fatty acid oxidation in adipocytes (p=0.05) and a 2301% increase in fatty acid oxidation in myotubes (p=0.039), and the piceatannol-HMB combination elicited a 60% increase in adipocytes (p=0.05) and a 6085% increase in myotubes (FIG. 36).

Ellagic Acid: Ellagic acid is a large polyphenol naturally occurring in strawberries, raspberries and grapes, as well as a number of other plant products. This polyphenol failed to exert a significant effect in most of our assays, and dose-response curves of ellagic acid indicated little activity, even at high concentrations (50 µM).

Figure 37:
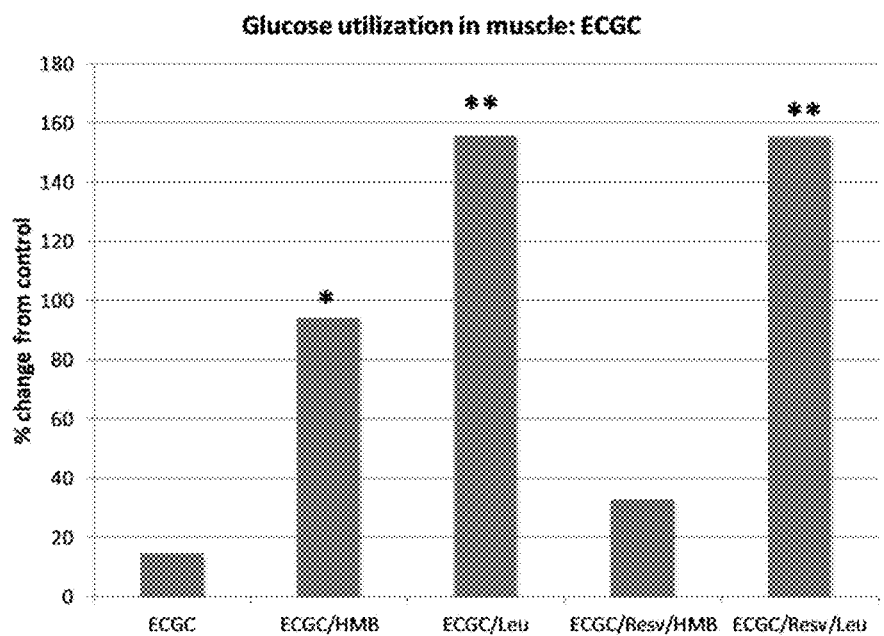
FIG. 37 depicts a graph showing interactive effects of epigallocatechin gallate (EGCG) (1 μM), HMB (5 μM), leucine (0.5 mM) and resveratrol (200 nM) on glucose utilization in C2C12 myotubes. Glucose utilization was measured as extracellular acidification response to glucose injection (*p=0.015; **p=0.017).

Epigallocatechin gallate (EGCG): EGCG is a polyphenol ester of epigallocatechin and gallic acid. EGCG is the predominant catechin in green tea. Despite claims to the contrary, we find this compound to be minimally active in directly stimulating fatty acid oxidation and do not detect synergistic effects with either HMB or leucine in stimulating fatty acid oxidation. However, EGCG (1 µM) did exert significant effects on glucose utilization as measured by extracellular acidification. This level of EGCG exerted no independent effect on glucose utilization, but stimulated a 94% increase in glucose utilization when combined with HMB (p=0.015; FIG. 37) and a 156% increase in glucose utilization when combined with leucine (p=0.017; FIG. 37). Notably, adding resveratrol to this combination exerted no additional effect, but also did not attenuate the observed effects. The effects of these combinations on AMPK and Sirt1 activities have not yet been determined.

Fucoxanthin: Fucoxanthin is a non-polyphenolic pigment found in brown seaweed ("Sea Mustard"; *Undaria pinnatifida*). Fucoxanthin dose-response curves indicate concentrations of 100 nM or below exert no effect; accordingly, this was the concentration used in synergy experiments.

Figure 38:
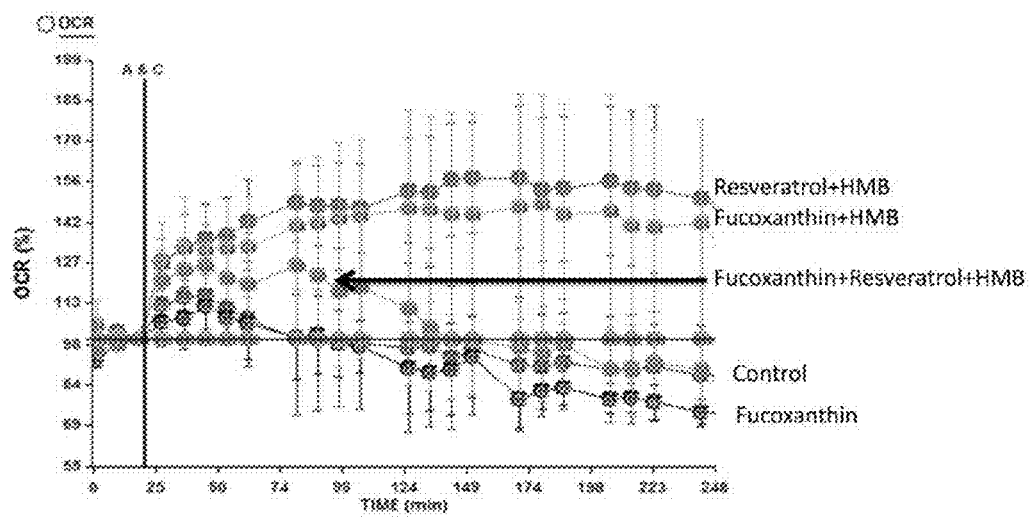
FIG. 38 depicts a graph showing effects of fucoxanthin (100 nM) with HMB (5 μM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 39:
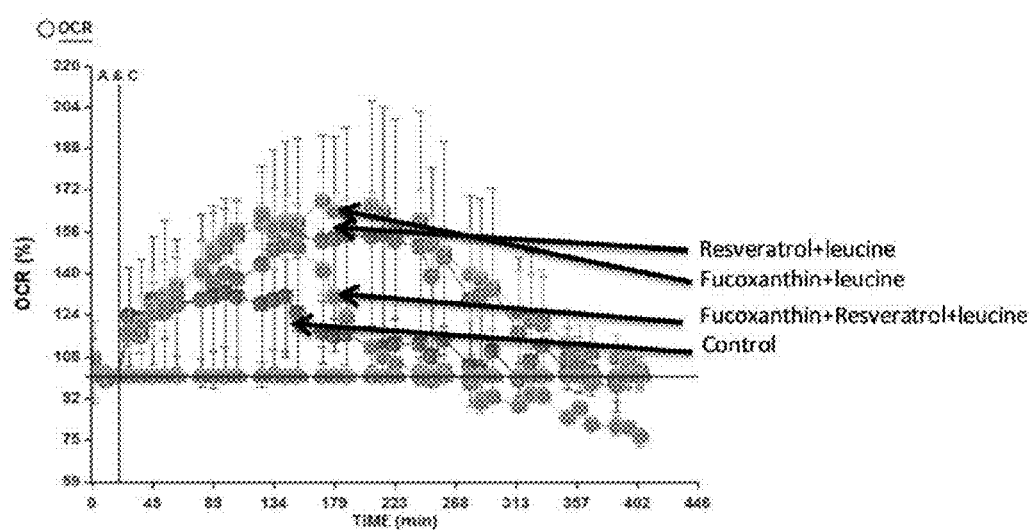
FIG. 39 depicts a graph showing interactive effects of fucoxanthin (100 nM) leucine (0.5 mM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 40:
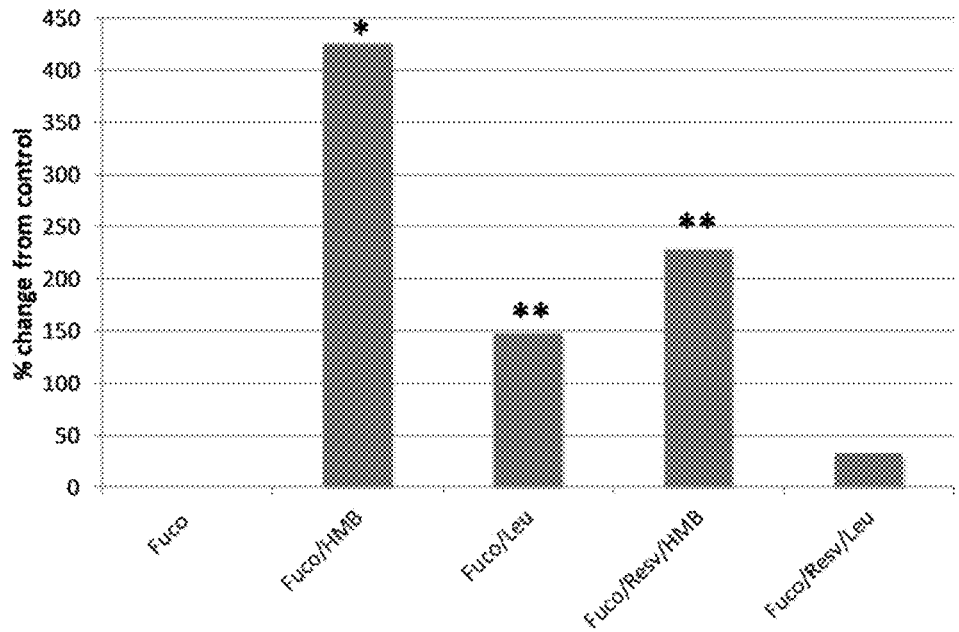
FIG. 40 depicts a graph showing interactive effects of fucoxanthin (100 nM) with HMB (5 µM), leucine (0.5 mM) and resveratrol (200 nM) on fatty acid oxidation in 3T3-L1 adipocytes (data expressed as % change from control value; *p=0.033; **p=0.05).

Fucoxanthin-HMB and fucoxanthin-leucine combinations both exerted potent effects on fatty acid oxidation in adipocytes (fucoxanthin-HMB, 425% increase, p=0.033; fucoxanthin-leucine, 148% increase, p=0.05; FIGS. 38-40) and myotubes (fucoxanthin-HMB, 236% increase, p=0.05; fucoxanthin-leucine, 82% increase, p=0.024). Addition of resveratrol neither attenuated nor augmented these effects.

Figure 41:
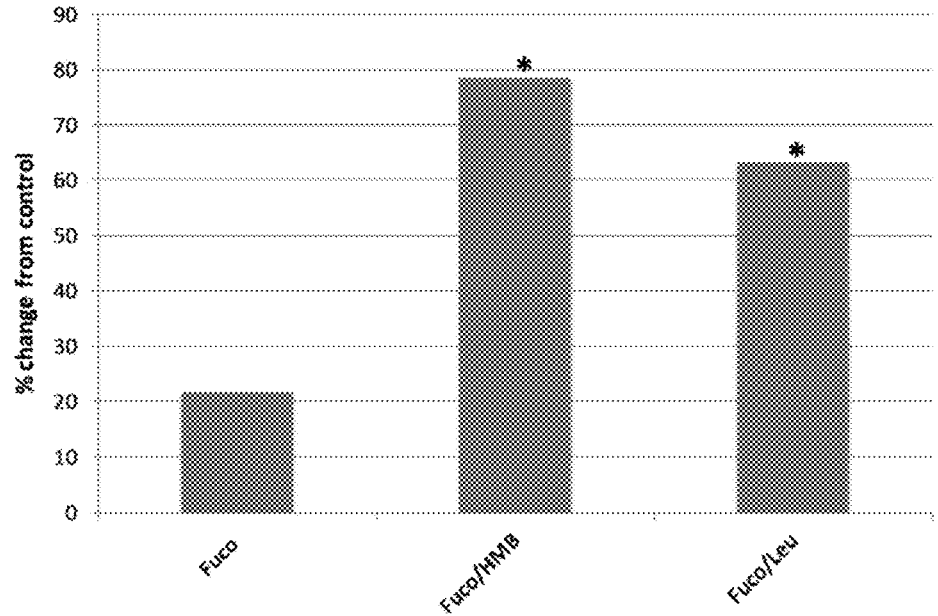
FIG. 41 depicts a graph showing interactive effects of fucoxanthin (100 nM), HMB (5 µM) and leucine (0.5 mM) on glucose utilization in C2C12 myotubes. Glucose utilization was measured as extracellular acidification response to glucose injection (*p<0.04).
Figure 42:
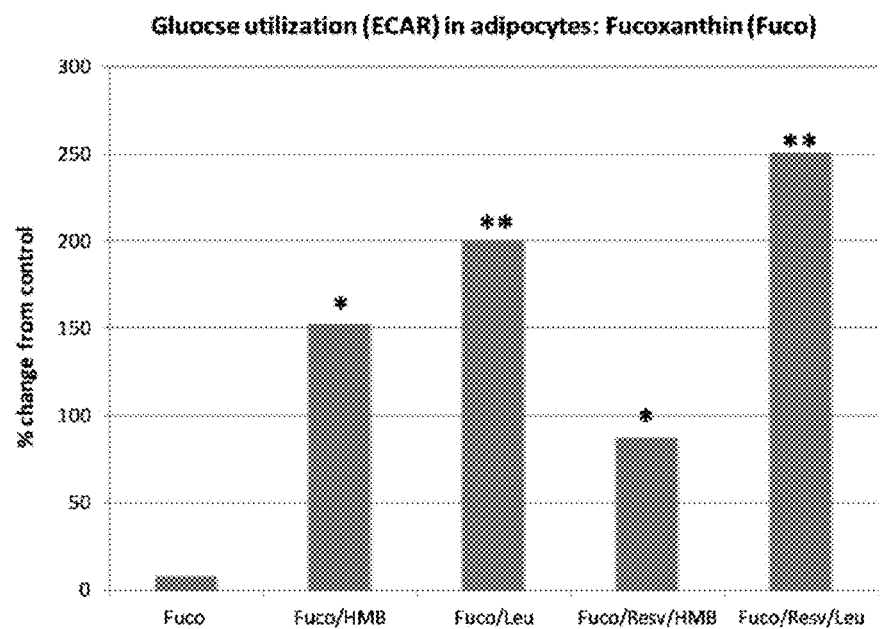
FIG. 42 depicts a graph showing interactive effects of fucoxanthin (100 nM), HMB (5 µM), leucine (0.5 mM) and resveratrol (200 nM) on glucose utilization in 3T3-L1 adipocytes. Glucose utilization was measured as extracellular acidification response to glucose injection (*p=0.02; **p=0.003).

Fucoxanthin combination with both HMB and leucine significantly augmented glucose utilization in myotubes and adipocytes (FIGS. 41 and 42). The fucoxanthin-HMB combination resulted in a 59% increase (p=0.038) and the fucoxanthin-leucine combination resulted in a 63% increase (p=0.034) in myotubes (FIG. 41). In adipocytes, the fucoxanthin-HMB combination resulted in a 321% increase (p=0.02) and the fucoxanthin-leucine combination resulted in a 557% increase (p=0.003; FIG. 42).

The effects of the fucoxanthin combinations on AMPK and Sirt1 activity have not yet been determined.

Figure 43:
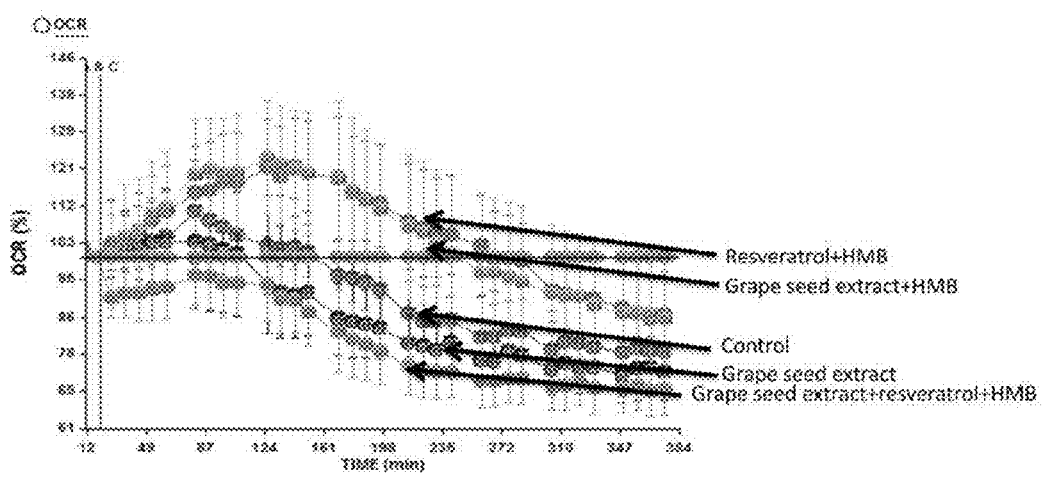
FIG. 43 depicts a graph showing interactive effects of grape seed extract (1 µg/mL) with HMB (5 µM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 44:
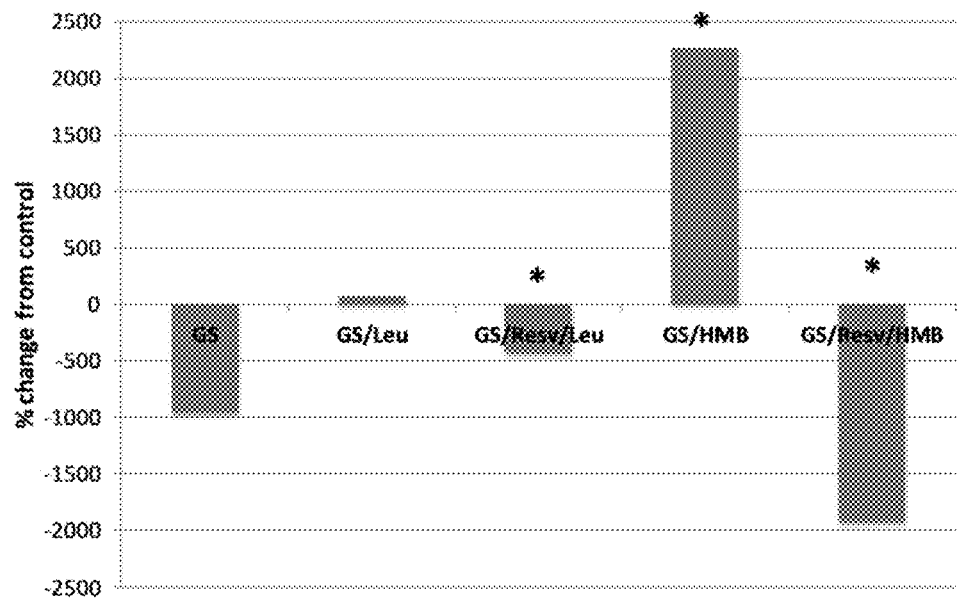
FIG. 44 depicts a graph showing interactive effects of grape seed extract (1 µg/mL) with HMB (5 µM) and resveratrol (200 nM) on fatty acid oxidation in 3T3-L1 adipocytes (data expressed as % change from control value; *p=0.04).
Figure 45:
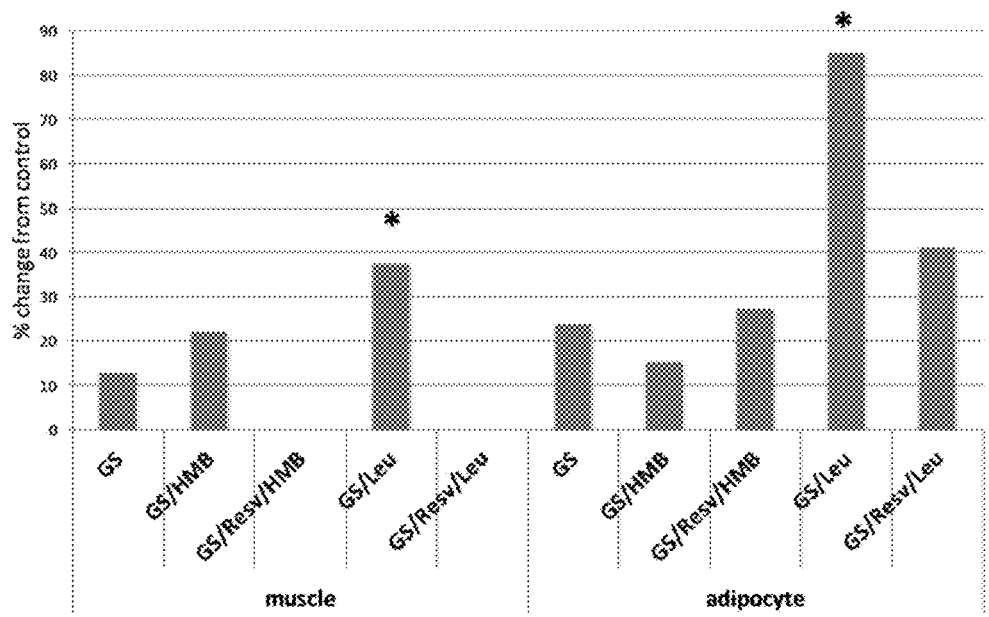
FIG. 45 depicts a graph showing interactive effects of grape seed extract (1 µg/mL) with HMB (5 µM), leucine (0.5 mM) and resveratrol (200 nM) on AMPK activity in 3T3-L1 adipocytes and C2C12 myotubes (data expressed as % change from control value; *p=0.01).

Grape seed extract: Grape seed extract (GSE) is an undifferentiated mixture of polyphenols, including resveratrol, and other naturally occurring compounds in grape. It was selected for study as a broad example of synergy with a naturally occurring group of polyphenols. Since it is a mixture, it is not possible to define concentrations in molar units, so mass units are used for this section. GSE dose-response curves indicate concentrations of 1 µg/mL or below exert no effect; accordingly, this was the concentration used in synergy experiments. GSE-leucine increased adipocyte fatty acid oxidation by 74%, but this did not reach statistical significance. The GSE-HMB combination increased fatty acid oxidation by 2262% (p=0.04; FIGS. 43 and 44). The effects of both combinations were attenuated by the addition of resveratrol to the combinations (FIG. 44). GSE-leucine and GSE-HMB combinations modestly increased both AMPK activity (40-80%, p<0.01; FIG. 45) and Sirt1 activity (15-20%, p<0.03).

Metformin: Metformin, a biguanide, is a commonly prescribed oral hypoglycemic agent. Its known mechanism of action is via stimulation of AMPK, resulting in increased insulin sensitivity as well as increased fat oxidation. Thus, metformin, HMB, leucine, and several of the polyphenols discussed above converge on the same signaling pathways. Accordingly, we sought to determine whether combinations of metformin with these compounds exert a synergistic effect, thereby lowering the concentration of metformin necessary to achieve therapeutic effect.

Figure 46:
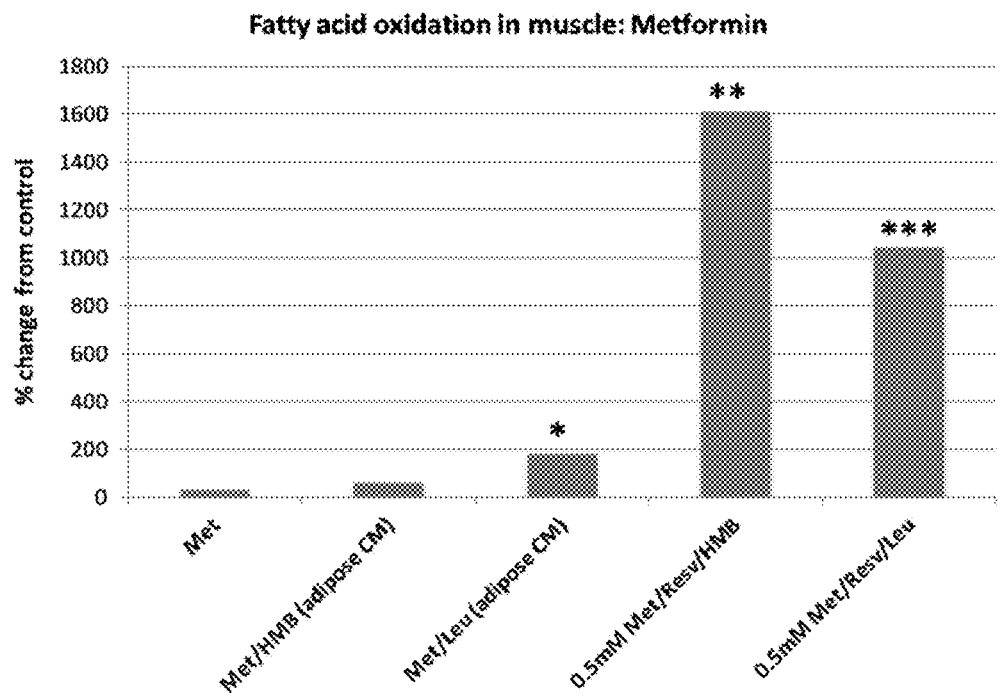
FIG. 46 depicts a graph showing interactive effects of metformin (0.1 mM) with HMB (5 µM), leucine (0.5 mM) and resveratrol (200 nM) on fatty acid oxidation in C2C12 myotubes (data expressed as % change from control value; *p=0.03; p=0.0001; *p=0.001).
Figure 47:
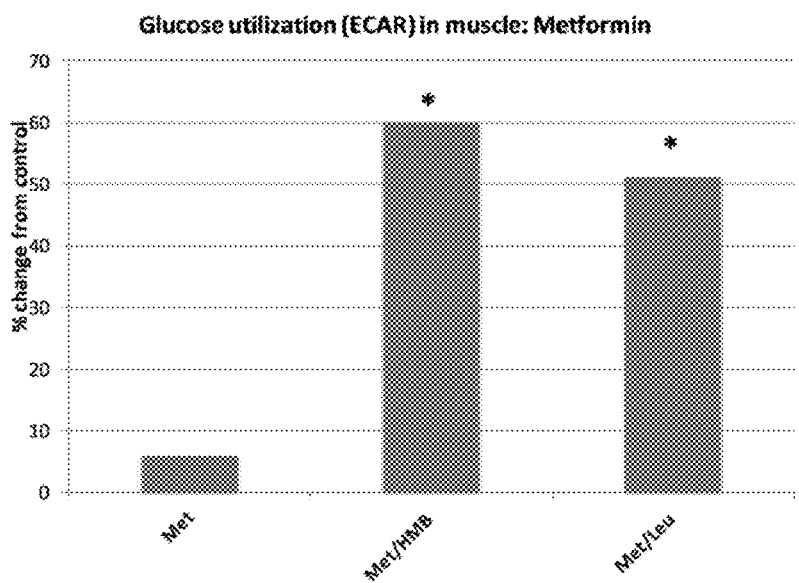
FIG. 47 depicts a graph showing interactive effects of metformin (0.1 mM) with HMB (5 µM) and leucine (0.5 mM) on glucose utilization in C2C12 myotubes. Glucose utilization was measured as extracellular acidification response to glucose injection (*p=0.03).

Metformin dose-response curves indicate concentrations of 0.1 mM or below exert no effect; accordingly, this was the concentration used in synergy experiments. This level is substantially lower than concentrations used to assess independent effects of metformin in cellular studies (2-10 mM). Combining metformin with resveratrol (200 nM) and HMB resulted in a 1607% increase in myotube fatty acid oxidation (p=0.0001; FIG. 46), while the metformin-leucine-resveratrol combination elicited a 1039% increase (p=0.001). Omitting resveratrol from the combinations resulted in statistically significant, but more modest, synergistic interactions with metformin (FIG. 46). Metformin-HMB elicited a 58% increase in myotube fatty acid oxidation (p=0.05) while metformin-leucine elicited a 176% increase (p=0.03). These combinations also significantly augmented glucose utilization in myotubes by 61 and 51%, respectively (p=0.028 for both). Both metformin-HMB and metformin-leucine stimulated myotube glucose utilization by 50-60% (p=0.03; FIG. 47).

Figure 48:
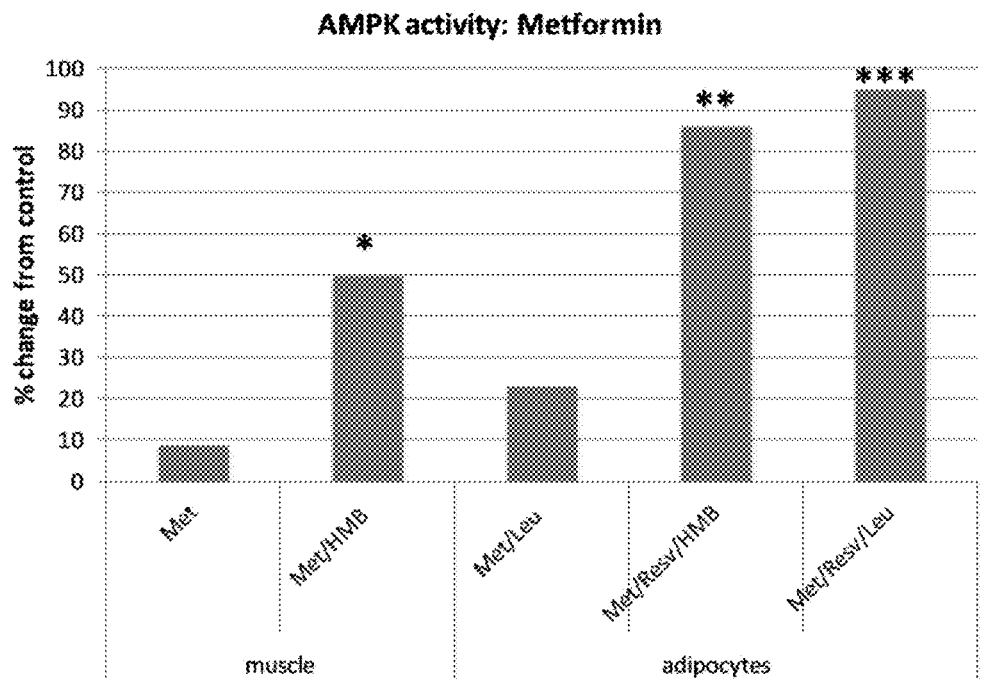
FIG. 48 depicts a graph showing interactive effects of metformin (0.1 mM) with HMB (5 µM), leucine (0.5 mM) and resveratrol (200 nM) on AMPK activity in C2C12 myotubes (data expressed as % change from control value; *p=0.031; p=0.026; *p=0.017)
Figure 49:
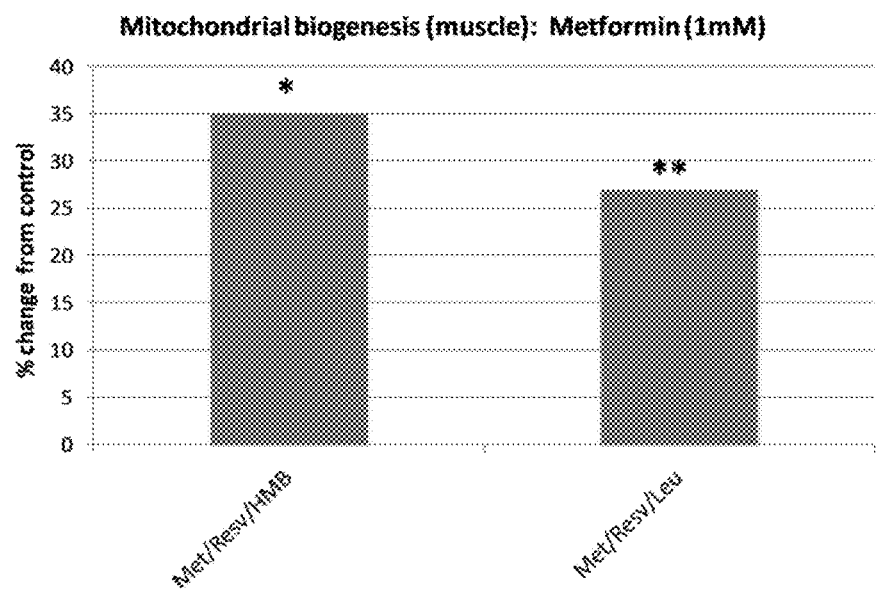
FIG. 49 depicts a graph showing interactive effects of metformin (0.1 mM) with HMB (5 µM) and leucine (0.5 mM) on mitochondrial biogenesis (*p=0.001; **p=0.013).

Consistent with these data, these combinations also significantly increased AMPK activity (FIG. 48). The metformin-HMB combination increased myotube AMPK activity by 50% (p=0.031) and the metformin-leucine combination by 22%. Inclusion of resveratrol (200 nM) significantly augmented these effects; metformin-HMB-resveratrol increased AMPK activity by 86% (p=0.026) and the metformin-leucine-resveratrol combination resulted in a 95% increase (p=0.017). These combinations exerted similar effects on Sirt1 activity. Metformin-HMB increased Sirt1 activity by 38% and 58% in adipocytes and myotubes, respectively (p=0.001 for both). Comparable effects were observed for mitochondrial biogenesis (metformin-HMB-resveratrol, 35%, p=0.001; metformin-leucine-resveratrol, 27%, p=0.013; FIG. 49).

Notably, combining metformin with either grape seed extract or chlorogenic acid resulted in similar stimulation of Sirt1 activity. Metformin-grape seed extract increased activity by 24% (p=0.001) and metformin-chlorogenic acid increased activity by 42% (p=0.004).

Rosiglitazone: Rosiglitazone is an oral hypoglycemic agent in the thiazolidinedione (TZD) class. Its adverse event profile has raised significant concern, limiting its current use, although it is still approved. TZDs act by binding to peroxisome proliferator-activated receptor gamma (PPARγ). One of the targets of PPARγ is peroxisome proliferator-activated receptor gamma coactivator 1-alpha (PGC-1α), a regulator of mitochondrial biogenesis and fatty acid oxidation that is a downstream mediator of Sirt1. Accordingly, we sought to determine whether combinations of rosiglitazone with the compounds investigated here exert a synergistic effect, thereby lowering the concentration of metformin necessary to achieve therapeutic effect.

Rosiglitazone dose-response curves indicate concentrations below 1 nM exert no effect; accordingly, this was the concentration used in synergy experiments. This level is lower than that typically used in cell culture experiments (10 nM-10 µM) and is markedly lower than plasma levels typically achieved following IV or oral dosing (400 nM-1.7 µM).

Figure 50:
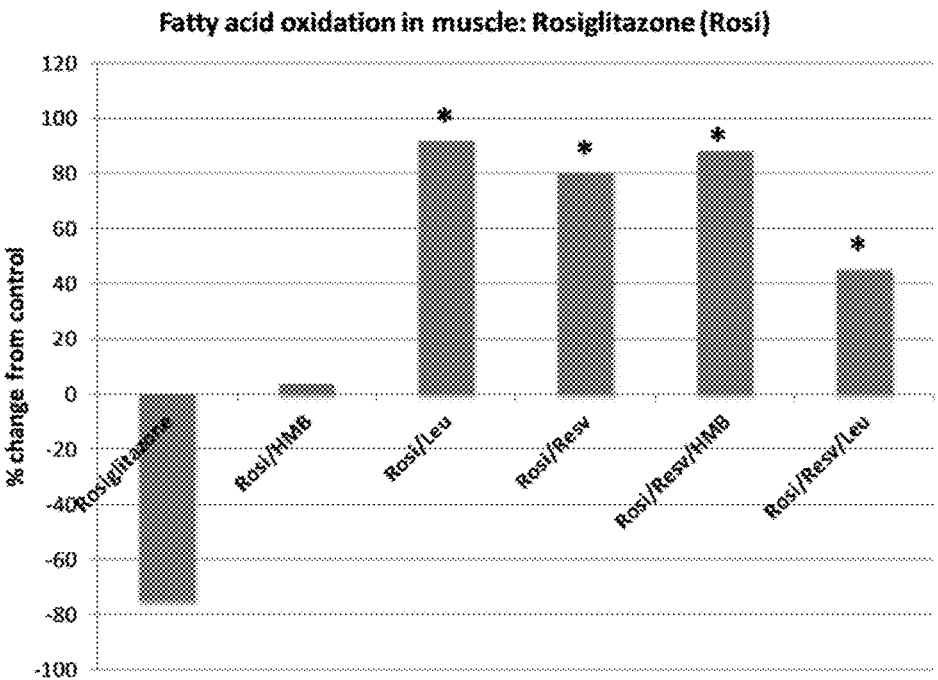
FIG. 50 depicts a graph showing interactive effects of rosiglitazone (1 nM) with HMB (5 µM), leucine (0.5 mM) and resveratrol (200 nM) on fatty acid oxidation in C2C12 myotubes (data expressed as % change from control value; *p=0.009).
Figure 51:
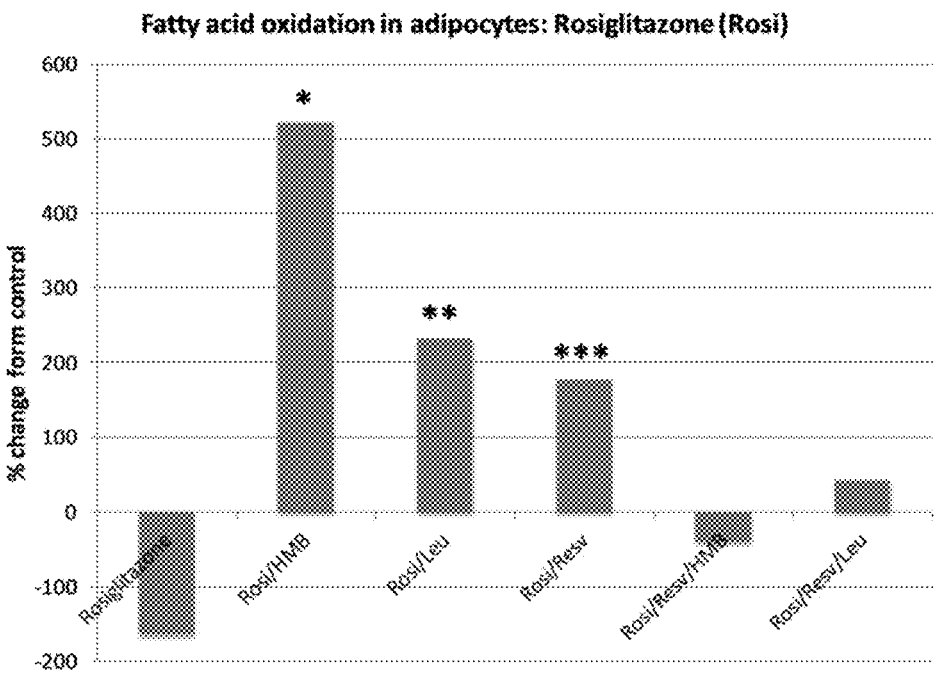
FIG. 51 depicts a graph showing interactive effects of rosiglitazone (1 nM) with HMB (5 µM), leucine (0.5 mM) and resveratrol (200 nM) on fatty acid oxidation in 3T3-L1 adipocytes (data expressed as % change from control value; *p=0.004; p=0.023; *p=0.003).

Combining rosiglitazone with either leucine or HMB resulted in significant stimulation of fatty acid oxidation in both mytubes (FIG. 50) and adipocytes (FIG. 51). The rosiglitazone-HMB combination stimulated fatty acid oxidation by 521% (p=0.004), and the rosiglitazone-leucine combination stimulated fatty acid oxidation by 231% (p=0.023) and myotube fatty acid oxidation by 92% (p=0.009). Combining rosiglitazone with resveratrol (200 nM) also resulted in stimulation of fatty acid oxidation (177%, p=0.003); however, adding resveratrol to the rosiglitazone-HMB or rosiglitazone-leucine combinations was not more effective than the combinations in the absence of resveratrol in myotubes and attenuated the effects of the combinations in adipocytes.

Figure 52:
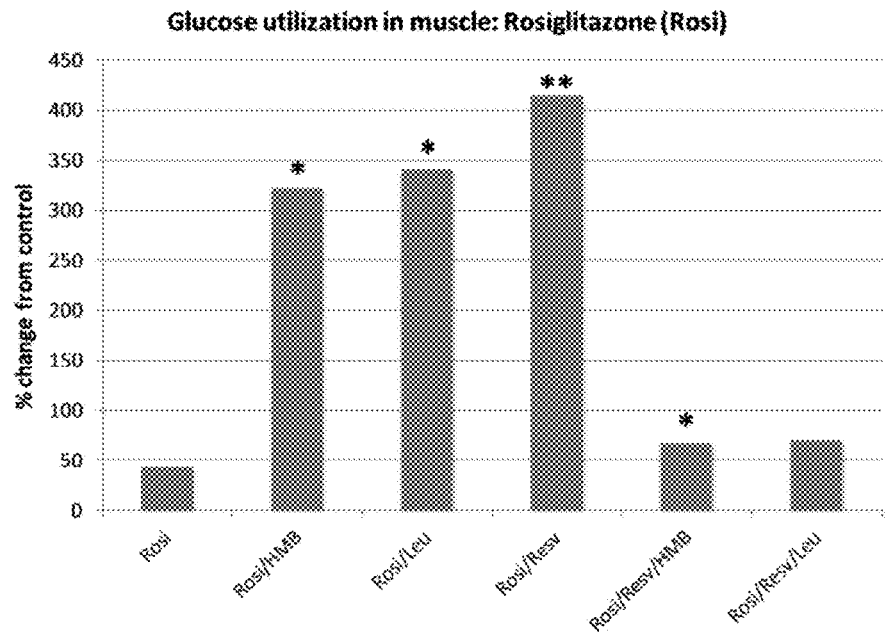
FIG. 52 depicts a graph showing interactive effects of rosiglitazone (1 nM) with HMB (5 µM), leucine (0.5 mM) and resveratrol (200 nM) on glucose utilization in C2C12 myotubes. Glucose utilization was measured as extracellular acidification response to glucose injection (*p=0.05; **p=0.001).

Combining rosiglitazone with either HMB or leucine resulted in marked increases in glucose utilization (FIG. 52). The rosiglitazone-HMB combination stimulated a 322% increase (p=0.05) and the rosiglitazone-leucine combination stimulated a 341% increase. A comparable increase was found when resveratrol (200 nM) was combined with rosiglitazone (415%, p=0.001), but adding resveratrol to either the rosiglitazone-HMB or rosiglitazone-leucine combinations did not further augment glucose utilization.

Phosphodiesterase (PDE) inhibitors: The effects of resveratrol on Sirt1 activation may be mediated, in part, via inhibiting cAMP Phosphodiesterase, resulting in upregulation of AMPK and subsequent activation of Sirt1 rather than a direct effect. However, other this effect may only be relevant at high (>50 µM) resveratrol concentrations. Accordingly we have evaluated the effects of various non-specific PDE inhibitors, as follows.

Figure 53:
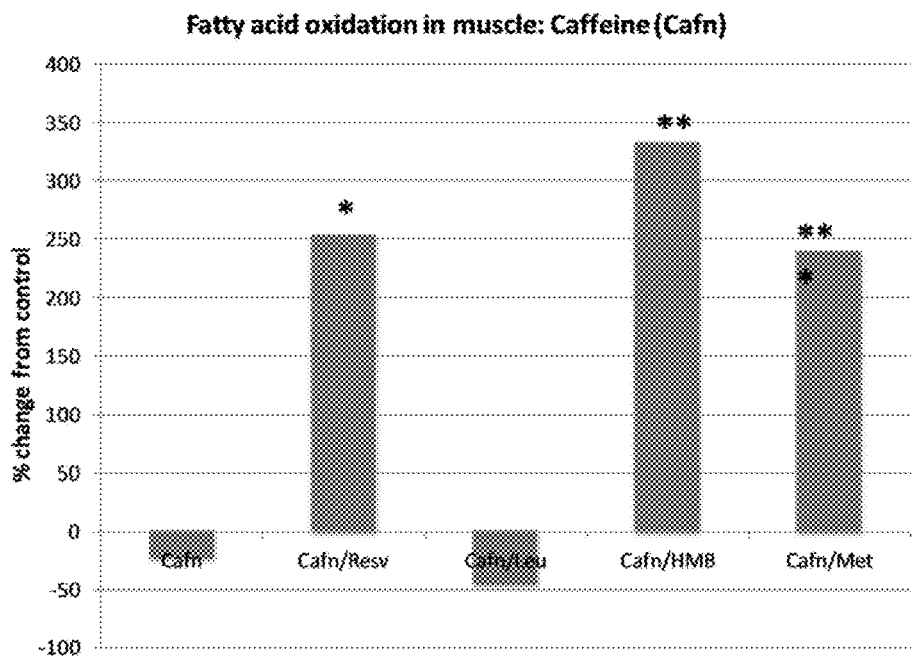
FIG. 53 depicts a graph showing interactive effects of caffeine (10 nM) with HMB (5 µM), leucine (0.5 mM), resveratrol (200 nM) and metformin (0.1 mM) on fatty acid oxidation in C2C12 myotubes (data expressed as % change from control value; *p=0.03; p=0.05; *p=0.013).
Figure 54:
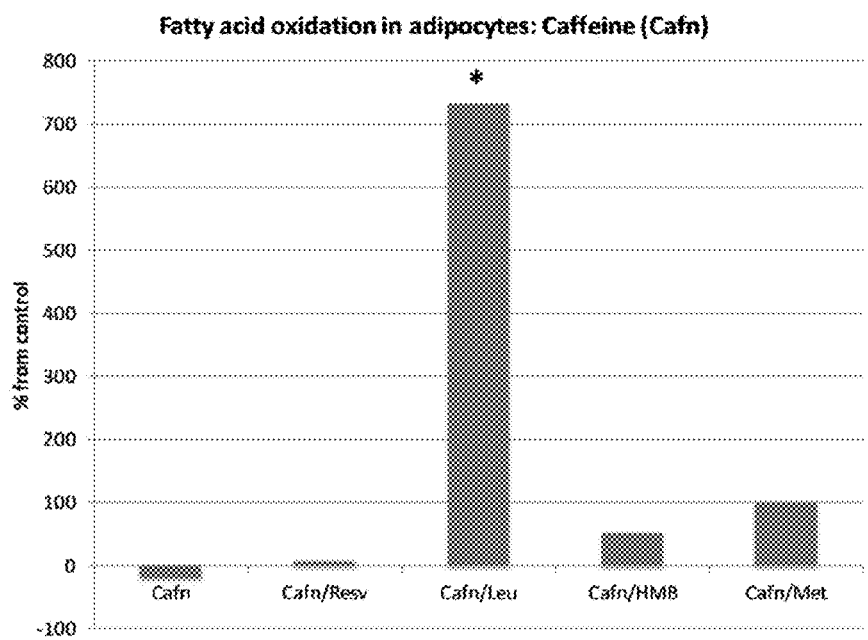
FIG. 54 depicts a graph showing interactive effects of caffeine (10 nM) with HMB (5 µM), leucine (0.5 mM), resveratrol (200 nM) and metformin (0.1 mM) on fatty acid oxidation in 3T3-L1 adipocytes (data expressed as % change from control value. *p=0.008).
Figure 55:
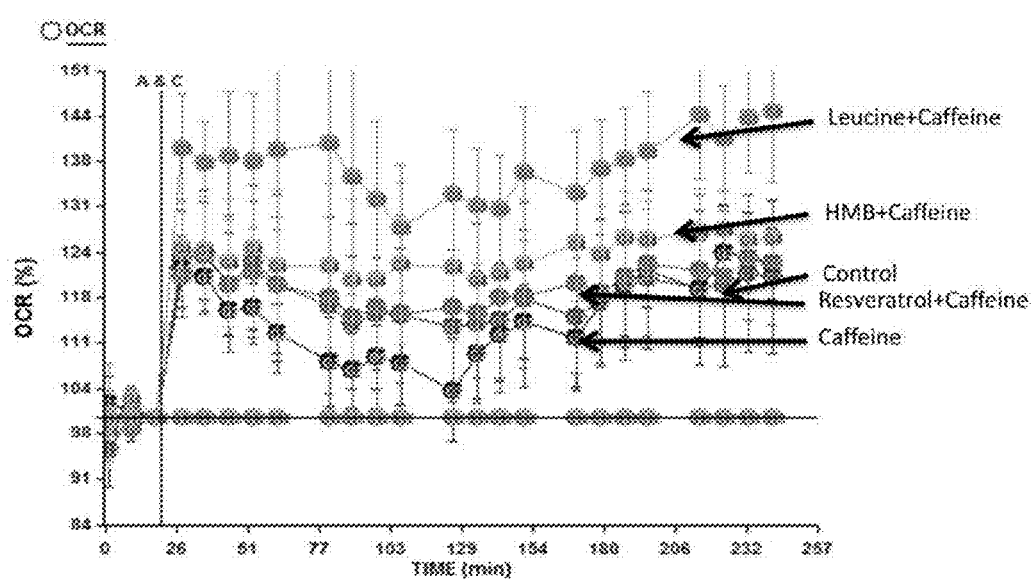
FIG. 55 depicts a graph showing interactive effects of caffeine (10 nM) with HMB (5 µM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).

Caffeine is a naturally occurring methyl-xanthine found primarily in coffee, tea, guarana and yerba mate. Caffeine is both an adenosine antagonist and a non-specific PDE inhibitor. Caffeine dose-response curves indicate concentrations below 10 nM exert no effect; accordingly, this was the concentration used in synergy experiments. This level is ~0.1% of the plasma concentration observed following caffeine consumption (1-10 µM). Combining 10 nM of caffeine with resveratrol (200 nM) resulted in a 254% increase in fatty acid oxidation in myotubes (p=0.03; FIG. 53), while neither component exerted an independent effect. Combining caffeine with 0.5 mM leucine stimulated adipocyte fatty acid oxidation by 732% (p=0.008; FIGS. 54 and 55), and combining caffeine with 5 µM HMB resulted in a 334% increase in fat oxidation in myotubes (p=0.05; FIG. 53). The caffeine-leucine combination also markedly improved muscle cell glucose utilization as measured by extracellular acidification responses to glucose addition (574% improvement, p=0.003). Caffeine also exhibited significant synergy with metformin (0.1 mM), resulting in a 240% increase in myotube fatty acid oxidation (p=0.013; FIG. 53), although it did not exert a synergistic effect on glucose utilization.

Figure 56:
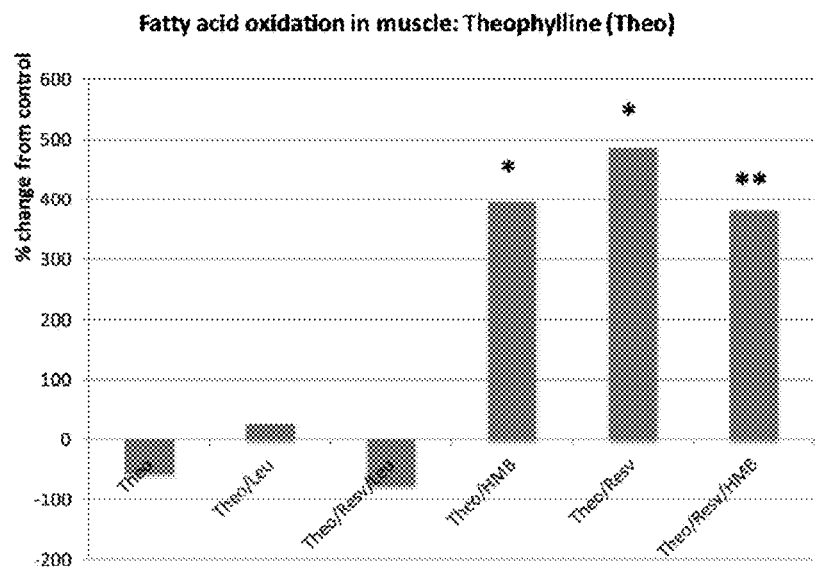
FIG. 56 depicts a graph showing interactive effects of theophylline (1 µM) with HMB (5 µM), leucine (0.5 mM) and resveratrol (200 nM) on fatty acid oxidation in C2C12 myotubes (data expressed as % change from control value; *p=0.03; **p=0.05).
Figure 57:
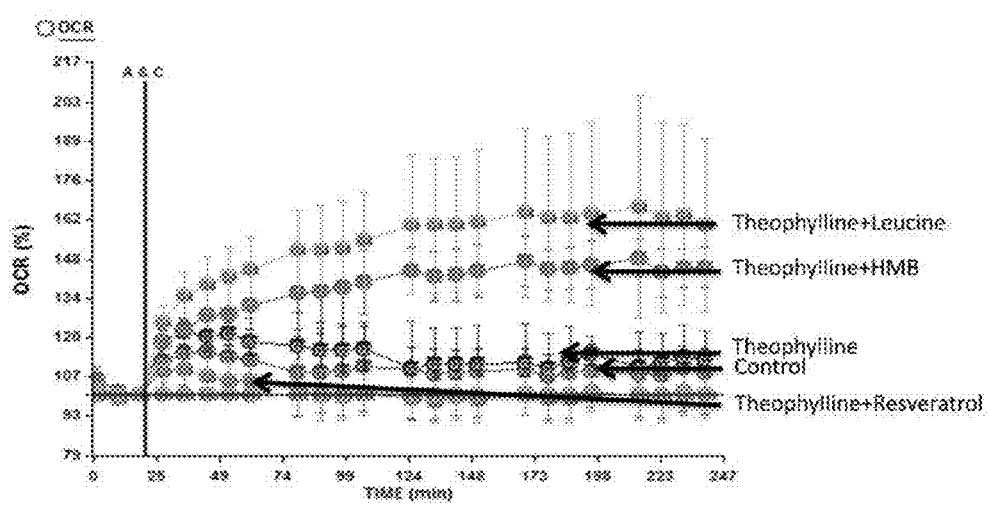
FIG. 57 depicts a graph showing interactive effects of theophylline (1 µM) with HMB (5 µM), leucine (0.5 mM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 58:
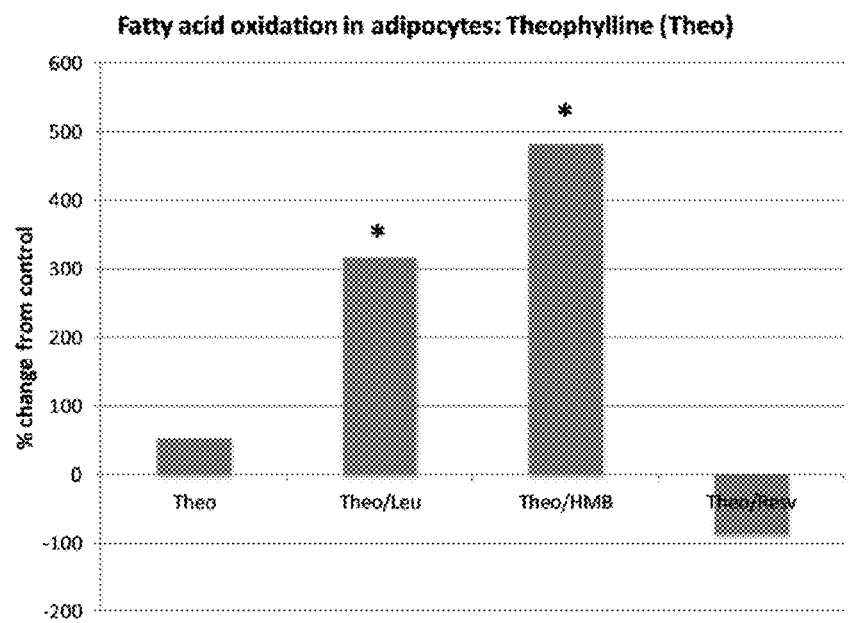
FIG. 58 depicts a graph showing interactive effects of theophylline (1 µM) with HMB (5 µM), leucine (0.5 mM) and resveratrol (200 nM) on fatty acid oxidation in 3T3-L1 adipocytes (data expressed as % change from control value; *p=0.006).

Theophylline is a metabolite of caffeine that is also naturally occurring in tea and cocoa. Theophylline dose-response curves indicate concentrations below 1 µM exert no effect; accordingly, this was the concentration used in synergy experiments. Combining theophylline with 5 µM HMB resulted in a 396% increase in myotube fatty acid oxidation (p=0.03; FIG. 56). Similar synergy occurred between theophylline and resveratrol (486%, p=0.03), while combining HMB, resveratrol and HMB did not further augment this effect (382%, p=0.05; FIG. 56). Theophylline exhibited a similar synergy with HMB and leucine in adipocytes (FIGS. 57 and 58), although no synergy was observed with resveratrol in adipocytes.

Figure 59:
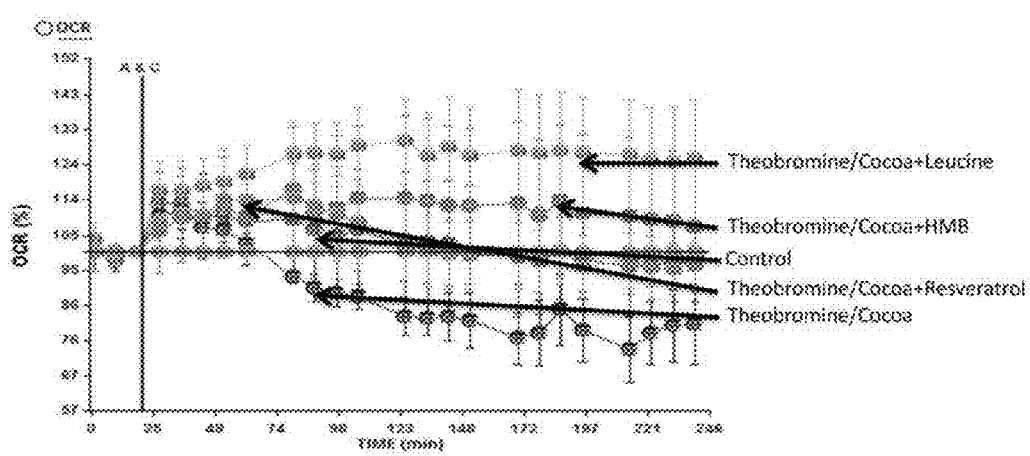
FIG. 59 depicts a graph showing interactive effects of cocoa extract/theobromine (0.1 µg/mL) with HMB (5 µM), leucine (0.5 mM) and resveratrol (200 nM) on fatty acid oxidation in 3T3-L1 adipocytes. Fatty acid oxidation was measured as $O_2$ consumption response to palmitate injection and is expressed as % change from pre-injection baseline (vertical line shows the time of palmitate injection; data points to the left of this line are baseline measurements and those to the right of the line show the $O_2$ consumption response).
Figure 60:
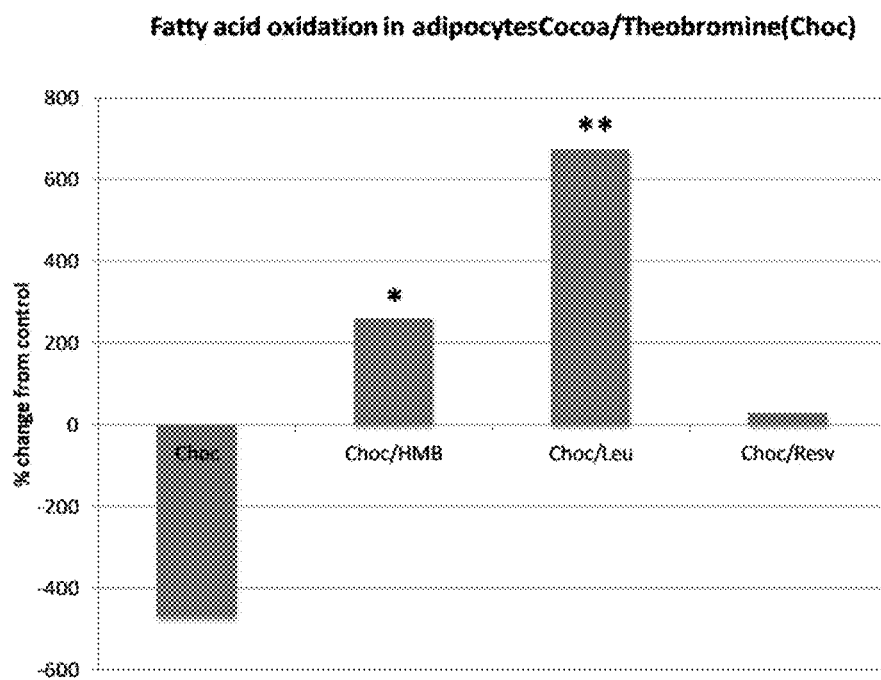
FIG. 60 depicts a graph showing interactive effects of cocoa extract/theobromine (0.1 µg/mL) with HMB (5 µM), leucine (0.5 mM) and resveratrol (200 nM) on fatty acid oxidation in 3T3-L1 adipocytes (data expressed as % change from control value; *p=0.021; **p=0.00035).

Theobromine is a naturally occurring methylxanthine found primarily in cocoa and dark chocolate, as well as yerba mate and tea. Experiments were conducted with a cocoa extract standardized to 12% theobromine; dose-response curves indicated concentrations below 0.1 µg/mL exert no effect; accordingly, this was the concentration used in synergy experiments. Combining cocoa extract/theobromine with 5 µM HMB resulted in a 260% increase in fat oxidation (p=0.021), and the cocoa extract/theobromine combination with 0.5 mM leucine resulted in a 673% increase (p=0.00035) (FIGS. 59 and 60). Combining the cocoa extract/theobromine with resveratrol exerted no significant effect on fat oxidation (FIGS. 59 and 60).

Isobutylmethylxanthine (3-isobutyl-1-methylxanthine; IBMX) is a methyl xanthine similar to caffeine. It serves as both an adenosine antagonist and a non-specific PDE inhibitor. IBMX dose-response curves indicate concentrations below 50 nM exert no effect; accordingly, this was the concentration used in synergy experiments. IBMX exhibited weak but statistically significant synergy with HMB, but not leucine, in stimulating fat oxidation (73% increase, p=0.05) and glucose utilization (66%, p=0.05) in myotubes.

These data demonstrate significant synergistic effects of a several naturally occurring polyphenols on fat oxidation and glucose utilization when these polyphenols are combined with either HMB or leucine. These effects occur at levels which produce no independent effects and which are readily achievable via diet or supplementation. These effects, mediated via Sirt1 and AMPK signaling, are significantly more robust for several of the polyphenols than those we previously observed for a low dose of resveratrol combined with either HMB or leucine and more robust than effects observed by us and others for high dose resveratrol. Chlorogenic acid (a hydroxycinnamic acid) and its hydrolysis product, quinic acid, as well as compounds structurally related to chlorogenic acid (cinnamic acid, ferulic acid) exerted especially robust effects. Highly significant effects were also observed with the resveratrol metabolite piceatannol as well as with a non-polyphenolic compound from seaweed (fucoxanthin, a xanthophyll that exhibits a highly resonant structure commonly observed in polyphenols). These effects can also be recapitulated with naturally occurring non-specific PDE inhibitors. Thus, moderate levels of leucine and HMB can be utilized in synergistic combinations with a number of polyphenols and related compounds to stimulate AMPK and sirtuin signaling and achieve benefits comparable to or exceeding those found with high-dose resveratrol.

These data also demonstrate that leucine and HMB exhibit significant synergies with pharmaceuticals that converge on the same signaling pathways, thereby conferring efficacy to otherwise non-therapeutic doses of these drugs. This can be an effective strategy for decreasing the levels of these drugs required to achieve therapeutic efficacy, thereby attenuating side effects and adverse events otherwise associated with them.

Example 6—Synergistic Effects of Metformin with Resveratrol-Hydroxymethylbutryate Blend on Insulin Sensitivity in Diabetic Mice Eight to ten week-old male diabetic db/db mice (C57BLKS/J-lepr$^{db}$/lepr$^{db}$) were randomized into six treatment groups (as described below) with 10 animals/group and kept on their diet for 2 weeks:

Group 1 (labeled "control group"): standard diet (AIN 93G) only

Group 2 (labeled "high Metformin" (here 300 mg/kg BW)): standard diet mixed with 1.5 g Metformin/kg diet (calculation: average food consumption=8 g/day, average BW=40 g, 300 mg×0.04 kg=12 mg Metformin/day/8 g food=1.5 mg Met/g diet)

Group 3 (labeled "low Metformin" (here 150 mg/kg BW): standard diet mixed with 0.75 g Metformin/kg diet Group 4 (labeled "very low Metformin" (here 50 mg/kg BW): standard diet mixed with 0.25 g Metformin/kg diet Group 5 (labeled "low Metformin plus Resv and CaHMB"): standard diet mixed with 0.75 g Metformin plus 12.5 mg Resveratrol and 2 g CaHMB/kg diet Group 6 (labeled "very low Metformin plus Resv and CaHMB"): standard-diet mixed with 0.25 g Metformin plus 12.5 mg of Resveratrol and 2 g CaHMB/kg diet.

Animals were housed in polypropylene cages at a room temperature of 22±2° C. and regime of 12 h light/dark cycle. The animals had free access to water and their experimental food throughout the experiment. At the of the treatment period (2 weeks) all animals were fasted overnight and humanely euthanized the next morning, and blood and tissues were collected for further experiments as described below.

Insulin Tolerance Test (ITT): Insulin tolerance tests were performed at 2 pm on day 7. The mice were injected with insulin (0.75 U/kg) in ~0.1 ml 0.9% NaCl intraperitoneally. A drop of blood (5 microliter) was taken from the cut tail vein before the injection of insulin and after 15, 30, 45, and 60 min for the determination of blood glucose. Change in blood glucose over the linear portion of the response curve was then calculated.

Insulin: Blood Insulin in serum was measured via Insulin ELISA kit from Millipore (Cat. # EZRMI-13K).

Glucose: Blood glucose was measured via Glucose Assay Kit from Cayman (Cat. # EZRMI-13K).

Statistical Analysis: All data is expressed as mean±STD. Data was analyzed by one-way ANOVA, and significantly different group means ($p<0.05$) were separated by the least significant difference test using SPSS (SPSS Inc, Chicago, Ill.).

Results

Figure 61:
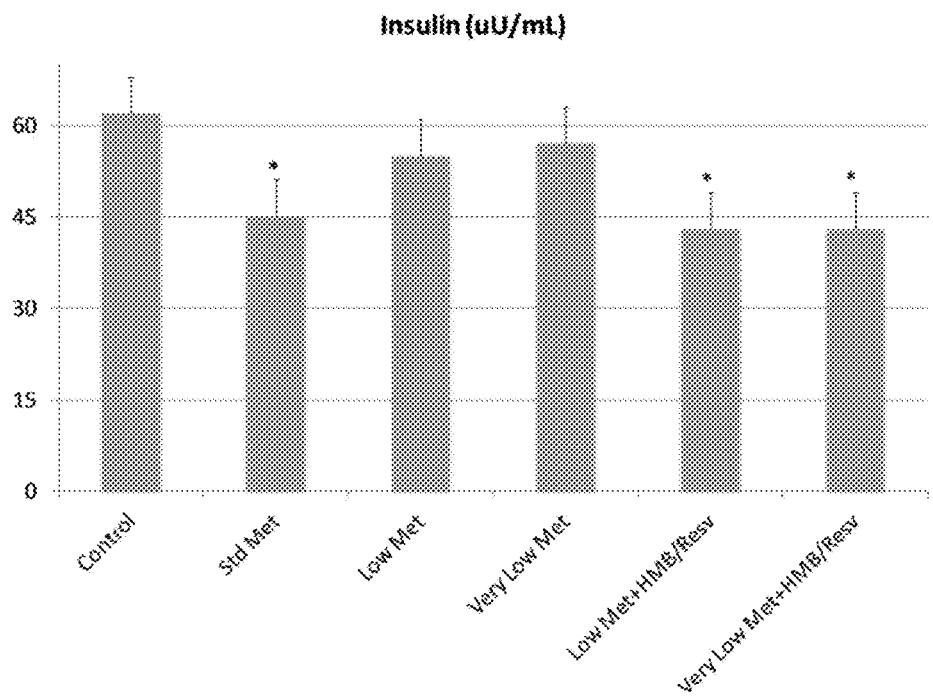
FIG. 61 depicts a graph showing effects of a standard dose of metformin (here 1.5 g metformin/kg diet), a low dose of metformin (here 0.75 g metformin/kg diet) and a very lose dose of metformin (here 0.25 g metformin/kg diet) compared with [the low dose of metformin+12.5 mg resveratrol and 2 g CaHMB/kg diet] and with [the very lose dose of metformin+12.5 mg resveratrol and 2 g CaHMB/kg diet] on plasma insulin in db/db mice (*p<0.02 vs. control).
Figure 62:
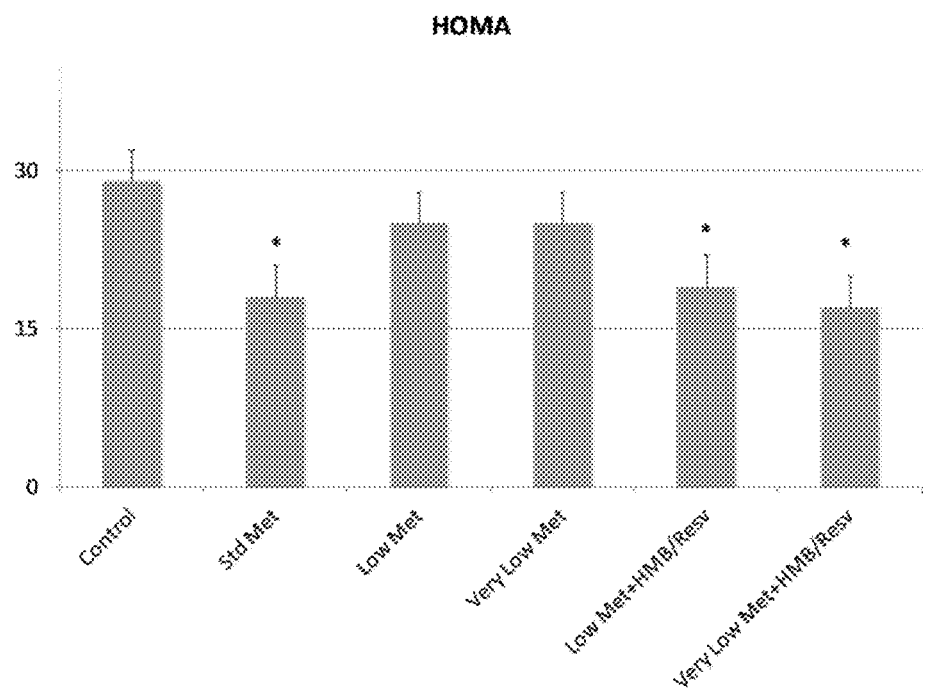
FIG. 62 depicts a graph showing effects of a standard dose of metformin (here 1.5 g metformin/kg diet), a low dose of metformin (here 0.75 g metformin/kg diet) and a very lose dose of metformin (here 0.25 g metformin/kg diet) compared with [the low dose of metformin+12.5 mg resveratrol and 2 g CaHMB/kg diet] and with [the very lose dose of metformin+12.5 mg resveratrol and 2 g CaHMB/kg diet] on HOMA$_{IR}$ (homeostatic assessment of insulin resistance) in db/db mice (*p<0.025 vs. control).
Figure 63:
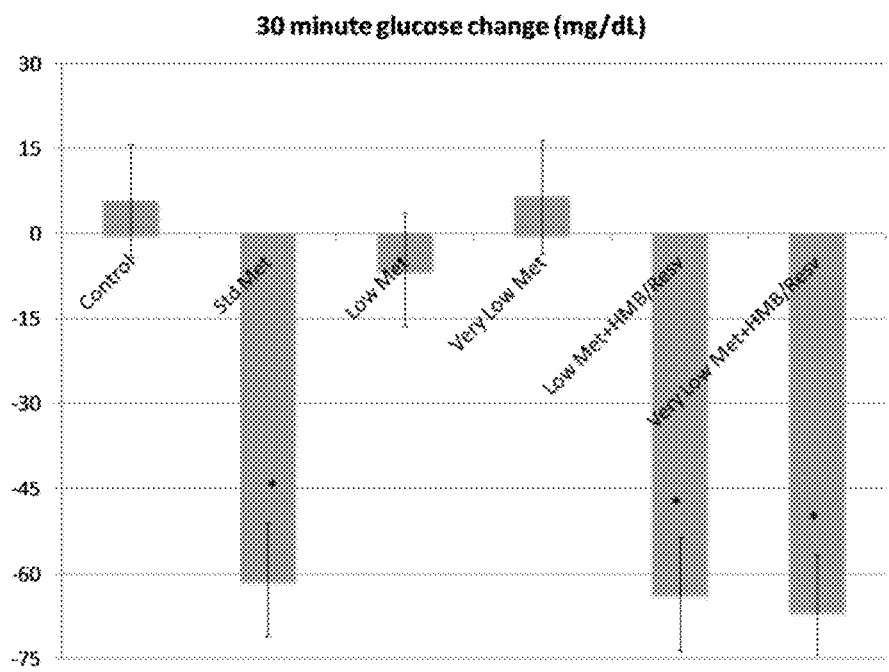
FIG. 63 depicts a graph showing effects of a standard dose of metformin (here 1.5 g metformin/kg diet), a low dose of metformin (here 0.75 g metformin/kg diet) and a very lose dose of metformin (here 0.25 g metformin/kg diet) compared with [the low dose of metformin+12.5 mg resveratrol and 2 g CaHMB/kg diet] and with [the very lose dose of metformin+12.5 mg resveratrol and 2 g CaHMB/kg diet] on 30-minute plasma glucose response to insulin (0.75 U/kg body weight) in db/db mice (*p<0.02 vs. control).
Figure 64:
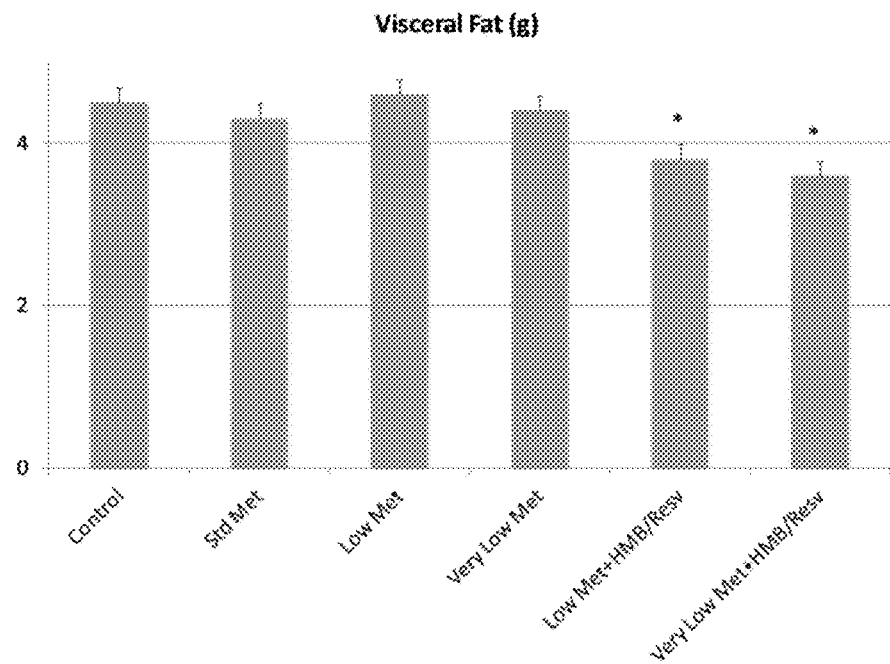
FIG. 64 depicts a graph showing effects of a standard dose of metformin (here 1.5 g metformin/kg diet), a low dose of metformin (here 0.75 g metformin/kg diet) and a very lose dose of metformin (here 0.25 g metformin/kg diet) compared with [the low dose of metformin+12.5 mg resveratrol and 2 g CaHMB/kg diet] and with [the very lose dose of metformin+12.5 mg resveratrol and 2 g CaHMB/kg diet] on visceral fat mass in db/db mice (*p<0.03 vs. control).
Figure 65:
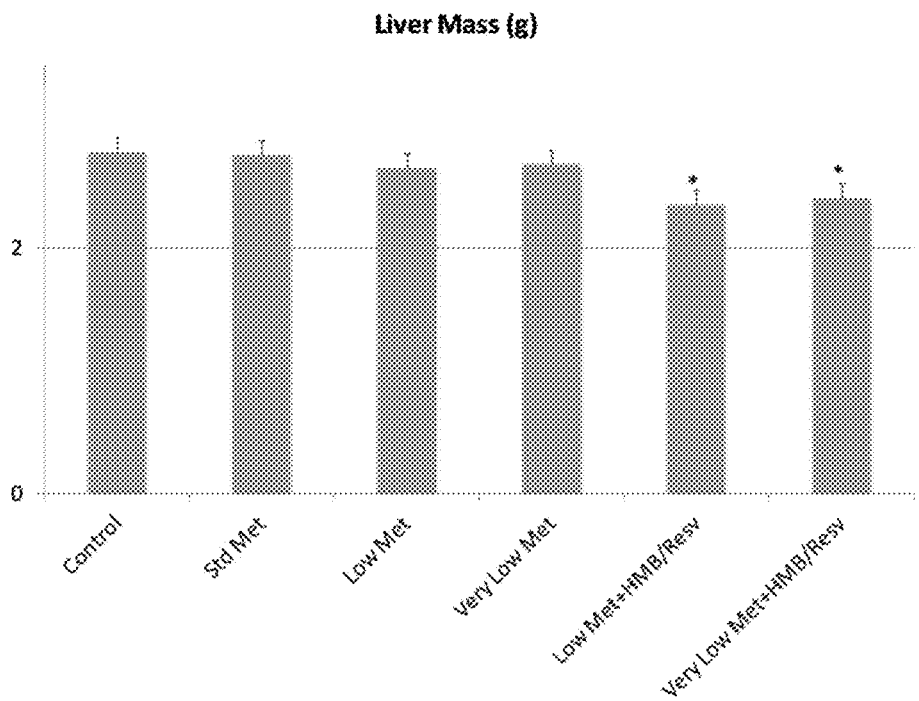
FIG. 65 depicts a graph showing effects of a standard dose of metformin (here 1.5 g metformin/kg diet), a low dose of metformin (here 0.75 g metformin/kg diet) and a very lose dose of metformin (here 0.25 g metformin/kg diet) compared with [the low dose of metformin+12.5 mg resveratrol and 2 g CaHMB/kg diet] and with [the very lose dose of metformin+12.5 mg resveratrol and 2 g CaHMB/kg diet] on visceral fat mass in db/db mice (*p<0.05 vs. control).

The high dose (300 mg/kg bw) reduced plasma insulin by 27% (from 62 to 45 uU/mL, $p<0.02$, FIG. 61) and in the $HOMA_{IR}$ index by 35% (from 29 to 18 units, $p<0.025$, FIG. 62), but exerted no significant effect on plasma glucose in these highly insulin resistant animals. However, there were no significant effects on body composition. A low dose of metformin (here 150 mg/kg) and a very low dose (50 mg/kg) exerted no significant independent effects on any variable studied. In contrast, combining either the low or very low dose of metformin with HMB resulted in significant decreases in plasma insulin from 62 uU/mL to 43 uU/mL ($p<0.02$, FIG. 61) comparable to that seen with high dose metformin, and there was no significant difference between the low metformin-HMB blend versus the very low metformin-HMB blend. Consistent with this observation, the $HOMA_{IR}$ index decreased from 29 units on the control diet to 19 on the low metformin-HMB blend and to 16 on the very low metformin-HMB blend ($p<0.025$, FIG. 62), reflecting an improvement in insulin sensitivity comparable to that found with high dose metformin. This is also reflected in the results of the insulin tolerance test; animals on the control, low-dose or very low-dose of metformin exhibited minimal changes in blood glucose in response to the insulin challenge (FIG. 63). In contrast, those on the standard metformin dose and those on either the low or very low dose of metformin combined with HMB exhibited ~60 mg/dL decreases in blood glucose over the 30 minute linear portion of the response curve ($p<0.02$; FIG. 63). Moreover, the metformin-HMB blends reduced visceral adiposity (FIG. 64). Animals on the control diet had a mean visceral fat mass of 4.5 g, and this was not affected by metformin at any dosage in the absence of HMB. A low dose of metformin+HMB and a very low dose of metformin+HMB reduced visceral fat by ~20%, to 3.8 and 3.6 g, respectively, ($p<0.03$; FIG. 64). These treatments also reduced liver mass, from 2.78 g (control) to 2.35 g and 2.41 g, respectively ($p<0.05$ for both, FIG. 65).

Example 7—Synergistic Cell Signalling Effects of Metformin with Resveratrol-Hydroxymethylbutryate Blend on Insulin Sensitivity in Diabetic Mice Six groups of mice are treated as in Example 6, including collection of blood and tissues for further experiments as described below.

SIRT1 Activity: SIRT1 activity in cell lysates is measured by using the SIRT1 Fluorimetric Drug Discovery Kit (BML-AK555, ENZO Life Sciences International, Inc. PA, USA). In this assay, SIRT1 activity is assessed by the degree of deacetylation of a standardized substrate containing an acetylated lysine side chain. The substrate utilized is a peptide containing amino acids 379-382 of human p53 (Arg-His-Lys-Lys[Ac]), a target of SIRT1 activity; SIRT1 activity is directly proportional to the degree of deacetylation of Lys-382. Samples are incubated with peptide substrate (25 µM), and $NAD^+$ (500 µM) in a phosphate-buffered saline solution at 37° C. on a horizontal shaker for 45 minutes. The reaction is stopped with the addition of 2 mM nicotinamide and a developing solution that binds to the deacetylated lysine to form a fluorophore. Following 10 minutes incubation at 37° C., fluorescence is read in a plate-reading fluorometer at an excitation wavelength of 360 nm and an emission wavelength of 450 nm. Resveratrol (100 mM) serves as a SIRT1 activator and suramin sodium (25 mM) as a SIRT1 inhibitor; wells including each are utilized as positive and negative controls in each set of reactions. A standard curve is constructed using deactylated substrate (0-10 µM). Data is normalized to cellular protein concentration measured via BCA-assay.

Mitochondrial extraction from cell lysates: Mitochondria from tissue are isolated and lysed by using the Mitochondrial Isolation Kit from BioChain (Cat# KC010100).

Sirt3 Activity: SIRT3 activity is measured by using the SIRT3 Fluorimetric Drug Discovery Kit (ENZO, BML-AK557) after mitochondrial extraction from cell lysates. This assay is similar to SIRT1 activity, but uses a different amino acid sequence of p53 (317-320: Gln-Pro-Lys(Ac)), as substrate. This substrate is most efficiently deacetylated by SIRT3.

Insulin signaling: Total and phosphorylated Akt, GSK-3β, IGF-1R, IR, IRS-1, p70S6K and PRAS40 in tissue lysates are measured via the Luminex Kits "Akt Pathway Total 7-Plex Panel" (Cat# LH00002) and "Akt Pathway Phospho 7-Plex Panel" (Cat# LHO0001) from Invitrogen Life Science.

AMPK activity: AMPK activity in cell lysates is measured via the Non-Radioisotopic AMPK Kinase Assay Kit from CycLex (Cat# CY-1182).

RNA extraction: The Ambion ToTALLY RNA isolation kit (Ambion, Inc., Austin, Tex., USA) is used to extract total RNA from tissue according to the manufacturer's instructions. The concentration, purity and quality of the isolated RNA are assessed by measuring the 260/280 ratio (1.8-2.0) and 260/230 ratio (close to 2.0) via Spectrophotometer.

Gene Expression: Expression of 18S, Sirt1, Sirt3, PGC1-α, cytochrome c oxidase subunit VIIc (COX 7), mitochondrial NADH dehydrogenase, nuclear respiratory factor 1 (NRF1), uncoupling protein (UCP2 (adipocyte)/UCP3 (myocyte), and GLUT4 are measured via quantitative real-time PCR using an ABI 7300 Real-Time PCR system (Applied Bioasystems, Branchburg, N.J.) with a TaqMan core reagent kit. All primers and probe sets are obtained from Applied Bioasystems TaqMan Assays-on-Demand and utilized accordingly to manufacturer's instructions. Pooled RNA from each cell type is serial-diluted in the range of 0.0156-50 ng and is used to establish a standard curve; total RNA for each unknown sample is also diluted in this range. RT-PCR reactions are performed according to the instructions of the ABI Real-Time PCR system and TaqMan Real Time PCR Core Kit. Expression of each gene of interest is then normalized using the corresponding 18S rRNA quantitation. Data for each gene is presented as a ratio to 18S rRNA.

Example 8—Syngergistic Effects of Leucine and its Metabolites with Polyphenols on Irisin Compounds at doses having no independent effects on fatty acid oxidation were tested for synergistic combinatorial effects on fatty acid oxidation and on irisin secretion. Compounds used included resveratrol (200 nM), cinnamic acid (1 µM), Chlorogenic acid (0.5 µM), quinic acid (500 nM), caffeine (10 nM), leucine (0.5 mM), and HMB (5 µM). As described in Example 5, C2C12 myotubes treated with the indicated combinations of compounds were used to produce conditioned media, with which 3T3-L1 adiposytes were then treated. Fatty acid oxidation was measured as in Example 5. Irisin levels were measured by Western blot and ELISA, both in conditioned media and in plasma from mice treated according to Example 4.

Western Blot: The FNDC5 antibody (which binds irisin) was obtained from Abcam (Cambridge, Mass.). C2C12 myotubes were treated as described in Example 5, with the indicated compound combinations, and the media and cellular fractions were prepared as described by Bostrom et al (Nature (2012) 481:463-468). Protein was measured by BCA kit (Thermo Scientific). For Western blot, 6 µg protein (media) or 25 µg (cell lysate) was resolved on 4-20% gradient polyacrylaminde gels (Criterion precast gel, Bio-Rad Laboratroies, Hercules, Calif.), transferred to PVDF membranes, incubated in blocking buffer (3% BSA in TBS) and then incubated with primary antibody (FNDC5), washed and incubated with secondary horseradish peroxidase-conjugated antibody. Visualization and chemiluminescent detection was conducted using BioRad ChemiDoc instrumentation and software (Bio-Rad Laboratories, Hercules, Calif.) and band intensity was assessed using Image Lab 4.0 (Bio-Rad Laboratories, Hercules, Calif.), with correction for background and loading controls. Purified FNDC5 (Abcam, Cambridge, Mass.) was used as a positive control in these blots. FNDC5 was detected at 26-28 kDA and irisin was detected at 22-24 kDA.

ELISA: Irisin was also detected in C2C12 incubation media from treated cells and in mouse plasma using a commercial enzyme immunoassay kit obtained from Phoenix Pharmaceuticals, Inc. (Burlingame, Calif.). This kit uses an irisin (FNDC5 [16-127] fragment) and streptavidin-horseradish peroxidase detection on a microplate reader at 450 nm.

Figure 66:
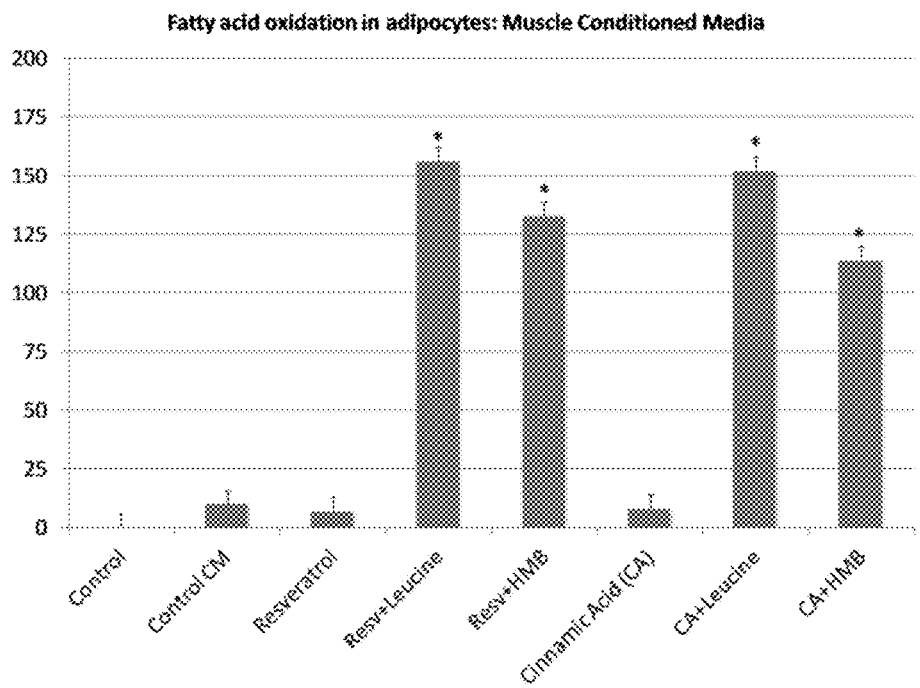
FIG. 66 depicts a graph showing interactive effects of resveratrol (200 nM), leucine (0.5 mM), HMB (5 μM) and cinnamic acid (1 μM) on fatty acid oxidation (*p=0.035 vs. control).
Figure 67:
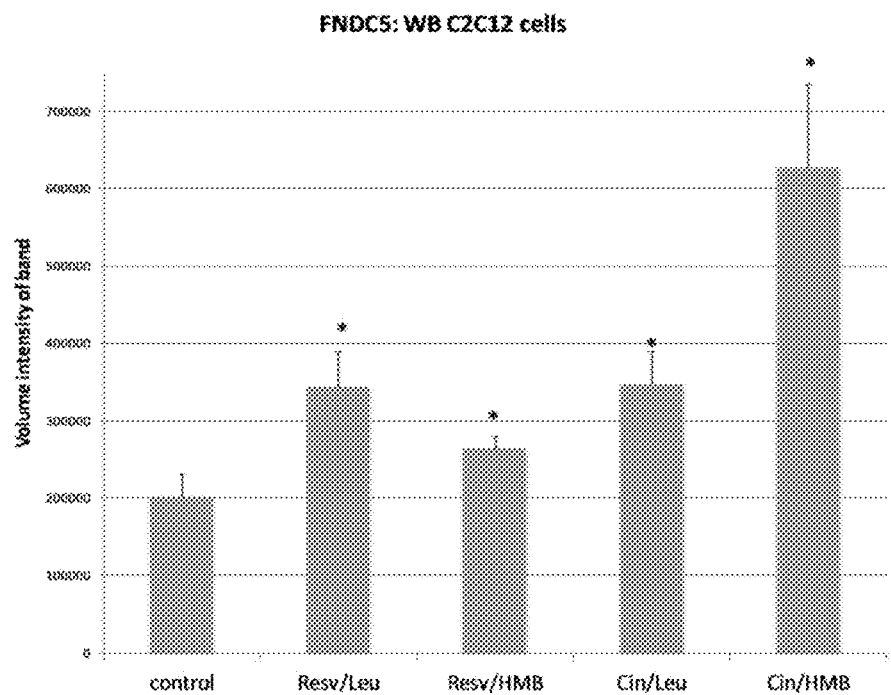
FIG. 67 depicts a graph showing interactive effects of resveratrol (200 nM), leucine (0.5 mM), HMB (5 μM) and cinnamic acid (1 μM) on expression of irisin precursor protein FNDC5 in C2C12 cellular lysates measured by Western blot (values are normalized band intensity units; *p<0.03 vs. control).
Figure 68:
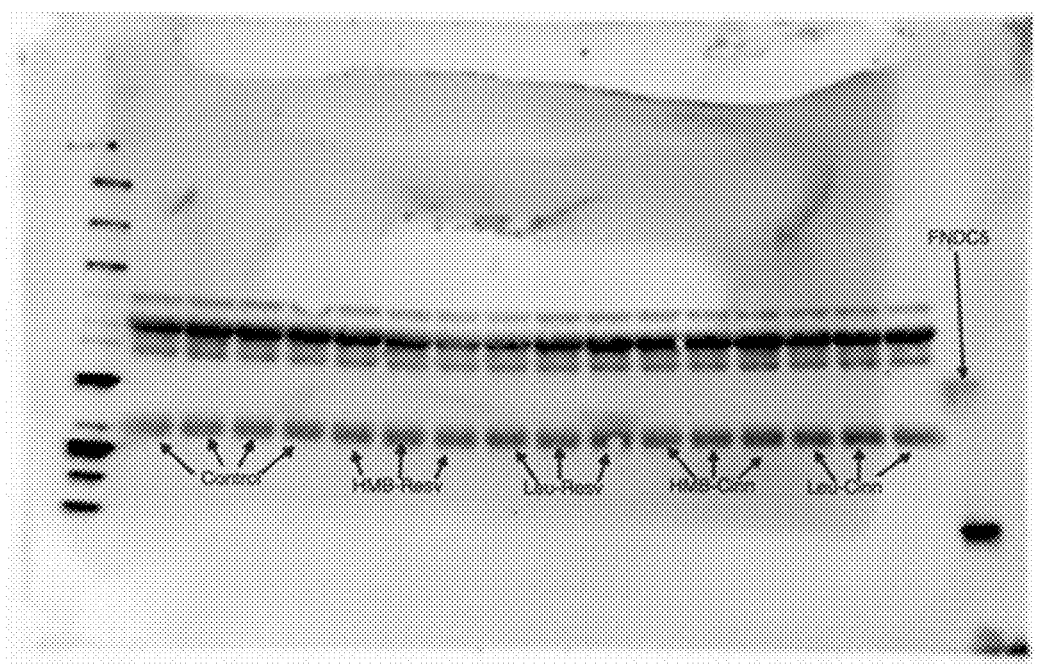
FIG. 68 depicts a representative Western blot of irisin secretion into culture media in response to leucine (0.5 mM) or HMB (5 μM) combined with either resveratrol (200 nM) or cinnamic acid (1 μM). Quantitative data normalized to control: resveratrol/HMB: 73% increase (p<0.01); resveratrol/leucine, 271% increase (p<0.01), cinnamic acid/HMB 7% (not significant), cinnamic acid/leucine, 238% (p<0.01).
Figure 69:
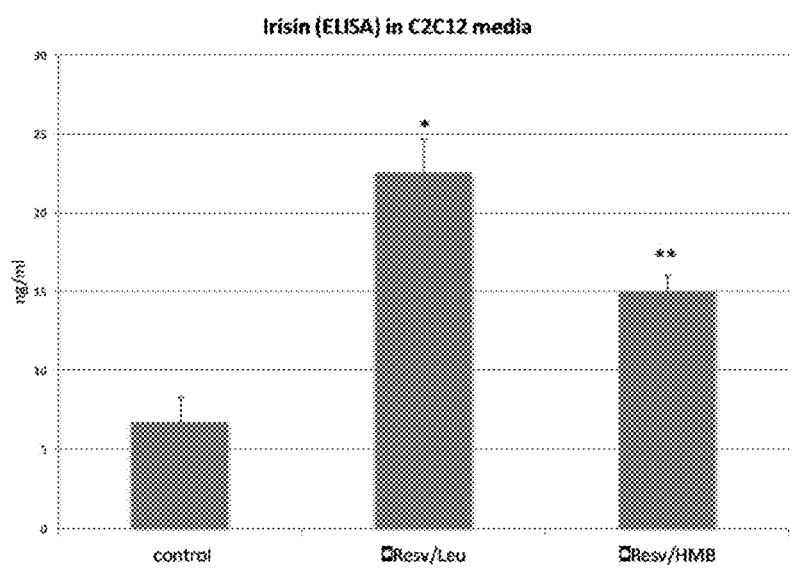
FIG. 69 depicts a graph showing interactive effects of resveratrol (200 nM), leucine (0.5 mM) and HMB (5 μM) on irisin secretion by C2C12 myotubes into culture media (*p=0.0008 vs. control; **p=0.00001 vs. control).
Figure 71:
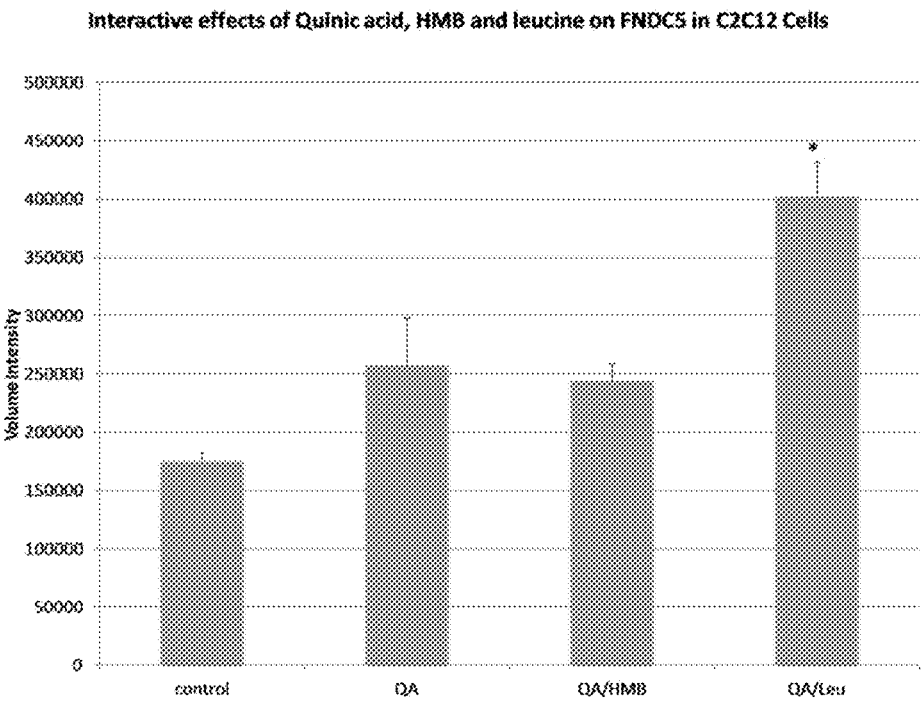
FIG. 71 depicts a graph showing interactive effects of quinic acid (QA; 500 nM), leucine (Leu; 0.5 mM), HMB (5 μM) on FNDC5 protein expression in C2C12 cellular lysates measured by Western blot. Values are normalized band intensity units (*p<0.005 vs. control).
Figure 72:
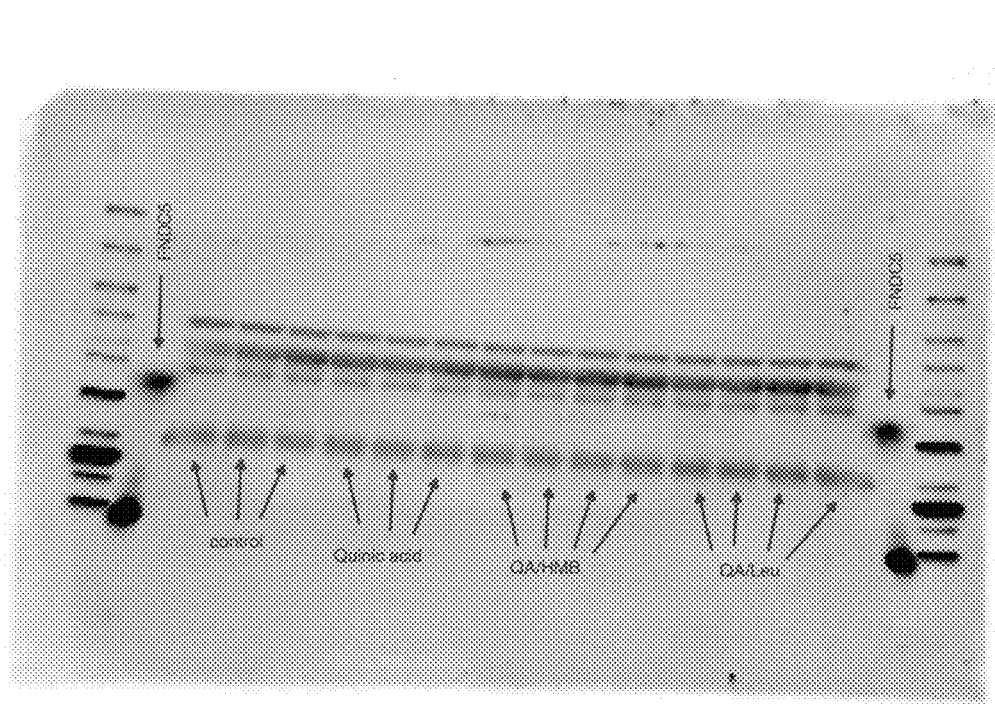
FIG. 72 depicts a representative Western blot of irisin secretion by C2C12 cells into the culture media in response to leucine (0.5 mM) or HMB (5 μM) combined with quinic acid (500 nM).
Figure 73:
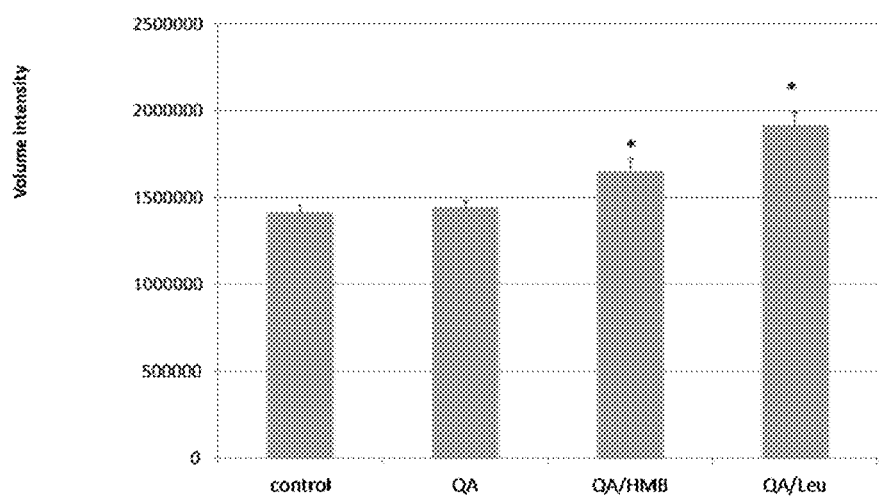
FIG. 73 depicts a graph showing quantitative assessment of the effects of leucine (0.5 mM) or HMB (5 μM) combined with quinic acid (500 nM) on irisin secretion by C2C12 cells into culture media (*p<0.05 vs. control).
Figure 74:
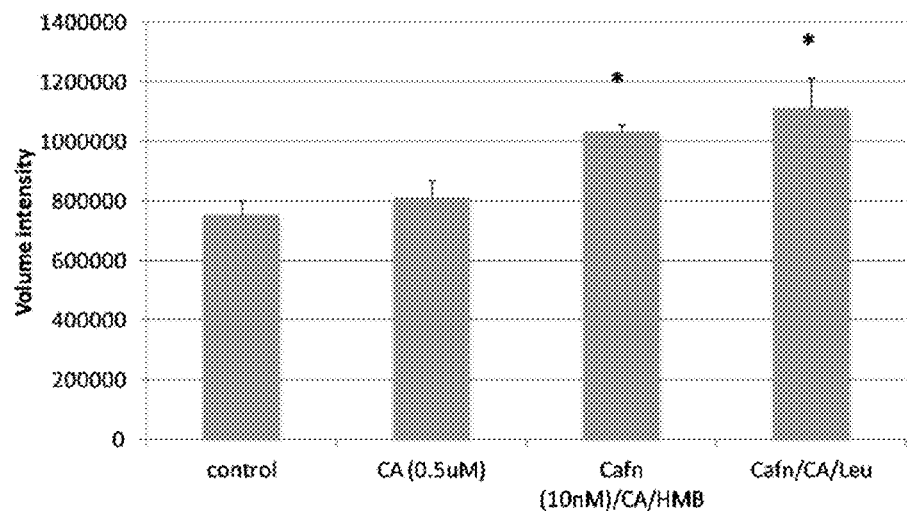
FIG. 74 depicts a graph showing interactive effects of chlorogenic acid (CA; 500 nM), caffeine (Cafn; 10 nM), leucine (Leu; 0.5 mM), and HMB (5 μM) on irisin secretion by C2C12 myotubes into culture media (*p<0.05 vs control).

Results:

In vitro: Conditioned media from cells treated with combinations of resveratrol and leucine, resveratrol and HMB, cinnamic acid and leucine, and cinnamic acid and HMB increased fatty acid oxidation in adipocytes, which was not observed for the compounds when used alone (FIG. 66). The combinations of resveratrol with either leucine or HMB, cinnamic acid with HMB, and chlorogenic acid with either leucine or HMB resulted in significant increases in FNDC5 protein expression in muscle cells (FIG. 67), while the individual components exerted no effect. Combining quinic acid with leucine also results in a significant increase in FNDC5 expression (FIG. 71), and in irisin secretion into the media (FIGS. 72 and 73), while the individual component exert no effect. Measurement of irisin secretion into the media was measured by Western blot (FIGS. 68 and 72) and by ELISA (FIG. 69). Combining resveratrol with leucine resulted in a 234% increase in irisin secretion, from 6.76 to 22.55 ng/ml (p=0.008) and the resveratrol-HMB combination elicited a 122.5% increase (p=0.00001, FIGS. 68 and 69). Similarly, the cinnamic acid-leucine combination stimulated a 40% increase (p=0.0005), while the cinnamic acid-HMB combination did not significantly stimulate irisin release into the media (FIG. 68). Although the chlorogenic acid combinations with leucine or HMB increased muscle FNDC5 protein expression, this combination resulted in only modest, non-significant increases in irisin secretion into the media. However, a three-way combination of chlorogenic acid, caffeine, and either leucine or HMB results in significant increases in both FNDC5 protein expression in skeletal muscle cells and of irisin secretion into the media (FIG. 74).

Figure 70:
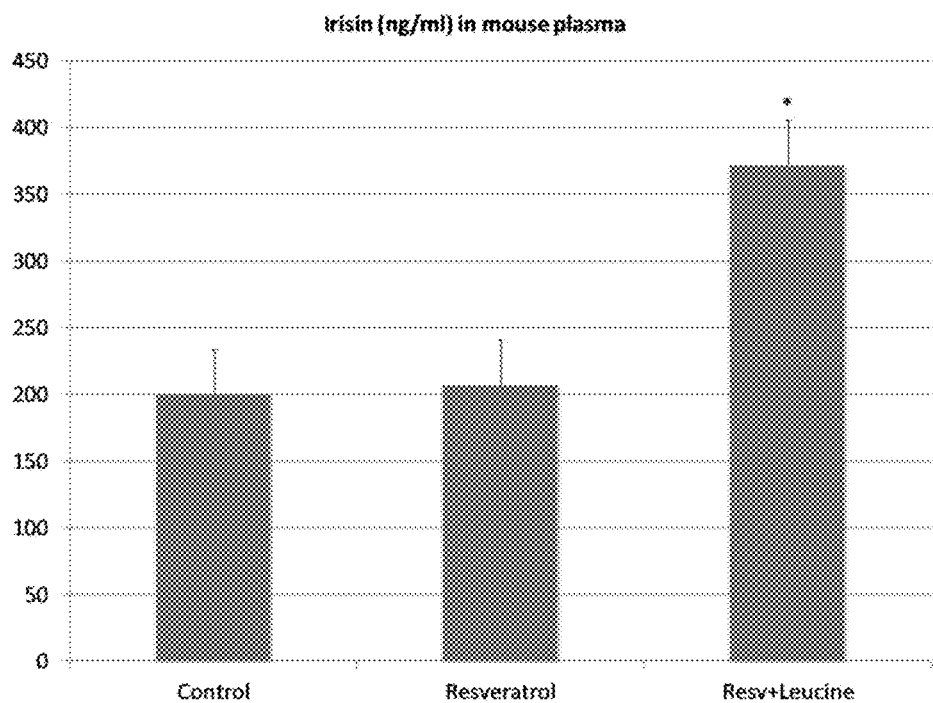
FIG. 70 depicts a graph showing interactive effects of resveratrol and resveratrol/leucine combination on plasma irisin in diet-induced obese mice (*p=0.03 vs. control).

In vivo: Supplementing the diets of diet-induced obese mice with a low dose of resveratrol (12.5 mg/kg diet) and a two-fold increase in dietary leucine (from 1.21 to 2.42%) for six weeks resulted in an 86% increase in plasma irisin, from 200±23 to 372±49 ng/ml (p=0.03, FIG. 70). The low-dose of resveratrol exerted no independent effect on this variable.

These data indicate that, in addition to direct stimulation of sirtuin signaling and fatty acid oxidation in skeletal muscle and fat cells, leucine-polyphenol combinations also stimulate irisin release from skeletal muscle, thereby further promoting adipocyte fat oxidation.

Example 9—Signaling of BCAA Plus Sirtuin Pathway Activator Compositions Through Irisin In Vitro C2C12 myotubes are treated a branched chain amino acid or a metabolite thereof (BCAA), a sirtuin pathway activator, both of these, or no treatment as a control, as in Example 5. The branched chain amino acid can be leucine, such as at 0.5 mM. The sirtuin pathway activator can be resveratrol, such as at 200 nM. Myotubes are treated according to one or more of the experiments described in Example 5 to produce conditioned media. Conditioned media is split into two samples, one that is untreated and one that is treated to reduce or remove irisin. Treatment to remove or inactivate irisin can include immunoprecipitation of irisin, addition of an irisin-neutralizing antibody, or size exclusion (e.g. by filtration or a co-culture of myotubes with adipocytes, where the two cell types are separated by a membrane having a pore size smaller than the size of irisin). Measurement of the mRNA and/or protein levels of FNDC5 (irisin precursor protein) is used to confirm increased FNDC5 expression, synergistically induced by treatment with the combination composition. Measurement of irisin levels before and after treatment of the conditioned media (such as by Western blot or ELISA as described in Example 8) is used to confirm increased irisin production in untreated media and degree of reduction in the treated media. 3T3-L1 adiposytes are then treated with either treated or untreated conditioned media. An output of mitochondrial biogenesis is then measured, such as fatty acid oxidation, glucose utilization, oxygen consumption, mitochondrial mass, or one or more indicia of fat cell browning (e.g. expression of browning-associated genes, such as Ucp1; and increase in fatty acid oxidation). Gene expression can be measured as in Example 4. Other measures of mitochondrial biogenesis can be measured as in Example 5. It is expected that combinations of BCAA (or BCAA metabolites) and sirtuin pathway activators synergistically increase irisin expression, and that adipocytes exposed to untreated media (as in Example 5) will show signs of synergistic increases in mitochondrial biogenesis. It is further expected that treatment of the conditioned media to remove or inactivate irisin from conditioned media giving a synergistic effect will significantly reduce the mitochondrial biogenesis otherwise observed. Such a result will indicate that combination compositions of this kind produce at least a portion of their synergistic effects through irisin signaling.

Example 10—Signaling of BCAA Plus Sirtuin Pathway Activator Compositions Through Irisin In Vivo Six week old male c57/BL6 mice were fed a high-fat diet with fat increased to 45% of energy (Research Diets D12451) for 6 weeks to induce obesity. At the end of this obesity induction period, animals were randomly divided into seven different diet treatment groups with 10 animals per group (overall 70 animals) and maintained on these diet for 6 weeks, according to groups in Example 4. Measurements, samples, and tissues were collected as in Example 4. Tissues collected included subcutaneous adipose tissue, which is ordinarily a white adipose tissue. RNA was extracted from the subcutaneous adipose tissue, and gene expression was evaluated according to methods described in Example 4. Gene expression analysis included determining the expression levels of PGC1α (a known activator of FNDC5 expression, which is the precursor of irisin) and UCP1 (a brown-fat-selective gene, an increase in expression of which is stimulated by irisin). Plasma levels of irisin were also evaluated, the results of which are described in Example 8 and illustrated in FIG. 70. Mice may also evaluated for increases in other indicators of induction of fat cell browning, including increased expression in subcutaneous fat and other adipose tissue of one or more other brown-fat-selective genes (e.g. Cidea, Prdm16, and Ndufs1). Protein expression may also be determined by Western blot or ELISA, as in Example 8. Fat cell browning is also indicated by an increase in fatty acid oxidation in fat cells.

Figure 75:
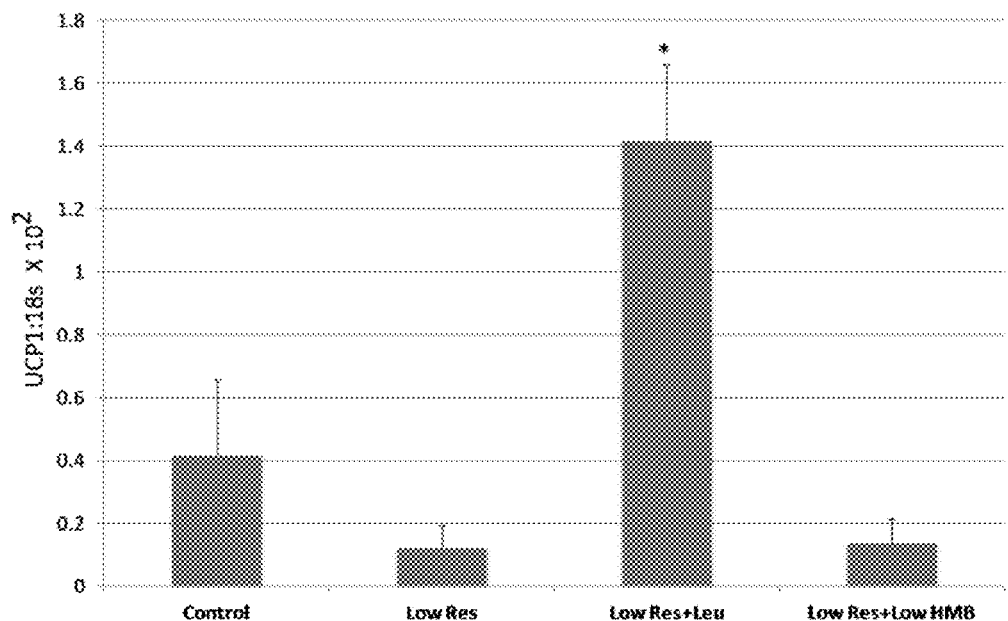
FIG. 75 depicts a graph showing the effects of resveratrol, resveratrol/leucine, and resveratrol/HMB combination on subcutaneous UCP1 mRNA expression in diet-induced obese mice. Data are normalized to 18S (*p=0.05 vs. control).
Figure 76:
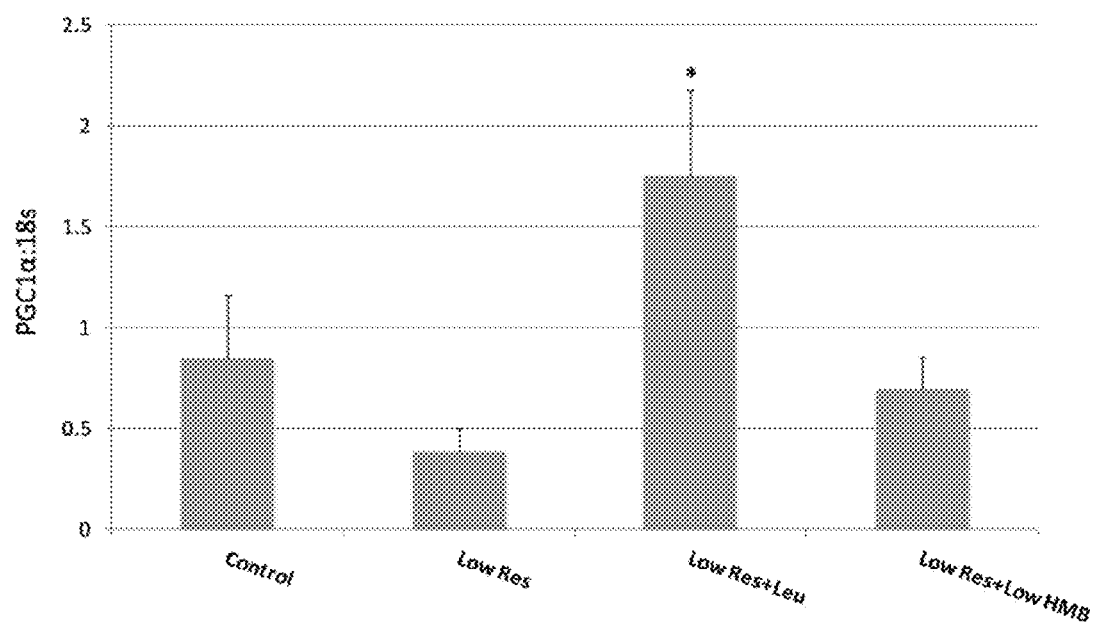
FIG. 76 depicts a graph showing effects of resveratrol, resveratrol/leucine, and resveratrol/HMB combination on subcutaneous PGC1α mRNA expression in diet-induced obese mice. Data are normalized to 18S (*p=0.04 vs. control).

Minimal UCP1 expression was detected in white subcutaneous adipose tissue in control mice. However, supplementing the diets of these diet-induced obese mice with a low dose of resveratrol (12.5 mg/kg diet) and a two-fold increase in dietary leucine (from 1.21 to 2.42%) for six weeks resulted in a 344% increase in UCP1 expression (p<0.05, FIG. 75). The low dose of resveratrol exerted no independent effect on this variable, and the HMB-resveratrol combination exerted no detectable effect. Consistent with these observations, there was a corresponding two-fold upregulation of PGC1α expression in white adipose tissue in response to feeding the resveratrol-leucine combination (p=0.04, FIG. 76).

These data indicate that, in addition to direct stimulation of sirtuin signaling and fatty acid oxidation in skeletal muscle and fat cells, the resveratrol-leucine combination also stimulates browning of white adipose tissue. This correlates with our observation that the leucine-resveratrol combination stimulates irsin release from muscle both in vitro and in vivo (see, e.g., Example 8).

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method for treating obesity in a subject in need thereof comprising:
   a) administering a composition comprising:
      i. at least about 500 mg of leucine and/or at least about 200 mg of one or more metabolites thereof, wherein the one or more leucine metabolites are selected from the group consisting of keto-isocaproic acid (KIC), alpha-hydroxy-isocaproic acid, and HMB; and
      ii. an amount of at least about 0.5 mg of a sirtuin pathway activator,
   wherein the composition is formulated as a tablet, capsule, gel capsule, beverage, snack bar or a food composition,
   wherein the composition is substantially free of the individual amino acids alanine, glutamic acid, glycine, isoleucine, valine, and proline,
   wherein when (a) is a metabolite of leucine the molar ratio of (a) to (b) is greater than 10; and wherein when (a) is leucine, the molar ratio of (a) to (b) is greater than 500.

2. The method of claim 1, wherein the sirtuin pathway activator activates one or more of SIRT1, SIRT3, AMPK, and PGC1α.

3. The method of claim 1, wherein the sirtuin pathway activator is a hydroxycinnamic acid, a stilbene, a polyphenol or a polyphenol precursor.

4. The method of claim 1, wherein the sirtuin pathway activator is a polyphenol or a polyphenol precursor.

5. The method of claim 4, wherein the polyphenol or polyphenol precursor is selected from the group consisting of chlorogenic acid, resveratrol, caffeic acid, cinnamic acid, ferulic acid, piceatannol, ellagic acid, epigallocatechin gallate, grape seed extract, and any analog thereof.

6. The method of claim 1, wherein the sirtuin pathway activator is resveratrol.

7. The method of claim 1, wherein the sirtuin pathway activator is a phosphodiesterase inhibitor.

8. The method of claim 1, wherein the sirtuin pathway activator is present in a sub-therapeutic amount.

9. The method of claim 1, wherein the amount of the sirtuin pathway activator is no more than 5 mg.

10. The method of claim 1, wherein the amount of the sirtuin pathway activator is no more than 50 mg.

11. The method of claim 1, wherein the composition further comprises an anti-diabetic agent.

12. The method of claim 11, wherein the anti-diabetic agent comprises metformin.

13. The method of claim 12, wherein the composition comprises at least about 25 mg of the metformin.

14. The method of claim 12, wherein the composition comprises at least about 250 mg of metformin.

15. The method of claim 12, wherein the composition comprises at least about 400 mg of metformin.

16. The method of claim 1, wherein the composition is formulated as a unit dose.

17. The method of claim 1, wherein the composition further comprises at least one pharmaceutically active agent.

18. The method of claim 17, wherein the pharmaceutically active agent is an anti-obesity agent.

19. The method of claim 18, wherein the anti-obesity agent is selected from group consisting of: lipase inhibitors, dopaminergic compounds, noradrenergic compounds, serotoninergic compounds, cannabinoid receptor antagonists, exenatide, pramlintide, and CNS agents.

20. The method of claim 1, wherein treating obesity is characterized by a reduction in body weight, weight gain, visceral adipose tissue mass, fat oxidation and heat production, and respiratory exchange ratio.

21. The method of claim 1, wherein the subject in need thereof is on a calorie restricted diet.

22. The method of claim 1, wherein the subject in need thereof is on an unrestricted diet.

23. The method of claim 1, wherein the subject in need thereof is human.

24. The method of claim 1, wherein the composition is administered to the subject twice a day.

25. The method of claim 1, wherein the composition is administered to the subject once a day.

* * * * *